(12) United States Patent
Masakari et al.

(10) Patent No.: US 11,078,517 B2
(45) Date of Patent: *Aug. 3, 2021

(54) HEMOGLOBIN A1C MEASUREMENT METHOD AND MEASUREMENT KIT

(71) Applicant: Kikkoman Corporation, Noda (JP)

(72) Inventors: Yosuke Masakari, Noda (JP); Atsushi Ichiyanagi, Noda (JP)

(73) Assignee: Kikkoman Corporation, Chiba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/031,037

(22) PCT Filed: Oct. 24, 2014

(86) PCT No.: PCT/JP2014/078363
§ 371 (c)(1),
(2) Date: Apr. 21, 2016

(87) PCT Pub. No.: WO2015/060429
PCT Pub. Date: Apr. 30, 2015

(65) Prior Publication Data
US 2016/0251695 A1 Sep. 1, 2016

(30) Foreign Application Priority Data
Oct. 25, 2013 (JP) .............................. JP2013-222774

(51) Int. Cl.
C12N 9/96 (2006.01)
C12Q 1/26 (2006.01)
C12N 9/06 (2006.01)
G01N 33/72 (2006.01)
C12Q 1/28 (2006.01)
G01N 21/78 (2006.01)

(52) U.S. Cl.
CPC ............. *C12Q 1/26* (2013.01); *C12N 9/0032* (2013.01); *C12Q 1/28* (2013.01); *C12Y 105/03* (2013.01); *G01N 21/78* (2013.01); *G01N 33/725* (2013.01); *C12Y 111/01* (2013.01); *G01N 2333/805* (2013.01); *G01N 2333/908* (2013.01); *G01N 2333/90672* (2013.01)

(58) Field of Classification Search
None
See application file for complete search history.

(56) References Cited

U.S. PATENT DOCUMENTS

| 5,370,990 | A | 12/1994 | Staniford et al. |
| 7,070,948 | B1 | 7/2006 | Sakaue et al. |
| 2006/0240501 | A1 | 10/2006 | Ebinuma |
| 2007/0054344 | A1 | 3/2007 | Ebinuma |
| 2008/0113381 | A1 | 5/2008 | Matsuoka et al. |
| 2008/0233605 | A1 | 9/2008 | Taniguchi et al. |
| 2011/0003361 | A1 | 1/2011 | Kurosawa et al. |
| 2011/0195444 | A1 | 8/2011 | Hirao et al. |
| 2013/0267007 | A1 | 10/2013 | Ichiyanagi et al. |
| 2014/0234886 | A1 | 8/2014 | Aisaka et al. |
| 2015/0118700 | A1* | 4/2015 | Ichiyanagi ........... C12N 9/0032 435/14 |
| 2015/0316541 | A1* | 11/2015 | Tetsumoto ........... G01N 33/721 435/7.1 |

FOREIGN PATENT DOCUMENTS

| JP | 05-033997 B2 | 5/1993 |
| JP | 11-127895 A | 5/1999 |
| JP | 2001-095598 A | 4/2001 |
| JP | 2003-235585 A | 8/2003 |
| JP | 2004-275013 A | 10/2004 |
| JP | 2004-275063 A | 10/2004 |
| JP | 2010-035469 A | 2/2010 |
| JP | 2010-057474 A | 3/2010 |
| JP | 2011-229526 A | 11/2011 |
| WO | WO 97/13872 A1 | 4/1997 |
| WO | WO 2004/104203 A1 | 12/2000 |
| WO | WO 2004/038033 A1 | 5/2004 |
| WO | WO 2004/038034 A1 | 5/2004 |
| WO | WO 2005/049857 A1 | 6/2005 |
| WO | WO 2008/108385 A1 | 9/2008 |
| WO | WO 2010/041419 A1 | 4/2010 |
| WO | WO 2010/041715 A1 | 4/2010 |
| WO | WO 2011/015325 A1 | 2/2011 |
| WO | WO 2012/018094 A1 | 2/2012 |

(Continued)

OTHER PUBLICATIONS

Young, (Clinical Chem., 56:4, 547-549, 2010).*
Whistler et al. (Advances in Carbohydrate Chemistry & Biochemistry, bol. 64, 2010, Academic Press, pp. 1-529).*
Monnier et al. (Biochem. Soc. Trans., Dec. 2003, pt6, vol. 31, pp. 1349-1353).*
Hirokawa et al., (FEMS Microbio. Letters, vol. 235, 2004, p. 157-162).*
Ferri et al. (J. of Diabetes Science & Technology, vol. 3, Iss. 3, May 2009, pp. 585-592).*
International Search Report dated Jan. 27, 2015 in PCT/JP2014/ 078363. Ferri et al., "Cloning and Expression of Fructosyl-amine Oxidase from Marine Yeast *Pichia* Species N1-1," Mar. Biotechnol., 2004, 6:625-632.
Ferri et al., "Cloning and Expression of Fructosyl-amine Oxidase from Marine Yeast *Pichia* Species N1-1," Mar. Biotechnol., 2004, 6:625-632.

(Continued)

*Primary Examiner* — Hope A Robinson

(74) *Attorney, Agent, or Firm* — Foley & Lardner LLP

(57) ABSTRACT

This invention provides an amadoriase that acts on the β-chain of hemoglobin A1c (HbA1c) and generates hydrogen peroxide, a method for measurement of HbA1c using such amadoriase, and a reagent kit for measurement of HbA1c using such amadoriase. The method for measurement of HbA1c involves the use of an amadoriase that has specific activity of 0.1 U/mg or greater to αF6P and oxidizes the HbA1c β-chain amino terminus so as to generate hydrogen peroxide, and the reagent kit for measurement of HbA1c comprises such amadoriase. The method and the kit for measurement of HbA1c enable quantification of HbA1c to be performed rapidly, simply, and accurately.

4 Claims, 20 Drawing Sheets

Specification includes a Sequence Listing.

(56) References Cited

FOREIGN PATENT DOCUMENTS

WO    WO 2013/162035 A1    10/2013

OTHER PUBLICATIONS

Ferri et al., "Isolation and characterization of a fructosyl-amine oxidase from an *Arthrobacter* sp.," Biotechnology Letters, 2005, 27:27-32.

Fujiwara et al., "Alteration of Substrate Specificity of Fructosyl-Amino Acid Oxidase from *Ulocladium* sp. JS-103," Journal of Bioscience and Bioengineering, 2006, 102(3):241-243.

Fujiwara et al., "Alteration of substrate specificity of fructosyl-amino acid oxidase from *Fusarium oxysporum*," Appl. Microbiol. Biotechnol., 2007, 74:813-819.

Hirokawa et al., "Molecular cloning and expression of novel fructosyl peptide oxidases and their application for the measurement of glycated protein," Biochemical and Biophysical Research Communications, 2003, 311:104-111.

Hirokawa et al., "Recombinant *Agrobacterium* AgaE-like Protein with Fructosyl Amino Acid Oxidase Activity," Biosci. Biotechnol. Biochem., 2002, 66(11):2323-2329.

Jeppsson et al., "Approved IFCC Reference Method for the Measurement of $HbA_{1c}$, in Human Blood," Clin. Chem. Lab. Med., 2002, 40(1):78-89.

Kim et al., "Motif-Based Search for a Novel Fructosyl Peptide Oxidase from Genome Databases," Biotechnology and Bioengineering, Jun. 15, 2010, 106(3):358-366.

Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.

Yoshida et al., "Primary structures of fungal fructosyl amino acid oxidases and their application to the measurement of glycated proteins," Eur. J. Biochem., 1996, 242:499-505.

Supplementary Partial European Search Report dated Apr. 7, 2017, in EP 14856134.3.

Database accession No. AZT55379, "*Coniochaeta* sp. Amadoriase protein mutant (D106A)," XP002768406, retrieved from EBI Accession No. GSP:AZT55379, Mar. 29, 2012, 1 page.

Office Action dated Mar. 9, 2018, in EP 14856134.3.

* cited by examiner

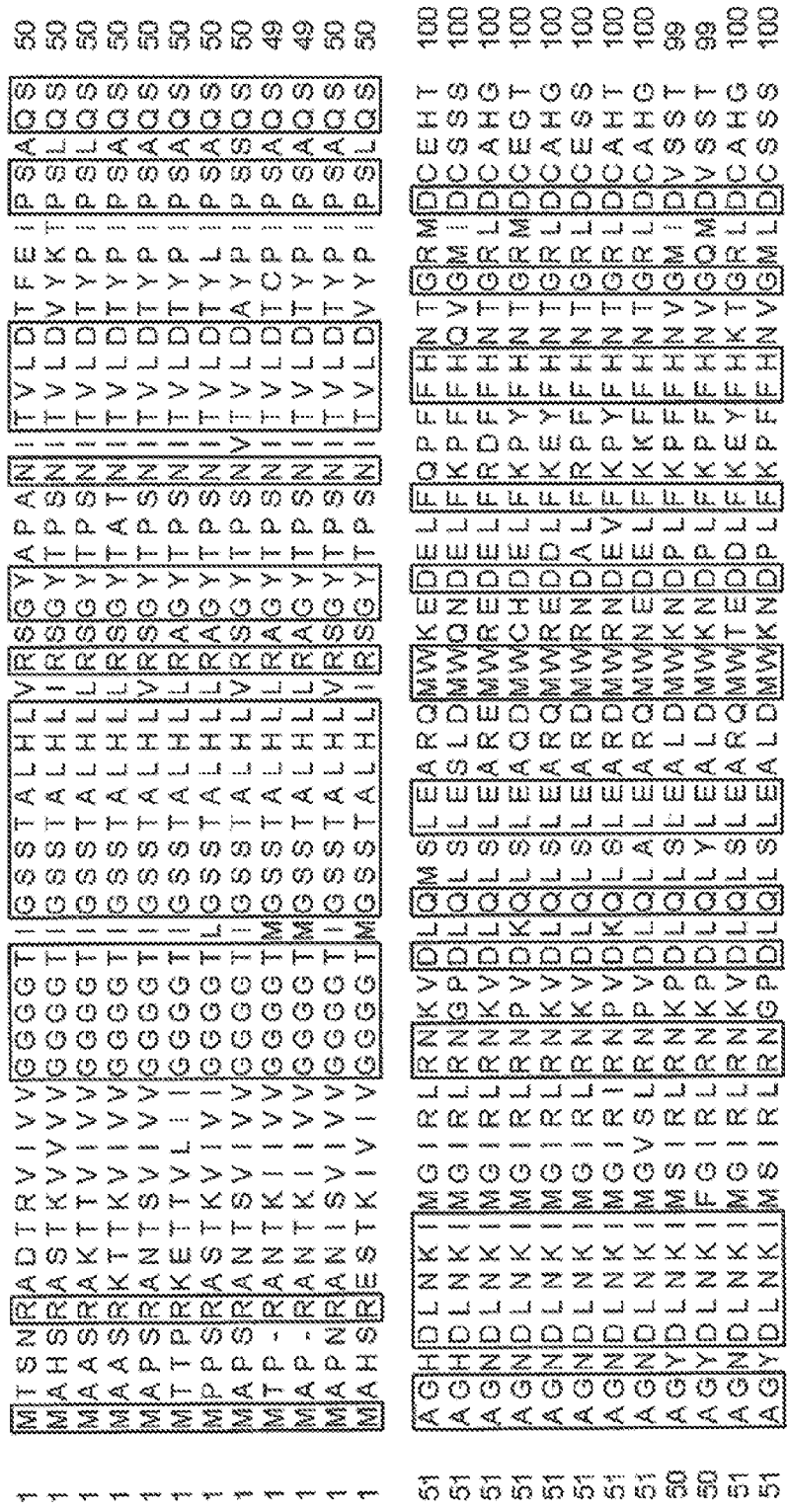

| | | | | | | |
|---|---|---|---|---|---|---|
| Co | 398 | EEMAYQ | WRWRPG- | GDALKSRRAAPP | KDLADMPGWKHDPKL------ | 437 |
| Et | 399 | QEMAGA | WRWRPG- | GDALRSRRGAPA | KDLAEMPGWKHDAHL------ | 437 |
| Py | 397 | ADLAHA | WRWRPG- | GDALQSRRAAPA | KDLADMPGWNHD-ESPRAKL- | 440 |
| Ar | 400 | DDLAQA | WRWRPGI | GDALKSRRAAPA | KDLADMPGWKHDGSQNATSGTSSE | 449 |
| Cc | 397 | EDLAEA | WRWRPGQ | GDALKSRRAAPA | KDLADMPGWKHD-DVVKSKL- | 440 |
| Nz | 399 | EDLAEA | WRWRPGS | GDALKSRRAAPA | RDLADLPGWNHD-DVKSESR- | 441 |
| Cn | 395 | DDLAHA | WRWRPGQ | GDALKS-IRRAA | PAKDLADMPGWNHDQDSESR- | 448 |
| Pf | 399 | SVFKDA | WRWRPGI | GDALKSRRAAPA | KDLADMPGWNHDEPSDDMDVKDVA | 437 |
| An | 399 | SVFKDA | WRWRPGS | GDALKSRRAAPA | KDLADMPGWRNE-KPRANL- | 438 |
| En | 397 | DDLAHA | WRWRPGT | GDALKSRRAARA | KDLADMPGWNHDGEAPRAKL- | 438 |
| Ut | 399 | DDLAGA | WRWRPG- | GDALKSKRSAPA | KDLAEMPGWKHDAKL------ | 441 |
| Pj | | | | | | 437 |

| | | | | | |
|---|---|---|---|---|---|
| Co | 437 | ------ | ------ | ------ | 437 (SEQ ID NO: 1) |
| Et | 437 | ------ | ------ | ------ | 437 (SEQ ID NO: 145) |
| Py | 440 | ------ | ------ | ------ | 440 (SEQ ID NO: 113) |
| Ar | 450 | -HKL-- | ------ | ------ | 452 (SEQ ID NO: 115) |
| Cc | 440 | ------ | ------ | ------ | 440 (SEQ ID NO: 117) |
| Nz | 441 | ------ | ------ | ------ | 441 (SEQ ID NO: 54) |
| Cn | 449 | VSLASVKIGENIGEKVVEDGARVGVKVLA | | | 477 (SEQ ID NO: 149) |
| Pf | 437 | ------ | ------ | ------ | 437 (SEQ ID NO: 38) |
| An | 438 | ------ | ------ | ------ | 438 (SEQ ID NO: 147) |
| En | 436 | ------ | ------ | ------ | 438 (SEQ ID NO: 119) |
| Ut | 441 | ------ | ------ | ------ | 441 (SEQ ID NO: 121) |
| Pj | 437 | ------ | ------ | ------ | 437 (SEQ ID NO: 123) |

```
Co 399 EEMAYQ WRWRPG -GDAL KISRRAAP PKDLADMPGWKHDPKL-------        437
Et 399 QEMAGA WRWRPG -GDAL RSRRGAP  AKDLAEMPGWKHDAHL-------        437
Py 397 ADLAHA WRWRPG IGDAL QSRRGAP  AKDLADMPGWNHD-ESPRAKL---       440
Ar 400 DDLAQA WRWRPG -GDAL KSRRAAP  AKDLADMPGWNHDGSGNATSGTSSE     449
Cc 397 EDLAHA WRWRPG -GDAL KSRRAAP  AKDLADLPGWNHD-DVVKSKL---       440
Nz 399 DDLAEA WRWRPG -GDDARKS-RRAAP  AKDLADMPGWKHD-DVKSKL---       441
Cn 399 EDLAES WRWRPG QGDDAL RSRRAAP AKDLADMPGWNHDEPSDDDMDVKDVA     448
Pn 395 SSVFKD WRWRPG SGDDAL ISRRAAP -AKDLADLPGWNHD--KPRAKM--       437
An 399 SSVFKD WRWRPG SGDDAL KSRRAAP  AKDLADMPGWRNEAKM-------       438
En 399 DDLAHA WRWRPG TGDDAL KSRRAAPAAKDLADMPGWNHDGEAPRAKL--        438
Ul 397 SVFKDA WRWRPG SGDDAL KSRRAAR  AKDLADMPGWKHDAPRAKL---        441
Pj 399 QDLAGA WRWRPG -GDAL KSKRSAP  AKDLAEMPGWKHDAKL-------        437
```

```
Co 437 ------------------------------------  437 (SEQ ID NO: 1)
Et 437 ------------------------------------  437 (SEQ ID NO: 145)
Py 440 ------------------------------------  440 (SEQ ID NO: 113)
Ar 450 --HKL-------------------------------  452 (SEQ ID NO: 115)
Cc 440 ------------------------------------  440 (SEQ ID NO: 117)
Nz 441 ------------------------------------  441 (SEQ ID NO: 54)
Cn 449 VSLASVKIGENIGEKVVEDGARVGVKVLA--------  477 (SEQ ID NO: 149)
Pn 437 ------------------------------------  437 (SEQ ID NO: 38)
An 438 ------------------------------------  438 (SEQ ID NO: 147)
En 438 ------------------------------------  438 (SEQ ID NO: 119)
Ul 441 ------------------------------------  441 (SEQ ID NO: 121)
Pj 437 ------------------------------------  437 (SEQ ID NO: 123)
```

HEMOGLOBIN A1C MEASUREMENT METHOD AND MEASUREMENT KIT

CROSS-REFERENCE TO RELATED APPLICATIONS

This application is a National Stage application of PCT/JP2014/078363, filed Oct. 24, 2014, which claims priority from Japanese application JP 2013-222774, filed Oct. 25, 2013.

REFERENCE TO SEQUENCE LISTING SUBMITTED ELECTRONICALLY

The content of the electronically submitted sequence listing in ASCII text file (Name: PH-6001-PCT; Size: 292,660 bytes) filed with the application is incorporated herein by reference in its entirety.

TECHNICAL FIELD

The present invention relates to a method for measurement of hemoglobin A1c in a sample and a reagent kit for implementing such method for measurement.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, hemoglobin A1c (HbA1c) has drawn attention as a glycemic control marker significant for diagnosis of diabetic patients and control of conditions in the field of clinical diagnosis of diabetes mellitus. HbA1c is a protein comprising glucose bound to the α-amino group at the N-terminal (amino-terminal) valine (Val) residue of the hemoglobin "β chain." The blood HbA1c level reflects the average blood glucose level for a given period of time in the past, and the measured value thereof serves as a significant indicator for diagnosis and control of diabetes conditions.

Several types of enzymatic methods involving the use of amadoriases have heretofore been known as methods for rapidly and simply measuring HbA1c.

Enzymes that oxidize iminodiacetic acid or a derivative thereof (also referred to as an "Amadori compound") in the presence of oxygen to catalyze a reaction to generate glyoxylic acid or α-ketoaldehyde, amino acid or peptide, and hydrogen peroxide are collectively referred to as "amadoriases." Amadoriases are known to be useful for measuring HbA1c by an enzymatic method. An example of a substrate that is known to be oxidized by amadoriases is α-fructosyl-valyl-histidine (hereafter referred to as "αFVH").

Amadoriases have been found in bacteria, yeast, and fungi. For example, amadoriases derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Debaryomyces, Corynebacterium, Agrobacterium*, and *Arthrobacter* have been reported (e.g., Patent Documents 1 and 6 to 15 and Non-Patent Documents 1 to 9). These genera may be referred to as the genera *Coniochaeta* etc. in this description. In some of the aforementioned documents, an amadoriase may also be referred to as, for example, ketoamine oxidase, fructosyl amino acid oxidase, fructosyl peptide oxidase, or fructosyl amine oxidase.

As a method for rapidly and readily measuring HbA1c with the use of various types of amadoriases as described above, a method in which HbA1c is degraded with a cleavage enzyme such as a protease or peptidase (hereafter referred to as "protease(s) or the like"), and a particular target substance released from the β-chain amino terminus of HbA1c is quantified with the use of amadoriases as described above is known (e.g., Patent Documents 1 to 7).

Specifically, a method in which HbA1c is degraded with a particular protease or the like, αFVH is released from the β-chain amino terminus thereof, and the released αFVH is quantified has been known. At present, such method is a major technique for measuring HbA1c by an enzymatic method.

According to a further method for measurement of HbA1c involving the use of amadoriases, HbA1c is digested using a Glu-C protease, releasing α-fructosyl hexapeptide comprising 6 amino acids including valine at the glycated β-chain amino terminus (α-fructosyl-valyl-histidyl-leucyl-threonyl-proryl-glutamic acid, hereafter referred to as "αF6P"), and then the released αF6P is quantified (e.g., Patent Documents 16 and 17). This method for measurement of HbA1c by an enzymatic method is defined by the International Federation of Clinical Chemistry and Laboratory Medicine (IFCC) (Non-Patent Document 10).

In the method for measurement of HbA1c involving the use of amadoriases, however, it is indispensable to perform a process comprising digesting HbA1c with a protease or peptidase (hereafter, referred to as a "protease or the like"), so as to release a glycated peptide including valine at the glycated β-chain amino terminus thereof. Accordingly, it is necessary to include a protease or the like in the reagent kit for measurement of HbA1c; however, such inclusion is not preferable for the reasons described below.

That is, a protease or the like is capable of protein hydrolysis and, therefore, enzymes which are proteins are also hydrolyzed by the protease or the like. As such, amadoriases will also be hydrolyzed by a protease and inactivated, and, as a result, the reaction consuming a glycated peptide and oxygen to generate hydrogen peroxide wall be inhibited. In order to address such problem, it is possible to increase the amount of amadoriases and to complete the measurement before amadoriases are completely inactivated. However, increasing the amount of amadoriases will lead to preferential hydrolysis of amadoriases rather than HbA1c, which intrinsically is not preferable.

When measuring HbA1c by allowing an amadoriase to react with a glycated peptide and quantifying the resulting hydrogen peroxide, hydrogen peroxide may be quantified using a peroxidase. In such a case, the peroxidase will also be hydrolyzed by the protease or the like and inactivated, which is not preferable.

As another aspect, when measuring HbA1c using enzymes, it is commonplace to use an automated analyzer. In such a case, a single sample is simultaneously subjected to analysis of various biomarkers including HbA1c. Since each biomarker is analyzed using an enzyme or antibody, upon contamination of a protease or the like, the enzyme or antibody contained in the biomarker reagent may be hydrolyzed. In such a case, biomarkers other than HbA1c may not be accurately analyzed. Accordingly, it is intrinsically preferable not to include a protease or the like in a reagent to be mounted on an automated analyzer.

Due to the reasons above, an amadoriase that can directly oxidize the HbA1c β-chain to generate hydrogen peroxide, and a method of measuring HbA1c using such amadoriase was needed. However, to date, amadoriases exhibiting such enzymatic activity were not found.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325
Patent Document 16: WO 2004/38034
Patent Document 17: WO 2008/108385

Non-Patent Documents

Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Appl. Microbiol. Biotechnol. 74, 813-9, 2007
Non-Patent Document 5: Eur. J. Biochem. 242, 499-505, 1996
Non-Patent Document 6: Mar. Biotechnol. 6, 625-32, 2004
Non-Patent Document 7: Biosci. Biotechnol. Biochem. 66, 1256-61, 2002
Non-Patent Document 8: Biosci. Biotechnol. Biochem. 66, 2323-29, 2002
Non-Patent Document 9: Biotechnol. Letters 27, 27-32, 2005
Non-Patent Document 10: Jeppsson J O, et al, Approved IFCC reference method for the measurement of HbA1c in human blood, Clin. Chem. Lab. Med. 40, 78-89, 2002

SUMMARY OF THE INVENTION

Objects to be Attained by the Invention

It is an object of the present invention to discover an amadoriase that oxidizes the HbA1c β chain and generates hydrogen peroxide, and to construct a method for measurement of HbA1c using such amadoriase.

Means for Attaining the Object

The present inventors have conducted concentrated studies in order to attain the above objects. As a result, the present inventors found that a modified amadoriase having several amino acid substitutions introduced into the amadoriase derived from the genus *Coniochaeta* or the like has the activity of oxidizing HbA1c and generating hydrogen peroxide, and put into practice a method for measurement of HbA1c using said modified amadoriase. By this the present invention has been accomplished.

Specifically, the present invention encompasses the following.

[1] A method for measurement of hemoglobin A1c in a sample comprising allowing an amadoriase capable of acting directly on hemoglobin A1c to act on a sample and measuring the resulting amount of hydrogen peroxide generated or oxygen consumed in the reaction.

[2] The method according to [1], wherein the amadoriase capable of acting directly on hemoglobin A1c has specific activity on α-fructosyl-valyl-histidyl-leucyl-threonyl-proryl-glutamic acid (αF6P) of 0.1 U/mg or greater.

[3] The method according to [1] or [2], wherein the amadoriase capable of acting directly on hemoglobin A1c has specific activity on α-fructosyl-valyl-histidyl-leucyl-threonyl-proryl-glutamic acid (αF6P) of 0.1 U/mg or greater and is selected from the group consisting of (i) to (iii) below:

(i) an amadoriase comprising an amino acid sequence, wherein when said amino acid sequence is aligned with the amino acid sequence of SEQ ID NO: 1, said amino acid sequence comprises one or more amino acid substitutions at positions corresponding to the positions of the amino acid sequence of SEQ ID NO: 1 selected from the group consisting of (a) to (j) below:
(a) position 62 in SEQ ID NO: 1;
(b) position 63 in SEQ ID NO: 1;
(c) position 102 in SEQ ID NO: 1;
(d) position 106 in SEQ ID NO: 1;
(e) position 110 in SEQ ID NO: 1;
(f) position 113 in SEQ ID NO: 1;
(g) position 355 in SEQ ID NO: 1;
(i) position 419 in SEQ ID NO: 1;
(i) position 68 in SEQ ID NO: 1; and
(j) position 356 in SEQ ID NO: 1;

(ii) the amadoriase as defined in (i), wherein the amadoriase consists of an amino acid sequence comprising substitution, deletion, or addition of one or several amino acids at positions other than those corresponding to positions 62, 63, 102, 106, 110, 113, 355, 419, 68, and 356 of the amino acid sequence of SEQ ID NO: 1; and (iii) the amadoriase as defined in (i), wherein the amadoriase comprises an amino acid sequence having 70% or higher sequence identity with the amino acid sequence as shown in SEQ ID NO: 1 over the full length and having 90% or higher sequence identity between the amino acid sequence of a homologous region consisting of amino acids at positions 10 to 32, to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region in corresponding positions of the amadoriase.

[4] The method according to [3], wherein the amadoriase capable of acting directly on hemoglobin A1c comprises an amino acid sequence in which, when aligned with the amino acid sequence as shown in SEQ ID NO: 1, amino acids at positions corresponding to one or more positions selected from the group consisting of (a) to (j) in SEQ ID NO: 1 below are one or more amino acids described in each of (a) to (j) below and has specific activity to α-fructosyl-valyl-histidyl-leucyl-threonyl-proryl-glutamic acid (αF6P) of 0.1 U/mg or greater;

(a) the amino acid at a position corresponding to position 62 in SEQ ID NO: 1 is alanine, aspartic acid, asparagine, glutamine, glutamic acid, glycine, valine, leucine, isoleucine, cysteine, serine, threonine, or proline;

(b) the amino acid at a position corresponding to position 63 in SEQ ID NO: 1 is alanine or histidine;

(c) the amino acid at a position corresponding to position 102 in SEQ ID NO: 1 is lysine;

(d) the amino acid at a position corresponding to position 106 in SEQ ID NO: 1 is alanine, lysine, or arginine;

(e) the amino acid at a position corresponding to position 110 in SEQ ID NO: 1 is leucine or tyrosine;

(f) the amino acid at a position corresponding to position 113 in SEQ ID NO: 1 is lysine or arginine;

(g) the amino acid at a position corresponding to position 355 in SEQ ID NO: 1 is serine;

(h) the amino acid at a position corresponding to position 419 in SEQ ID NO: 1 is lysine;

(i) the amino acid at a position corresponding to position 68 in SEQ ID NO: 1 is asparagine; and (j) the amino acid at a position corresponding to position 356 in SEQ ID NO: 1 is threonine.

[5] The method according to [4], wherein the amadoriase capable of acting directly on hemoglobin A1c comprises an amino acid sequence in which, when aligned with the amino acid sequence as shown in SEQ ID NO: 1, amino acids at positions corresponding to two or more positions selected from the group consisting of (a) to (j) in SEQ ID NO: 1 are two or more amino acids described in each of (a) to (j) and has specific activity to α-fructosyl-valyl-histidyl-leucyl-threonyl-proryl-glutamic acid (αF6P) of 0.1 U/mg or greater.

[6] The method according to [5], wherein the amadoriase capable of acting directly on hemoglobin A1c comprises an amino acid sequence in which, when aligned with the amino acid sequence as shown in SEQ ID NO: 1, amino acids at positions corresponding to three or more positions selected from the group consisting of (a) to (j) in SEQ ID NO: 1 are three or more amino acids described in each of (a) to (j) and has specific activity to α-fructosyl-valyl-histidyl-leucyl-threonyl-proryl-glutamic acid (αF6P) of 0.1 U/mg or greater.

[7] The method according to [6], wherein the amadoriase capable of acting directly on hemoglobin A1c comprises an amino acid sequence in which, when aligned with the amino acid sequence as shown in SEQ ID NO: 1, amino acids at positions corresponding to four or more positions selected from the group consisting of (a) to (j) in SEQ ID NO: 1 are four or more amino acids described in each of (a) to (j) and has specific activity to α-fructosyl-valyl-histidyl-leucyl-threonyl-proryl-glutamic acid (αF6P) of 0.1 U/mg or greater.

[8] The method according to [7], wherein the amadoriase capable of acting directly on hemoglobin A1c comprises an amino acid sequence in which, when aligned with the amino acid sequence as shown in SEQ ID NO: 1, amino acids at positions corresponding to five or more positions selected from the group consisting of (a) to (j) in SEQ ID NO: 1 are five or more amino acids described in each of (a) to (j) and has specific activity to α-fructosyl-valyl-histidyl-leucyl-threonyl-proryl-glutamic acid (αF6P) of 0.1 U/mg or greater.

[9] The method according to [8], wherein the amadoriase capable of acting directly on hemoglobin A1c comprises an amino acid sequence in which, when aligned with the amino acid sequence as shown in SEQ ID NO: 1, amino acids at positions corresponding to six or more positions selected from the group consisting of (a) to (j) in SEQ ID NO: 1 are six or more amino acids described in each of (a) to (j) and has specific activity to α-fructosyl-valyl-histidyl-leucyl-threonyl-proryl-glutamic acid (αF6P) of 0.1 U/mg or greater.

[10] The method for measurement of hemoglobin A1c in a sample according to any one of [1] to [9], wherein the amadoriase capable of acting directly on hemoglobin A1c is derived from the genus *Coniochaeta*, *Eupenicillium*, *Pyrenochaeta*, *Arthrinium*, *Curvularia*, *Neocosmospora*, *Cryptococcus*, *Phaeosphaeria*, *Aspergillus*, *Emericella*, *Ulocladium*, or *Penicillium*.

[11] The method for measurement of hemoglobin A1c in a sample according to any one of [1] to [10], wherein the amadoriase capable of acting directly on hemoglobin A1c is derived from *Coniochaeta* sp., *Eupenicillium terrenum*, *Pyrenochaeta* sp., *Arthrinium* sp., *Curvularia clavata*, *Neocosmospora vasinfecta*, *Cryptococcus neoformans*, *Phaeosphaeria nodorum*, *Aspergillus nidulans*, *Emericella nidulans*, *Ulocladium* sp., *Penicillium janthinelum*, or *Penicillium chrysogenum*.

[12] The method for measurement of hemoglobin A1c in a sample according to [1], wherein the amadoriase capable of acting directly on hemoglobin A1c is an amadoriase selected from (i) or (ii) below;

(i) an amadoriase comprising an amino acid sequence of SEQ ID NO: 141 or 143 substitution, deletion, or addition of one or several amino acids; or (ii) the amadoriase as defined in (i), wherein the amadoriase comprises an amino acid sequence having 70% or higher sequence identity with the amino acid sequence as shown in SEQ ID NO: 141 or 143 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase.

[13] The method of measurement according to any one of [3] to [12], wherein the amadoriase comprises one or more amino acid substitutions at positions corresponding to positions of the amino acid sequence of SEQ ID NO: 1 selected from the group consisting of (i) to (xiv) below:

(i) asparagine at position 262;
(ii) valine at position 257;
(iii) glutamic acid at position 249;
(iv) glutamic acid at position 253;
(v) glutamine at position 337;
(vi) glutamic acid at position 340;
(vii) aspartic acid at position 232;
(viii) aspartic acid at position 129;
(ix) aspartic acid at position 132;
(x) glutamic acid at position 133;
(xi) glutamic acid at position 44;

(xii) glycine at position 256;
(xiii) glutamic acid at position 231; and
(xiv) glutamic acid at position 81,
and wherein, optionally, the 3 amino acid residues from the carboxyl terminus of the amadoriase may be deleted.

[14] A reagent kit for measurement of hemoglobin A1c in a sample comprising ingredients (1) and (2) below:
(1) an amadoriase capable of acting directly on hemoglobin A1c and generating hydrogen peroxide; and
(2) a reagent for measurement of hydrogen peroxide.

[15] The kit according to [14], wherein the amadoriase capable of acting directly on hemoglobin A1c has specific activity on α-fructosyl-valyl-histidyl-leucyl-threonyl-proryl-glutamic acid (αF6P) of 0.1 U/mg or greater.

[16] The kit according to [14] or [15], wherein the amadoriase capable of acting directly on hemoglobin A1c has specific activity on α-fructosyl-valyl-histidyl-leucyl-threonyl-proryl-glutamic acid (αF6P) of 0.1 U/mg or greater and is selected from the group consisting of (i) to (iii):
(i) an amadoriase comprising an amino acid sequence, wherein when said amino acid sequence is aligned with the amino acid sequence of SEQ ID NO: 1, said amino acid sequence comprises one or more amino acid substitutions at positions corresponding to the positions of the amino acid sequence of SEQ ID NO: 1 selected from the group consisting of (a) to (j) below:
(a) position 62 in SEQ ID NO: 1;
(b) position 63 in SEQ ID NO: 1;
(c) position 102 in SEQ ID NO: 1;
(d) position 106 in SEQ ID NO: 1;
(e) position 110 in SEQ ID NO: 1;
(f) position 113 in SEQ ID NO: 1;
(g) position 355 in SEQ ID NO: 1;
(h) position 419 in SEQ ID NO: 1;
(i) position 68 in SEQ ID NO: 1; and
(j) position 356 in SEQ ID NO: 1;
(ii) the amadoriase as defined in (i), wherein the amadoriase consists of an amino acid sequence comprising substitution, deletion, or addition of one or several amino acids at positions other than those corresponding to positions 62, 63, 102, 106, 110, 113, 355, 419, 68, and 356 of the amino acid sequence of SEQ ID NO: 1; and
(iii) the amadoriase as defined in (i), wherein the amadoriase comprises an amino acid sequence having 70% or higher sequence identity with the amino acid sequence as shown in SEQ ID NO: 1 over the full length and having 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 234 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region in corresponding positions of the amadoriase.

[17] The kit according to [16], wherein the amadoriase capable of acting directly on hemoglobin A1c comprises an amino acid sequence in which, when aligned with the amino acid sequence as shown in SEQ ID NO: 1, amino acids at positions corresponding to one or more positions selected from the group consisting of (a) to (j) in SEQ ID NO: 1 below are one or more amino acids described in each of (a) to (j) below and has specific activity to α-fructosyl-valyl-histidyl-leucyl-threonyl-proryl-glutamic acid (αF6P) of 0.1 U/mg or greater;
(a) the amino acid at a position corresponding to position 62 in SEQ ID NO: 1 is alanine, aspartic acid, asparagine, glutamine, glutamic acid, glycine, valine, leucine, isoleucine, cysteine, serine, threonine, or proline;
(b) the amino acid at a position corresponding to position 63 in SEQ ID NO: 1 is alanine or histidine;
(c) the amino acid at a position corresponding to position 102 in SEQ ID NO: 1 is lysine;
(d) the amino acid at a position corresponding to position 106 in SEQ ID NO: 1 is alanine, lysine, or arginine;
(e) the amino acid at a position corresponding to position 110 in SEQ ID NO: 1 is leucine or tyrosine;
(f) the amino acid at a position corresponding to position 113 in SEQ ID NO: 1 is lysine or arginine;
(g) the amino acid at a position corresponding to position 355 in SEQ ID NO: 1 is serine;
(h) the amino acid at a position corresponding to position 419 in SEQ ID NO: 1 is lysine;
(i) the amino acid at a position corresponding to position 68 in SEQ ID NO: 1 is asparagine; and
(j) the amino acid at a position corresponding to position 356 in SEQ ID NO: 1 is threonine.

[18] The kit according to [17], wherein the amadoriase capable of acting directly on hemoglobin A1c comprises an amino acid sequence in which, when aligned with the amino acid sequence as shown in SEQ ID NO: 1, amino acids at positions corresponding to two or more positions selected from the group consisting of (a) to (j) in SEQ ID NO: 1 are two or more amino acids described in each of (a) to (j) and has specific activity to α-fructosyl-valyl-histidyl-leucyl-threonyl-proryl-glutamic acid (αF6P) of 0.1 U/mg or greater.

[19] The kit according to [18], wherein the amadoriase capable of acting directly on hemoglobin A1c comprises an amino acid sequence in which, when aligned with the amino acid sequence as shown in SEQ ID NO: 1, amino acids at positions corresponding to three or more positions selected from the group consisting of (a) to (j) in SEQ ID NO: 1 are three or more amino acids described in each of (a) to (j) and has specific activity to α-fructosyl-valyl-histidyl-leucyl-threonyl-proryl-glutamic acid (αF6P) of 0.1 U/mg or greater.

[20] The kit according to [19], wherein the amadoriase capable of acting directly on hemoglobin A1c comprises an amino acid sequence in which, when aligned with the amino acid sequence as shown in SEQ ID NO: 1, amino acids at positions corresponding to four or more positions selected from the group consisting of (a) to (j) in SEQ ID NO: 1 are four or more amino acids described in each of (a) to (j) and has specific activity to α-fructosyl-valyl-histidyl-leucyl-threonyl-proryl-glutamic acid (αF6P) of 0.1 U/mg or greater.

[21] The kit according to [20], wherein the amadoriase capable of acting directly on hemoglobin A1c comprises an amino acid sequence in which, when aligned with die amino acid sequence as shown in SEQ ID NO: 1, amino acids at positions corresponding to five or more positions selected from the group consisting of (a) to (j) in SEQ ID NO: 1 are five or more amino acids described in each of (a) to (j) and has specific activity to α-fructosyl-valyl-histidyl-leucyl-threonyl-proryl-glutamic acid (αF6P) of 0.1 U/mg or greater.

[22] The kit according to [21], wherein the amadoriase capable of acting directly on hemoglobin A1c comprises an amino acid sequence in which, when aligned with the amino acid sequence as shown in SEQ ID NO: 1, amino acids at positions corresponding to six or more positions selected from the group consisting of (a) to (j) in SEQ ID NO: 1 are six or more amino acids described in each of (a) to (j) and has specific activity to α-fructosyl-valyl-histidyl-leucyl-threonyl-proryl-glutamic acid (αF6P) of 0.1 U/mg or greater.

[23] The kit according to any one of [14] to [22], wherein the amadoriase capable of acting directly on hemoglobin A1c and generating hydrogen peroxide is derived from the genus *Coniochaeta, Eupenicillium, Pyrenochaeta, Arthrinium, Curvularia, Neocosmospora, Cryptococcus, Phaeosphaeria, Aspergillus, Emericella, Ulocladium,* or *Penicillium.*

[24] The kit according to any one of [14] to [23], wherein the amadoriase capable of acting directly on hemoglobin A1c and generating hydrogen peroxide is:

(i) an amadoriase comprising an amino acid sequence of SEQ ID NO: 141 or 143 substitution, deletion, or addition of one or several amino acids; or (ii) the amadoriase as defined in (i), wherein the amadoriase comprises an amino acid sequence having 70% or higher sequence identity with the amino acid sequence as shown in SEQ ID NO: 141 or 143 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, to 316, 324 to 329, 332 to 334, 341 to 344, 346 to 355, 357 to 363, 370 to 383, 385 to 387, to 394, 405 to 410, and 423 to 431 of SEQ ID NO: 141 and the amino acid sequence of the homologous region in corresponding positions of the amadoriase.

[25] The kit according to any one of [16] to [24], wherein the amadoriase capable of acting directly on hemoglobin A1c and generating hydrogen peroxide comprises one or more amino acid substitutions at positions corresponding to positions of the amino acid sequence of SEQ ID NO: 1 selected from the group consisting of (i) to (xiv) below:

(i) asparagine at position 262;
(ii) valine at position 257;
(iii) glutamic acid at position 249;
(iv) glutamic acid at position 253;
(v) glutamine at position 337;
(vi) glutamic acid at position 340;
(vii) aspartic acid at position 232;
(viii) aspartic acid at position 129;
(ix) aspartic acid at position 132;
(x) glutamic acid at position 133;
(xi) glutamic acid at position 44;
(xii) glycine at position 256;
(xiii) glutamic acid at position 231; and
(xiv) glutamic acid at position 81, and wherein, optionally, the 3 amino acid residues from the carboxyl terminus of the amadoriase may be deleted.

[26] An amadoriase selected from the group consisting of (i) to (iii) below:

(i) an amadoriase comprising an amino acid sequence in which, when aligned with the amino acid sequence as shown in SEQ ID NO: 1, the amino acid at the position corresponding to position 68 in the amino acid sequence as shown in SEQ ID NO: 1 is asparagine or the amino acid at the position corresponding to position 356 in the amino acid sequence as shown in SEQ ID NO: 1 is threonine and having activity on α-fructoryl hexapeptide (αF6P);

(ii) the amadoriase as defined in (i), wherein the amadoriase consists of an amino acid sequence comprising substitution, deletion, or addition of one or several amino acids at positions other than those corresponding to positions 68 or 356 of the amino acid sequence of SEQ ID NO: 1 and has activity on αF6P; and (iii) the amadoriase as defined in (i) comprising an amino acid sequence in which the amino acid at the position corresponding to position 68 in the amino acid sequence as shown in SEQ ID NO: 1 is asparagine or the amino acid at the position corresponding to position 356 in the amino acid sequence as shown in SEQ ID NO: 1 is threonine, and wherein the amino acid sequence of the amadoriase has 70% or higher sequence identity with the amino acid sequence as shown in SEQ ID NO: 1 over the full length and has 90% or higher sequence identity between the amino acid sequence of a homologous region consisting of amino acids at positions 10 to 32, 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of the amino acid sequence as shown in SEQ ID NO: 1 and the amino acid sequence of the homologous region in corresponding positions of the amadoriase, and wherein the amadoriase has activity on αF6P.

[27] The method according to any of [1] to [13], wherein the hemoglobin A1c is denatured hemoglobin A1c.

[28] The method according to [27], wherein the denaturation is caused by heating, surfactant treatment, acid or base treatment, or a combination of any thereof.

The present specification encompasses the contents described in the description and/or drawings of Japanese Patent Application No. 2013-222774, which is a priority document of the present application.

Effects of the Invention

The present invention can provide an amadoriase that enables quantification of HbA1c to be performed rapidly, simply, accurately, and satisfactorily. By using such amadoriase, a method for measurement of HbA1c by an enzymatic method and a kit for measurement of HbA1c without including a protease or the like can be provided. Since a protease or the like need not be included, the kit can be simplified, reaction efficiency and measurement accuracy can be improved, and unfavorable reactions of a protease or the like on other protein reagents can be avoided.

BRIEF DESCRIPTION OF THE DRAWINGS

FIG. 1-1 is a first diagram showing amino acid sequence identity among various known amadoriases. In addition to Co (*Coniochaeta* sp.) (SEQ ID NO: 1), Et (*Eupenicillium terrenum*) (SEQ ID NO: 145), Py (*Pyrenochaeta* sp.) (SEQ ID NO: 113), Ar (*Arthrinium* sp.) (SEQ ID NO: 115), Cc (*Curvularia clavata*) (SEQ ID NO: 117), and Nv (*Neocosmospora vasinfecta*) (SEQ ID NO: 54), Cn (*Cryptococcus neoformans*) (SEQ ID NO: 149), Pn (*Phaeosphaeria nodorum*) (SEQ ID NO: 38), An (*Aspergillus nidulans*) (SEQ ID NO: 147), En (*Emericella nidulans*) (SEQ ID NO: 119), Ul (*Ulocladium* sp.) (SEQ ID NO: 121), and Pj (*Penicillium janthinelum*) (SEQ ID NO: 123) were aligned.

FIG. 1-2 is a continuation from FIG. 1-1.

FIG. 1-3 is a continuation from FIG. 1-2.

FIG. 1-4 is a continuation from FIG. 1-3.

FIG. 1-5 is a continuation from FIG. 1-4.

FIG. 2-1 is a second diagram showing amino acid sequence identity and similar amino acids among various known amadoriases. In addition to Co (SEQ ID NO: 1), Et (SEQ ID NO: 145), Py (SEQ ID NO: 113), Ar (SEQ ID NO: 115), Cc (SEQ ID NO: 117), and Nv (SEQ ID NO: 54), Cn(SEQ ID NO: 149), Pn(SEQ ID NO: 38), An(SEQ ID NO: 147), En(SEQ ID NO: 119), Ul(SEQ ID NO: 121), and Pj (SEQ ID NO: 123) were aligned.

FIG. 2-2 is a continuation from FIG. 2-1.

FIG. 2-3 is a continuation from FIG. 2-2.

FIG. 2-4 is a continuation from FIG. 2-3.

FIG. 2-5 is a continuation from FIG. 2-4.

FIG. 3 shows the correlation between the time elapsed after the sample diluent (Reagent A2) has been mixed with a measurement reagent and absorbance, wherein HbA1c is measured using a modified amadoriase. The amadoriase solution is added at the time point of elapse of 300 seconds.

FIG. 4-1 shows the results of HbA1c measurement conducted by diluting an HbA1c-containing sample with an n-dodecyl-β-D-maltoside solution.

FIG. 4-2 shows the results of HbA1c measurement conducted by diluting an HbA1c-containing sample with an n-tetradecyl-β-D-maltoside solution.

FIG. 5 shows the correlation between the time elapsed after the sample diluent (Reagent D1) has been mixed with a measurement reagent and absorbance, wherein HbA1c is measured using a modified amadoriase. An amadoriase solution is added after the elapse of 300 seconds.

FIG. 6-1 shows the results of HbA1c measurement conducted by diluting an HbA1c-containing sample with a hydrochloric-acid-containing n-dodecyl-β-D-maltoside solution (Reagent D1) and using Amadoriase 25.

FIG. 6-2 shows the results of HbA1c measurement conducted by diluting an HbA1c-containing sample with a hydrochloric-acid-containing polyoxyethylene (20) cetyl ether solution (Reagent D2).

FIG. 6-3 shows the results of HbA1c measurement conducted by diluting an HbA1c-containing sample with a hydrochloric-acid-containing n-dodecyl-β-D-maltoside solution (Reagent D1) and using Amadoriase 28.

FIG. 8-1 shows the results of HbA1c measurement conducted by diluting an HbA1c-containing sample with a tetradecyltrimethylammonium bromide solution (Reagent G1).

FIG. 8-2 shows the results of HbA1c measurement conducted by diluting an HbA1c-containing sample with a hexadecyltrimethylammonium bromide solution (Reagent G2).

EMBODIMENTS FOR CARRYING OUT THE INVENTION

Figure 3:
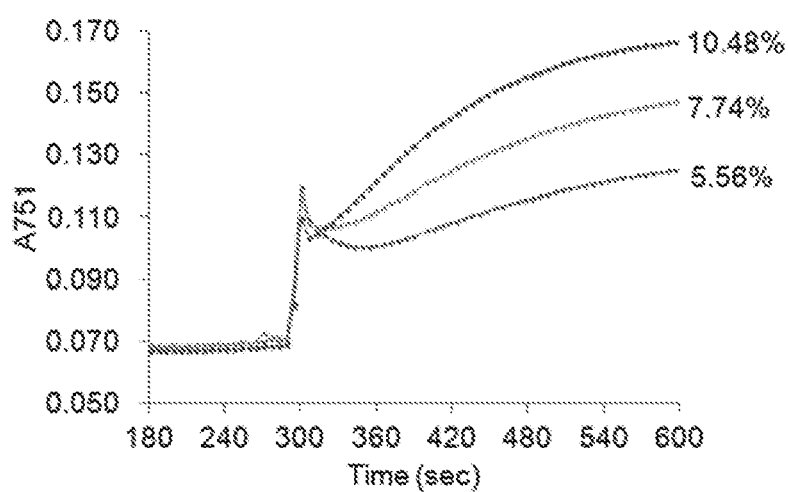

The present invention is described in detail as follows.
(Glycated Protein and Hemoglobin A1c)

The term "glycated protein" used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.
(Glycated Peptide and Fructosyl Peptide)

The term "glycated peptide" used herein refers to a non-enzymatically-glycated peptide derived from a glycated protein. Peptides that are directly and non-enzymatically glycated, products of degradation of glycated proteins by a protease or the like, and products of glycation of (poly) peptides constituting glycated proteins are included in glycated peptides. A "glycated peptide" is also referred to as a "fructosyl peptide." Regarding glycated proteins, examples of amino groups in the glycated peptide side chain include an amino terminal α-amino group and a ε-amino group in the lysine side chain within a peptide. However, in the present invention, more specifically, the glycated peptide is an α-glycated peptide (α-fructosyl peptide). An α-glycated peptide is released and formed from a glycated protein having a glycated N-terminal α-amino acid by an arbitrary means, such as limited degradation with a protease or the like. When the glycated protein of interest is hemoglobin A1c (HbA1c), for example, the α-glycated peptide is a glycated peptide cleaved from the HbA1c β-chain having the glycated N terminus. The HbA1c β-chain composed of 146 amino acids also falls under an α-glycated peptide.

According to an embodiment of the present invention, the target substance to which the amadoriase of the present invention acts on is HbA1c and more specifically, is the β-chain of HbA1c. According to another embodiment, the target substance to which the amadoriase of the present invention acts on is αF6P cleaved from the HbA1c β-chain and, more specifically, is α-fructosyl-valyl-histidyl-leucyl-threonyl-proryl-glutamic acid. According to another embodiment, the target substance to which the amadoriase of the present invention acts on is αFVH (α-fructosyl-valyl-histidine) or αFV (α-fructosyl valine).
(Amadoriase)

An amadoriase is also referred to as ketoamine oxidase, fructosyl amino acid oxidase, fructosyl peptide oxidase, or fructosyl amine oxidase, and it is an enzyme that oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria.

The amadoriase of the present invention acts directly on HbA1c. In the present specification, the phrase an amadoriase acts directly on HbA1c as used herein refers to the amadoriase acting on the fructosyl group at the N-terminus of the HbA1c β-chain in the presence of oxygen, and generating 2-keto-D-glucose, hydrogen peroxide, and hemoglobin β-chain. This however does not exclude said amadoriase acting on fructosyl peptides derived from the HbA1c β-chain, such as αF6P. That is, according to one embodiment, the amadoriase of the present invention not only acts directly on HbA1c but also has reactivity to fructosyl peptides derived from the HbA1c β-chain, such as αF6P.
(Modified Amadoriase)

The present invention provides a modified amadoriase having reactivity with αF6P, and capable of acting directly on HbA1c, which is produced based on a wild-type amadoriase comprising the amino acid sequence as shown in SEQ ID NO: 1, SEQ ID NO: 38, SEQ ID NO: 40, SEQ ID NO: 54, SEQ ID NO: 62, SEQ ID NO: 89, or SEQ ID NO: 99. In the present specification, the terms "modified amadoriase" and "amadoriase variant" are used interchangeably and refer to amadoriases which comprise an amino acid sequence derived from the amino acid sequence of a wild-type amadoriase having substitutions, deletions, or additions of some amino acids. The term "addition(s)" used in this context encompasses "insertion(s)."

Further, the present invention provides a modified amadoriase having reactivity with αF6P and capable of acting directly on HbA1c, which is produced based on a wild-type amadoriase comprising the amino acid sequence as shown in SEQ ID NO: 113, SEQ ID NO: 115, SEQ ID NO: 117, SEQ ID NO: 119, SEQ ID NO: 121, SEQ ID NO: 123, SEQ ID NO: 145, or SEQ ID NO: 149.

Further, based on findings of the present invention, a modified amadoriase that acts directly on HbA1c can be obtained from other wild-type amadoriases derived from the genus *Coniochaeta* or the like.

The modified amadoriase of the present invention can comprise a further mutation that alters other properties of the enzyme, provided that the modified amadoriase retains activity to αF6P and acts directly on HbA1c.

(Modified Amadoriase Based on Amadoriase from *Coniochaeta* sp. NISL 9330)

According to an embodiment, the amadoriase of the present invention is a modified amadoriase that acts directly on HbA1c, which is prepared from the amadoriase derived from the genus *Coniochaeta* comprising the amino acid sequence as shown in SEQ ID NO: 1.

Amadoriases comprising amino acid sequences exhibiting high sequence identity with the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 (double variants), SEQ ID NO: 137, SEQ ID NO: 139, SEQ ID NO: 165, SEQ ID NO: 167, SEQ ID NO: 169, SEQ ID NO: 171, and SEQ ID NO: 173 (triple variants), SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 and SEQ ID NO: 185 (quintuple variants) (e.g., sequence identity of 50% or higher, preferably 60% or higher, 70% or higher, 75% or higher, or 80% or higher, more preferably 85% or higher, further preferably 90% or higher, 95% or higher, or 98% or higher, and most preferably 99% or higher) and having activity on αF6P can act directly on HbA1c. For example, the amadoriase comprising the amino acid sequence as shown in SEQ ID NO: 141 has activity on αF6P and acts directly on HbA1c.

Amadoriases comprising amino acid sequences derived from the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 variants), SEQ ID NO: 137, SEQ ID NO: 139, SEQ ID NO: 165, SEQ ID NO: 167, SEQ ID NO: 169, SEQ ID NO: 171, and SEQ ID NO: 173 (triple variants), SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 SEQ ID NO: 185 (septuple variants) by modification, mutation, deletion, substitution, addition, and/or insertion of 1 or several amino acids and having activity on αF6P can act directly on HbA1c. The term "one or several amino acids" used herein refers to 1 to 15, preferably 1 to 10, more preferably 1 to 5, still more preferably 1 to 4, further preferably 1 to 3, and still further preferably 1 or 2 amino acids, when the full-length amino acid sequence comprises more than 400 amino acids. Also, the term "one or several amino acids" refers to 1 to 10, preferably 1 to 7, more preferably 1 to 5, still more preferably 1 to 4, further preferably 1 to 3, and still further preferably 1 or 2 amino acids, when the full-length amino acid sequence comprises 200 to 400 amino acids. The term "one or several amino acids" refers to 1 to 5, preferably 1 to 4, more preferably 1 to 3, and further preferably 1 or 2 amino acids, when the full-length amino acid sequence comprises 40 to less than 200 amino acids. The term "one or several amino acids" refers to 1 or 2 amino acids, when the full-length amino acid sequence comprises less than 40 amino acids.

Amadoriases encoded by nucleotide sequences hybridizing under stringent conditions to sequences complementary to the nucleotide sequences as shown in SEQ ID NO: 152, SEQ ID NO: 154, and SEQ ID NO: 156 (single variants), SEQ ID NO: 158, SEQ ID NO: 160, SEQ ID NO: 162, and SEQ ID NO: 164 (double variants), SEQ ID NO: 138, SEQ ID NO: 140, SEQ ID NO: 166, SEQ ID NO: 168, SEQ ID NO: 170, SEQ ID NO: 172, and SEQ ID NO: 174 (triple variants), SEQ ID NO: 134, SEQ ID NO: 136, SEQ ID NO: 176, and SEQ ID NO: 190 (quadruple variants), SEQ ID NO: 178 and SEQ ID NO: 180 (quintuple variants), SEQ ID NO: 144, SEQ ID NO: 182, SEQ ID NO: 184, SEQ ID NO: 188, and SEQ ID NO: 192 (sextuple variants), and SEQ ID NO: 142 and SEQ ID NO: 186 (septuple variants) and having activity on αF6P can act directly on HbA1c. Stringent hybridization conditions are described in, for example, Sambrook et al., Molecular Cloning, Vol. 2 (Cold Spring Harbor Laboratory Press) or Current Protocols in Molecular Biology (Frederick, M. Ausubel et al. (ed.), 1987). Under stringent conditions, for example, hybridization is carried out by conducting incubation with the use of a hybridization solution (50% formamide, 6 to 10×SSC (0.15 to 1.5 M NaCl, 15 mM sodium citrate, pH 7.0), 5×Denhardt solution, 1% SDS, 10% dextran sulfate, 10 μg/ml denatured salmon sperm DNA, and 50 mM phosphate buffer (pH 7.5)) at about 42° C. to about 50° C. followed by washing with 0.1×SSC and 0.1% SDS at about 65° C. to about 70° C. Under other stringent conditions, hybridization is carried out with the use of, for example, a hybridization solution of 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5).

The variant according to the present invention may be obtained from amadoriases derived from other organism species, such as the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaetidium, Pichia, Corynebacterium, Agrobacterium,* or *Arthrobacter,* provided that the conditions concerning substrate specificity and/or amino acid sequences described in the claims are satisfied.

A modified amadoriase obtained from the amadoriase derived from *Coniochaeta* sp. NISL 9330 (SEQ ID NO: 1) can comprise one or a plurality of amino acid substitutions at the positions described below. The term "one or a plurality of amino acid substitutions" used with regard to the modified amadoriase refers to substitution of 1, 2, 3, 4, 5, 6, 7, 8, 9, 10, 11, 13, 14, 15, 16, 17 or 18 amino acids. For example, the term refers to substitution of 1, 2, 4, 5, 6, 7, 8, 9, 10, 11, 12, 13, 14, or 15 amino acids, substitution of 1, 2, 3, 4, 5, 6, 7, 8, 9, or 10, amino acids, or substitution of 1, 2, 3, 4, 5, 6, 7, or 8 amino acids. According to one embodiment, the term "one or a plurality of amino acid substitutions" used with regard to the modified amadoriase refers to substitution of 1, 2, 3, 4, 5, 6, or 7 amino acids:

(a) arginine at position 62;
 (b) leucine at position 63;
 (c) glutamic acid at position 102;
 (d) aspartic acid at position 106;
 (e) glutamine at position 110;
 (f) alanine at position 113;
 (g) alanine at position 355;
 (h) alanine at position 419;
 (i) aspartic acid at position 68; and
 (j) alanine at position 356.

In the amadoriase derived from *Coniochaeta* sp. NISL 9330 (SEQ ID NO: 1), preferably, (a) arginine at position 62 is substituted with alanine, asparagine, aspartic acid, glutamine, glutamic acid, glycine, valine, leucine, isoleucine, cysteine, serine, threonine, or proline. Preferably, (b) leucine at position 63 is substituted with histidine or alanine. Preferably, (c) glutamic acid at position 102 is substituted with lysine. Preferably, (d) aspartic acid at position 106 is substituted with alanine, lysine, or arginine. Preferably, (e) glutamine at position 110 is substituted with leucine or tyrosine. Preferably, (f) alanine at position 113 is substituted with lysine or arginine. Preferably, (g) alanine at position 355 is substituted with serine. Optionally, (h) alanine at position 419 may be substituted with lysine. Optionally, (i) aspartic acid at position 68 may be substituted with asparagine. Optionally, (j) alanine at position 356 may be substituted with threonine.

A modified amadoriase obtained from the amadoriase derived from *Phaeosphaeria nodorum* (PnFX, SEQ ID NO: 38) can comprise one or a plurality of amino acid substitutions at the positions described below:

(a) serine at position 62;
 (b) leucine at position 63;
 (c) lysine at position 102;
 (d) aspartic acid at position 106;
 (e) glycine at position 110;
 (f) alanine at position 113;
 (g) alanine at position 351;
 (h) serine at position 416;
 (i) aspartic acid at position 68; and
 (j) alanine at position 352.

In the amadoriase derived from *Phaeosphaeria nodorum* (SEQ ID NO: 38), (a) serine at position 62 may, optionally, not be substituted. Alternatively, (a) serine at position 62 may be substituted with alanine, aspartic acid, asparagine, glutamine, glutamic acid, glycine, valine, leucine, isoleucine, cysteine, threonine, or proline. Preferably, (b) leucine at position 63 is substituted with histidine. Optionally, (c) lysine at position 102 may not be substituted. Preferably, (d) aspartic acid at position 106 is substituted with lysine. Preferably, glycine at position 110 is substituted with leucine. Preferably, alanine at position 113 is substituted with lysine. Preferably, alanine at position 351 is substituted with serine. Optionally, (h) serine at position 416 may be substituted with lysine. Optionally, (i) aspartic acid at position 68 may be substituted with asparagine. Optionally, (j) alanine at position 352 may be substituted with threonine.

A modified amadoriase obtained from the amadoriase derived from *Neocosmospora vasinfecta* (NvFX, SEQ ID NO: 54) can comprise one or a plurality of amino acid substitutions at the positions described below:

(a) arginine at position 62;
 (b) leucine at position 63;
 (c) glutamic acid at position 102;
 (d) glycine at position 106;
 (e) glutamic acid at position 110;
 (f) lysine at position 113;
 (g) serine at position 355;
 (h) alanine at position 420;
 (i) aspartic acid at position 68; and
 (j) alanine at position 356.

In the amadoriase derived from *Neocosmospora vasinfecta* (SEQ ID NO: 54), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Preferably, (c) glutamic acid at position 102 is substituted with lysine. Preferably, (d) glycine at position 106 is substituted with lysine. Preferably, glutamic acid at position 110 is substituted with leucine. Optionally, lysine at position 113 may not be substituted, and serine at position 355 may not be substituted. Optionally, (h) alanine at position 420 may be substituted with lysine. Optionally, (i) aspartic acid at position 68 may be substituted with asparagine. Optionally, (j) alanine at position 356 may be substituted with threonine.

A modified amadoriase obtained from the amadoriase derived from *Aspergillus nidulans* (AnFX, SEQ ID NO: 62) can comprise one or a plurality of amino acid substitutions at the positions described below:

(a) arginine at position 61;
 (b) leucine at position 62;
 (c) glutamic acid at position 101;
 (d) glycine at position 105;
 (e) lysine at position 109;
 (f) serine at position 112;
 (g) alanine at position 355;
 (h) alanine at position 420;
 (i) aspartic acid at position 67; and
 (j) asparagine at position 356.

In the amadoriase derived from *Aspergillus nidulans* (SEQ ID NO: 62), preferably, (a) arginine at position 61 may be substituted with alanine, aspartic acid, asparagine, glutamine, glutamic acid, glycine, valine, leucine, isoleucine, cysteine, serine, threonine, or proline. Preferably, (b) leucine at position 62 is substituted with histidine. Preferably, (c) glutamic acid at position 101 is substituted with lysine. Preferably, (d) glycine at position 105 is substituted with lysine. Preferably, lysine at position 109 is substituted with leucine. Preferably, serine at position 112 is substituted with lysine. Preferably, alanine at position 355 is substituted with serine. Optionally, (h) alanine at position 420 may be substituted with lysine. Optionally, (i) aspartic acid at position 67 may be substituted with asparagine. Optionally, (j) asparagine at position 356 may be substituted with threonine.

A modified amadoriase obtained from the amadoriase derived from *Eupenicillium terrenum* (SEQ ID NO: 40) can comprise one or a plurality of amino acid substitutions at the positions described below:

(a) arginine at position 62;
 (b) leucine at position 63;
 (c) glutamic acid at position 102;
 (d) asparagine at position 106;

(e) lysine at position 110;
(f) threonine at position 113;
(g) alanine at position 355;
(h) glycine at position 419;
(i) aspartic acid at position 68; and
(j) alanine at position 356.

In the amadoriase derived from EFP-T5 (SEQ ID NO: 40), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Preferably, (c) glutamic acid at position 102 is substituted with lysine. Preferably, (d) asparagine at position 106 is substituted with lysine. Preferably, lysine at position 110 is substituted with leucine. Preferably, threonine at position 113 is substituted with lysine. Preferably, alanine at position 355 is substituted with serine. Optionally, (h) glycine at position 419 may be substituted with lysine. Optionally, (i) aspartic acid at position 68 may be substituted with asparagine. Optionally, (j) asparagine at position 356 may be substituted with threonine.

A modified amadoriase obtained from fructosyl amino acid oxidase derived from *Cryptococcus neoformans* (SEQ ID NO: 89 or 149) can comprise one or a plurality of amino acid substitutions at the positions described below:
(a) arginine at position 62;
(b) isoleucine at position 63;
(c) glutamic acid at position 102;
(d) serine at position 106;
(e) serine at position 110;
(f) alanine at position 113;
(g) alanine at position 355;
(h) alanine at position 420;
(i) aspartic acid at position 68; and
(j) asparagine at position 356.

In the fructosyl amino acid oxidase derived from *Cryptococcus neoformans* (CnFX, SEQ ID NO: 89 or 149), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) isoleucine at position 63 is substituted with histidine. Preferably, (c) glutamic acid at position 102 is substituted with lysine. Preferably, (d) serine at position 106 is substituted with lysine. Preferably, serine at position 110 is substituted with leucine. Preferably, alanine at position 113 is substituted with lysine. Preferably, alanine at position 355 is substituted with serine. Optionally, (h) alanine at position 420 may be substituted with lysine. Optionally, (i) aspartic acid at position 68 may be substituted with asparagine. Optionally, (j) asparagine at position 356 be substituted with threonine.

A modified amadoriase obtained from ketoamine oxidase derived from *Pyrenochaeta* sp. (SEQ ID NO: 113) can comprise one or a plurality of amino acid substitutions at the positions described below:
(a) arginine at position 62;
(b) leucine at position 63;
(c) lysine at position 102;
(d) aspartic acid at position 106;
(e) alanine at position 110;
(f) threonine at position 113;
(g) alanine at position 353;
(h) alanine at position 418;
(i) aspartic acid at position 68; and
(j) alanine at position 356.

In the ketoamine oxidase derived from *Pyrenochaeta* sp. (SEQ ID NO: 113), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Optionally, (c) lysine at position 102 may not be substituted. Preferably, (d) aspartic acid at position 106 is substituted with lysine. Preferably, alanine at position 110 is substituted with leucine. Preferably, threonine at position 113 is substituted with lysine. Preferably, alanine at position 353 is substituted with serine. Optionally, (h) alanine at position 418 may be substituted with lysine. Optionally, (i) aspartic acid at position 68 may be substituted with asparagine. Optionally, (j) alanine at position 354 may be substituted with threonine.

A modified amadoriase obtained from ketoamine oxidase derived from *Arthrinium* sp. (SEQ ID NO: 115) can comprise one or a plurality of amino acid substitutions at the positions described below:
(a) arginine at position 62;
(b) leucine at position 63;
(c) lysine at position 102;
(d) alanine at position 106;
(e) glutamine at position 110;
(f) threonine at position 113;
(g) alanine at position 356;
(h) alanine at position 421;
(i) aspartic acid at position 68; and
(j) alanine at position 357.

In the ketoamine oxidase derived from *Arthrinium* sp. (SEQ ID NO: 115), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Optionally, (c) lysine at position 102 may not be substituted. Preferably, (d) alanine at position 106 is substituted with lysine. Preferably, glutamine at position 110 is substituted with leucine. Preferably, threonine at position 113 is substituted with lysine. Preferably, alanine at position 356 is substituted with serine. Optionally, (h) alanine at position 421 may be substituted with lysine. Optionally, (i) aspartic acid at position 68 may be substituted with asparagine. Optionally, (j) alanine at position 357 may be substituted with threonine.

A modified amadoriase obtained from ketoamine oxidase derived from *Curvularia clavata* (SEQ ID NO: 117) can comprise one or a plurality of amino acid substitutions at the positions described below:
(a) arginine at position 62;
(b) leucine at position 63;
(c) glutamic acid at position 102;
(d) aspartic acid at position 106;
(e) alanine at position 110;
(f) alanine at position 113;
(g) alanine at position 353;
(h) alanine at position 418;
(i) aspartic acid at position 68; and
(j) alanine at position 354.

In the ketoamine oxidase derived from *Curvularia clavata* (SEQ ID NO: 117), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Preferably, (e) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) alanine at position 418 may be substituted with lysine. Optionally, (i) aspartic acid at position 68 may be substituted with asparagine. Optionally, (j) alanine at position 354 may be substituted with threonine.

A modified amadoriase obtained from ketoamine oxidase (Cc95FX, SEQ ID NO: 99) having 95% amino acid sequence identity with ketoamine oxidase derived from *Curvularia clavata* (SEQ ID NO: 117) can comprise one or a plurality of amino acid substitutions at the positions described below:
(a) arginine at position 62;
(b) leucine at position 63;
(c) glutamic acid at position 102;
(d) aspartic acid at position 106;
(e) alanine at position 110;
(f) alanine at position 113;
(g) alanine at position 353;
(h) serine at position 418;
(i) aspartic acid at position 68; and
(j) alanine at position 354.

In the ketoamine oxidase (SEQ ID NO: 99) having 95% amino acid sequence identity with the ketoamine oxidase derived from *Curvularia clavata* (SEQ ID NO: 117), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Preferably, (c) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) serine at position 418 may be substituted with lysine. Optionally, (i) aspartic acid at position 68 may be substituted with asparagine. Optionally, (j) alanine at position 354 may be substituted with threonine.

A modified amadoriase obtained from fructosyl peptide oxidase derived from *Emericella nidulans* (SEQ ID NO: 119) can comprise one or a plurality of amino acid substitutions at the positions described below:
(a) arginine at position 61;
(b) leucine at position 62;
(c) glutamic acid at position 101;
(d) lysine at position 105;
(e) arginine at position 109;
(f) serine at position 112;
(g) alanine at position 355;
(h) alanine at position 420;
(i) aspartic acid at position 67; and
(j) asparagine at position 356.

In the fructosyl peptide oxidase derived from *Emericella nidulans* (SEQ ID NO: 119), preferably, (a) arginine at position 61 may be substituted with alanine, aspartic acid, asparagine, glutamine, glutamic acid, glycine, valine, leucine, isoleucine, cysteine, serine, threonine, or proline. Preferably, (b) leucine at position 62 is substituted with histidine. Preferably, (c) glutamic acid at position 101 is substituted with lysine. Optionally, (d) lysine at position 105 may not be substituted. Preferably, arginine at position 109 is substituted with leucine. Preferably, serine at position 112 is substituted with lysine. Preferably, alanine at position 355 is substituted with serine. Optionally, (h) alanine at position 420 may be substituted with lysine. Optionally, (i) aspartic acid at position 67 may be substituted with asparagine. Optionally, (j) asparagine at position 356 may be substituted with threonine.

A modified amadoriase obtained from fructosyl amino acid oxidase derived from *Ulocladium* sp. (SEQ ID NO: 121) can comprise one or a plurality of amino acid substitutions at the positions described below:
(a) arginine at position 62;
(b) leucine at position 63;
(c) lysine at position 102;
(d) aspartic acid at position 106;
(e) alanine at position 110;
(f) alanine at position 113;
(g) alanine at position 353;
(h) alanine at position 418;
(i) aspartic acid at position 68; and
(j) alanine at position 354.

In the fructosyl amino acid oxidase derived from *Ulocladium* sp. (SEQ ID NO: 121), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Optionally, (e) lysine at position 102 may not be substituted. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) alanine at position 418 may be substituted with lysine. Optionally, (1) aspartic acid at position 68 may be substituted with asparagine. Optionally, (j) alanine at position 354 may be substituted with threonine.

A modified amadoriase obtained from fructosyl amino acid oxidase derived from *Penicillium janthinellum* (SEQ ID NO: 123) can comprise one or a plurality of amino acid substitutions at the positions described below:
(a) arginine at position 62;
(b) leucine at position 63;
(c) glutamic acid at position 102;
(d) serine at position 106;
(e) lysine at position 110;
(f) aspartic acid at position 113;
(g) alanine at position 355;
(h) serine at position 419;
(i) aspartic acid at position 68; and
(j) asparagine at position 356.

In the fructosyl amino acid oxidase derived from *Penicillium janthinellum* (SEQ ID NO: 123), preferably, (a) arginine at position 62 may be substituted with alanine, aspartic acid, asparagine, glutamine, glutamic acid, glycine, valine, leucine, isoleucine, cysteine, serine, threonine, or proline. Preferably, (b) leucine at position 63 is substituted with histidine. Preferably, (c) glutamic acid at position 102 is substituted with lysine. Preferably, (d) serine at position 106 is substituted with lysine. Preferably, lysine at position 110 is substituted with leucine. Preferably, aspartic acid at position 113 is substituted with lysine. Preferably, alanine at position 355 is substituted with serine. Optionally, (h) serine at position 419 may be substituted with lysine. Optionally, (i) aspartic acid at position 68 may be substituted with asparagine. Optionally, (j) asparagine at position 356 may be substituted with threonine. The same applies to the fructosyl amino acid oxidase derived from *Penicillium chrysogenum*.

According to one embodiment of the present invention, the amadoriase of the present invention that acts directly on hemoglobin A1c may preferably be an amadoriase that:

recognizes the β chain of hemoglobin A1c as a substrate.

oxidizes the β chain of hemoglobin A1c and generates hydrogen peroxide.

has an optimal pH range between pH 6 and 8.

has an operable pH range between pH 5 and 9, has an operable temperature between 25° C. and 40° C., and has a molecular weight according to SDS-PAGE of about 45 to 55 KDa (e.g., about 48 to 50 KDa).

Amadoriases exhibiting no activity on HbA1c at all are excluded from the scope of the amadoriase variant or the modified amadoriase according to the present invention.

(Obtaining a Gene Encoding an Amadoriase)

In order to obtain a gene encoding the amadoriases described above (hereinafter, also referred to as merely "amadoriase gene"), gene cloning methods that are used in general can be employed. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the aforementioned amadoriase and selecting an amadoriase gene from a chromosomal DNA or cDNA library using the probe DNA. Alternatively, an appropriate primer DNA may be produced based on the aforementioned amino acid sequence, a DNA including the target gene fragment encoding the amadoriase gene may be amplified by using an appropriate polymerase chain reaction (PCR) technique, such as the 5' RACE or 3' RACE method, and the resulting DNA fragments may then be linked.

A preferable example of a gene encoding an amadoriase thus obtained is an amadoriase gene derived from the genus *Coniochaeta* (JP 2003-235585 A).

Other preferable examples include amadoriase genes derived from the genus *Phaeosphaeria*, amadoriase genes derived from the genus *Neocosmospora*, amadoriase genes derived from the genus *Aspergillus*, amadoriase genes derived from the genus *Cryptococcus*, amadoriase genes derived from the genus *Curvularia*, and amadoriase genes derived from the genus *Eupenicillium*.

Such amadoriase genes are preferably linked to various vectors according to a conventional technique from the viewpoint of handleability. For example, a DNA encoding an amadoriase gene can be obtained by subjecting a recombinant plasmid pKK223-3-CFP-T7 DNA encoding an amadoriase gene derived from a strain of *Coniochaeta* sp. NISL9330 (WO 2007/125779) to extraction and purification using the GenElute Plasmid Mini prep Kit (Sigma-Aldrich). A person skilled in the art would be able to obtain DNA of amadoriase genes derived from other organisms in a similar manner using conventional techniques. More specifically, DNA encoding an amadoriase gene can be obtained by culturing *E. coli* strains carrying the recombinant plasmid pUTE100K'-EFP-T5 including DNA encoding an amadoriase gene derived from a strain of *Eupenicillium terrenum* ATCC 18547 (WO 2007/125779) and extracting and purifying the recombinant plasmid pUTE100K'-EFP-T5 including DNA encoding an amadoriase gene from the cells using the GenElute Plasmid Miniprep Kit. Also, DNA encoding an amadoriase gene can be obtained by culturing *E. coli* strains carrying the recombinant plasmid pET22b-AnFX including DNA encoding an amadoriase gene derived from a strain of *Aspergillus nidulans* FGSC A26 (WO 2012/018094) and extracting and purifying the recombinant plasmid pET22b-AnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-CnFX including DNA encoding an amadoriase gene derived from a strain of *Cryptococcus neoformans* (WO 2012/018094) and extracting and purifying the recombinant plasmid pET22b-CnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-NvFX including DNA encoding an amadoriase gene derived from a strain of *Neocosmospora vasinfecta* (WO 2012/018094) and extracting and purifying the recombinant plasmid pET22b-NvFX including DNA encoding an amadoriase gene therefrom with the use of the GenElute Plasmid Miniprep Kit.

(Vector)

Vectors that can be used in the present invention are not limited to the aforementioned plasmid vectors. For example, any other vectors known in the art, such as bacteriophage or cosmid vectors, can be used. Specifically, for example, pBluescriptII SK+ (manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein, an ultraviolet irradiation method, a genetic engineering technique, a method of making full use of a protein engineering technique, or various other methods can be extensively used.

Examples of chemical mutagens used in the aforementioned mutation include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the aforementioned drug at the concentration of 0.5 M to 12 M. The ultraviolet irradiation may be also performed according to a conventional technique as described above (Gendai Kagaku, pp. 24-30, June, 1989).

As the method of making full use of the protein engineering technique, in general, a technique known as site-specific mutagenesis can be used. Examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acid. Sci. U.S.A., 82, 488, 1985; Methods Enzymol., 154, 367, 1987).

A technique known as a general PCR technique can also be used (Technique, 1, 11, 1989). In addition to the conventional genetic mutation technique, by an organic synthesis method or synthetic method of an enzyme, the modified amadoriase genes of interest can be also directly synthesized.

The nucleotide sequences of DNAs encoding the amadoriase genes obtained by the aforementioned methods may be determined or verified by, for example, using a multi-capillary DNA analysis system, Applied Biosystems 3130x Genetic Analyzer (Life Technologies).

(Transformation/Transduction)

The amadoriase genes obtained as described above are integrated into a vector such as a bacteriophage vector, a cosmid vector, or a plasmid vector used in transformation of a procaryotic or eucaryotic cell by a conventional technique, and a host corresponding to each vector can be transformed or transduced by a conventional technique. For example, a microorganism belonging to the genus *Escherichia*, such as the obtained recombinant DNA, is used as the host to transform a strain of *E. coli* K-12, and preferably a strain of *E. coli* JM109 or *E. coli* DH5α (manufactured by Takara Bio Inc.), or such microorganism is transduced into such strain. Thus, transformed or transduced strains of interest can be obtained.

(Amino Acid Sequence Homology, Identity, or Similarity)

The amino acid sequence homology, identity, or similarity can be calculated by a program such as maximum matching or search homology of GENETYX (manufactured by (GENETYX program such as maximum matching or multiple alignment of DNASIS Pro (manufactured by Hitachi Solutions, Ltd.), or a program such as multiple alignment of CLUSTALW. In order to calculate amino acid sequence identity, two or more amadoriases may be aligned, and the positions of identical amino acids in such two or more amadoriases may be determined. The identical regions in amino acid sequences can be determined based on such information. The percent identity of two or more amino acid sequences is determined by subjecting two or more amino acid sequences to alignment using the algorithm such as Blosum62 by designating the total number of amino acids in the aligned region as the denominator and the number of identical amino acids relative to the total number as the numerator. If no identity is found in parts of the two or more amino acid sequences, for example, an amino acid sequence comprises at its C terminus an additional sequence in which no identity is observed, in general, such regions cannot be aligned. Accordingly, such regions are not used for calculation of the percent identity.

Also, positions of similar amino acids in two or more amadoriases can be inspected. For example, a plurality of amino acid sequences can be subjected to alignment with the use of CLUSTALW. In such a case, Blosum62 is used as the algorithm and a plurality of amino acid sequences are subjected to alignment. Amino acids determined to be similar as a result of alignment may be referred to as "similar amino acids." In the variant of the present invention, amino acid substitution can be carried out between such similar amino acids. Through such alignment, amino acid sequences composed of the identical amino acids or similar amino acids among a plurality of amino acid sequences can be simultaneously investigated. Based on such information, homologous regions (conserved regions) in the amino acid sequences can be determined.

Figures 1, 4:
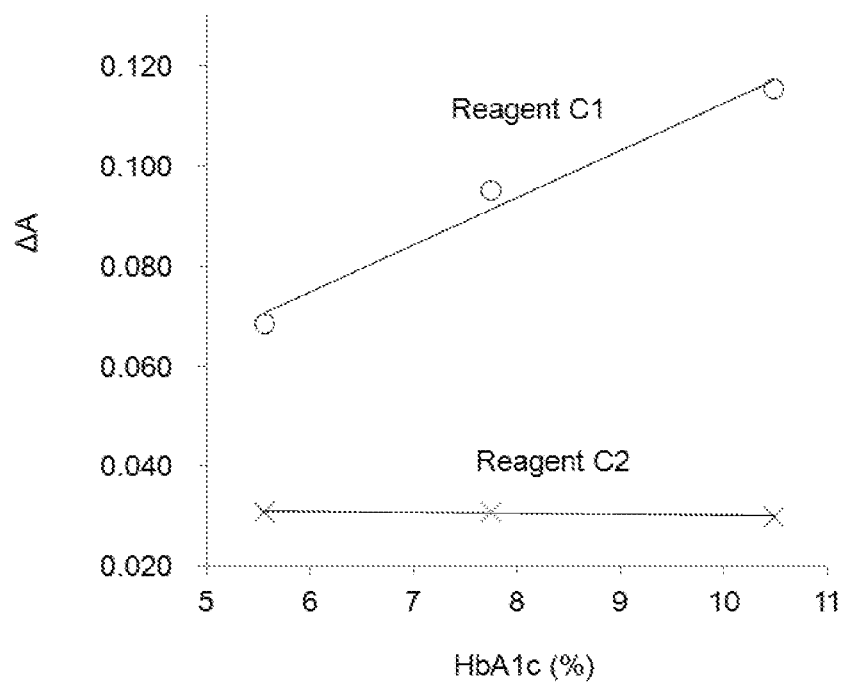

The term "homologous region(s)" used herein refers to region(s) consisting of identical or similar amino acids at corresponding positions in the reference amadoriase and in the amadoriase being compared, when two or more amadoriases are aligned, wherein said region(s) consists of 3 or more, 4 or more, 5 or more, 6 or more, 7 or more, 8 or more, 9 or more, or 10 or more continuous amino acids. For example, FIG. 1 shows the alignment of amadoriases exhibiting sequence identity of 74% or higher over the full-length amino acid sequences. In such sequences, the region of positions 10 to 32 with reference to the sequence of the amadoriase derived from *Coniochaeta* sp, as shown in SEQ ID NO: 1 consists of identical or similar amino acids, and such region is considered to be a homologous region. Similarly, regions of positions 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, to 308, 310 to 316, 324 to 329, 332 to 334, 341 to 344, 346 to 355, 357 to 363, 370 to 383, to 387, 389 to 394, 405 to 410, and 423 to 431 with reference to the sequence of the amadoriase derived from *Coniochaeta* sp. as shown in SEQ ID NO: 1 can be homologous regions.

Preferably, the homologous region of an amadoriases is composed of amino acid sequences of positions 11 to 32, 36 to 41, 50 to 52, 54 to 58, 84 to 86, 88 to 90, 145 to 150, to 168, 202 to 205, 207 to 212, 215 to 225, 236 to 248, 258 to 261, 266 to 268, 270 to 273, to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of an amadoriases is composed of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1, the sequence identity is 50% or higher, preferably 60% or higher, 70% or higher, 75% or higher, 80% or higher, or 85% or higher, more preferably 90% or higher or 95% or higher, and most preferably 99% or higher, and such amadoriase variant has high reactivity with αF6P. In addition, the amino acid sequence in the homologous region of the amadoriase variant according to the present invention exhibits 80%, preferably 85% or higher, 90%, 95%, or 98%, and further preferably 99% or higher sequence identity with the amino acid sequence in the homologous region of SEQ ID NO: 1.

According to one embodiment, the homologous region of an amadoriase is, with reference to the amadoriase sequence as shown in SEQ ID NO: 141, a region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431; preferably a region consisting of amino acids at positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410; and more preferably a region consisting of amino acids at positions 11 to 18, 20 to 32, 50 to 52, 54 to 58, 266 to 268, to 273, 277 to 286, and 370 to 383.

According to an embodiment of the present invention, the amadoriase is (i) or (ii) below:

(i) an amadoriase comprising an amino acid sequence in which substitution, deletion, or addition of 1 or several amino acids has been carried out on the amino acid sequence as shown in SEQ ID NO: 141; or (ii) the amadoriase as defined in (i), wherein the amadoriase comprises an amino acid sequence having 70% or higher sequence identity with the amino acid sequence as shown in SEQ ID NO: 141 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase. According to one embodiment, the amadoriase of the present invention comprises an amino acid sequence exhibiting 95% or higher sequence identity between the amino acid sequence of the homologous region as defined in (ii) above and the amino acid sequence of the homologous region in corresponding positions of said amadoriase.

In addition to, or independent of the substitutions described above, the amadoriase according to an embodiment of the present invention comprises one or more amino acid substitutions at positions corresponding to the amino acids selected from the group consisting of (i) and (ii) in the amino acid sequence as shown in SEQ ID NO: 1:

(i) aspartic acid at position 68; or
(ii) alanine at position 356.

In addition to the substitutions described above, the amadoriase according to an embodiment of the present invention comprises one or more amino acid substitutions at positions corresponding to positions selected from the group consisting of (i) to (xiv) in the amino acid sequence as shown in SEQ ID NO: 1:

(i) asparagine at position 262;
(ii) valine at position 257;
(iii) glutamic acid at position 249;
(iv) glutamic acid at position 253;
(v) glutamine at position 337;
(vi) glutamic acid at position 340;
(vii) aspartic acid at position 232;
(viii) aspartic acid at position 129;
(ix) aspartic acid at position 132;
(x) glutamic acid at position 133;
(xi) glutamic acid at position 44;
(xii) glycine at position 256;
(xiii) glutamic acid at position 231; and
(xiv) glutamic acid at position 81.

In addition to the substitutions described above, the amadoriase according to another embodiment of the present invention may optionally lack 3 amino acid residues from the carboxyl terminus.

(Identifying a Position Corresponding to an Amino Acid)

When an amino acid at a particular position in the reference amino acid sequence corresponds to an amino acid at a particular position in another similar amino acid sequence, in the present invention, such amino acid is referred to as a corresponding amino acid, and the position of such amino acid is referred to as the corresponding or equivalent position. A method of identifying the "position corresponding to an amino acid position" may be also performed by comparing amino acid sequences using a known algorithm such as a Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Homologous positions are considered to exist in the same positions in the three-dimensional structures, and amino acid residues at such homologous positions are expected to exert similar effects in terms of specificity of the amadoriase of interest.

In the present invention, the amino acid at "the position corresponding to arginine at position 62 in the amino acid sequence as shown in SEQ ID NO: 1" is the amino acid corresponding to arginine at position 62 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to arginine at position 62 in the amino acid sequence as shown in SEQ ID NO: 1" is arginine at position 62 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), the fructosyl amino acid oxidase derived from *Ulocladium* sp. (SEQ ID NO: 121), and the fructosyl amino acid oxidase derived from *Penicillium janthinellum* (SEQ ID NO: 123); it is serine at position 62 in the case of the fructosyl peptide oxidase derived from *Phaeosphaeria nodorum* (SEQ ID NO: 38); it is arginine at position 61 in the case of the fructosyl peptide oxidase derived from *Emericella nidulans* (SEQ ID NO: 119); and it is arginine at position 61 in the case of the fructosyl amino acid oxidase derived from *Aspergillus nidulans* (SEQ ID NOs: 62 and 147).

In the present invention, the amino acid at "the position corresponding to leucine at position 63 in the amino acid sequence as shown in SEQ ID NO: 1" is the amino acid corresponding to leucine at position 63 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to leucine at position 63 the amino acid sequence as shown in SEQ ID NO: 1" is leucine at position 63 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl peptide oxidase derived from *Phaeosphaeria nodorum* (SEQ ID NO: 38), the fructosyl amino acid oxidase derived from *Ulocladium* sp. (SEQ ID NO: 121), and the fructosyl amino acid oxidase derived from *Penicillium janthinellum* (SEQ ID NO: 123); it is isoleucine at position 63 in the case of the fructosyl amino acid oxidase derived from *Cryptococcus neoformans* (SEQ ID NOs: 89 and 149); and it is leucine at position 62 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119).

In the present invention, the amino acid at "the position corresponding to glutamic acid at position 102 in the amino acid sequence as shown in SEQ ID NO: 1" is the amino acid corresponding to glutamic acid at position 102 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to glutamic acid at position 102 in the amino acid sequence as shown in SEQ ID NO: 1" is glutamic acid at position 102 in the case of the amadoriase derived from *Eupenicillium terrenum* (SEQ ID NOs: 40 and 145), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl amino acid oxidase derived from *Penicillium janthinellum* (SEQ ID NO: 123); it is lysine at position 102 in the case of the ketoamine oxidase derived from *Pyrenochaeta* sp. (SEQ ID NO: 113), the ketoamine oxidase derived from *Arthrinium* sp. (SEQ ID NO: 115), the fructosyl peptide oxidase derived from *Phaeosphaeria nodorum* (SEQ ID NO: 38), and the fructosyl amino acid oxidase derived from *Ulocladium* sp. (SEQ ID NO: 121); and it is glutamic acid at position 101 in the case of the fructosyl peptide oxidase derived from *Emericella nidulans* (SEQ ID NO: 119) and the fructosyl amino acid oxidase derived from *Aspergillus nidulans* (SEQ ID NOs: 62 and 147).

In the present invention, the amino acid at "the position corresponding to aspartic acid at position 106 in the amino acid sequence as shown in SEQ ID NO: 1" is the amino acid corresponding to aspartic acid at position 106 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to aspartic acid at position 106 in the amino acid sequence as shown in SEQ ID NO: 1" is asparagine at position 106 in the case of the amadoriase derived from *Eupenicillium terrenum* (SEQ ID NOs: 40 and 145); it is aspartic acid at position 106 in the case of the ketoamine oxidase derived from *Pyrenochaeta* sp. (SEQ ID NO: 113), the ketoamine oxidase derived from *Curvularia clavata* (SEQ ID NO: 117), the fructosyl peptide oxidase derived from *Phaeosphaeria nodorum* (SEQ ID NO: 38), and the fructosyl amino acid oxidase derived from *Ulocladium* sp. (SEQ ID NO: 121); it is alanine at position 106 in the case of the ketoamine oxidase derived from *Arthrinium* sp. (SEQ ID NO: 115); it is glycine at position 106 in the case of the ketoamine oxidase derived from *Neocosmospora vasinfecta* (SEQ ID NO: 54); it is serine at position 106 the case of the fructosyl amino acid oxidase derived from *Cryptococcus neoformans* (SEQ ID NOs: 89 and 149) and the fructosyl amino acid oxidase derived from *Penicillium janthinellum* (SEQ ID NO: 123); it is lysine at position 105 in the case of the fructosyl peptide oxidase derived from *Emericella nidulans* (SEQ ID NO: 119); and it is glycine at position 105 the case of the fructosyl amino acid oxidase derived from *Aspergillus nidulans* (SEQ ID NOs: 62 and 147).

In the present invention, the amino acid at "the position corresponding to glutamine at position 110 in the amino acid sequence as shown in SEQ ID NO: 1" is the amino acid corresponding to glutamine at position 110 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to glutamine at position 110 in the amino acid sequence as shown in SEQ ID NO: 1" is lysine at position 110 in the case of the amadoriase derived from *Eupenicillium terrenum* (SEQ ID NOs: 40 and 145) and the fructosyl amino acid oxidase derived from *Penicillium janthinellum* (SEQ ID NO: 123); it is alanine at position 110 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is glutamine at position 110 in the case of the ketoamine oxidase derived from *Arthrinium* sp. (SEQ ID NO: 115); it is glutamic acid at position 110 in the case of the ketoamine oxidase derived from *Neocosmospora vasinfecta* (SEQ ID NO: 54); it is serine at position 110 in the case of the fructosyl amino acid oxidase derived from *Cryptococcus neoformans* (SEQ ID NOs: 89 and 149); it is glycine at position 110 in the case of the fructosyl peptide oxidase derived from *Phaeosphaeria nodorum* (SEQ ID NO: 38); it is arginine at position 109 in the case of the fructosyl peptide oxidase derived from *Emericella nidulans* (SEQ ID NO: 119); and it is lysine at position 109 in the case of the fructosyl amino acid oxidase derived from *Aspergillus nidulans* (SEQ ID NOs: 62 and 147).

In the present invention, the amino acid at "the position corresponding to alanine at position 113 in the amino acid sequence as shown in SEQ ID NO: 1" is the amino acid corresponding to alanine at position 113 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 113 the amino acid sequence as shown in SEQ ID NO: 1" is threonine at position 113 in the case of the amadoriase derived from *Eupenicillium terrenum* (SEQ ID NOs: 40 and 145), the ketoamine oxidase derived from *Pyrenochaeta* sp. (SEQ ID NO: 113), and the ketoamine oxidase derived from *Arthrinium* sp. (SEQ ID NO: 115); it is alanine at position 113 in the case of the ketoamine oxidase derived from *Curvularia clavata* (SEQ ID NO:

117), the fructosyl amino acid oxidase derived from *Cryptococcus neoformans* (SEQ ID NOs: 89 and 149), the fructosyl peptide oxidase derived from *Phaeosphaeria nodorum* (SEQ ID NO: 38), and the fructosyl amino acid oxidase derived from *Ulocladium* sp. (SEQ ID NO: 121); it is lysine at position 113 in the case of the ketoamine oxidase derived from *Neocosmospora vasinfecta* (SEQ ID NO: 54); it is serine at position 112 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119); and it is aspartic acid at position 113 in the case of the fructosyl amino acid oxidase derived from *Penicillium janthinellum* (SEQ ID NO: 123).

In the present invention, the amino acid at "the position corresponding to alanine at position 355 in the amino acid sequence as shown in SEQ ID NO: 1" is the amino acid corresponding to alanine at position 355 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 355 the amino acid sequence as shown in SEQ ID NO: 1" is alanine at position 355 in the case of the amadoriase derived from *Eupenicillium terrenum* (SEQ ID NOs: 40 and 145), the fructosyl amino acid oxidase derived from *Cryptococcus neoformans* (SEQ ID NOs: 89 and 149), the fructosyl amino acid oxidase derived from *Aspergillus nidulans* (SEQ ID NOs: 62 and 147), the fructosyl peptide oxidase derived from *Emericella nidulans* (SEQ ID NO: 119), and the fructosyl amino acid oxidase derived from *Penicillium janthinellum* (SEQ ID NO: 123); it is alanine at position 353 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 356 in the case of the ketoamine oxidase derived from *Arthrinium* sp. (SEQ ID NO: 115); it is serine at position 355 in the case of the ketoamine oxidase derived from *Neocosmospora vasinfecta* (SEQ ID NO: 54); and it is alanine at position 351 in the case of the fructosyl peptide oxidase derived from *Phaeosphaeria nodorum* (SEQ ID NO: 38).

In the present invention, the amino acid at "the position corresponding to alanine at position 419 in the amino acid sequence as shown in SEQ ID NO: 1" is the amino acid corresponding to alanine at position 419 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 419 the amino acid sequence as shown in SEQ ID NO: 1" is glycine at position 419 in the case of the amadoriase derived from *Eupenicillium terrenum* (SEQ ID NOs: 40 and 145); it is alanine at position 418 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 421 in the case of the ketoamine oxidase derived from *Arthrinium* sp. (SEQ ID NO: 115); it is alanine at position 420 in the case of the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl peptide oxidase derived from *Emericella nidulans* (SEQ ID NO: 119); it is serine at position 416 in the case of the fructosyl peptide oxidase derived from *Phaeosphaeria nodorum* (SEQ ID NO: 38); it is serine at position 419 in the case of the fructosyl amino acid oxidase derived from *Penicillium janthinellum* (SEQ ID NO: 123); and it is alanine at position 420 in the case of the fructosyl amino acid oxidase derived from *Aspergillus nidulans* (SEQ ID NOs: 62 and 147).

In the present invention, the amino acid at "the position corresponding to aspartic acid at position 68 in the amino acid sequence as shown in SEQ ID NO: 1" is the amino acid corresponding to aspartic acid at position 68 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to aspartic acid at position 68 in the amino acid sequence as shown in SEQ ID NO: 1" is aspartic acid at position 68 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), the fructosyl peptide oxidase derived from *Phaeosphaeria nodorum* (SEQ ID NO: 38), the fructosyl amino acid oxidase derived from *Ulocladium* sp. (SEQ ID NO: 121), and the fructosyl amino acid oxidase derived from *Penicillium janthinellum* (SEQ ID NO: 123); and it is aspartic acid at position 67 in the case of the fructosyl peptide oxidase derived from *Emericella nidulans* (SEQ ID NO: 119) and the fructosyl amino acid oxidase derived from *Aspergillus nidulans* (SEQ ID NOs: 62 and 147).

In the present invention, the amino acid at "the position corresponding to alanine at position 356 in the amino acid sequence as shown in SEQ ID NO: 1" is the amino acid corresponding to alanine at position 356 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 356 the amino acid sequence as shown in SEQ ID NO: 1" is asparagine at position 356 in the case of the amadoriase derived from *Eupenicillium terrenum* (SEQ ID NOs: 40 and 145); it is alanine at position 354 in the case of the ketoamine oxidase derived from *Pyrenochaeta* sp. (SEQ ID NO: 113); alanine at position 357 in the case of the ketoamine oxidase derived from *Arthrinium* sp.

(SEQ ID NO: 115); it is alanine at position 354 in the case of the ketoamine oxidase derived from *Curvularia clavata* (SEQ ID NO: 117); it is alanine at position 356 in the case of the ketoamine oxidase derived from *Neocosmospora vasinfecta* (SEQ ID NO: 54); it is asparagine at position 356 in the case of the fructosyl amino acid oxidase derived from *Cryptococcus neoformans* (SEQ ID NOs: 89 and 149); it is alanine at position 352 in the case of the fructosyl peptide oxidase derived from *Phaeosphaeria nodorum* (SEQ ID NO: 38); it is asparagine at position 356 in the case of the fructosyl amino acid oxidase derived from *Aspergillus nidulans* (SEQ ID NOs: 62 and 147); it is asparagine at position 356 in the case of the fructosyl peptide oxidase derived from *Emericella nidulans* (SEQ ID NO: 119); it is alanine at position 354 in the case of the fructosyl amino acid oxidase derived from *Ulocladium* sp. (SEQ ID NO: 121); and it is asparagine at position 356 in the case of the fructosyl amino acid oxidase derived from *Penicillium janthinellum* (SEQ ID NO: 123).

The amadoriase variant of the present invention may be a single variant or a multiple variant comprising two or more amino acid substitutions. The present inventors found that an amadoriase having substitutions at positions corresponding to positions 62, 63, 102, 106, 113, and 355 of the amino acid sequence as shown in SEQ ID NO: 1 surprisingly exhibits activity on HbA1c. The present inventors further discovered that an amadoriase having substitutions at positions corresponding to positions 68 and 356 of the amino acid sequence as shown in SEQ ID NO: 1 surprisingly exhibited enhanced activity on αF6P.

In the present description, mutations at these positions (at positions 62, 63, 102, 106, 113, 355, 419, as well as positions 68 and 356) may also be referred to as "mutations that alter substrate specificity of an amadoriase" or "amino acid substitutions that alter substrate specificity of an amadoriase."

According to one embodiment, the specific activity (U/mg) of the amadoriase of the present invention on αF6P is 0.1 U/mg or higher, 0.2 U/mg or higher, 0.3 U/mg or higher, 0.4 or higher, 0.5 U/mg or higher, 0.6 U/mg or higher, 0.7 U/mg or higher, 0.8 U/mg or higher, or 0.9 U/mg or higher, such as 1 U/mg or higher. Such amadoriase can comprise 1 more, 2 or more, 3 or more, 4 or more, 5 or more, 6 or more, 7 or more, 8 or more, 9 or more, or 10 or more amino acid substitutions that alter substrate specificity. Such amadoriase of the present invention acts directly on HbA1c and can be used for the method of HbA1c measurement according to the present invention.

According to one embodiment, the amadoriase of the present invention having a specific activity (U/mg) on αF6P of 0.1 U/mg or higher may be an amadoriase having 1 or more, 2 or more, 3 or more, 4 or more, 5 or more, 6 or more, 7 or more, 8 or more, or 9 or more, for example 10 amino acid substitutions at positions corresponding to positions selected from (a) to (j) below, when aligned with the amino acid sequence as shown in SEQ ID NO: 1:

(a) arginine at position 62 in SEQ ID NO: 1;
(b) leucine at position 63 in SEQ ID NO: 1;
(c) glutamic acid at position 102 in SEQ ID NO: 1;
(d) aspartic acid at position 106 in SEQ ID NO: 1;
(e) glutamine at position 110 in SEQ ID NO: 1;
(f) alanine at position 113 in SEQ ID NO: 1;
(g) alanine at position 355 in SEQ ID NO: 1;
(h) alanine at position 419 in SEQ ID NO: 1;
(i) aspartic acid at position 68 in SEQ ID NO: 1; and
(j) alanine at position 356 in SEQ ID NO: 1.

Incidentally, in the case of the fructosyl peptide oxidase derived from *Phaeosphaeria nodorum* (SEQ ID NO: 38), the amino acid at "the position corresponding to arginine at position 62 in the amino acid sequence as shown in SEQ ID NO: 1" is serine at position 62. From the perspective of the amino acid sequence of SEQ ID NO: 1, this can be recognized as the amino acid at the position corresponding to arginine at position 62 being serine, i.e., equivalent to the amino acid being substituted with serine. Accordingly, a naturally occurring amadoriase comprising an amino acid sequence in which the amino acid at the position corresponding to arginine at position 62 in the amino acid sequence of SEQ ID NO: 1 serine, such as the fructosyl peptide oxidase derived from *Phaeosphaeria nodorum* (SEQ ID NO: 38) is also, for the sake of convenience, encompassed within the scope of an amadoriase comprising an amino acid substitution at a position corresponding to (a) arginine at position 62 in SEQ ID NO: 1, when aligned with the amino acid sequence as shown in SEQ ID NO: 1, according to the present specification.

According to one embodiment, the amadoriase of the present invention having a specific activity (U/mg) on αF6P of 0.1 U/mg or higher may comprise 1 or more, 2 or more, 3 more, 4 or more, 5 or more, 6 or more, 7 or more, 8 or more, or 9 or more, such as 10 of the amino acid residues as described below at positions corresponding to the positions of the amino acid sequence of SEQ ID NO: 1 selected from the group consisting of (a) to (j) below:

(a) the amino acid at a position corresponding to position 62 in SEQ ID NO: 1 is alanine, aspartic acid, asparagine, glutamine, glutamic acid, glycine, valine, leucine, isoleucine, cysteine, serine, threonine, or proline;
(b) the amino acid at a position corresponding to position 63 in SEQ ID NO: 1 is alanine or histidine;
(c) the amino acid at a position corresponding to position 102 in SEQ ID NO: 1 is lysine;
(d) the amino acid at a position corresponding to position 106 in SEQ ID NO: 1 is alanine, lysine, or arginine;
(e) the amino acid at a position corresponding to position 110 in SEQ ID NO: 1 is leucine or tyrosine;
(f) the amino acid at a position corresponding to position 113 in SEQ ID NO: 1 is lysine or arginine;
(g) the amino acid at a position corresponding to position 355 in SEQ ID NO: 1 is serine;
(h) the amino acid at a position corresponding to position 419 in SEQ ID NO: 1 is lysine;
(i) the amino acid at a position corresponding to position 68 in SEQ ID NO: 1 is asparagine; and
(j) the amino acid at a position corresponding to position 356 in SEQ ID NO: 1 is threonine.

(Auxiliary Substitution)

It has been reported that when the amino acid at the position corresponding to position 60 in the amino acid sequence of SEQ ID NO: 1 is serine, substituting the same with glycine renders the amadoriase which did not exhibit activity on αFVH prior to substitution to exhibit activity on αFVH post substitution (see JP 2010-35469 A and WO 2012/018094). Therefore, when an amadoriase used in the present invention comprises serine at the position corresponding to position 60 in the amadoriase sequence of SEQ ID NO: 1, such serine may be substituted with glycine in advance. Alternatively, a wild-type amadoriase comprising a sequence in which the amino acid at the position corresponding to position 60 in the sequence of SEQ ID NO: 1 is glycine may be used to introduce mutations into positions corresponding to positions 62, 63, 102, 106, 110, 113, 355, and 419 and positions 68 and 356 of SEQ ID NO: 1. Unless otherwise specified, an amadoriase comprising a sequence in which the amino acid at a position corresponding to position 60 in the sequence as shown in SEQ ID NO: 1 is glycine is encompassed within the scope of the amadoriase variant of the present invention. In the case of the amadoriase derived from *Aspergillus nidulans*, for example, the amino acid at position 59 in SEQ ID NO: 147 that corresponds to position 60 in SEQ ID NO: 1 is serine in the wild-type amadoriase. An amadoriase having this serine substituted with glycine (i.e., SEQ ID NO: 62) may be used as a basis amadoriase to obtain a variant of the present invention. The same applies to the amadoriase from *Penicillium janthinellum* (Pj) (SEQ ID NO: 123).

(Additional Auxiliary Substitutions-Mutations that Improve Surfactant Resistance)

The present inventors have confirmed that surfactant resistance of an amadoriase can be improved via substitution of amino acid residues of the amadoriase. The amadoriase of the present invention can, optionally, further comprise such amino acid substitution(s).

Examples of amino acid substitutions that can improve surfactant resistance include those at positions corresponding to the amino acids (1) to (14) below in the amino acid sequence as shown in SEQ ID NO: 1:

(1) substitution of asparagine at position 262 with, for example, histidine;
(2) substitution of valine at position 257 with, for example, cysteine, serine, or threonine;
(3) substitution of glutamic acid at position 249 with, for example, lysine or arginine;
(4) substitution of glutamic acid at position 253 with, for example, lysine or arginine;
(5) substitution of glutamine at position 337 with, for example, lysine or arginine;
(6) substitution of glutamic acid at position 340 with, for example, proline;
(7) substitution of aspartic acid at position 232 with, for example, lysine or arginine;
(8) substitution of aspartic acid at position 129 with, for example, lysine or arginine;
(9) substitution of aspartic acid at position 132 with, for example, lysine or arginine;
(10) substitution of glutamic acid at position 133 with, for example, alanine, methionine, lysine, or arginine;
(11) substitution of glutamic acid at position 44 with, for example, proline;
(12) substitution of glycine at position 256 with, for example, lysine or arginine;
(13) substitution of glutamic acid at position 231 with, for example, lysine or arginine;
(14) substitution of glutamic acid at position 81 with, for example, lysine or arginine.

It is sufficient that an amadoriase variant exhibiting improved surfactant resistance comprises at least one of the amino acid substitutions described above. An amadoriase variant may comprise a plurality of amino acid substitutions. For example, an amadoriase variant may comprise 1, 2, 3, 4, 5, 6, 7, 8, 9, 10, 11, 12, 13, or 14 of the amino acid substitutions described above.

In the present invention, the amino acid at "the position corresponding to glutamic acid at position 44 in the amino acid sequence as shown in SEQ ID NO: 1" is the amino acid corresponding to glutamic acid at position 44 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method for identifying "amino acid residues at corresponding positions" with reference to FIG. 1 in which amino acid sequences are aligned.

Specifically, it is lysine at position 44 in the amadoriase derived from *Eupenicillium terrenum*, proline at position 44 in the case of the ketoamine oxidase derived from *Pyrenochaeta* sp., proline at position 44 in the case of the ketoamine oxidase derived from *Arthrinium* sp., proline at position 44 in the case of the ketoamine oxidase derived from *Curvularia clavata*, proline at position 44 in the case of the ketoamine oxidase derived from *Neocosmospora vasinfecta*, leucine at position 44 in the case of the fructosyl amino acid oxidase derived from *Cryptococcus neoformans*, proline at position 44 in the case of the fructosyl peptide oxidase derived from *Phaeosphaeria nodorum*, proline at position 43 in the case of the fructosyl amino acid oxidase derived from *Aspergillus nidulans*, proline at position 43 in the case of the fructosyl peptide oxidase derived from *Emericella nidulans*, proline at position 44 in the case of the fructosyl amino acid oxidase derived from *Ulocladium* sp., and proline at position 44 in the case of the fructosyl amino acid oxidase derived from *Penicillium janthinelum*.

The amino acid at "the position corresponding to glutamic acid at position 81 in the amino acid sequence as shown in SEQ ID NO: I" is the amino acid corresponding to glutamic acid at position 81 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is asparagine at position 81 in the case of the amadoriase derived from *Eupenicillium terrenum*, glutamic acid at position 81 in the case of the ketoamine oxidase derived from *Pyrenochaeta* sp., histidine at position 81 in the case of the ketoamine oxidase derived from *Arthrinium* sp., glutamic acid at position 81 in the case of the ketoamine oxidase derived from *Curvularia clavata*, asparagine at position 81 in the case of the ketoamine oxidase derived from *Neocosmospora vasinfecta*, asparagine at position 81 in the case of the fructosyl amino acid oxidase derived from *Cryptococcus neoformans*, glutamic acid at position 81 in the case of the fructosyl peptide oxidase derived from *Phaeosphaeria nodorum*, asparagine at position 80 in the case of the fructosyl amino acid oxidase derived from *Aspergillus nidulans*, asparagine at position 80 in the case of the fructosyl peptide oxidase derived from *Emericella nidulans*, glutamic acid at position 81 in the case of the fructosyl amino acid oxidase derived from *Ulocladium* sp., and asparagine at position 81 in the case of the fructosyl amino acid oxidase derived from *Penicillium janthinelum*.

The amino acid at "the position corresponding to glutamic acid at position 133 in the amino acid sequence as shown in SEQ ID NO: 1" is the amino acid corresponding to glutamic acid at position 133 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is glutamic acid at position 133 in the case of the amadoriase derived from *Eupenicillium terrenum*, glutamic acid at position 133 in the case of the ketoamine oxidase derived from *Pyrenochaeta* sp., alanine at position 133 in the case of the ketoamine oxidase derived from *Arthrinium* sp., glutamic acid at position 133 in the case of the ketoamine oxidase derived from *Curvularia clavata*, alanine at position 133 in the case of the ketoamine oxidase derived from *Neocosmospora vasinfecta*, glutamic acid at position 133 in the case of the fructosyl amino acid oxidase derived from *Cryptococcus neoformans*, glutamic acid at position 131 in the case of the fructosyl peptide oxidase derived from *Phaeosphaeria nodorum*, glutamic acid at position 132 in the case of the fructosyl amino acid oxidase derived from *Aspergillus nidulans*, glutamic acid at position 132 in the case of the fructosyl peptide oxidase derived from *Emericella nidulans*, lysine at position 133 in the case of the fructosyl amino acid oxidase derived from *Ulocladium* sp., and aspartic acid at position 133 in the case of the fructosyl amino acid oxidase derived from *Penicillium janthinelum*.

The amino acid at "the position corresponding to glutamic acid at position 253 in the amino acid sequence as shown in SEQ ID NO: 1" is the amino acid corresponding to glutamic acid at position 253 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is alanine at position 253 in the case of the amadoriase derived from *Eupenicillium terrenum*, alanine at position 251 in the case of the ketoamine oxidase derived from *Pyrenochaeta* sp., glutamic acid at position 253 in the case of the ketoamine oxidase derived from *Arthrinium* sp., glutamic acid at position 251 in the case of the ketoamine oxidase derived from *Curvularia clavata*, valine at position 253 in the case of the ketoamine oxidase derived from *Neocosmospora vasinfecta*, glutamic acid at position 253 in the case of the fructosyl amino acid oxidase derived from *Cryptococcus neoformans*, arginine at position 249 in the case of the fructosyl peptide oxidase derived from *Phaeosphaeria nodorum*, alanine at position 253 in the case of the fructosyl amino acid oxidase derived from *Aspergillus nidulans*, alanine at position 253 in the case of the fructosyl peptide oxidase derived from *Emericella nidulans*, glutamic acid at position 251 in the case of the fructosyl amino acid oxidase derived from *Ulocladium* sp., and glutamine at position 253 in the case of the fructosyl amino acid oxidase derived from *Penicillium janthinelum*.

The amino acid at "the position corresponding to glycine at position 256 in the amino acid sequence as shown in SEQ ID NO: 1" is the amino acid corresponding to glycine at position 256 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is asparagine at position 256 in the case of the amadoriase derived from *Eupenicillium terrenum*, aspartic acid at position 254 in the case of the ketoamine oxidase derived from *Pyrenochaeta* sp., glycine at position 256 in the case of the ketoamine oxidase derived from *Arthrinium* sp., asparagine at position 254 in the case of the ketoamine oxidase derived from *Curvularia clavata*, glycine at position 256 in the case of the ketoamine oxidase derived from *Neocosmospora vasinfecta*, glutamic acid at position 256 in the case of the fructosyl amino acid oxidase derived from *Cryptococcus neoformans*, asparagine at position 252 in the case of the fructosyl peptide oxidase derived from *Phaeosphaeria nodorum*, asparagine at position 256 in the case of the fructosyl amino acid oxidase derived from *Aspergillus nidulans*, asparagine at position 256 in the case of the fructosyl peptide oxidase derived from *Emericella nidulans*, asparagine at position 254 in the case of the fructosyl amino acid oxidase derived from *Ulocladium* sp., and aspartic acid at position 256 in the case of the fructosyl amino acid oxidase derived from *Penicillium janthinelum*.

Further, the amino acid at "the position corresponding to valine at position 257 in the amino acid sequence as shown in SEQ ID NO: 1" is the amino acid corresponding to valine at position 257 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is valine at position 257 in the case of the amadoriase derived from *Eupenicillium terrenum*, threonine at position 255 in the case of the ketoamine oxidase derived from *Pyrenochaeta* sp., cysteine at position 257 in the case of the ketoamine oxidase derived from *Arthrinium* sp., valine at position 255 in the case of the ketoamine oxidase derived from *Curvularia clavata*, cysteine at position 257 in the case of the ketoamine oxidase derived from *Neocosmospora vasinfecta*, cysteine at position 257 in the case of the fructosyl amino acid oxidase derived from *Cryptococcus neoformans*, serine at position 253 the case of the fructosyl peptide oxidase derived from *Phaeosphaeria nodorum*, threonine at position 257 in the case of the fructosyl amino acid oxidase derived from *Aspergillus nidulans*, threonine at position 257 in the case of the fructosyl peptide oxidase derived from *Emericella nidulans*, valine at position 255 in the case of the fructosyl amino acid oxidase derived from *Ulocladium* sp., and valine at position 257 in the case of the fructosyl amino acid oxidase derived from *Penicillium janthinelum*.

Further, the amino acid at "the position corresponding to asparagine at position 262 the amino acid sequence as shown in SEQ ID NO: 1" is the amino acid corresponding to asparagine at position 262 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is aspartic acid at position 262 in the case of the amadoriase derived from *Eupenicillium terrenum*, asparagine at position 260 in the case of the ketoamine oxidase derived from *Pyrenochaeta* sp., histidine at position 262 in the case of the ketoamine oxidase derived from *Arthrinium* sp., asparagine at position 260 in the case of the ketoamine oxidase derived from *Curvularia clavata*, histidine at position 262 in the case of the ketoamine oxidase derived from *Neocosmospora vasinfecta*, asparagine at position 262 in the case of the fructosyl amino acid oxidase derived from *Cryptococcus neoformans*, asparagine at position 258 in the case of the fructosyl peptide oxidase derived from *Phaeosphaeria nodorum*, aspartic acid at position 262 in the case of the fructosyl amino acid oxidase derived from *Aspergillus nidulans*, aspartic acid at position 262 in the case of the fructosyl peptide oxidase derived from *Emericella nidulans*, asparagine at position 260 in the case of the fructosyl amino acid oxidase derived from *Ulocladium* sp., and aspartic acid at position 262 in the case of the fructosyl amino acid oxidase derived from *Penicillium janthinelum*.

Further, the amino acid at "the position corresponding to glutamine at position 337 in the amino acid sequence as shown in SEQ ID NO: 1" is the amino acid corresponding to glutamine at position 337 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is lysine at position 337 in the case of the amadoriase derived from *Eupenicillium terrenum*, lysine at position 335 in the case of the ketoamine oxidase derived from *Pyrenochaeta* sp., glutamine at position 338 in the case of the ketoamine oxidase derived from *Arthrinium* sp., threonine at position 335 in the case of the ketoamine oxidase derived from *Curvularia clavata*, lysine at position 337 in the case of the ketoamine oxidase derived from *Neocosmospora vasinfecta*, lysine at position 337 in the case of the fructosyl amino acid oxidase derived from *Cryptococcus neoformans*, lysine at position 333 in the case of the fructosyl peptide oxidase derived from *Phaeosphaeria nodorum*, asparagine at position 337 in the case of the fructosyl amino acid oxidase derived from *Aspergillus nidulans*, asparagine at position 337 in the case of the fructosyl peptide oxidase derived from *Emericella nidulans*, threonine at position 335 in the case of the fructosyl amino acid oxidase derived from *Ulocladium* sp., and lysine at position 337 in the case of the fructosyl amino acid oxidase derived from *Penicillium janthinelum*.

Further, the amino acid at "the position corresponding to glutamic acid at position 340 in the amino acid sequence as shown in SEQ ID NO: 1" is the amino acid corresponding to glutamic acid at position 340 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is glutamic acid at position 340 in the case of the amadoriase derived from *Eupenicillium terrenum*, glutamic acid at position 338 in the case of the ketoamine oxidase derived from *Pyrenochaeta* sp., glutamic acid at position 341 in the case of the ketoamine oxidase derived from *Arthrinium* sp., glutamic acid at position 338 in the case of the ketoamine oxidase derived from *Curvularia clavata*, proline at position 340 in the case of the ketoamine oxidase derived from *Neocosmospora vasinfecta*, glutamic acid at position 340 the case of the fructosyl amino acid oxidase derived from *Cryptococcus neoformans*, lysine at position 336 in the case of the fructosyl peptide oxidase derived from *Phaeosphaeria nodorum*, glutamic acid at position 340 in the case of the fructosyl amino acid oxidase derived from *Aspergillus nidulans*, glutamic acid at position 340 in the case of the fructosyl peptide oxidase derived from *Emericella nidulans*, glutamic acid at position 338 in the case of the fructosyl amino acid oxidase derived from *Ulocladium* sp., and glutamic acid at position 340 the case of the fructosyl amino acid oxidase derived from *Penicillium janthinelum*.

Further, the amino acid at "the position corresponding to aspartic acid at position 129 the amino acid sequence as shown in SEQ ID NO: 1" is the amino acid corresponding to aspartic acid at position 129 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is glutamic acid at position 129 in the case of the amadoriase derived from *Eupenicillium terrenum*, aspartic acid at position 129 in the case of the ketoamine oxidase derived from *Pyrenochaeta* sp., aspartic acid at position 129 in the case of the ketoamine oxidase derived from *Arthrinium* sp., aspartic acid at position 129 in the case of the ketoamine oxidase derived from *Curvularia clavata*, aspartic acid at position 129 in the case of the ketoamine oxidase derived from *Neocosmospora vasinfecta*, serine at position 129 in the case of the fructosyl amino acid oxidase derived from *Cryptococcus neoformans*, aspartic acid at position 127 in the case of the fructosyl peptide oxidase derived from *Phaeosphaeria nodorum*, glutamic acid at position 128 in the case of the fructosyl amino acid oxidase derived from *Aspergillus nidulans*, glutamic acid at position 128 in the case of the fructosyl peptide oxidase derived from *Emericella nidulans*, aspartic acid at position 129 in the case of the fructosyl amino acid oxidase derived from *Ulocladium* sp., and glutamic acid at position 129 the case of the fructosyl amino acid oxidase derived from *Penicillium janthinelum*.

Further, the amino acid at "the position corresponding to aspartic acid at position 132 the amino acid sequence as shown in SEQ ID NO: 1" is the amino acid corresponding to aspartic acid at position 132 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is aspartic acid at position 132 in the case of the amadoriase derived from *Eupenicillium terrenum*, aspartic acid at position 132 in the case of the ketoamine oxidase derived from *Pyrenochaeta* sp., aspartic acid at position 132 in the case of the ketoamine oxidase derived from *Arthrinium* sp., aspartic acid at position 132 in the case of the ketoamine oxidase derived from *Curvularia clavata*, glutamic acid at position 132 in the case of the ketoamine oxidase derived from *Neocosmospora vasinfecta*, aspartic acid at position 132 in the case of the fructosyl amino acid oxidase derived from *Cryptococcus neoformans*, aspartic acid at position 130 in the case of the fructosyl peptide oxidase derived from *Phaeosphaeria nodorum*, aspartic acid at position 131 in the case of the fructosyl amino acid oxidase derived from *Aspergillus nidulans*, aspartic acid at position 131 in the case of the fructosyl peptide oxidase derived from *Emericella nidulans*, aspartic acid at position 132 in the case of the fructosyl amino acid oxidase derived from *Ulocladium* sp., and aspartic acid at position 132 in the case of the fructosyl amino acid oxidase derived from *Penicillium janthinelum*.

Further, the amino acid at "the position corresponding to glutamic acid at position 231 in the amino acid sequence as shown in SEQ ID NO: 1" is the amino acid corresponding to glutamic acid at position 231 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is glutamic acid at position 231 in the case of the amadoriase derived from *Eupenicillium terrenum*, glutamic acid at position 229 in the case of the ketoamine oxidase derived from *Pyrenochaeta* sp., glutamic acid at position 231 in the case of the ketoamine oxidase derived from *Arthrinium* sp., glutamic acid at position 229 in the case of the ketoamine oxidase derived from *Curvularia clavata*, glutamic acid at position 231 in the case of the ketoamine oxidase derived from *Neocosmospora vasinfecta*, glutamic acid at position 231 in the case of the fructosyl amino acid oxidase derived from *Cryptococcus neoformans*, histidine at position 227 in the case of the fructosyl peptide oxidase derived from *Phaeosphaeria nodorum*, glutamic acid at position 231 in the case of the fructosyl amino acid oxidase derived from *Aspergillus nidulans*, glutamic acid at position 231 in the case of the fructosyl peptide oxidase derived from *Emericella nidulans*, glutamine at position 229 in the case of the fructosyl amino acid oxidase derived from *Ulocladium* sp., and glutamic acid at position 231 in the case of the fructosyl amino acid oxidase derived from *Penicillium janthinelum*.

Further, the amino acid at "the position corresponding to aspartic acid at position 232 the amino acid sequence as shown in SEQ ID NO: 1" is the amino acid corresponding to aspartic acid at position 232 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is aspartic acid at position 232 in the case of the amadoriase derived from *Eupenicillium terrenum*, aspartic acid at position 230 in the case of the ketoamine oxidase derived from *Pyrenochaeta* sp., glutamic acid at position 232 in the case of the ketoamine oxidase derived from *Arthrinium* sp., aspartic acid at position 230 in the case of the ketoamine oxidase derived from *Curvularia clavata*, glutamic acid at position 232 in the case of the ketoamine oxidase derived from *Neocosmospora vasinfecta*, glycine at position 232 in the case of the fructosyl amino acid oxidase derived from *Cryptococcus neoformans*, glutamic acid at position 228 in the case of the fructosyl peptide oxidase derived from *Phaeosphaeria nodorum*, glutamic acid at position 232 in the case of the fructosyl amino acid oxidase derived from *Aspergillus nidulans*, glutamic acid at position 232 in the case of the fructosyl peptide oxidase derived from *Emericella nidulans*, aspartic acid at position 230 in the case of the fructosyl amino acid oxidase derived from *Ulocladium* sp., and aspartic acid at position 232 in the case of the fructosyl amino acid oxidase derived from *Penicillium janthinelum*.

Further, the amino acid at "the position corresponding to glutamic acid at position 249 in the amino acid sequence as shown in SEQ ID NO: 1" is the amino acid corresponding to glutamic acid at position 249 in the amadoriase sequence as shown in SEQ ID NO: 1, when the identified amino acid sequence of an amadoriase is compared with the amino acid sequence of the amadoriase derived from the genus *Coniochaeta* as shown in SEQ ID NO: 1. This can be specified by the aforementioned method with reference to FIG. 1 in which amino acid sequences are aligned.

Specifically, it is lysine at position 249 in the case of the amadoriase derived from *Eupenicillium terrenum*, lysine at position 247 in the case of the ketoamine oxidase derived from *Pyrenochaeta* sp., histidine at position 249 in the case of the ketoamine oxidase derived from *Arthrinium* sp., glutamic acid at position 247 in the case of the ketoamine oxidase derived from *Curvularia clavata*, glutamic acid at position 249 in the case of the ketoamine oxidase derived from *Neocosmospora vasinfecta*, glutamic acid at position 249 in the case of the fructosyl amino acid oxidase derived from *Cryptococcus neoformans*, glutamic acid at position 245 in the case of the fructosyl peptide oxidase derived from *Phaeosphaeria nodorum*, alanine at position 249 in the case of the fructosyl amino acid oxidase derived from *Aspergillus nidulans*, alanine at position 249 in the case of the fructosyl peptide oxidase derived from *Emericella nidulans*, serine at position 247 in the case of the fructosyl amino acid oxidase derived from *Ulocladium* sp., and glutamine at position 249 in the case of the fructosyl amino acid oxidase derived from *Penicillium janthinelum*.

In the present description, mutations at the positions described above (at positions 44, 253, 257, 262, 337, 340, 249, 232, 129, 132, 256, 231, and 81) are also referred to as "mutations that improve surfactant resistance of an amadoriase" or "amino acid substitutions that improve surfactant resistance of an amadoriase." According to an embodiment, the amadoriase of the present invention can, in addition to mutations that alter substrate specificity, further comprise a mutation that improves surfactant resistance.

(Further Auxiliary Deletion-Deletion of 3 Amino Acid Residues from the Carboxyl Terminus)

In the past, the present inventors reported that heat stability of an amadoriase can be improved by deletion of 3 amino acid residues from the carboxyl terminus of the amadoriase (see WO 2013/100006, all of the contents as disclosed therein are incorporated herein by reference in their entirely). According to an embodiment, the amadoriase of the present invention may further involve deletion of 3 amino acid residues from the carboxyl terminus, in addition to the mutation described above.

(Position Corresponding to Deletion at the Carboxyl Terminus)

The 3 amino acid residues at "the position corresponding to 3 amino acid residues from the carboxyl terminus of the amadoriase sequence as shown in SEQ ID NO: 1" refers to 3 amino acid residues from the carboxyl terminus in the amino acid sequence as shown in SEQ ID NO: 1, when the amino acid sequence of an amadoriase is compared with the amino acid sequence of the amadoriase derived from the genus *Coniochaeta* as shown in SEQ ID NO: 1. In the amadoriase from the genus *Coniochaeta*, the sequence of the 3 residues at these positions consist of proline at position 435, lysine at position 436, and leucine at position 437. The amino acid sequence at positions corresponding thereto can be specified by the aforementioned method with reference to FIG. 1 in which amino acid sequences are aligned.

Specifically, 3 amino acids at the carboxyl terminus are alanine at position 435, histidine at position 436, and leucine at position 437 in the case of the amadoriase derived from *Eupenicillium terrenum*, alanine at position 438, lysine at position 439, and leucine at position 440 in the case of the ketoamine oxidase derived from *Pyrenochaeta* sp., histidine at position 450, lysine at position 451, and leucine at position 452 in the case of the ketoamine oxidase derived from *Arthrinium* sp., serine at position 438, lysine at position 439, and leucine at position 440 in the case of the ketoamine oxidase derived from *Curvularia clavata*, alanine at position 435, asparagine at position 436, and leucine at position 437 in the case of the fructosyl peptide oxidase derived from *Phaeosphaeria nodorum*, alanine at position 436, lysine at position 437, and methionine at position 438 in the case of the fructosyl amino acid oxidase derived from *Aspergillus nidulans*, alanine at position 436, lysine at position 437, and methionine at position 438 in the case of the fructosyl peptide oxidase derived from *Emericella nidulans*, alanine at position 439, lysine at position 440, and leucine at position 441 in the case of the fructosyl amino acid oxidase derived from *Ulocladium* sp., and alanine at position 435, lysine at position 436, and leucine at position 437 in the case of the fructosyl amino acid oxidase derived from *Penicillium janthinelum*.

In the present description, a deletion of the amino acid residues from the carboxyl terminus in an amadoriase is also referred to as a "deletion that improves heat stability of an amadoriase." According to an embodiment, the amadoriase of the present invention can further comprise a deletion that improves heat stability, in addition to a mutation that alters substrate specificity and a mutation that improves surfactant resistance.

(Production of Amadoriase)

In order to produce the amadoriase obtained as described above using a strain having the ability to produce such amadoriase, the strain may be cultured by a conventional solid culture method, although liquid culture is preferable.

Thus, the present invention provides a method for producing an amadoriase comprising a step of culturing a strain capable of producing an amadoriase under conditions where the amadoriase protein can be expressed and a step of isolating an amadoriase from a culture product or culture solution. In such method, a host cell transformed with a vector comprising a gene encoding the amadoriase of the present invention can be used. The phrase "under conditions where the amadoriase protein can be expressed" means conditions where an amadoriase gene is transcribed, translated, and a polypeptide encoded by such gene is produced.

Examples of media to culture the aforementioned strains include media prepared by adding one or more inorganic salts, such as sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

Further, a substrate with which the amadoriase can react or a compound similar thereto, such as a glycated protein, including a glycated amino acid, a glycated peptide, a degradation product of glycated protein, glycated hemoglobin, or glycated albumin, may be added to the media, so as to increase the amount of the target enzyme to be produced.

It is appropriate to adjust the initial pH of the media to 7 to 9. Culture is preferably performed at 20° C. to 42° C. and more preferably at about 25° C. to 37° C. for 4 to 24 hours, and further preferably at about 25° C. to 37° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and nucleic acid is removed with the aid of streptomycin sulfate, protamine sulfate, or manganese sulfate, according to need. Ammonium sulfate, alcohol, or acetone is added thereto, so as to fractionate the solution, and sediments are then collected to obtain the crude enzymes of the amadoriases.

The purified amadoriase enzyme preparation can be obtained from the crude enzyme of the aforementioned amadoriase by a method appropriately selected from: gel filtration methods using Sephadex, Superdex, or Ultrogel; adsorption-elution methods using ion exchange carriers, hydrophobic carriers, or hydroxyapatite; electrophoretic methods using polyacrylamide gels, etc.; sedimentation methods such as sucrose density-gradient centrifugation; affinity chromatographic methods; and fractionation methods using a molecular sieve membrane, a hollow-fiber membrane, etc. Alternatively, the aforementioned methods can adequately be performed in combination. The amadoriase of interest can thus be obtained.

(Reactivity of the Amadoriase of the Present Invention on HbA1c)

The amadoriase obtained by the means described above can act directly on HbA1c as a result of mutation in the amino acid sequence caused by genetic modification or other means.

Further, the amadoriase of the present invention may have improved reactivity with αF6P compared with an amadoriase prior to modification. Specifically, the ratio of "reactivity with αF6P" relative to "reactivity with αFVH" designated to be "1" may be increased, compared with such ratio before modification.

For example, αF6P/αFVH of the amadoriase of the present invention, indicating the ratio of reactivity with αF6P relative to reactivity with αFVH designated to be 1, may be preferably 10% or higher, more preferably 20% or higher, still more preferably 30% or higher, and further preferably 40% or higher, compared with that prior to modification.

Also, αF6P/αFV of the amadoriase of the present invention, indicating the ratio of reactivity with αF6P relative to reactivity with αFV designated to be 1, is preferably 10% or higher, more preferably 20% or higher, still more preferably 30% or higher, and further preferably 40% or higher, compared with that prior to modification. The "reactivity with αFV" may also be referred to as "αFV oxidation activity."

An example of the amadoriase of the present invention acting directly on HbA1c is an amadoriase produced by a strain of *E. coli* JM109 (pKK223-3-CFP-T7-H35). Since the amadoriase of the present invention acts directly on HbA1c, such amadoriase is highly useful industrially since it enables realization of an enzymatic measurement system in which HbA1c in a sample is directly assayed, without the need for treating HbA1c with a protease or the like.

(Method of Measuring Activity of Amadoriase)

The activity of an amadoriase can be measured by various methods. An example of the method of measuring the activity of an amadoriase as used herein is described below.

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

For measurement of the activity of the amadoriase of the present invention, αFV, αFVH, or αF6P is used as a substrate, unless otherwise specified. Regarding an enzyme titer, the amount of enzyme used to generate 1 μmol of hydrogen peroxide per minute is defined as 1 U, when measurement is carried out using αFV, αFVH, or αF6P as a substrate.

Specific activity (U/mg) is an enzyme titer (U) per mg of an enzyme. When for example the specific activity of a particular enzyme on αF6P is 0.1 U/mg or greater, the amount of an enzyme may be increased 10-fold, to achieve an enzyme titer that is the same as the enzyme titer of an enzyme having specific activity of 1 U/mg.

When the amadoriase "has reactivity with αF6P" herein, specific activity thereof on αF6P (U/mg) may be 0.1 U/mg or higher, 0.2 U/mg or higher, 0.3 U/mg or higher, 0.4 U/mg or higher, 0.5 U/mg or higher, 0.6 U/mg or higher, 0.7 U/mg or higher, 0.8 U/mg or higher, or 0.9 U/mg or higher, such as 1 U/mg, unless otherwise specified. A glycated peptide, such as αFV or αFVH, synthesized and purified with reference to the method of, for example, Sakaue et al. can be used (JP 2001-95598 A). Upon treatment of glycated hemoglobin (HbA1c) with endoproteinase Glu-C, for example, α-glycated hexapeptide derived from the β chain subunit of glycated hemoglobin (HbA1c) (i.e., fructosyl Val-His-Leu-Thr-Pro-Glu) is released (Clin. Chem., 43, 1994-1951, 1997), and it can be used as an αF6P substrate. A substance that is identical with such α-glycated hexapeptide; that is, a synthetic substrate, fructosyl Val-His-Leu-Thr-Pro-Glu (manufactured by Peptide Institute, Inc.), can also be used.

A: Preparation of Reagents (Preparation Example of Reagent Used for Measuring Activity of Amadoriase on αF6P, αFVH, or αFV)

(Reagent 1) 0.1 M Phosphate Buffer (pH 6.5) Containing 5 U/Ml Peroxidase and 0.49 mM 4-aminoantipyrine Peroxidase (5.0 kU, manufactured by Kikkoman Corporation) and 100 mg of 4-aminoantipyrine (manufactured by Wako Pure Chemical Industries, Ltd.) are dissolved in a 0.1 M potassium phosphate buffer (pH 6.5), and the volume of the solution is fixed to 1.000 ml.

(Reagent 2) 15 mM TOOS Solution 500 mg of TOOS (N-ethyl-N-(2-hydroxy-3-sulfopropyl)-m-toluidine sodium, manufactured by Dojindo Laboratories) is dissolved in ion-exchange water, and the volume of the solution is fixed to 100 ml.

(Reagent 3) Substrate Solution (30 mM; Final Concentration: 1 mM)

αF6P (257.1 mg, manufactured by Peptide Institute, Inc.), αFVH (124.9 mg, manufactured by Kikkoman Corporation), or αFV (83.8 mg, manufactured by Kikkoman Corporation) is dissolved in ion-exchange water, and the volume of the solution is fixed to 10 ml.

B: Method for Measuring Activity (Example of Method for Measurement of Activity of Amadoriase on αF6P, αFVH, or αFV)

Reagent 1 (2.7 ml), 100 µl of Reagent 2, and 100 µl of an enzyme solution are mixed, and the mixture is preliminarily heated at 37° C. for 5 minutes. Subsequently, 100 µl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute (ΔAs) at 555 nm. A control solution is prepared in the manner as described above, except that 100 µl of ion-exchange water is added instead of 100 µl of Reagent 3, and the change in absorbance per minute (ΔA0) at 555 nm thereof is determined. The number of micromoles of hydrogen peroxide generated per minute at 37° C. is calculated using the equation shown below in terms of the unit of activity (U) in the enzyme solution.

$$\text{Activity (U/ml)} = \{(\Delta As - \Delta A0) \times 3.0 \times df\}/(39.2 \times 0.5 \times 0.1)$$

ΔAs: the change in absorbance of the reaction solution per minute

ΔA0: the change in absorbance of the control solution per minute 39.2: millimole absorbance index of quinoneimine dye generated by the reaction ($mM^{-1} \cdot cm^{-1}$)

0.5: number of moles of quinoneimine dye generated by 1 mol of hydrogen peroxide df: dilution factor (Example of Method of Quantification of Heat-Treated HbA1c)

Reagents for measurement of HbA1c described below are prepared.

Sample: HbA1c Solution

The certified reference material for measurement of HbA1c, JCCRM-423 (Reference Material Institute for Clinical Chemistry Standards)

Total hemoglobin concentration: 133 g/l

Three HbA1c concentration levels (NGSP levels: about 5.6%, about 7.7%, and about 10.5%)

Reagent A1: Sample Pre-Treatment Solution 5.0% n-dodecyl-β-D-maltoside (Dojindo Laboratories)

Reagent A2: Sample Pre-Treatment Solution 5.0% n-tetradecyl-β-D-maltoside (Sigma-Aldrich Co. LLC.)

Reagent B: Leucodye, Peroxidase Solution 150 mM potassium phosphate buffer (pH 6.5)

0.30 mM N-(carboxymethylaminocarbonyl)-4,4'-bis(dimethylamino)diphenylamine sodium (DA-64, Wako Pure Chemical Industries, Ltd.)

15 U/ml peroxidase (Kikkoman Corporation)

Reagent C1: Amadoriase Solution 120 mM potassium phosphate buffer (pH 6.5)

120 U/ml of the amadoriase of the present invention (e.g., CFP-T7-H35)

(Example of Method of Measurement of Activity of Amadoriase on HbA1c)

A sample diluted 30 fold with Reagent A1 or Reagent A2 (also referred to as a sample diluent herein) is incubated at high temperature for a given period of time, for example, at 98° C. for 2 minutes, 25 µl of the sample diluent is added to 50 µl of Reagent B, the resultant is incubated at 37° C. for 5 minutes, 25 µl of Reagent C1 is added thereto, and quantification of hydrogen peroxide generated upon oxidation of the HbA1c β-chain amino terminus is allowed to proceed at 37° C. for 5 minutes. When hydrogen peroxide is generated in the solution, a leucodye develops color by the action of peroxidase, and the absorbance of light at 751 nm increases. On the basis of the results attained depending on the HbA1c concentration in the sample, the HbA1c concentration in the sample (i.e., the NGSP level) and a difference in the absorbance of light at 751 nm before and after hydrogen peroxide quantification (ΔA) can be plotted on a chart.

ΔA is calculated in accordance with the equation below.

$$\Delta A = (\text{absorbance 5 minutes after the addition of Reagent C1}) - (\text{absorbance immediately before the addition of Reagent C1} \times 0.75)$$

According to the example above, the volume of the reaction solution is increased 1.33 fold with the addition of Reagent C1. Accordingly, the value attained by multiplying the absorbance immediately before the addition of Reagent C1 by 0.75 is regarded as the absorbance immediately after the addition of Reagent C1.

(Example of Method of Quantification of Acid-Treated HbA1c)

Reagents for measurement of HbA1c having the compositions described below are prepared and HbA1c is measured with the use of Bio Majesty JCA-BM1650 (JEOL Ltd.).

Sample: HbA1c Solution
The certified reference material for measurement of HbA1c, JCCRM-423 (Reference Material Institute for Clinical Chemistry Standards)
Total hemoglobin concentration: 133 g/l
Three HbA1c concentration levels (NGSP levels: about 5.6%, about 7.7%, and about 10.5%)
Reagent D: Sample Pre-Treatment Solution
  8.3% n-dodecyl-β-D-maltoside (Dojindo Laboratories) or polyoxyethylene (20) cetyl ether (Brij58, Wako Pure Chemical Industries, Ltd.)
  0.1 M hydrochloric acid
Reagent E: Leucodye Solution
  30 mM Tris-potassium phosphate buffer (pH 9.0)
  290 mM potassium phosphate buffer (pH 6.5)
  0.16 mM N-(carboxymethylaminocarbonyl)-4,4'-bis(dimethylamino)diphenylamine sodium (DA-64, Wako Pure Chemical Industries, Ltd.)
Reagent F1: Peroxidase, Amadoriase Solution
  100 mM potassium phosphate buffer (pH 6.5)
  40 U/ml peroxidase (Kikkoman Corporation)
  180 U/ml of the amadoriase of the present invention (e.g., CFP-T7-H35)

A sample diluted 30 fold with Reagent D (25 µl) is added to 125 µl of Reagent L, the mixture is incubated at 37° C. for 5 minutes, 50 µl of Reagent F1 is added thereto, and quantification of hydrogen peroxide generated upon oxidation of the HbA1c β-chain amino terminus is allowed to proceed at 37° C. for 5 minutes.

For example, ΔA can be calculated in accordance with the equation below.

$$\Delta A = \text{(absorbance 5 minutes after the addition of Reagent } F1\text{)} - \text{(absorbance immediately before the addition of Reagent } F1 \times 0.75\text{)}$$

(Example of Method of Quantification of Surfactant-Treated HbA1c)

Reagents for measurement of HbA1c having the compositions described below are prepared and HbA1c is measured with the use of Bio Majesty JCA-BM1650 (JEOL Ltd.).

Sample: HbA1c Solution
The certified reference material for measurement of HbA1c, JCCRM-423 (Reference Material Institute for Clinical Chemistry Standards)
Total hemoglobin concentration: 133 g/l
Three HbA1c concentration levels (NGSP levels: about 5.6%, about 7.7%, and about 10.5%)
Reagent G1: Sample Pre-Treatment Solution
  0.80% tetradecyltrimethylammonium bromide (Tokyo Chemical Industry Co., Ltd.)
Reagent G2: Sample Pre-Treatment Solution
  0.70% hexadecyltrimethylammonium bromide (Tokyo Chemical Industry Co., Ltd.)
Reagent H1: Leucodye Solution
  120 mM MOPS-NaOH buffer (pH 6.5)
  1.6% n-dodecyl-β-D-maltoside (Dojindo Laboratories)
  0.16 mM N-(carboxymethylaminocarbonyl)-4,4'-bis(dimethylamino)diphenylamine sodium (DA-64, Wako Pure Chemical Industries, Ltd.)
Reagent H2: Leucodye Solution
  120 mM PIPES-NaOH buffer (pH 6.5)
  1.6% n-dodecyl-β-D-maltoside (Dojindo Laboratories)
  0.16 mM N-(carboxymethylaminocarbonyl)-4,4'-bis(dimethylamino)diphenylamine sodium (DA-64, Wako Pure Chemical Industries, Ltd.)
Reagent I1: Peroxidase, Amadoriase Solution
  100 mM MOPS-NaOH buffer (pH 6.5)
  40 U/ml peroxidase (Kikkoman Corporation)
  160 U/ml of the amadoriase of the present invention (e.g., DFP-DH2)
Reagent I2: Peroxidase, Amadoriase Solution
  100 mM PIPES-NaOH buffer (pH 6.5)
  40 U/ml peroxidase (Kikkoman Corporation)
  160 U/ml the amadoriase of the present invention (e.g., DFP-DH2)

A sample diluted 25 fold with Reagent G1 (25 µl) is added to 125 µl of Reagent H1, the mixture is incubated at 37° C. for 5 minutes, 50 µl of Reagent I1 is added thereto, and quantification of hydrogen peroxide generated upon oxidation of the HbA1c β-chain amino terminus is allowed to proceed at 37° C. for 5 minutes. When the sample is diluted 25 fold with Reagent G2, 25 µl of the diluted sample is added to 125 µl of Reagent H2, the mixture is incubated at 37° C. for 5 minutes, 50 µl of Reagent I2 is added thereto, and quantification of hydrogen peroxide generated upon oxidation of the HbA1c β-chain amino terminus is allowed to proceed at 37° C. for 5 minutes.

For example, ΔA can be calculated in accordance with the equation below.

$$\Delta A = \text{(absorbance 5 minutes after the addition of Reagent } I1 \text{ or } I2\text{)} - \text{(absorbance immediately before the addition of Reagent } I1 \text{ or } I2 \times 0.75\text{)}$$

(Measurement of HbA1c)

HbA1c oxidase (amadoriase) is allowed to react with the sample containing HbA1c. The duration of the reaction may be, for example, 5 seconds or longer, 10 seconds or longer, or 20 seconds or longer, shorter than 180 minutes or shorter than 150 minutes. More specifically, the duration may be, for example, 0.5 to 120 minutes, preferably 0.5 to 60 and more preferably 1 to 30 minutes. If the duration of the reaction is too short, HbA1c in the sample cannot be sufficiently measured and measurement cannot be performed satisfactorily. If the duration of the reaction is too long, in contrast, the duration of measurement is prolonged, and measurement efficiency becomes poor. In addition thereto, the sample and the reagent are exposed to the measurement conditions for a long period of time, and this disadvantageously causes problems such as degradation or denaturation of the substrate in the sample or components of the reagent. In microassay systems, in particular, the sample may be dehydrated with the elapse of time, which leads to a decrease in the volume of the sample and a change in concentrations which may cause errors. Allowing HbA1c oxidase to react with the sample for preferably 0.5 to 60 minutes, more preferably 1 to 30 minutes, and further preferably 1 to 10 minutes, enables rapid and good measurement of HbA1c. While the reaction temperature may vary depending on the optimal temperature for the enzyme being used, it is, for example, from 20° C. to 45° C., and a temperature that is generally employed for an enzymatic reaction can adequately be selected.

The preferable amount of an amadoriase to be used in the present invention may vary depending on the amount of the substrate contained in the sample solution. For example, the amadoriase may be added, so as to adjust the final concentration of the amadoriase to 0.1 to 50 U/ml, and preferably 0.2 to 10 U/ml in the solution. The pH level is preferably adjusted to an adequate level for the reaction with the use of a buffer by taking the optimal pH level for the amadoriase into consideration, although the pH level is not particularly limited, provided that the amadoriase is capable of reaction. For example, the pH level is preferably 3 to 11, and particularly preferably 5 to 9, such as 6 to 8.

In the method of measurement according to the present invention, it is preferable to use various types of buffers, according to need, in order to adjust and/or maintain the pH level for the purpose of stabilization of an enzyme or a reagent or improvement in reactivity. Examples of buffers that can be used include N-[tris(hydroxymethyl)methyl] glycine, phosphate, acetate, carbonate, tris(hydroxymethyl)-aminomethane, borate, citrate, dimethyl glutamate, Tricine, HEPES, MES, Bis-Tris, ADA, PIPES, ACES, MOPSO, BES, MOPS, TES, DIPSO, TAPSO, POPSO, HEPPSO, EPPS, Tricine, Bieine, TAPS, phthalate, and tartrate. In addition, solubilizers, stabilizers, reaction-improving agents, or, as HbA1c denaturation agents, surfactants (e.g., n-octyl-β-D-glucoside, n-octyl-β-D-thioglucoside, n-dodecyl-β-D-maltoside, n-tetradecyl-β-D-maltoside, n-octyl-β-D-maltoside, 1-dodecylpyridinium salt, hexadecyltrimethyl ammonium salt, tetradecyltrimethyl ammonium salt, dodecyltrimethyl ammonium salt, triton X-100, Brij 35, Brij 58, Tween 80, cholate, n-heptyl-β-D-thioglucoside, 3-oxatridecyl-α-D-mannoside, n-nonyl-β-D-thiomaltoside, n-decyl-β-D-maltoside, n-undecyl-β-D-maltoside, trehalose C8, trehalose C10, trehalose C12, trehalose C14, trehalose C16, BIGCHAP, deoxy-BIGCHAP, MEGA-8, MEGA-9, MEGA-10, hexadecylpyridinium salt, octadecyltrimethyl ammonium salt, decyltrimethyl ammonium salt, nonyltrimethyl ammonium salt, octyltrimethyl ammonium salt, hexyltrimethyl ammonium salt, or sodium dodecyl sulfate), reducing agents (e.g., dithiothreitol, mercaptoethanol, or L-cysteine), bovine serum albumin, or saccharides (e.g., glycerine, lactose, or sucrose), may be adequately added, according to need.

The surfactant used in the present invention is not particularly limited, provided that the method of measuring HbA1c of the present invention can be carried out in the presence of the surfactant, and examples of surfactants include a nonionic surfactant and an ionic surfactant, such as a cationic surfactant, an anionic surfactant, and an amphoteric surfactant. The term "surfactant" used herein refers to one or more surfactants, unless otherwise specified.

Examples of the nonionic surfactant include polyoxyethylene alkyl ether, sorbitan fatty acid ester, alkyl polyglucoside, fatty acid diethanol amide, and alkyl monoglyceryl ether.

Examples of the cationic surfactant include alkyltrimethylammonium salt, dialkyldimethylammonium salt, alkylbenzyldimethyl ammonium salt, pyridinium salt, such as alkylpyridinium salt, phosphonium salt, such as alkylphosphonium salt, imidazolium salt, such as alkylimidazolium salt, and isoquinolinium salt, such as alkylisoquinolinium salt.

Examples of the cationic surfactant of the present invention include quaternary ammonium salt (I), pyridinium salt (II), and phosphonium salt (III) represented by the following general formulae:

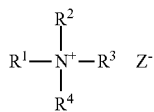

wherein $R^1$ to $R^4$, which may be the same or different, each represent a substituted or unsubstituted $C_1$ to $C_{20}$ alkyl, alkenyl, aryl, or benzyl; and $Z^-$ represents a monovalent anion;

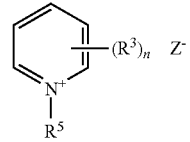

wherein $R^5$ represents substituted or unsubstituted $C_1$ to $C_{20}$ alkyl; each $R^a$, which may be the same or different, represents a hydrogen atom or a substituted or unsubstituted $C_1$ to $C_{20}$ alkyl, alkenyl, aryl or benzyl; n represents an integer of 1 to 5; and $Z^-$ represents a monovalent anion; and

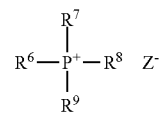

wherein, $R^6$ to $R^9$, which may be the same or different, each represent substituted or unsubstituted $C_1$ to $C_{20}$ alkyl, alkenyl, aryl or benzyl; and $Z^-$ represents a monovalent anion.

Examples of the quaternary ammonium salt include octyltrimethylammonium chloride (OTAC), octyltrimethylammonium bromide (OTAB), decyltrimethylammonium chloride, decyltrimethylammonium bromide (DTAB), dodecyltrimethylammonium chloride, dodecyltrimethylammonium bromide, tetradecyltrimethyl ammonium chloride (TTAC), tetradecyltrimethylammonium bromide (TTAB), hexadecyltrimethylammonium chloride (CTAC), hexadecyltrimethylammonium bromide, octadecyltrimethyl ammonium chloride, octadecyltrimethylammonium bromide (STAB), eicosyltrimethylammonium chloride, eicosyltrimethylammonium bromide, benzyldodecyldimethylammonium chloride, benzyldodecyldimethylammonium bromide (BDDAB), benzyltetradecyldimethylammonium chloride (BDTAC), benzyltetradecyldimethyl ammonium bromide, benzylcetyldimethyl ammonium chloride (BCDAC), benzylcetyldimethylammonium bromide, dioctyldimethylammonium chloride, and dioctyldimethylammonium bromide.

Examples of the pyridinium salt include 1-decylpyridinium chloride, 1-decylpyridinium bromide, 1-dodecylpyridinium chloride (1-DPC), 1-dodecylpyridinium bromide, 1-tetradecylpyridinium chloride, 1-tetradecylpyridinium bromide, 1-hexadecylpyridinium chloride, (1-CPC) and bromide (1-CPB), N-cetyl-2-methylpyridinium chloride and bromide, N-cetyl-3-methylpyridinium chloride and bromide, N-cetyl-4-methylpyridinium chloride (4Me-1-CPC) and bromide, 1-octadecylpyridinium chloride and bromide, 1-eicosylpyridinium chloride and bromide.

Examples of the phosphonium salt include tetraethylphosphonium chloride and bromide, tributylmethylphosphonium chloride and bromide and iodide, tetrabutylphosphonium chloride and bromide, tetra-n-octylphosphonium chloride and bromide, tributyldodecylphosphonium chloride and bromide, tributylhexadecylphosphonium chloride and bromide (TBCPB), methyltriphenylphosphonium chloride and bromide and iodide, tetraphenylphosphonium chloride and bromide.

Anion Z⁻ to be paired with a cationic surfactant can, for example, be Cl⁻, Br⁻ or I⁻.

Examples of the anionic surfactant include linear alkylbenzene sulfonate, alkyl sulfate, alpha-olefin sulfonate, polyoxyethylene alkyl ether sulfate, α-sulfo fatty acid ester salt, and alkali metal salt of natural fatty acid. An example of such surfactant is sodium dodecyl sulfate (SDS).

Examples of the amphoteric surfactant include alkyl dimethyl amine oxide and alkylcarboxybetaine.

The present invention provides a method for measurement of HbA1c by measuring the amount of substances produced or consumed by the reaction of an amadoriase. An example of a product that can be easily measured and is preferable as a target of measurement is hydrogen peroxide. Hydrogen peroxide generated by the action of the amadoriase may be detected with the use of a color substrate or the like. Examples of color substrates used in the present invention include, in addition to 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), and DA-64 (N-(carboxymethylaminocarbonyl)-4,4'-bis(dimethylamino)-diphenylamine). ADOS, ALOS, and TOOS develop color when condensed with 4-aminoantipyrine. DA-64 and DA-67 are each able to develop color alone without 4-aminoantipyrine. In either case, color development is catalyzed by peroxidase. In general, it is preferable that measurement of hydrogen peroxide be carried out simultaneously with the step of generating hydrogen peroxide, and it is preferable that measurement be allowed to proceed simultaneously with the reaction with an amadoriase. An example of the substance consumed by the reaction to be measured is dissolved oxygen, and the amount of dissolved oxygen in the reaction solution can be measured with the use of a dissolved oxygen meter or the like.

The present invention provides reagents for measurement of HbA1c including the measurement reagent amadoriase and hydrogen peroxide described above and further supplemented with a buffer or the like, according to need. Such reagent can be adequately supplemented with various known components, such as a surfactant, a salt, a buffer, a pH adjuster, or a preservative. The reagent for measurement of HbA1c according to the present invention may be prepared to separately contain various reagents in different containers. For example, it can be provided in the form of a liquid product, a frozen product of a liquid product, or a freeze-dried product. Alternatively, such reagents for measurement may be used in a dried or dissolved state, or a carrier on a thin film, such as paper, may be impregnated with such reagent and used. Enzymes used for the reagent for measurement can be solidified and repeatedly used in accordance with a conventional technique. According to one embodiment, the reagent for measurement of HbA1c of the present invention does not contain a protease or the like for cleaving α-fructosyl peptide from glycated protein.

The optimal specification or conditions for the use of the reagent for measurement of HbA1c according to the present invention may be selected in accordance with the components thereof or other properties. For example, the reagent, can be prepared to be used for measurement conducted at 20° C. to 45° C. The time necessary for measurement can be adequately determined in accordance with various measurement conditions. For example, it is 0.5 to 60 minutes, preferably 0.5 to 30 minutes, and further preferably 1 to 10 minutes. For example, an extent of the reagent colored (i.e., a change in the absorbance) may be measured using a spectrophotometer, and the measured absorbance may be compared with the reference absorbance. Thus, the glycated peptide or glycated protein contained in the sample can be measured. Measurement can be carried out with the use of a common automated analyzer.

(Quantification of HbA1c)

The method for measurement of HbA1c according to the present invention may be a qualitative or quantitative method. According to the quantitative method for measurement of HbA1c of the present invention, concentration of HbA1c in the sample is determined. Specifically, an aspect of the present invention provides a method for quantification of HbA1c in a sample involving the use of an amadoriase. This quantitative method comprises a step of bringing a HbA1c-containing sample into contact with the amadoriase of the present invention and a step of measuring the amount of substances produced or consumed by the reaction of the amadoriase with HbA1c. Here, HbA1c may be in a naturally occurring or denatured state. The "contact" that is carried out in accordance with the method of quantification can be any form of physical contact between the amadoriase of the present invention and a sample, so that the amadoriase can catalyze the oxidation reaction of HbA1c. In addition to the case in which a free enzyme is mixed with HbA1c in a solution, for example, a liquid sample containing HbA1c can be added or added dropwise to the amadoriase of the present invention immobilized to a solid support.

A sample used for the method for measurement of HbA1c of the present invention can be any type of biological sample that can contain glycated hemoglobin, such as a sample derived from blood, body fluid, or lymph. A sample can adequately be a processed sample.

Denatured HbA1c may be subjected to the reaction with an amadoriase, in order to improve the reaction efficiency between the amadoriase and HbA1c. Denatured HbA1c can be obtained by mixing HbA1c with an adequate surfactant, via heat treatment, with the addition of a surfactant in combination with heat treatment, or via denaturing treatment with the aid of an acid or alkali condition. When denaturation is to be achieved by the addition of a surfactant and heat treatment, either treatment can be carried out at first. Heat treatment may be carried out at a temperature and for a period of lime sufficient to denature all HbA1c or a portion of the same. Treatment can be carried out at, for example, 60° C. or higher, 70° C. or higher, 80° C. or higher, or 90° C. or higher, such as at 98° C. While the duration of treatment varies depending on temperature, it can be, for example, 10 seconds or longer, 20 or longer, 30 seconds or longer, 1 minute or longer, or 2 minutes or longer. Any of the surfactants mentioned above can be added at adequate concentrations.

When the amount of the amadoriase variant used and the duration of the reaction are maintained at constant levels and the amount of added HbA1c is altered, by investigating the range of HbA1c concentration in which the absorbance of the detected luminescent substrate proportionally decreases as the amount of added HbA1c is decreased, it is possible to determine the lowest HbA1c concentration that can be detected with the use of the amadoriase. Such concentration is also referred to as the "detection limit concentration" herein. According to the method for quantification of HbA1c of the present invention, the amount of the enzyme and the duration of the reaction are preferably determined so as to adjust the detection limit of HbA1c to a level lower than the HbA1c concentration in the sample or the glycated hemoglobin level in the blood.

According to the quantitative method of measurement of the present invention, a calibration curve can be prepared in advance by performing regression analysis such as the method of least squares based on the measured absorbance of the control sample containing HbA1c at a known concentration. The measured value of the sample containing HbA1c at an unknown concentration may be plotted on the calibration curve prepared as such, to quantify the HbA1c concentration in the sample.

The present inventors have demonstrated that HbA1c in the sample can be satisfactorily quantified using an amadoriase variant derived from *Coniochaeta*, such as CFP-T7-H35. This is a surprising discovery. See FIGS. 4-1 and 4-2. Further, CFP-T7-H35 also has activity on αF6P. Based on such findings, a person skilled in the art will appreciate that other amadoriases exhibiting satisfactory activity on a α-fructosyl oligopeptide, such as αF6P, also may possibly act directly on HbA1c and may possibly be used for quantitative analysis of HbA1c. For example, it is highly plausible that an amadoriase having high specific activity on α-fructosyl oligopeptide, such as αF6P, will also act directly on HbA1c and such amadoriase may be used for quantification of HbA1c. A person skilled in the art can adequately determine the conditions for such quantification, such as the amount (concentration) of an enzyme and the duration of the reaction.

(Screening Method)

According to an embodiment, whether or not an amadoriase of interest acts directly on HbA1c can be determined by the method described above (i.e., the method for measurement of HbA1c). Examples of candidate amadoriases include various naturally occurring amadoriases and amadoriases modified therefrom, such as amadoriases having αFV activity, amadoriases having αFVH activity, amadoriases having αF6P activity, amadoriases exhibiting activity on α-fructosyl peptide, and amadoriases modified therefrom (e.g., those described in the (Modified amadoriase) section above). Screening may be carried out rapidly with high-throughput on numerous candidates by using a 96-well plate or the like. Whether or not a candidate amadoriase acts directly on HbA1c can be screened. Alternatively, candidate amadoriases may be first subjected to primary selection, so as to determine whether or not they have αFV activity, αFVH activity, αF6P activity, or other activity, and those determined to have such activity may then be subjected to secondary selection, so as to determine whether or not they act directly on HbA1c. A crude enzyme extract prepared from a biological sample or a product purified therefrom can be subjected to screening. A gene of an amadoriase exhibiting activity on α-fructosyl peptide may be obtained in accordance with a conventional technique, an enzyme may be produced via genetic engineering, and the resulting enzyme may be used for selection. According to conventional techniques, an amadoriase exhibiting activity on α-fructosyl peptide can be purified, the amino acid sequence thereof can be determined, and primers for PCR can be designed based on the sequence information. Thus, a gene of interest can be obtained. Alternatively, a gene of interest can be obtained from the genomic library or cDNA library of an organism whose PCR primers have already been designed based on the sequence information of a known amadoriase. However, methods for obtaining a gene of interest are not limited to these (also see the (Obtaining a gene encoding an amadoriase) section above). An adequate mutation may be introduced into an obtained amadoriase gene using conventional genetic engineering techniques, and whether or not the resulting variant acts directly on HbA1c can be tested.

Further, an adequate mutation may be introduced into an obtained amadoriase gene using genetic engineering techniques, so as to prepare an amadoriase variant exhibiting activity on long-chain α-fructosyl peptide, such as αF6P, and whether or not the resulting variant has specific activity of 0.1 U/mg ore more on, for example, αF6P, and whether or not it acts directly on HbA1c, can be tested. Such variant may be prepared via, for example, (a) substitution of an amino acid at a position corresponding to position 62 with alanine, asparagine, or aspartic acid, (b) substitution of an amino acid at a position corresponding to position 63 with histidine or alanine, (c) substitution of an amino acid at a position corresponding to position 102 with lysine, (d) substitution of an amino acid at a position corresponding to position 106 with alanine, lysine, or arginine, (e) substitution of an amino acid at a position corresponding to position 110 with leucine or tyrosine, (1) substitution of an amino acid at a position corresponding to position 113 with lysine or arginine, (g) substitution of an amino acid at a position corresponding to position 355 with serine, and/or (h) substitution of an amino acid at a position corresponding to position 419 lysine, (i) substitution of an amino acid at a position corresponding to position 68 with asparagine, and/or (j) substitution of an amino acid at a position corresponding to position 356 threonine in the amino acid sequence as shown in SEQ ID NO: 1. However, it should be noted that a mutation to be introduced is not limited to these, and techniques involving introduction of random mutations can also be employed. Introduction of a mutation and examination of activity can be repeatedly performed a plurality of times, and a variant having higher activity on α-fructosyl peptide or activity on HbA1c can be obtained by techniques involving introduction of random mutations. Also see the (Mutation of an amadoriase gene) section above.

The mutation that improves surfactant resistance described above may be introduced into an amadoriase to be used and/or the deletion that improves heat stability may be performed. So long as activity on HbA1c is retained, mutation(s) that alters other properties of the enzyme can also be introduced.

In addition to the reagents for measurement of HbA1c described above, the kit for measurement of HbA1c of the present invention may include other known stabilizer(s), a system that deletes contaminants, and the like. Techniques that are employed for various conventional reagents or kits for the purpose of measuring HbA1c by enzymatic methods using a protease or the like may be adequately modified, and such modified technique(s) can be employed for the kit for measurement of HbA1c comprising the amadoriase of the present invention. However, the kit for measurement of HbA1c of the present invention does not require such protease or the like. According to an embodiment, specifically, the kit for measurement of HbA1c of the present invention does not comprise a protease or the like for cleaving α-fructosyl peptide from HbA1c.

Hereafter, the present invention is described in greater detail with reference to the examples, although the technical scope of the present invention is not limited to these examples.

Example 1

(1) Preparation of DNA of Recombinant Plasmid pKK223-3-CFP-T7

A strain of *E. coli* JM109 (pKK223-3-CFP-T7) having the recombinant plasmid of an amadoriase gene derived from the genus *Coniochaeta* (SEQ ID NO: 2) (WO 2007/125779) was inoculated into 3 ml of LB-amp media (1% (w/v) bactotrypton, 0.5% (w/v) peptone, 0.5% (w/v) NaCl, and 50 μg/ml ampicillin) and shake culture was conducted at 37° C. for 16 to obtain a culture product.

The culture product was centrifuged at 10,000×g for 1 minute to collect strains. A recombinant plasmid pKK223-3-CFP-T7 was extracted and purified therefrom using the GenElute Plasmid Mini-Prep Kit (manufactured by Sigma-Aldrich Corporation), and 2.5 μl of DNA of the recombinant plasmid pKK223-3-CFP-T7 was obtained.

(2) Site-Directed Modification Operation of DNA of Recombinant Plasmid pKK223-3-CFP-T7

PCR was carried out under conditions described below using DNA of the recombinant plasmid pKK223-3-CFP-T7 as a template, synthetic oligonucleotides of SEQ ID NOs: 3 and 4, and KOD-Plus- (Toyobo Co., Ltd.).

Specifically, 5 μl of 10×KOD-Plus-buffer, 5 μl of a dNTPs mixture in which each dNTP was adjusted at 2 mM, 2 μl of a 25 mM $MgSO_4$ solution, 50 ng of DNA of pKK223-3-CFP-T7 as a template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was electrophoresed on 1.0% agarose gel, and specific amplification of about 6.000 bp DNA was confirmed. The DNAs obtained in such a manner were treated with a restriction enzyme DpnI (manufactured by New England Biolabs), the remaining template DNAs were cleaved, strains of *E. coli* JM109 were transformed, and the transformants were then spread on LB-amp agar media. The grown colonies were inoculated into LB-amp media and shake-cultured therein, and plasmid DNAs were isolated in the same manner as in (1) above. The nucleotide sequences of DNAs encoding amadoriases in the plasmids were determined using a multi-capillary DNA analysis system (Applied Biosystems 3130xl Genetic Analyzer; manufactured by Life Technologies). Thus, the recombinant plasmid encoding the modified amadoriase resulting from substitution of arginine at position 62 with alanine in the amino acid sequence as shown in SEQ ID NO: 1 obtained (pKK223-3-CFP-T7-H1).

(3) Production of Various Types of Modified Amadoriases

Strains of *E. coli* JM109 (pKK223-3-CFP-T7-H1) carrying pKK223-3-CFP-T7-H1 were cultured in 3 ml of LB-amp media supplemented with 0.1 mM IPTG (final concentration) at 25° C. for 16 hours. The resulting cultured strains were washed with 10 mM potassium phosphate buffer (pH 7.0), the washed strains were suspended in the same buffer, the resulting suspension was ultrasonically disintegrated, and the resultant was centrifuged at 20,000×g for 10 minutes to prepare 0.6 ml of a crude enzyme solution containing the modified amadoriase (CFP-T7-H1).

(4) Measurement of αF6P/αFVH and αF6P/αFV

The enzyme solution containing CFP-T7-H1 was subjected to measurement of oxidation activity on αFV, αFVH, and αF6P by the method described in the "B: Method of activity measurement" above. For the purpose of comparison, the enzyme solution containing CFP-T7 produced from the *E. coli* JM109 strain (pKK223-3-CFP-T7) was subjected to measurement in the same manner. Table 1 shows the oxidation activity on αFV, αFVH, and αF6P, αF6P/αFVH, and αF6P/αFV of amadoriases, relative to the oxidation activity on αFVH designated to be 100.

TABLE 1

| Amadoriase | Amino acid substitution | αFV oxidation activity | αFVH oxidation activity | αF6P oxidation activity | αF6P/αFVH | αF6P/αFV |
|---|---|---|---|---|---|---|
| CFP-T7 (Comparative Example) | None | 67.1 | 100 | 0 | 0 | 0 |
| CFP-T7-H1 (Amadoriase 1) | R62A | 142 | 100 | 0.0316 | 0.000316 | 0.000222 |

As shown in Table 1, CFP-T7 exhibited αFV oxidation activity and αFVH oxidation activity, although it did not exhibit αF6P oxidation activity. This indicates that CFP-T7 has very high specificity with α-fructosyl dipeptide but it does not react with α-fructosyl hexapeptide.

Variant CFP-T7-H1, on the other hand, exhibited αF6P oxidation activity, in addition αFV oxidation activity and αFVH oxidation activity.

Thus, it was found that, as a result of introduction of amino acid substitution (R62A) into CFP-T7, a new trait; i.e., αF6P oxidation activity, could be conferred to CFP-T7, and reactivity (substrate specificity) with αF6P was improved.

Subsequently, in the same manner as in (2) above, PCR was carried out with the use of DNA of the recombinant plasmid pKK223-3-CFP-T7-H1 as a template, oligonucleotides as shown in SEQ ID NOs: 5 to 8, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with alanine and glutamine at position 110 with leucine, phenylalanine, or tyrosine were obtained (pKK223-3-CFP-T7-H2, pKK223-3-CFP-T7-H3, and pKK223-3-CFP-T7-H4).

Strains of *E. coli* JM109 carrying pKK223-3-CFP-T7-H2, pKK223-3-CFP-T7-H3, or pKK223-3-CFP-T7-H4 were cultured in the manner described in (3) above, and crude enzyme solutions (0.6 ml each) containing various types of modified amadoriases (i.e., CFP-T7-H2, CFP-T7-H3, or CFP-T7-H4) were prepared.

The crude enzyme solutions thus prepared were subjected to measurement of oxidation activity on αFV, αFVH, and αF6P by the method described in the "B: Method of activity measurement" above. For the purpose of comparison, the enzyme solution containing CFP-T7-H1 produced from the *E. coli* JM109 strain (pKK223-3-CFP-T7-H1) was subjected to measurement in the same manner, table 2 shows the oxidation activity on αFV, αFVH, and αF6P, αF6P/αFVH, and αF6P/αFV of amadoriases, relative to the oxidation activity on αFVH designated to be 100.

TABLE 2

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H1 (Amadoriase 1) | R62A | 142 | 100 | 0.0316 | 0.000316 | 0.000222 |
| CFP-T7-H2 (Amadoriase 2) | R62A, Q110L | 137 | 100 | 0.0735 | 0.000735 | 0.000536 |
| CFP-T7-H3 (Amadoriase 3) | R62A, Q110F | 145 | 100 | 0.0298 | 0.000298 | 0.000205 |
| CFP-T7-H4 (Amadoriase 4) | R62A, Q110Y | 107 | 100 | 0.0341 | 0.000341 | 0.000319 |

Specifically, CFP-T7-H2 and CFP-T7-H4 were found to have improved reactivity (substrate specificity) with αF6P, compared with that of CFP-T7-H1.

Subsequently, in the same manner as in (2) above, PCR was carried out with the use of DNA of the recombinant plasmid pKK223-3-CFP-T7-H2 as a template, oligonucleotides as shown in SEQ ID NOs: 4 and 9 to 12, and KOD-Plus-, strains of E. coli JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of glutamine at position 110 with leucine and arginine at position 62 with asparagine, aspartic acid, glutamine, or glutamic acid were obtained (pKK223-3-CFP-T7-H2-62N, pKK223-3-CFP-T7-H6, pKK223-3-CFP-T7-H2-62Q, and pKK223-3-CFP-T7-H2-62E).

Strains of E. coli JM109 carrying pKK223-3-CFP-T7-H2-62N, pKK223-3-CFP-T7-H6, pKK223-3-CFP-T7-H2-62Q, or pKK223-3-CFP-T7-H2-62E were cultured in the manner described in (3) above, and crude enzyme solutions (0.6 ml each) containing various types of modified amadoriases (CFP-T7-H2-62N, CFP-T7-H6, CFP-T7-H2-62Q, or CFP-T7-H2-62E) were prepared.

The crude enzyme solutions thus prepared were subjected to measurement of oxidation activity on αF6P by the method described in the "B: Method of activity measurement" above. For the purpose of comparison, the enzyme solution containing CFP-T7-H2 produced from the E. coli JM109 strain (pKK223-3-CFP-T7-H2) was subjected to measurement in the same manner. Table 3 shows αF6P oxidation activity of crude enzyme solutions containing amadoriases, relative to αF6P oxidation activity of a crude enzyme solution containing CFP-T7-H2 designated to be 100.

TABLE 3

| Amadoriase | Amino acid substitution | αF6P oxidation activity ratio |
|---|---|---|
| CFP-T7-H2 (Amadoriase 2) | R62A, Q110L | 100 |
| CFP-T7-H2-62N (Amadoriase 5) | R62N, Q110L | 120 |
| CFP-T7-H6 (Amadoriase 6) | R62D, Q110L | 513 |
| CFP-T7-H2-62Q (Amadoriase 7) | R62Q, Q110L | 11 |
| CFP-T7-H2-62E (Amadoriase 8) | R62E, Q110L | 21 |

Specifically, CFP-T7-H2-62N and CFP-T7-H16 were found to have improved αF6P oxidation activity, compared with that of CFP-T7-H2. Incidentally, as shown in Table 1, a wild-type enzyme comprising an amino acid sequence in which amino acid 62 is arginine does not exhibit activity on αF6P. Compared with such wild-type enzyme, variants resulting from substitution of arginine at position 62 with glutamine or glutamic acid, respectively, each have improved activity on αF6P. Substitutive amino acids exhibiting activity on αF6P at position 62, i.e., alanine, asparagine, aspartic acid, glutamine, and glutamic acid, have relatively small molecular weights. Accordingly, amino acid substitution at position 62 with glycine, valine, leucine, isoleucine, cysteine, serine, threonine, or proline similarly having a small molecular weight are thought to result in a modified amadoriase having αF6P activity. In this description, alanine, asparagine, aspartic acid, glutamine, glutamic acid, glycine, valine, leucine, isoleucine, cysteine, serine, threonine, and proline may collectively be referred to as "small-molecular-weight amino acids."

A crude enzyme solution containing CFP-T7-H2 or CFP-T7-H6 was subjected to measurement of oxidation activity on αFV, αFVH, and αF6P by the method described in the "B: Method of activity measurement" above. Table 4 shows oxidation activity on substrates, αF6P/αFVH, and αF6P/FV of amadoriases, relative to αFVH oxidation activity designated to be 100.

TABLE 4

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H2 (Amadoriase 2) | R62A, Q110L | 137 | 100 | 0.0735 | 0.000735 | 0.000535 |
| CFP-T7-H6 (Amadoriase 6) | R62D, Q110L | 864 | 100 | 3.00 | 0.0300 | 0.00347 |

Specifically, CFP-T7-H6 was found to have significantly improved αF6P oxidation activity and improved reactivity (substrate specificity) with αF6P, compared with those of CFP-T7-H2.

Subsequently, in the same manner as in (2) above, PCR was carried out with the use of DNA of the recombinant plasmid pKK223-3-CFP-T7-H6 as a template, oligonucleotides as shown in SEQ ID NOs: 13 to 24, and KOD-Plus-, strains of E. coli JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and arginine at position 64 with alanine, glutamic acid, or histidine were obtained (pKK223-3-CFP-T7-H7, pKK223-3-CFP-T7-H8, and pKK223-3-CFP-T7-H9), recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and aspartic acid at position 106 with alanine, lysine, or arginine were obtained (pKK223-3-CFP-T7-H10, pKK223-3-CFP-T7-H11, and pKK223-3-CFP-T7-H12), and recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and alanine at position 113 with lysine or arginine were obtained (pKK223-3-CFP-T7-H13 and pKK223-3-CFP-T7-H14).

Strains of E. coli JM109 carrying pKK223-3-CFP-T7-H7, pKK223-3-CFP-T7-H8, pKK223-3-CFP-T7-H9, pKK223-3-CFP-T7-H10, pKK223-3-CFP-T7-H11, pKK223-3-CFP-T7-H12, pKK223-3-CFP-T7-H13, or pKK223-3-CFP-T7-H14 were cultured in the manner described in (3) above, and crude enzyme solutions (0.6 ml each) containing various types of modified amadoriases (CFP-T7-H7, CFP-T7-H8, CFP-T7-H9, CFP-T7-H10, CFP-T7-H11, CFP-T7-H12, CFP-T7-H13, or CFP-T7-H14) were prepared.

The crude enzyme solutions thus prepared were subjected to measurement of oxidation activity on αF6P by the method described in the "B: Method of activity measurement" above. For the purpose of comparison, the enzyme solution containing CFP-T7-H6 produced from the E. coli JM109 strain (pKK223-3-CFP-T7-H6) was subjected to measurement in the same manner. Table 5 shows αF6P oxidation activity of crude enzyme solutions containing amadoriases, relative to the αF6P oxidation activity of a crude enzyme solution containing CFP-T7-H6 designated to be 100.

TABLE 5

| Amadoriase | Amino acid substitution | αF6P oxidation activity ratio |
|---|---|---|
| CFP-17-H6 (Amadoriase 6) | R62D, Q110L | 100 |
| CFP-T7-H7 (Amadoriase 9) | R62D, R64A, Q110L | 17 |
| CFP- T7-H8 (Amadoriase 10) | R62D, R64E, Q110L | 2 |
| CFP- T7-H9 (Amadoriase 11) | R62D, R64H, Q110L | 44 |
| CFP-T7-H10 (Amadoriase 12) | R62D, D106A, Q110L | 301 |
| CFP-T7-H11 (Amadoriase 13) | R62D, D106K, Q110L | 951 |
| CFP-T7-H12 (Amadoriase 14) | R62D, D106R, Q110L | 636 |
| CFP-T7-H13 (Amadoriase 15) | R62D, Q110L, A113K | 207 |
| CFP-T7-H14 (Amadoriase 16) | R62D, Q110L, A113R | 183 |

Specifically, CFP-T7-H10, CFP-T7-H11, CFP-T7-H12, CFP-T7-H13, and CFP-T7-H14 were each found to exhibit significantly improved αF6P oxidation activity ratio, compared with that of CFP-T7-H6, and the levels of improvement in some of the variants were remarkable.

Crude enzyme solutions containing CFP-T7-H6, CFP-T7-H11, CFP-T7-H12, CFP-T7-H13, and CFP-T7-H14 were subjected to measurement of oxidation activity on αFV, αFVH, and αF6P by the method described in the "B: Method of activity measurement" above. Table 6 shows oxidation activity on substrates, αF6P/αFVH, and αF6P/FV of amadoriases, relative to αFVH oxidation activity designated to be 100.

TABLE 6

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H6 (Amadoriase 6) | R62D, Q110L | 864 | 100 | 3.00 | 0.0300 | 0.00347 |
| CFP-T7-H11 (Amadoriase 13) | R62D, Q106K, Q110L | 511 | 100 | 12.5 | 0.125 | 0.0245 |
| CFP-T7-H12 (Amadoriase 14) | R62D, Q106R, Q110L | 700 | 100 | 11.6 | 0.116 | 0.0165 |
| CFP-T7-H13 (Amadoriase 15) | R62D, Q110L, A113K | 747 | 100 | 4.33 | 0.0433 | 0.00579 |
| CFP-T7-H14 (Amadoriase 16) | R62D, Q110L, A113R | 814 | 100 | 4.22 | 0.0422 | 0.00519 |

As shown in Table 6, specifically, CFP-T7-H11, CFP-T7-H12, CFP-T7-H13, and CFP-T7-H14 were found to have significantly improved reactivity (substrate specificity) with αF6P, compared with that of CFP-T7-H6.

Subsequently, in the same manner as in (2) above, PCR was earned out with the use of DNA of the recombinant plasmid pKK223-3-CFP-T7-H11 as a template, oligonucleotides as shown in SEQ ID NOs: 21 to 24, and KOD-Plus-, strains of E. coli JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, and alanine at position 113 with lysine or arginine were obtained (pKK223-3-CFP-T7-H20 and pKK223-3-CFP-T7-H21).

Strains of E. coli JM109 carrying pKK223-3-CFP-T7-H20 or pKK223-3-CFP-T7-H21 were cultured in the manner described in (3) above, and crude enzyme solutions (0.6 ml each) containing various types of modified amadoriases (CFP-T7-H20 or CFP-T7-H21) were prepared.

Crude enzyme solutions containing CFP-T7-H11, CFP-T7-H20, and CFP-T7-H21 were subjected to measurement of oxidation activity on αFV, αFVH, and αF6P by the method described in the "B: Method of activity measurement" above. Table 7 shows oxidation activity on substrates, αF6P/αFVH, and αF6P/αFV of amadoriases, relative to the αFVH oxidation activity designated to be 100.

TABLE 7

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H11 (Amadoriase 13) | R62D, D106K, Q110L | 511 | 100 | 12.5 | 0.125 | 0.0245 |
| CFP-T7-H20 (Amadoriase 17) | R62D, D106K, Q110L, A113K | 544 | 100 | 20.5 | 0.205 | 0.0377 |
| CFP-T7-H21 (Amadoriase 18) | R62D, D106K, Q110L, A113R | 558 | 100 | 20.8 | 0.208 | 0.0372 |

Specifically, CFP-T7-H20 and CFP-T7-H21 were found to have improved reactivity (substrate specificity) with αF6P, compared with that of CFP-T7-H11.

Subsequently, in the same manner as in (2) above, PCR was carried out with the use of DNA of the recombinant plasmid pKK223-3-CFP-T7-H20 as a template, oligonucleotides as shown in SEQ ID NOs: 25 to 29, and KOD-Plus-, strains of E. coli JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, alanine at position 113 with lysine, and leucine at position 63 with alanine, aspartic acid, histidine, or lysine were obtained (pKK223-3-CFP-T7-H24, pKK223-3-CFP-T7-H25, pKK223-3-CFP-T7-H26, and pKK223-3-CFP-T7-H27).

Strains of E. coli JM109 carrying pKK223-3-CFP-T7-H24, pKK223-3-CFP-T7-H25, pKK223-3-CFP-T7-H26, or pKK223-3-CFP-T7-H27 were cultured in the manner described in (3) above, and crude enzyme solutions (0.6 ml each) containing various types of modified amadoriases (CFP-T7-H24, CFP-T7-H25, CFP-T7-H26, or CFP-T7-H27) were prepared.

The crude enzyme solutions thus prepared were subjected to measurement of oxidation activity on αF6P by the method described in the "B: Method of activity measurement" above. For the purpose of comparison, the enzyme solution containing CFP-T7-H20 produced from the E. coli JM109 strain (pKK223-3-CFP-T7-H20) was subjected to measurement in the same manner. Table 8 shows αF6P oxidation activity of crude enzyme solutions containing amadoriases, relative to the αF6P oxidation activity of a crude enzyme solution containing CFP-T7-H20 designated to be 100.

TABLE 8

| Amadoriase | Amino acid substitution | αF6P oxidation activity ratio |
|---|---|---|
| CFP-T7-H20 (Amadoriase 17) | R62D, D106K, Q110L, A113K | 100 |
| CFP-T7-H24 (Amadoriase 19) | R62D, L63A, D106K, Q110L, A113K | 123 |
| CFP-T7-H25 (Amadoriase 20) | R62D, L63D, D106K, Q110L, A113K | 24 |
| CFP-T7-H26 (Amadoriase 21) | R62D, L63H, D106K, Q110L, A113K | 142 |
| CFP-T7-H27 (Amadoriase 22) | R62D, L63K, D106K, Q110L, A113K | 7 |

As shown in Table 8, specifically, CFP-T7-H24 and CFP-T7-H26 were found to have improved αF6P oxidation activity, compared with that of CFP-T7-H20.

Crude enzyme solutions containing CFP-T7-H20, CFP-T7-H24, or CFP-T7-H26 subjected to measurement of oxidation activity on αFV, αFVH, and αF6P by the method described in the "B: Method of activity measurement" above. Table 9 shows oxidation activity on substrates, αF6P/αFVH, and αF6P/αFV of amadoriases, relative to the αFVH oxidation activity designated to be 100.

TABLE 9

| Amadoriase | Amino acid substitution | αFV oxidation activity | αFVH oxidation activity | αF6P oxidation activity | αF6P/αFVH | αF6P/αFV |
|---|---|---|---|---|---|---|
| CFP-T7-H20 (Amadoriase 17) | R62D, D106K, Q110L, A113K | 544 | 100 | 20.5 | 0.205 | 0.0377 |
| CFP-T7-H24 (Amadoriase 19) | R62D, L63A, D106K, Q110L, A113K | 1880 | 100 | 86.7 | 0.867 | 0.0461 |
| CFP-T7-H26 (Amadoriase 21) | R62D, L63H, D106K, Q110L, A113K | 1090 | 100 | 84.3 | 0.843 | 0.0773 |

As shown in Table 9, specifically, CFP-T7-H24 and CFP-T7-H26 were found to have improved reactivity (substrate specificity) with αF6P, compared with that of CFP-T7-H20.

Subsequently, in the same manner as in (2) above, PCR was carried out with the use of DNA of the recombinant plasmid pKK223-3-CFP-T7-H26 as a template, oligonucleotides as shown in SEQ ID NOs: 30 to 33, and KOD-Plus-, strains of E. coli JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, aspartic acid at position 106 with lysine, glutamine at position 110 with leucine, alanine at position 113 with lysine, and glutamic acid at position 102 with lysine was obtained (pKK223-3-CFP-T7-H28), and a recombinant plasmid encoding a modified amadoriase comprising an amino acid sequence derived from the amino acid sequence as shown in SEQ ID NO: 1 by substitution of arginine at position 62 aspartic acid, leucine at position 63 with histidine, aspartic acid at position 106 with lysine, glutamine at position 110 with leucine, alanine at position 113 with lysine, and alanine at position 419 with lysine was obtained (pKK223-3-CFP-T7-H29).

Strains of E. coli JM109 carrying pKK223-3-CFP-T7-H26, pKK223-3-CFP-T7-H28, or pKK223-3-CFP-T7-H29 were cultured in the manner described in (3) above, and crude enzyme solutions (0.6 ml each) containing various types of modified amadoriases (CFP-T7-H26, CFP-T7-H28, or CFP-T7-H29) were prepared.

The crude enzyme solutions thus prepared were subjected to measurement of oxidation activity on αF6P by the method described in the "B: Method of activity measurement" above. For the purpose of comparison, the enzyme solution containing CFP-T7-H26 produced from the E. coli JM109 strain (pKK223-3-CFP-T7-H26) was subjected to measurement in the same manner. Table 10 shows αF6P oxidation activity of crude enzyme solutions containing amadoriases, relative to the αF6P oxidation activity of a crude enzyme solution containing CFP-T7-H26 designated to be 100.

TABLE 10

| Amadonase | Amino acid substitution | αF6P oxidation activity ratio |
|---|---|---|
| CFP-T7-H26 (Amadoriase 21) | R62D, L63H, D106K, Q110L, A113K | 100 |
| CFP-T7-H28 (Amadoriase 23) | R62D, L63H, E102K, D106K, Q110L, A113K | 117 |
| CFP-T7-H29 (Amadoriase 24) | R62D, L63H, D106K, Q110L, A113K, A419K | 102 |

As shown in Table 10, specifically, CFP-T7-H28 and CFP-T7-H29 were found to have improved αF6P oxidation activity, compared with that of CFP-T7-H26.

Crude enzyme solutions containing CFP-T7-H26, CFP-T7-H28, or CFP-T7-H29 subjected to measurement of oxidation activity on αFV, αFVH, and αF6P by the method described in the "B: Method of activity measurement" above. Table 11 shows oxidation activity on substrates, αF6P/αFVH, and αF6P/αFV of amadoriases, relative to the αFVH oxidation activity designated to be 100.

TABLE 11

| Amadoriase | Amino acid substitution | αFV oxidation activity | αFVH oxidation activity | αF6P oxidation activity | αF6P/αFVH | αF6P/αFV |
|---|---|---|---|---|---|---|
| CFP-T7-H26 (Amadoriase 21) | R62D, L63H, D106K, Q110L, A113K | 1090 | 100 | 84.3 | 0.843 | 0.0773 |
| CFP-T7-H28 (Amadoriase 23) | R62D, L63H, E102K, D106K, Q110L, A113K | 1080 | 100 | 134 | 1.34 | 0.124 |
| CFP-T7-H29 (Amadoriase 24) | R62D, L63H, D106K, Q110L, A113K, A419K | 1000 | 100 | 111 | 1.11 | 0.111 |

As shown in Table 11, specifically, CFP-T7-H28 and CFP-T7-H29 were found to have improved reactivity (substrate specificity) with αF6P, compared with that of CFP-T7-H126.

Subsequently, in the same manner as in (2) above, PCR was carried out with the use of DNA of the recombinant plasmid pKK223-3-CFP-T7-H28 as a template, oligonucleotides as shown in SEQ ID NOs: 34 and 35, and KOD-Plus-, strains of E. coli JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, glutamic acid at position 102 with lysine, aspartic acid at position 106 with lysine, glutamine at position 110 with leucine, alanine at position 113 with lysine, and alanine at position 355 with serine was obtained (pKK223-3-CFP-T7-H35). Strains of E. coli JM109 carrying pKK223-3-CFP-T7-H35 were cultured in the manner described in (3) above, and a crude enzyme solution (0.6 ml) containing a modified amadoriase (CFP-T7-H35) was prepared.

The crude enzyme solution thus prepared was subjected to measurement of oxidation activity on αF6P by the method described in the "B: Method of activity measurement" above. For the purpose of comparison, the enzyme solution containing CFP-T7-H20 produced from the strain of E. coli JM109 (pKK223-3-CFP-T7-H28) was subjected to measurement in the same manner. Table 12 shows αF6P oxidation activity of crude enzyme solutions containing amadoriases, relative to the αF6P oxidation activity of a crude enzyme solution containing CFP-T7-H126 designated to be 100.

TABLE 12

| Amadoriase | Amino acid mutation | αF6P oxidation activity ratio |
|---|---|---|
| CFP-T7-H28 (Amadoriase 23) | R62D, L63H, E102K, D106K, Q110L, A113K | 100 |
| CFP-T7-H35 (Amadoriase 25) | R62D, L63H, E102K, D106K, Q110L, A113K, A355S | 206 |

As shown in Table 12, specifically, CFP-T7-H35 was found to have improved αF6P oxidation activity, compared with that of CFP-T7-H28.

Subsequently, in the same manner as in (2) above, PCR was carried out with the use of DNA of the recombinant plasmid pKK223-3-CFP-T7 as a template, oligonucleotides as shown in SEQ ID NOs: 4 and 10, and KOD-Plus-, strains of E. coli JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid was obtained (pKK223-3-CFP-T7-62D). Subsequently, a strain of E. coli JM109 carrying pKK223-3-CFP-T7-62D was prepared.

Subsequently, in the same manner as in (2) above, PCR was carried out with the use of DNA of the recombinant plasmid pKK223-3-CFP-T7-H35 as a template, oligonucleotides as shown in SEQ ID NOs: 193 and 194, and KOD-Plus-, strains of E. coli JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, glutamic acid at position 102 with lysine, aspartic acid at position 106 with lysine, glutamine at position 110 with leucine, alanine at position 113 with lysine, alanine at position 355 with serine, and aspartic acid at position 68 asparagine was obtained (pKK223-3-CFP-T7-H36).

Subsequently, in the same manner as in (2) above, PCR was carried out with the use of DNA of the recombinant plasmid pKK223-3-CFP-T7-H36 as a template, oligonucleotides as shown in SEQ ID NOs: 195 and 196, and KOD-Plus-, strains of E. coli JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, glutamic acid at position 102 with lysine, aspartic acid at position 106 with lysine, glutamine at position 110 with leucine, alanine at position 113 with lysine, alanine at position 355 with serine, aspartic acid at position 68 with asparagine, and alanine at position 356 with threonine was obtained (pKK223-3-CFP-T7-H37).

In order to obtain a variant of CFP-T7-H36 exhibiting improved stability, a mutation that improves stability was introduced into CFP-T7-H36 and 3 amino acids were deleted from the C terminus thereof, so as to obtain a modified CFP-T7-H36 comprising a sequence of 434 acids as shown in SEQ ID NO: 199 (hereafter referred to as "CFP-DH1"), and expression thereof was attempted in *E. coli*. A 1,305-bp gene sequence as shown in SEQ ID NO: 200 encoding the amino acid sequence as shown in SEQ ID NO: 199 and having an optimized codon for expression in *E. coli* (including the termination codon TAA) was obtained in accordance with a conventional technique, i.e., total synthesis of a gene fragment via PCR. Through this procedure, the EcoRI site and the HindIII site were added to the 5' terminus and the 3' terminus of the sequence as shown in SEQ ID NO: 200, respectively.

Subsequently, the procedure described below was implemented so as to subclone the obtained CFP-DH1 gene into a plasmid for expression in *E. coli*. First, the gene obtained via total synthesis above and the pKK223-3 Vector (Novagen) were treated with two types of restriction enzymes (EcoRI and HindIII, TakaraBio. Co., Ltd.), the gene and the vector were ligated to each other, and DNA of the recombinant plasmid pKK223-3-CFP-DH1 resulting from insertion of the CFP-DH1 gene into the multicloning site of the pKK223-3 vector was obtained. Strains of *E. coli* JM109 were transformed with the resulting recombinant plasmid, and the transformants were then spread on LB-amp agar medium. The grown colonies were inoculated into LB-amp media and shake-cultured therein, and plasmid DNAs were isolated in the same manner as in (1) above. Nucleotide sequences of DNAs encoding amadoriases in the plasmids were determined using a multi-capillary DNA analysis system (Applied Biosystems 3130xl Genetic Analyzer; manufactured by Life Technologies). It was thus confirmed that DNA of the recombinant plasmid pKK223-3-CFP-DH1 comprising the CFP-DH1 gene inserted into the multicloning site of the pKK223-3 vector was actually obtained.

Subsequently, in the same manner as in (2) above, PCR was carried out with the use of DNA of the recombinant plasmid pKK223-3-CFP-DH1 as a template, oligonucleotides as shown in SEQ ID NOs: 201 and 202, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 199 by substitution of alanine at position 356 with threonine was obtained (pKK223-3-CFP-DH2).

Example 2

Production and Purification of Various Types of Amadoriases

Production and Purification of Modified Amadoriase Derived from the Genus *Coniochaeta*

*E. coli* JM109 producing the wild-type amadoriases from the genus *Coniochaeta* and *E. coli* JM109 (pKK223-3-CFP-T7), *E. coli* JM109 (pKK223-3-CFP-T7-62D), *E. coli* JM109 (pKK223-3-CFP-T7-H20), *E. coli* JM109 (pKK223-3-CFP-T7-H21), and *E. coli* JM109 (pKK223-3-CFP-T7-H35) producing modified amadoriases obtained in the manner described above were inoculated into 120 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 24 ml of a crude enzyme solution.

The resulting crude enzyme solution was allowed to adsorb to 12 ml of Toyopearl Butyl-650C resin (manufactured by Tosoh) equilibrated with a 10 mM potassium phosphate buffer (pH 7.0) containing 1.35 M $(NH_4)_2SO_4$, the resin was washed with 120 ml of the same buffer, and the amadoriases adsorbed to the resin were then eluted and collected with the aid of a 10 mM potassium phosphate buffer (pH 7.0) containing 84 ml of 1.05 M $(NH_4)_2SO_4$.

The resulting crude enzyme solution containing the amadoriases was introduced into Spectra/Por dialysis tubing (MWCO: 12,000-14,000) and dialyzed against a 10-fold amount of 5 mM potassium phosphate buffer (pH 7.5). This procedure was repeated 3 times to completely remove $(NH_4)_2SO_4$ from the crude enzyme solution containing the amadoriases. Subsequently, the crude enzyme solution containing the amadoriases was applied to HiScreen Capto Q ImpRes (manufactured by GE Healthcare) equilibrated with a 10 mM potassium phosphate buffer (pH 7.5) to allow amadoriases to bind to anion-exchange resin. Thereafter, the concentration of NaCl contained in a 10 mM potassium phosphate buffer (pH 7.5) was linearly increased from 0 mM to 160 mM to elute proteins bound to the resin, and fractions exhibiting amadoriase activity were collected. The obtained fractions exhibiting amadoriase activity were analyzed via SDS-PAGE to confirm that the fractions were sufficiently purified, so that no other contaminating proteins were present therein, and these fractions were designated to be purified samples of the CFP-T7, CFP-T7-62D, CFP-T7-H20, CFP-T7-H21, and pKK223-3-CFP-T7-H35 enzymes.

*E. coli* JM109 (pKK223-3-CFP-T7-H36), *E. coli* JM109 (pKK223-3-CFP-T7-H37), and *E. coli* JM109 (pKK223-3-CFP-DH2) producing modified amadoriases obtained in Example 1 were inoculated into 200 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 40 ml of a crude enzyme solution. Only the cultured strains of *E. coli* JM109 (pKK223-3-CFP-DH2) were washed with 2 mM potassium phosphate buffer (pH 8.0), the washed strains were suspended in the same buffer, the resulting suspension was ultrasonically disintegrated, and the resultant was centrifuged at 20,000×g for 10 minutes to prepare 40 ml of a crude enzyme solution.

After the column loaded with Q-sepharose FF (GE Healthcare) was equilibrated with a 10 mM potassium phosphate buffer (pH 7.5), the crude enzyme solutions each containing CFP-T7-H36 and CFP-T7-H37 were applied, so as to allow amadoriases to bind to the anion-exchange resin. Then, a 10 mM potassium phosphate buffer (pH 7.5) containing 30 mM NaCl was applied at an amount equivalent to 20 column volumes, so as to elute contaminating proteins, and then proteins bound to the resin were eluted with the aid of a 10 potassium phosphate buffer (pH 7.5) containing 80 mM NaCl, and fractions exhibiting amadoriase activity were collected.

After the column loaded with Q-sepharose FF (GE Healthcare) was equilibrated with a 2 mM potassium phosphate buffer (pH 8.0), the crude enzyme solution containing CFP-DH2 was applied, so as to allow amadoriases to bind to the anion-exchange resin. Then, a 4 mM potassium phosphate buffer (pH 8.0) was applied at an amount equivalent to 20 volumes, so as to elute contaminating proteins, and then proteins bound to the resin were eluted with the aid of a 4 mM potassium phosphate buffer (pH 8.0) containing 3.0 mM NaCl, and fractions exhibiting amadoriase activity were collected.

Each of the obtained fractions exhibiting amadoriase activity were concentrated using Amicon Ultra Ultracel-30K (Millipore) and purified using HiLoad 26/60 Superdex 200. Resin equilibration and elution were carried out using a 10 mM potassium phosphate buffer (pH 6.5) containing 150 mM NaCl. Purity of the eluted fractions was evaluated via SDS-PAGE, and fractions containing no contaminating proteins were collected, and the collected fractions were designated to be purified samples of the CFP-T7-H36, CFP-T7-H37, and CFP-DH2 enzymes.

(Production and Purification of Fructosyl Amino Acid Oxidase Derived from *Aspergillus oryzae* RIB40)

SEQ ID NO: 36 shows the amino acid sequence of fructosyl amino acid oxidase derived from *Aspergillus oryzae* RIB40 (hereafter referred to as "FAOAo2"), a recombinant plasmid obtained by insertion of the gene (SEQ ID NO: 37) encoding the amino acid sequence as shown in SEQ ID NO: 36 (hereafter referred to as "pUC19-FAOAo2") is allowed to express in *E. coli* DH5α to produce FAOAo2, and FAOAo2 reacts with fructosyl hexapeptide (see WO 2008/108385).

The strains of *E. coli* DH5α capable of producing FAOAo2 (pUC9-FAOAo2) were inoculated into LB-amp media supplemented with IPTG (final concentration: 0.1 mM) and cultured therein at 25° C. for 16 hours. The resulting cultured strains were washed with a 10 Tris-HCl buffer (pH 8.5), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM Tris-HCl buffer (pH 8.5), the resin was washed with a 10 mM Tris-HCl buffer (pH 8.5) containing 50 mM NaCl, and the FAOAo2 adsorbed to the resin was then eluted and collected with the aid of a 10 mM Tris-HCl buffer (pH 8.5) containing 100 mM NaCl.

The resulting crude enzyme solution containing FAOAo2 was applied to the HiLoad 26/600 Superdex 200 column equilibrated with a 20 mM MES-NaOH buffer (pH 7.0) containing 150 mM NaCl so as to elute FAOAo2 with the same buffer, and a fraction exhibiting amadoriase activity was collected. The obtained fraction was analyzed via SDS-PAGE to confirm that the fraction was sufficiently purified, so that no other contaminating proteins were present therein, and the fraction was designated to be a purified enzyme sample of FAOAo2.

(Preparation of Strain Producing Fructosyl Peptide Oxidase Derived from *Phaeosphaeria nodorum*)

SEQ ID NO: 38 shows the amino acid sequence of fructosyl peptide oxidase derived from *Phaeosphaeria nodorum* (hereafter referred to as "PnFX") (see Biotechnology and Bioengineering, 106, 358-366, 2010). The gene (SEQ ID NO: 39) encoding the amino acid sequence as shown in SEQ ID NO: 38 was obtained via total synthesis of cDNA by a conventional technique of PCR of a gene fragment. The NdeI site and the BamHI were added to the 5' terminus and the 3' terminus of SEQ ID NO: 39, respectively. Also, the full-length amino acid sequence that is deduced based on the cloned gene sequence was confirmed to be consistent with the PnFX sequence as shown in FIG. 1.

In order to express the gene shown in SEQ ID NO: 39 in *E. coli*, subsequently, the following procedures were performed. The gene obtained via total synthesis above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-PnFX was obtained. Strains of *E. coli* BL21 (DE3) were transformed under the conditions as described above to obtain a strain of *E. coli* BL21 (DE3) (pET22b-PnFX).

(Production and Purification of Fructosyl Peptide Oxidase Derived from *Phaeosphaeria nodorum*)

The strains of *E. coli* BL21 (DE3) (pET22b-PnFX) capable of producing PnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution containing PnFX was purified in accordance with the method described in the non-patent document (Biotechnology and Bioengineering, 106, 358-366, 2010). Specifically, the crude enzyme solution was fractionated with ammonium sulfate, dialyzed against a 10 mM potassium phosphate buffer (pH 8.0), purified via anion-exchange chromatography (Q Sepharose Fast Flow was used in Example 2), and then purified via gel filtration chromatography (HiLoad 26/600 Superdex 200 was used in Example 2). The obtained fraction was analyzed via SDS-PAGE to confirm that the fraction was sufficiently purified, so that no other contaminating proteins were present therein, and the fraction was designated to be a purified sample of PnFX.

By using the purified samples of CFP-T7, CFP-T7-62D, CFP-T7-H20, CFP-T7-H21, CFP-T7-H35, FAOAo2, and PnFX, specific activities thereof relative to αFV, αFVH, and αF6P as substrates were measured. Results are shown in Table 13-1. Incidentally, the concentration of the protein used for calculating specific activity was determined by using the ultraviolet absorption method which utilizes absorbance at 280 nm (see Protein Sci., 4, 2411-23, 1995).

TABLE 13-1

| Amadoriase | Amino acid mutation | Specific activity (U/mg) 1 mM αFV | 1 mM αFVH | 1 mM αF6P | αF6P/ αFVH | αF6P/ αFV |
|---|---|---|---|---|---|---|
| CFP-T7 (Comparative Example 1) | None | 11.1 | 16.5 | 0 | 0 | 0 |
| FAOAo2 (Comparative Example 2) | None | Not measured | Not measured | 0.0022 | | |
| PnFX (Comparative Example 3) | None | Not measured | Not measured | 0.0091 | | |
| CFP-T7-62D (Amadoriase 26) | R62D | 13.6 | 1.62 | 0.018 | 0.00132 | 0.00113 |
| CFP-T7-H20 (Amadoriase 17) | R62D, D106K, Q110L, A113K | 21.8 | 4.28 | 0.850 | 0.198 | 0.0389 |
| CFP-T7-H21 (Amadoriase 18) | R62D, D106K, Q110L, A113R | 21.0 | 4.05 | 0.795 | 0.196 | 0.0377 |
| CFP-T7-H35 (Amadoriase 25) | R62D, L63H, E102K, D106K, Q110L, A113K, A355S | 13.2 | 1.90 | 4.27 | 2.25 | 0.323 |

With the use of the purified samples of CFP-T7-H36, CFP-T7-H37, and CFP-DH2, specific activities thereof relative to αF6P as a substrate were measured. The results are shown in Table 13-2. Incidentally, the concentration of the protein used for calculating specific activity was determined by using the ultraviolet absorption method which utilizes absorbance at 280 nm (see Protein Sci., 4, 2411-23, 1995).

TABLE 13-2

| Amadoriase | Amino acid mutation relative to CFP-T7 | Specific activity (U/mg) 1 mM αF6P |
|---|---|---|
| CFP-T7-H36 (Amadoriase 36) | R62D, L63H, D68N, E102K, D106K, Q110L, A113K, A355S | 4.65 |
| CFP-T7-H37 (Amadoriase 37) | R62D, L63H, D68N, E102K, D106K, Q110L, A113K, A355S, A356T | 7.19 |
| CFP-DH2 (Amadoriase 39) | R62D, L63H, D68N, E102K, D106K, Q110L, A113K, A355S, A356T E44P, E133A, E253K, V257C, N262H, Q337K, E340P, ΔP435, ΔK436, ΔL437 | 5.30 |

While purified CFP-T7 exhibited oxidation activity on αFV and αFVH, it did not exhibit oxidation activity on αF6P. In contrast, CFP-T7-H35 exhibited oxidation activity on αF6P, in addition to oxidation activity on αFV and αFVH, and specific activity of the αF6P oxidation reaction reached a high level of 4.27 U/mg.

Specific activity of CFP-T7-62D, CFP-T7-H20, and CFP-77-H21 relative to αF6P were 0.018 U/mg, 0.850 U/mg, and 0.795 U/mg, respectively. That is, sufficiently high reactivity with αF6P was observed even in a measurement method that eliminated the influence of protease/peptidase from the E. coli host.

Specific activity of the amadoriase reacting with αF6P (i.e., FAOAo2, see WO 2008/108385) and that of PnFX (see WO 2011/15326, referred to as "P.n FPOX" therein) relative to αF6P were 0.0022 U/mg and 0.0091 U/mg, respectively.

The modified amadoriase derived from the genus Coniochaeta prepared in accordance with the procedure described herein exhibited specific activity that is 2 times (Amadoriase 26/Comparative Example 3) to 1.940 times (Amadoriase 25/Comparative Example 2) greater than those of the amadoriases reacting with αF6P. That is, an amadoriase exhibiting high reactivity with αF6P was obtained in accordance with the procedure described herein.

There were no significant discrepancies between the αF6P/αFVH values of CFP-T7-H20 and CFP-T7-H21 measured with the use of crude enzyme solutions and those measured with the use of purified enzymes.

Specific activity of CFP-T7-H36 and CFP-T7-H37 relative to αF6P was 4.65 U/mg and 7.19 U/mg, respectively. Such specific activity was improved as amino acid substitution was added, compared with specific activity of CFP-T7-H35 before amino acid substitution (i.e., 4.27 U/mg). Also, CFP-DH2 exhibited higher specific activity (5.30 U/mg) than CFP-T7-H35 (Table 13-2).

The present inventors had confirmed that the mutations which were introduced into CFP-DH2 (E44P/E133A/ H253K/V257C/N262H/Q337K/E340P), improve surfactant resistance of amadoriases. Specifically, residual activity in an enzyme derived from CFP without mutations is 29.2% even when 0.04% tetradecyltrimethylammonium chloride (TTAC) is allowed to react with the amadoriase in a 20 mM potassium phosphate buffer (pH 7.0), whereas residual activity in CFP-DH2, to which mutations (E44P/E133A/E253K/ V257C/N262H/Q337K/E340P) were introduced, was 100%. The effects of such mutations are described in JP Patent Application No. 2013-221515 and the specification of PCT/JP2014/071036, which are incorporated herein by reference in their entirety. In addition, the present inventors have previously reported that deletion of amino acids from the carboxyl terminus of CFP-DH2 improve heat stability of amadoriases. The effects of such deletion are described in WO 2013/100006.

Amadoriases not having such mutations retain activity even after treatment with surfactants. Thus, HbA1c can be measured with the use of an adequate amount of enzymes. With the use of amadoriases with improved surfactant resistance or heat stability, the amount of enzymes required for measurement can also be reduced.

Example 3

Introduction of Point Mutations into Various Amadoriases

By introducing the mutations described above, reactivity of the amadoriase from the genus Coniochaeta with αF6P was enhanced. Thus, enhanced reactivity with αF6P can also be expected by introducing similar mutations into corresponding positions in the amino acid sequence of an amadoriase derived from other organism species by referencing information attained by a known sequence alignment processing based on sequence identity. Accordingly, mutations were actually introduced into the corresponding positions of a plurality of amadoriases other than the amadoriase from the genus Coniochaeta.

1. Introduction of Point Mutation into Gene of Fructosyl Peptide Oxidase Derived from Eupenicillium terrenum SEQ ID NO: 40 shows the amino acid sequence of fructosyl peptide oxidase derived from Eupenicillium terrenum (hereafter referred to as "EFP-T5"), and it can be prepared by E. coli strains carrying the recombinant plasmid pUTE100K'-EFP-T5 into which the gene (SEQ ID NO: 41)

encoding the amino acid sequence as shown in SEQ ID NO: 40 has been inserted. EFP-T5 is confirmed to exhibit oxidation activity on αFV and αFVH (see WO 2007/125779 WO 2008/018094).

In order to introduce a mutation aimed at improvement of substrate specificity into EFP-T5, in the same manner as in Example 1, PCR was carried out with the use of the recombinant plasmid pUTE100K'-EFP-T5 as a template, synthetic oligonucleotides as shown in SEQ ID NOs: 42 and 43, and KOD-Plus- (manufactured by TOYOBO CO., LTD.), strains of E. coli JM109 were transformed, and nucleotide sequences of DNAs encoding the EFP-T5 in the plasmid DNAs carried on the grown colonies were determined. As a result, a recombinant plasmid encoding the EFP-T5 gene comprising an amino acid sequence derived from the amino acid sequence as shown in SEQ ID NO: 40 by substitution of arginine at position 62 with aspartic acid was obtained (pUTE100K'-EFP-T5-62D).

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid and asparagine at position 106 with lysine (pUTE100K'-EFP-T5-62D/106K) was obtained with the use of pUTE100K'-EFP-T5-62D as a template and synthetic oligonucleotides as shown in SEQ ID NOs: 44 and 45.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, and lysine at position 110 with leucine (pUTE100K'-EFP-T5-62D/106K/110L) was obtained with the use of pUTE100K'-EFP-T5-62D/106K as a template and synthetic oligonucleotides as shown in SEQ ID NOs: 46 and 47.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, and threonine at position 113 with lysine (pUTE100K'-EFP-T5-62D/106K/110L/113K) was obtained with the use of pUTE100K'-EFP-T5-62D/106K/110L as a template and synthetic oligonucleotides as shown in SEQ ID NOs: 48 and 49.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, threonine at position 113 with lysine, and alanine at position 355 with serine (pUTE100K'-EFP-T5-62D/106K/110L/113K/355S) was obtained with the use of pUTE100K'-EFP-T5-62D/106K/110L/113K as a template and synthetic oligonucleotides as shown in SEQ ID NOs: 50 and 51.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, leucine at position 63 with histidine, asparagine at position 106 with lysine, lysine at position 110 with leucine, threonine at position 113 with lysine, and alanine at position 355 serine (pUTE100K'-EFP-T5-62D/63H/106K/110L/113K/355S) was obtained with the use of pUTE100K'-EFP-T5-62D/106K/110L/113K/355S as a template and synthetic oligonucleotides as shown in SEQ ID NOs: 52 and 53.

2. Introduction of Point Mutation into Gene of Ketoamine Oxidase Derived from *Neocosmospora vasinfecta*

SEQ ID NO: 54 shows the amino acid sequence of ketoamine oxidase derived from *Neocosmospora vasinfecta* (hereafter referred to as "NvFX"), and it can be prepared by E. coli strains carrying the recombinant plasmid pET22b-NvFX into which the gene (SEQ ID NO: 55) encoding the amino acid sequence as shown in SEQ ID NO: 54 has been inserted. NvFX is confirmed to exhibit oxidation activity on αFV and αFVH (see WO 2012/018094).

In order to introduce a mutation aimed at improvement of substrate specificity into NvFX, in the same manner as in Example 1, PCR was carried out with the use of the recombinant plasmid pET22b-NvFX as a template, synthetic oligonucleotides as shown in SEQ ID NOs: 56 and 57, and KOD-Plus- (manufactured by TOYOBO CO., LTD.), strains of *E. coli* JM109 were transformed, and nucleotide sequences of DNAs encoding the NvFX variant in the plasmid DNAs carried on the grown colonies were determined. As a result, a recombinant plasmid encoding the NvFX gene comprising an amino acid sequence derived from the amino acid sequence as shown in SEQ ID NO: 54 by substitution of arginine at position 62 with aspartic acid was obtained (pET22b-NvFX-62D).

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid and glycine at position 106 with lysine (pET22b-NvFX-62D/106K) was obtained with the use of pET22b-NvFX-62D as a template and synthetic oligonucleotides as shown in SEQ ID NOs: 58 and 59.

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid, arginine at position 106 with lysine, and glutamic acid at position 110 with leucine (pET122b-NvFX-62D/106K/110L) was obtained with the use of PET22b-NvFX-62D/106K as a template and synthetic oligonucleotides as shown in SEQ ID NOs: 60 and 61.

Strains of *E. coli* BL21 (DE3) were transformed under the same conditions as in Example 1 to obtain strains of *E. coli* BL21 (DE3) (pET22b-NvFX-62D/106K/110L).

3. Introduction of Point Mutation into Gene of Fructosyl Amino Acid Oxidase Derived from *Aspergillus nidulans*

SEQ ID NO: 62 shows the amino acid sequence of fructosyl amino acid oxidase derived from *Aspergillus nidulans* resulting from substitution of serine at position 59 with glycine so as to impart the activity of fructosyl peptide oxidase (hereafter referred to as "AnFX"), and it can be prepared by *E. coli* strains carrying the recombinant plasmid pET22b-AnFX into which the gene (SEQ ID NO: 63) encoding the amino acid sequence as shown in SEQ ID NO: 62 has been inserted. AnFX is confirmed to exhibit oxidation activity on αFV and αFVH (see WO 2012/018094).

In order to introduce a mutation aimed at improvement of substrate specificity into AnFX, in the same manner as in Example 1, PCR was carried out with the use of the recombinant plasmid pET22b-AnFX as a template, synthetic oligonucleotides as shown in SEQ ID NOs: 64 and 65, and KOD-Plus- (manufactured by TOYOBO CO., LTD.), strains of *E. coli* JM109 were transformed, and nucleotide sequences of DNAs encoding the AnFX variant in the plasmid DNAs earned on the grown colonies were determined. As a result, a recombinant plasmid encoding the AnFX gene comprising an amino acid sequence derived from the amino acid sequence as shown in SEQ ID NO: 62 by substitution of arginine at position 61 with aspartic acid was obtained (pET22b-AnFX-61D).

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid and glycine at position 105 with lysine (pET22b-AnFX-61D/105K) was obtained with the use of pET22b-AnFX-61D as a template and synthetic oligonucleotides as shown in SEQ ID NOs: 66 and 67.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, and lysine at position 109 with leucine (pET22b-AnFX-61D/105K/109L) was obtained with the use of pET22b-AnFX-61D/105K as a template and synthetic oligonucleotides as shown in SEQ ID NOs: 68 and 69.

Strains of *E. coli* BL21 (DE3) were transformed under the same conditions as in Example 1 to obtain strains of *E. coli* BL21 (DE3) (pET22b-AnFX-61D/105K/109L).

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, and serine at position 112 with lysine (pET22b-AnFX-61D/105K/109L/112K) was obtained with the use of pET22b-AnFX-61D/105K/109L as a template and synthetic oligonucleotides as shown in SEQ ID NOs: 112 and 70.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, serine at position 112 with lysine, and alanine at position 355 with serine (pET22b-AnFX-61D/105K/109L/112K/355S) was obtained with the use of pET22b-AnFX-61D/105K/109L/112K as a template and synthetic oligonucleotides as shown in SEQ ID NOs: 71 and 72.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glycine at position 105 with lysine, lysine at position 109 with leucine, serine at position 112 with lysine, and alanine at position 355 with serine (pET22b-AnFX-61D/62H/105K/109L/112K/355S) was obtained with the use of pET22b-AnFX-61D/105K/109L/112K/355S as a template and synthetic oligonucleotides as shown in SEQ ID NOs: 73 and 74.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glutamic acid at position 101 with lysine, glycine at position 105 with lysine, lysine at position 109 with leucine, serine at position 112 with lysine, and alanine at position 355 with serine (pET22b-AnFX-61D/62H/101K/105K/109L/112K/355S) was obtained with the use of pET22b-AnFX-61D/62H/105K/109L/112K/355S as a template and synthetic oligonucleotides as shown in SEQ ID NOs: 75 and 76.

Strains of *E. coli* BL21 (DE3) were transformed under the same conditions as in Example 1 to obtain strains of *E. coli* BL21 (DE3) (pET22b-AnFX-61D/62H/101K/105K/109L/112K/355S).

4. Introduction of Point Mutation into Gene of Fructosyl Peptide Oxidase Derived from *Phaeosphaeria nodorum*

In order to introduce a mutation aimed at improvement of substrate specificity into PnFX, in the same manner as in Example 1, PCR was carried out with the use of the recombinant plasmid pET22b-PnFX prepared in the manner as described above as a template, synthetic oligonucleotides as shown in SEQ ID NOs: 77 and 78, and ROD Plus (manufactured by TOYOBO CO., LTD.), strains of *E. coli* JM109 were transformed, and nucleotide sequences of DNAs encoding the PnFX variant in the plasmid DNAs carried on the grown colonies were determined. As a result, a recombinant plasmid encoding the PnFX gene comprising an amino acid sequence derived from the amino acid sequence as shown in SEQ ID NO: 38 by substitution of serine at position 62 with aspartic acid was obtained (pET22b-PnFX-62D).

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid and aspartic acid at position 106 with lysine (pET22b-PnFX-62D/106K) was obtained with the use of pET22b-PnFX-62D as a template and synthetic oligonucleotides as shown in SEQ ID NOs: 79 and 80.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, and glycine at position 110 with leucine (pET22b-PnFX-62D/106K/110L) was obtained with the use of pET22b-PnFX-62D/106K as a template and synthetic oligonucleotides as shown in SEQ ID NOs: 81 and 82.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, and alanine at position 113 with lysine (pET22b-PnFX-62D/106K/110L/113K) was obtained with the use of pET22b-PnFX-62D/106K/110L as a template and synthetic oligonucleotides as shown in SEQ ID NOs: 83 and 84.

Strains of *E. coli* BL21 (DE3) were transformed under the same conditions as in Example 1 to obtain strains of *E. coli* BL21 (DE3) (PET22b-PnFX-62D/106K/110L/113K).

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, alanine at position 113 with lysine, and alanine at position 351 with serine (pET22b-PnFX-62D/106K/110L/113K/351S) was obtained with the use of pET22b-PnFX-62D/106K/110L/113K as a template and synthetic oligonucleotides as shown in SEQ ID NOs: 85 and 86.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, leucine at position 63 with histidine, aspartic acid at position 106 with lysine, glycine at position 110 with leucine, alanine at position 113 with lysine, and alanine at position 351 with serine (pET22b-PnFX-62D/63H/106K/110L/113K/351S) was obtained with the use of pET22b-PnFX-62D/106K/110L/113K/351S as a template and synthetic oligonucleotides as shown in SEQ ID NOs: 87 and 88.

Strains of *E. coli* BL21 (DE3) were transformed under the same conditions as in Example 1 to obtain strains of *E. coli* BL21 (DE3) (pET22b-PnFX-62D/63H/106K/110L/113K/351S).

5. Introduction of Point Mutation into Gene of Fructosyl Peptide Oxidase Derived from *Cryptococcus neoformans*

SEQ ID NO: 89 shows the amino acid sequence of fructosyl amino acid oxidase derived from *Cryptococcus neoformans* (hereafter referred to as "CnFX"), and it can be prepared by *E. coli* strains carrying the recombinant plasmid pET22b-CnFX into which the gene (SEQ ID NO: 90) encoding the amino acid sequence as shown in SEQ ID NO: 89 has been inserted. CnFX is confirmed to exhibit oxidation activity on αFV and αFVH (see WO 2012/018094).

In order to introduce a mutation aimed at improvement of substrate specificity into CnFX, in the same manner as in Example 1, PCR was carried out with the use of the recombinant plasmid pET22b-CnFX prepared in the manner as described above as a template, synthetic oligonucleotides as shown in SEQ ID NOs: 91 and 92, and KOD-Plus- (manufactured by TOYOBO CO., LTD.), strains of *E. coli* JM109 were transformed, and nucleotide sequences of DNAs encoding the CnFX variant in the plasmid DNAs carried on the grown colonies were determined. As a result, a recombinant plasmid encoding the CnFX gene comprising an amino acid sequence derived from the amino acid sequence as shown in SEQ ID NO: 89 by substitution of arginine at position 62 with aspartic acid was obtained (pET22b-CnFX-62D).

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid and serine at position 106 with lysine (pET22b-CnFX-62D/106K) was obtained with the use of pET22b-CnFX-62D as a template and synthetic oligonucleotides as shown in SEQ ID NOs: 93 and 94.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, and serine at position 110 with leucine, (pET22b-CnFX-62D/106K/110L) was obtained with the use of pET22b-CnFX-62D/106K as a template and synthetic oligonucleotides as shown in SEQ ID NOs: 95 and 96.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, serine at position 110 with leucine, and alanine at position 113 with lysine (pET22b-CnFX-62D/106K/110L/113K) was obtained with the use of pET22b-PnFX-62D/106K/110L as a template and synthetic oligonucleotides as shown in SEQ ID NOs: 97 and 98.

Strains of *E. coli* BL21 (DE3) were transformed under the same conditions as in Example 1 to obtain strains of *E. coli* BL21 (DE3) (pET22b-CnFX-62D/106K/110L/113K).

6. Introduction of Point Mutation into Amadoriase Gene Exhibiting 95% Sequence Identity with Ketoamine Oxidase Derived from *Curvularia clavata*

(Preparation of Amadoriase-Producing Strain Exhibiting 95% Sequence Identity with Ketoamine Oxidase Derived from *Curvularia clavata*)

SEQ ID NO: 99 shows the amino acid sequence of an amadoriase exhibiting 95% sequence identity with ketoamine oxidase derived from *Curvularia clavata* (hereafter referred to as "Cc95FX"). The gene (SEQ ID NO: 100) encoding the amino acid sequence as shown in SEQ ID NO: 99 was obtained via total synthesis of cDNA by a conventional technique of PCR of a gene fragment. The NdeI site and the BamHI were added to the 5' terminus and the 3' terminus of SEQ ID NO: 100, respectively.

In order to express the gene as shown in SEQ ID NO: 100 in *E. coli*, subsequently, the following procedures were performed. The gene obtained via total synthesis above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-Cc95FX was obtained. Strains of *E. coli* BL21 (DE3) were transformed under the conditions as described above to obtain strains of *E. coli* BL21 (DE3) (pET22b-Cc95FX).

(Introduction of Point Mutation into Amadoriase Gene Exhibiting 95% Sequence Identity with Ketoamine Oxidase Derived from *Curvularia clavata*)

In order to introduce a mutation aimed at improvement of substrate specificity into Cc95FX, in the same manner as in Example 1, PCR was carried out with the use of the recombinant plasmid pET22b-Cc95FX prepared in the manner as described above as a template, synthetic oligonucleotides as shown in SEQ ID NOs: 101 and 102, and KOD-Plus- (manufactured by TOYOBO CO., LTD.), strains of *E. coli* JM109 were transformed, and nucleotide sequences of DNAs encoding the Cc95FX variant in the plasmid DNAs carried on the grown colonies were determined. As a result, a recombinant plasmid encoding the Cc95FX gene comprising an amino acid sequence derived from the amino acid sequence as shown in SEQ ID NO: 99 by substitution of arginine at position 62 with aspartic acid was obtained (pET22b-Cc95FX-62D).

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid and aspartic acid at position 106 with lysine (pET22b-Cc95FX-62D/106K) was obtained with the use of pET22b-Cc95FX-62D as a template and synthetic oligonucleotides as shown in SEQ ID NOs: 103 and 104.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, and alanine at position 110 with leucine (pET22b-Cc95FX-62D/106K/110L) was obtained with the use of pET22b-Cc95FX-62D/106K as a template and synthetic oligonucleotides as shown in SEQ ID NOs: 105 and 106.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, and alanine at position 113 with lysine (pET22b-Cc95FX-62D/106K/110L/113K) was obtained with the use of pET22b-Cc95FX-62D/106K/110L as a template and synthetic oligonucleotides as shown in SEQ ID NOs: 107 and 108.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, alanine at position 113 with lysine, and alanine at position 353 with serine (pET22b-Cc95FX-62D/106K/110L/113K/353S) was obtained with the use of pET22b-Cc95FX-62D/106K/110L/113K as a template and synthetic oligonucleotides as shown in SEQ ID NOs: 109 and 110.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, leucine at position 63 with histidine, aspartic acid at position 106 with lysine, alanine at position 110 with leucine, alanine at position 113 with lysine, and alanine at position 353 serine (pET22b-Cc95EX-62D/63H/106K/110L/113K/353S) was obtained with the use of pET22b-Cc95FX-62D/106K/110L/113K/353S as a template and synthetic oligonucleotides as shown in SEQ ID NOs: 111 and 102.

Strains of E. coli BL21 (DE3) were transformed under the same conditions as in Example 1 to obtain strains of E. coli BL21 (DE3) (pET22b-Cc95FX-62D/63H/106K/110L/113K/353S).

Example 4

Production and Purification of Various Types of Amadoriases

Production and Purification of Fructosyl Peptide Oxidase Derived from *Eupenicillium terrenum*

E. coli JM109 producing wild-type EFP-T5 and E. coli JM109 E. coli JM109 (pUTE100K'-EFP-T5-62D), and E. coli JM109 (pUTE100K'-EFP-T5-62D/63H/106K/110L/113K/355S) producing the modified EFP-T5 in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

To the resulting crude enzyme solution containing the wild-type or modified EFP-T5 ammonium sulfate was added to bring the concentration of the solution to 35% saturation, the mixture was agitated, and the resultant was centrifuged at 20,000×g for 10 to collect a supernatant. Subsequently, ammonium sulfate was further added to the supernatant to bring the concentration of the solution to 70% saturation, the mixture was agitated, and the resultant was centrifuged at 20,000×g for 10 minutes. The supernatant was then discarded and the precipitate was dissolved in 10 mM potassium phosphate buffer (pH 7.0).

The resulting crude enzyme solution containing the wild-type or modified EFP-T5 dialyzed against 10 mM potassium phosphate buffer (pH 6.5), the resultant was applied to 4 ml of Q Sepharose Fast Flow resin (manufactured by GE Healthcare) equilibrated with the buffer, and proteins not adsorbed on the resin were eluted with the aid of the buffer. Subsequently, the resulting crude enzyme solution containing the wild-type or modified EFP-T5M enzyme was dialyzed against a 10 mM potassium phosphate buffer (pH 8.0), the resultant was allowed to adsorb to the HiLoad 26/10 Q Sepharose HP column (manufactured by GE Healthcare) equilibrated with the buffer, and the resin was washed with the same buffer. While linearly increasing the concentration of NaCl in the buffer from 0 mM to 100 the wild-type or modified EFP-T5 enzyme which were adsorbed to the resin were then eluted and collected.

The resulting crude enzyme solution containing the wild-type or modified EFP-T5 was applied to the HiLoad 26/600 Superdex 200 column equilibrated with a 10 mM potassium phosphate buffer (pH 7.0) containing 150 mM NaCl so as to elute the wild-type or modified EFP-T5 enzyme with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified EFP-T5 enzyme.

(Production and Purification of Ketoamine Oxidase Derived from *Neocosmospora vasinfecta*)

E. coli BL21 (DE3) producing the wild-type NvFX and E. coli BL21 (DE3) (pET22b-NvFX) and E. coli BL21 (DE3) (pET22b-NvFX-62D/106K/110L) producing the modified NvFX obtained in the manner described above were inoculated into LB-amp media supplemented with IPTG (final concentration: 0.1 mM) and cultured therein at 25° C. for 16 The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and the wild-type or modified NvFX that were adsorbed to the resin were then eluted and collected with the aid of a 10 mM potassium phosphate buffer (pH 8.0) containing 300 mM NaCl.

The resulting crude enzyme solution containing the wild-type or modified NvFX was applied to the HiLoad 26/600 Superdex 200 column equilibrated with a 20 mM MES-NaOH buffer (pH 7.0) containing 150 mM NaCl so as to elute the wild-type or modified NvFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified NvFX.

(Production and Purification of Fructosyl Amino Acid Oxidase Derived from *Aspergillus nidulans*)

*E. coli* BL21 (DE3) producing the wild-type AnFX and *E. coli* BL21 (DE3) (pET22b-AnFX-61D/105K/109L) and *E. coli* BL21 (DE3) (pET22b-AnFX-61D/62H/101K/105K/109L/112K/355S) producing the modified AnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 6.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to SP Sepharose Fast Flow resin (manufactured by GE Healthcare) equilibrated with a 10 mM potassium phosphate buffer (pH 6.0), the resin was washed with a 10 mM potassium phosphate buffer (pH 6.0) containing 20 mM NaCl, and the modified AnFX that was adsorbed to the resin was then eluted and collected with the aid of a 10 mM potassium phosphate buffer (pH 6.0) containing 100 mM NaCl.

The resulting crude enzyme solutions containing the modified AnFX were applied to the HiLoad 26/600 Superdex 200 column equilibrated with a 20 mM MES-NaOH buffer (pH 7.0) containing 150 mM NaCl so as to elute modified AnFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the modified AnFX.

(Production and Purification of Fructosyl Peptide Oxidase Derived from *Phaeosphaeria nodorum*)

*E. coli* BL21 (DE3) (pET22b-PnFX-62D/106K/110L/113K) and *E. coli* BL21 (DE3) (pET22b-PnFX-62D/63H/106K/110L/113K/351S) producing the modified AnFX obtained in the manner described above were purified in accordance with the method for purification of the wild-type PnFX described above. After the completion of purification with the HiLoad 26/600 Superdex 200 column, the degree of purification was analyzed via SDS-PAGE to confirm that the fraction was sufficiently purified, so that no other contaminating proteins were present therein, and the fraction was designated to be a purified sample of the modified PnFX.

(Production and Purification of Ketoamine Oxidase Derived from *Cryptococcus neoformans*)

*E. coli* BL21 (DE3) producing the wild-type CnFX and *E. coli* BL21 (DE3) (pET22b-CnFX) and *E. coli* BL21 (DE3) (pET22b-CnFX-62D/106K/110L/113K) producing the modified CnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and the wild-type or modified CnFX that were adsorbed to the resin were then eluted and collected with the aid of a 10 mM potassium phosphate buffer (pH 8.0) containing 300 mM NaCl.

The resulting crude enzyme solution containing the wild-type or modified CnFX was applied to the HiLoad 26/600 Superdex 200 column equilibrated with a 20 mM MES-NaOH buffer (pH 7.0) containing 150 mM NaCl so as to elute the wild-type or modified CnFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified CnFX.

(Preparation of Amadoriase Exhibiting 95% Sequence Identity with Ketoamine Oxidase Derived from *Curvularia clavata*)

*E. coli* JM109 producing the wild-type Cc95FX and *E. coli* JM109 and *E. coli* JM109 (pET22b-Cc95FX-62D/63H/106K/110L/113K/355S) producing the modified Cc95FX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

With the use of the purified samples of various types of wild-type amadoriases and modified enzymes, specific activity thereof relative to αF6P as substrates was measured. The results are shown in Table 14. Concentration of a protein used for calculation of specific activity was determined by the ultraviolet absorption method involving the use of the absorbance at 280 nm (see Protein Sci., 4, 2411-23, 1995).

A crude enzyme solution containing Cc95FX or Cc95FX-62D/63H/106K/110L/113K/355S was subjected to measurement of oxidation activity on αFV, αFVH, and αF6P by the method described in the "B: Method of activity measurement" above. Oxidation activity on substrates, αF6P/αFVH, and αF6P/FV of amadoriases relative to αFVH oxidation activity designated to be 100 are as shown in Table 15.

TABLE 14

| Amadoriase | Amino acid mutation | Specific activity (U/mg) 1 mM αF6P |
|---|---|---|
| EFP-T5 (Comparative Example 4) | None | 0 |
| EFP-T5-R62D (Amadoriase 27) | R62D | 0.0043 |
| EFP-T5-62D/63H/106K/110L/113K/355S (Amadoriase 28) | R62D, L63H, N106K, K110L, T113K, A355S | 1.12 |
| NvFX (Comparative Example 5) | None | 0 |

TABLE 14-continued

| Amadoriase | Amino acid mutation | Specific activity (U/mg) 1 mM αF6P |
|---|---|---|
| NvFX-62D/106K/110L (Amadoriase 29) | R62D, G106K, E110L | 0.0030 |
| AnFX (Comparative Example 6) | None | 0 |
| AnFX-61D/105K/109L (Amadoriase 30) | R61D, G105K, K109L | 0.106 |
| AnFX-61D/62H/101K/ 105K/109L/112K/355S (Amadoriase 31) | R61D, L62H, E101K, G105K, K109L, S112K, A355S | 0.283 |
| PnFX (Comparative Example 3) | None | 0.0091 |
| PnFX-62D/106K/110L/113K (Amadoriase 32) | S62D, D106K, G110L, A113K | 0.125 |
| PnFX-62D/63H/106K/110L/ 113K/351S (Amadoriase 33) | S62D, L63H, D106K, G110L, A113K, A351S | 0.667 |
| CnFX (Comparative Example 7) | None | 0 |
| CnFX-62D/106K/110L/113K (Amadoriase 34) | R62D, S106K, S110L, A113K | 0.342 |

TABLE 15

| Amadoriase | Amino acid substitution | αFV oxidation activity | αFVH oxidation activity | αF6P oxidation activity | αF6P/ αFVH | αF6P/ αFV |
|---|---|---|---|---|---|---|
| Cc95FX (Comparative Example 8) | None | 100 | 0 | 0 | 0 | |
| Cc95FX-62D/ 63H/106K/ 110L/113K/ 353S (Amadoriase 35) | R62D/ L63H/ D106K/ A110L/ A113K/ A353S | 16400 | 100 | 237 | 2.37 | 0.0144 |

As a result of introducing into various amadoriases the amino acid substitutions which confer or enhance reactivity with αF6P in comparison with the amadoriase from Coniochaeta introduced in accordance with the procedure described herein (CFP-T7; Comparative Example 1), reactivity with αF6P, was newly conferred upon EFP-T5, NvFX, AnFX, and CnFX, as expected. While PnFX had exhibited a minor level of reactivity with αF6P prior to mutation, specific activity on αF6P was elevated by 13.7 fold as a result of introduction of the amino acid substitution described herein.

Further, amino acid substitution aimed at addition or enhancement of reactivity with αF6P relative to the amadoriase derived from Coniochaeta obtained in accordance with the procedure described herein (CFP-T7; Comparative Example 1) was introduced into an amadoriase (Cc95FX; Comparative Example 8) exhibiting 95% sequence identity with the ketoamine oxidase derived from Curvularia clavata obtained in accordance with the procedure described herein. As a result and as expected, reactivity with αF6P, was newly conferred upon Cc95FX, and regarding Cc95FX-62D/63H/ 106K/110L/113K/355S, αF6P oxidation activity exceeded αFVH oxidation activity.

Figures 2, 4:
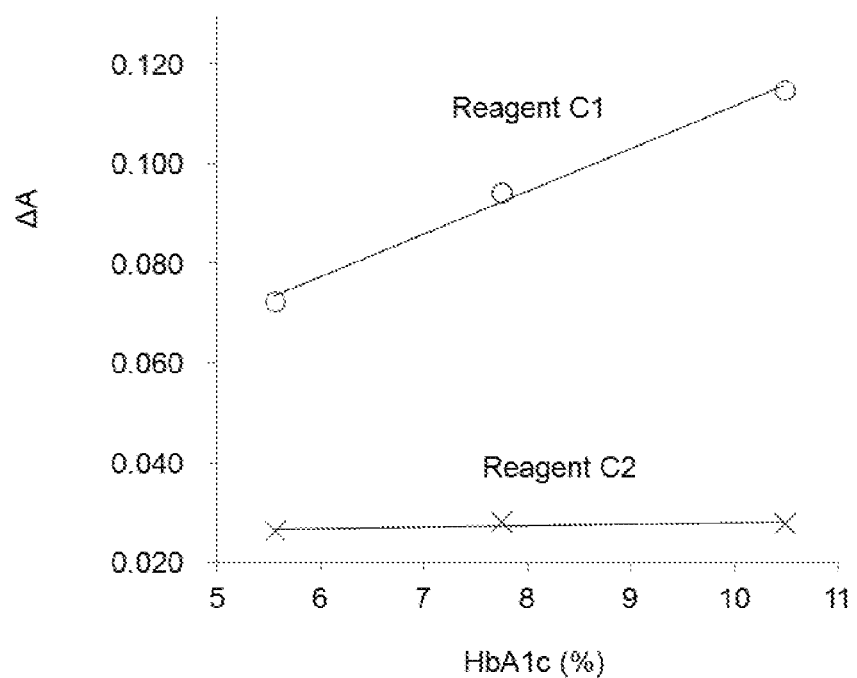

That is, the effects of amino acid substitution aimed at addition or enhancement of reactivity with αF6P to the amadoriase derived from Coniochaeta described herein are not limited to the amadoriase derived from Coniochaeta but rather, reactivity with αF6P was added to or enhanced similarly in general in amadoriases exhibiting 74% or higher sequence identity with the amadoriase derived from Coniochaeta as shown in FIGS. 1 and 2.

Table 14 demonstrates that Amadoriases 30 resulting from introduction of mutations (61D/105K/110L) into AnFX exhibits 0.1 or higher specific activity on αF6P. That is, a modified amadoriase exhibiting 0.1 or higher specific activity on αF6P was obtained through introduction of triple mutations into an enzyme. Also, Amadoriases 32 resulting from introduction of 62D/106K/110L/113K into PnFX exhibited 0.1 or higher specific activity on αF6P. That is, a modified amadoriase exhibiting 0.1 or higher specific activity on αF6P was obtained through introduction of quadruple mutations into an enzyme. In addition, specific activity on αF6P was further enhanced through introduction of additional mutations.

It was shown in this description that the effects of introduced substitutions accumulate. Accordingly, a person skilled in the art will appreciate that a mutation that improves activity of an amadoriase on αF6P is not limited to a particular mutation or a particular combination of mutations and that mutations at positions 62, 63, 102, 106, 110, 113, 355, 419, 68, and 356 described herein and mutations that enhance activity on αF6P at positions other than those described above can be employed in any combination. As described in Examples 5 to 7 below, a person skilled in the art will also understand that amadoriases having activity on αF6P can be used for the method of HbA1c measurement according to the present invention.

The tables below show the amino acids at positions 62, 63, 102, 106, 110, 113, 355, and 419 and amino acids after substitution, if any, of the variants of the present invention and of the Comparative Examples.

TABLE 16

| Name | Comparative Example 1 CFP-T7 Coniochaeta sp. | Comparative Example 3 PnFX Phaeosphaeria nodorum | Comparative Example 5 NvFX Neocosmospora vasinfecta | Comparative Example 6 AnFX Aspergillus nidulans | Comparative Example 4 EFP-T5 Eupenicillium terrenum | Comparative Example 7 CnFX Cryptococcus neoformans | Comparative Example 8 Cc95FX Curvularia clavata | Comparative Example 2 FAOAo2 Aspergillus oryzae |
|---|---|---|---|---|---|---|---|---|
| Origin | | | | | SEQ ID NO | | | |
| aa position | SEQ 1 | SEQ 38 | SEQ 54 | SEQ 62 (SEQ 147) | SEQ 40 (SEQ 145) | SEQ 89 (SEQ 149) | SEQ 99 | SEQ 36 |
| 62 | R | S | R | R61 | R | R | R | |
| 63 | L | L | L | L62 | L | I | L | |
| 102 | E | K | E | E101 | E | E | E | |
| 106 | D | D | G | G105 | N | S | D | |
| 110 | Q | G | E | K109 | K | S | A | |

TABLE 16-continued

| Name | Comparative Example 1 CFP-T7 | Comparative Example 3 PnFX | Comparative Example 5 NvFX | Comparative Example 6 AnFX | Comparative Example 4 EFP-T5 | Comparative Example 7 CnFX | Comparative Example 8 Cc95FX | Comparative Example 2 FAOAo2 |
|---|---|---|---|---|---|---|---|---|
| Origin | Coniochaeta sp. | Phaeosphaeria nodorum | Neocosmospora vasinfecta | Aspergillus nidulans | Eupenicillium terrenum | Cryptococcus neoformans | Curvularia clavata | Aspergillus oryzae |
| | | | | SEQ ID NO | | | | |
| aa position | SEQ 1 | SEQ 38 | SEQ 54 | SEQ 62 (SEQ 147) | SEQ 40 (SEQ 145) | SEQ 89 (SEQ 149) | SEQ 99 | SEQ 36 |
| 113 | A | A | K | S112 | T | A | A | |
| 355 | A | A351 | S | A | A | A | A353 | |
| 419 | A | S416 | A420 | A420 | G | A420 | S418 | |

TABLE 17

| Name | PyFX | ArFX | CcFX | EnFx | UlFX | PjFX |
|---|---|---|---|---|---|---|
| Origin | Pyrenochaeta sp. | Arthrinium sp. | Curvularia clavata | Emericella nidulans | Ulocladium sp. | Penicillium janthinellum |
| | | | SEQ ID NO | | | |
| aa position | SEQ 113 | SEQ 115 | SEQ 117 | SEQ 119 | SEQ 121 | SEQ 123 |
| 62 | R | R | R | R61 | R | R |
| 63 | L | L | L | L62 | L | L |
| 102 | K | K | E | E101 | K | E |
| 106 | D | A | D | K105 | D | S |
| 110 | A | Q | A | R109 | A | K |
| 113 | T | T | A | S112 | A | D |
| 355 | A353 | A356 | A353 | A | A353 | A |
| 419 | A418 | A421 | A418 | A420 | A418 | S |

TABLE 18

| Name | Amadoriase 26 CFP-T7-62D | Amadoriase 1 CFP-T7-H1 | Amadoriase 2 CFP-T7-H2 | Amadoriase 4 CFP-T7-H4 | Amadoriase 5 CFP-T7-H2-62N | Amadoriase 6 CFP-T7-H6 | Amadoriase 27 eFP-T5-R62D |
|---|---|---|---|---|---|---|---|
| Origin | Coniochaeta sp. | Coniochaeta sp. | Coniochaeta sp. | Coniochaeta sp. | Coniochaeta sp. | Coniochaeta sp. | Eupenicillium terrenum |
| | | | | SEQ ID NO | | | |
| aa position | SEQ 153 | SEQ 151 | SEQ 157 | SEQ 159 | SEQ 161 | SEQ 163 | SEQ 155 |
| 62 | R62D | R62A | R62A | R62A | R62N | R62D | R62D |
| 63 | | | | | | | |
| 102 | | | | | | | |
| 106 | | | | | | | |
| 110 | | | Q110L | Q110Y | Q110L | Q110L | |
| 113 | | | | | | | |
| 355 | | | | | | | |
| 419 | | | | | | | |

TABLE 19

| Name | Amadoriase 12 CPF-T7-H10 | Amadoriase 13 CPF-T7-H11 | Amadoriase 14 CPF-T7-H12 | Amadoriase 15 CPF-T7-H13 | Amadoriase 16 CPF-T7-H14 | Amadoriase 29 NvFX-62D/106K/110L | Amadoriase 30 AnFX-61D/105K/109L |
|---|---|---|---|---|---|---|---|
| Origin | Coniochaeta sp. | Coniochaeta sp. | Coniochaeta sp. | Coniochaeta sp. | Coniochaeta sp. | Neocosmospora vasinfecta | Aspergillus nidulans |
| | | | | SEQ ID NO | | | |
| aa position | SEQ 165 | SEQ 167 | SEQ 169 | SEQ 171 | SEQ 173 | SEQ 137 | SEQ 139 |
| 62 | R62D | R62D | R62D | R62D | R62D | R62D | R61D |
| 63 | | | | | | | |
| 102 | | | | | | | |
| 106 | D106A | D106K | D106R | | | G106K | G105K |
| 110 | Q110L | Q110L | Q110L | Q110L | Q110L | E110L | K109L |

TABLE 19-continued

| Name | Amadoriase 12 CPF-T7-H10 | Amadoriase 13 CPF-T7-H11 | Amadoriase 14 CPF-T7-H12 | Amadoriase 15 CPF-T7-H13 | Amadoriase 16 CPF-T7-H14 | Amadoriase 29 NvFX-62D/ 106K/110L | Amadoriase 30 AnFX-61D/ 105K/109L |
|---|---|---|---|---|---|---|---|
| Origin | Coniochaeta sp. | Coniochaeta sp. | Coniochaeta sp. | Coniochaeta sp. | Coniochaeta sp. | Neocosmospora vasinfecta | Aspergillus nidulans |
| | | | | SEQ ID NO | | | |
| aa position | SEQ 165 | SEQ 167 | SEQ 169 | SEQ 171 | SEQ 173 | SEQ 137 | SEQ 139 |
| 113 | | | | A113K | A113R | | |
| 355 | | | | | | | |
| 419 | | | | | | | |

TABLE 20

| Name | Amadoriase 17 CPF-T7-H20 | Amadoriase 18 CPF-T7-H21 | Amadoriase 19 CPF-T7-H24 | Amadoriase 21 CPF-T7-H26 | Amadoriase 32 PnFX-62D/ 106K/110L/113K | Amadoriase 34 CnFX-62D/ 106K/110L/113K |
|---|---|---|---|---|---|---|
| Origin | Coniochaeta sp. | Coniochaeta sp. | Coniochaeta sp. | Coniochaeta sp. | Phaeosphaeria nodorum | Cryptococcus neoformans |
| | | | | SEQ ID NO | | |
| aa position | SEQ 133 | SEQ 175 | SEQ 177 | SEQ 179 | SEQ 135 | SEQ 189 |
| 62 | R62D | R62D | R62D | R62D | S62D | R62D |
| 63 | | | L63A | L63H | | |
| 102 | | | | | | |
| 106 | D106K | D106K | D106K | D106K | D106K | S106K |
| 110 | Q110L | Q110L | Q110L | Q110L | G110L | S110L |
| 113 | A113K | A113R | A113K | A113K | A113K | A113K |
| 355 | | | | | | |
| 419 | | | | | | |

TABLE 21

| Name | Amadoriase 23 CPF-T7-H28 | Amadoriase 24 CPF-T7-H29 | Amadoriase 25 CFP-T7-H35 | Amadoriase 33 PnFX-62D/ 106K/110L/ 113K/351S | Amadoriase 31 AnFX-61D/ 101K/105K/ 109L/112K/355S | Amadoriase 28 EFP-T5-62D/ 63H/106K/110L/ 113K/355S | Amadoriase 35 Cc95FX-62D/ 63H/106K/110L/ 113K/353S |
|---|---|---|---|---|---|---|---|
| Origin | Coniochaeta sp. | Coniochaeta sp. | Coniochaeta sp. | Phaeosphaeria nodorum | Aspergillus nidulans | Eupenicillium terrenum | Curvularia clavata |
| | | | | SEQ ID NO | | | |
| aa position | SEQ 181 | SEQ 183 | SEQ 141 | SEQ 187 | SEQ 185 | SEQ 143 | SEQ 191 |
| 62 | R62D | R62D | R62D | S62D | R61D | R62D | R62D |
| 63 | L63H | L63H | L63H | L63H | L62H | L63H | L63H |
| 102 | E102K | | E102K | | E101K | | |
| 106 | D106K | D106K | D106K | D106K | G105K | N106K | D106K |
| 110 | Q110L | Q110L | Q110L | G110L | K109L | K110L | A110L |
| 113 | A113K | A113K | A113K | A113K | S112K | T113K | A113K |
| 355 | | | A355S | A351S | A355S | A355S | A353S |
| 419 | | A419K | | | | | |

Example 5

Quantification of HbA1c

Reagents for measurement of HbA1c having the compositions described below were prepared and HbA1c was measured with the use of Bio Majesty JCA-BM1650 (JEOL Ltd.) in the manner as described below.
Sample: HbA1c Solution
 the certified reference material for measurement of HbA1c, JCCRM-423-8 (Reference Material Institute for Clinical Chemistry Standards),
 total hemoglobin concentration: 133 g/l,
 three HbA1c concentration levels (NGSP levels: 5.56%, 7.74%, 10.48%)
Reagent A1: Sample Pre-Treatment Solution
 5.0% n-dodecyl-β-D-maltoside (Dojindo Laboratories)

Reagent A2: Sample Pre-Treatment Solution
 5.0% n-tetradecyl-β-D-maltoside (Sigma-Aldrich Co. LLC.)
Reagent B: Leucodye, Peroxidase Solution
 150 mM potassium phosphate buffer (pH 6.5)
 0.30 mM N-(carboxymethylaminocarbonyl)-4,4'-bis(dimethylamino)diphenylamine sodium (DA-64, Wako Pure Chemical Industries, Ltd.)
 15 U/ml peroxidase (Kikkoman Corporation)
Reagent C1: CFP-T7-H35 Solution
 120 mM potassium phosphate buffer (pH 6.5)
 120 U/ml (28 mg/ml) CFP-T7-H35 (Amadoriase 25)
Reagent C2: CFP-T7 Solution
 120 mM potassium phosphate buffer (pH 6.5)
 28 mg/ml CFP-T7 (Comparative Example 1)
A sample diluted 30 fold with Reagent A1 or Reagent A2 (hereafter, it is referred to as a "sample diluent") was incubated at 98° C. for 2 minutes, 25 μl of the sample diluent was added to 50 μl of Reagent B, the mixture was incubated at 37° C. for 5 minutes, 25 μl of Reagent C1 or Reagent C2 was added thereto, and quantification of hydrogen peroxide generated upon oxidation of the HbA1c β-chain amino terminus was then allowed to proceed at 37° C. for 5 minutes. When hydrogen peroxide is generated in the solution, a leucodye develops color by the action of peroxidase, and the absorbance of light at 751 nm increases. As an example, the correlation between the time elapsed after the sample diluent was mixed with Reagent B and the absorbance when HbA1c is measured with the use of Reagent A2 and Reagent C1 is shown in FIG. 3. In this case, an increased absorbance caused by generation of hydrogen peroxide was observed immediately after the addition of the CFP-T7-H35 (Reagent C1). On the basis of the results attained depending on the HbA1c concentration in the sample, a chart showing the HbA1c concentration in the sample (i.e., the NGSP level) plotted along the horizontal axis and a difference in the absorbance of light at 751 nm before and after hydrogen peroxide quantification (ΔA) plotted along the vertical axis was prepared.

ΔA was calculated in accordance with the equation below.

$\Delta A$=(absorbance 5 minutes after the addition of Reagent $C1$ or Reagent $C2$)−(absorbance immediately before the addition of Reagent $C1$ or Reagent $C2$×0.75)

Since the volume of the reaction solution was increased 1.33 fold with the addition of Reagent C1 or Reagent C2, the value attained by multiplying the absorbance immediately before the addition of Reagent C1 or Reagent C2 by 0.75 was considered to be the absorbance immediately after the addition of Reagent C1 or Reagent C2. FIG. 4-1 shows the results attained when the sample was diluted with Reagent A1, and FIG. 4-2 shows the results attained when the sample was diluted with Reagent A2.

When Reagent C1 was used, a good correlation was established between the HbA1c concentration and ΔA. When Reagent C2 was used, however, no correlation was observed between the HbA1c concentration and ΔA. Such tendency was not influenced by the type of sample pretreatment solution (Reagent A1 or A2). Thus, an amadoriase exhibiting αF6P oxidation activity was found to exhibit oxidation activity on the HbA1c β-chain, and such amadoriase was found to be able to perform HbA1c quantification rapidly and accurately without the use of a protease or the like.

Example 6

Quantification of HbA1c Pre-Treated with Acid

Reagents for measurement of HbA1c having the compositions described below were prepared and HbA1c was measured with the use of Bio Majesty JCA-BM1650 (JEOL Ltd.) in the manner described below. In Example 6, an acidified nonionic surfactant was used as a pretreatment solution for the HbA1c sample.
Sample: HbA1c Solution
  the certified reference material for measurement of HbA1c, JCCRM-423-8 (Reference Material Institute for Clinical Chemistry Standards)
  total hemoglobin concentration: 133 g/l,
  three HbA1c concentration levels (NGSP levels: 5.56%, 7.74%, and 10.48%); or the certified reference material for measurement of HbA1c, JCCRM-423-9b (Reference Material Institute for Clinical Chemistry Standards),
  total hemoglobin concentration: 133 g/l,
  three HbA1c concentration levels (NGSP levels: 5.61%, 7.71%, and 10.55%)
Reagent D1: Sample Pre-t Real Merit Solution
  8.3% n-dodecyl-β-D-maltoside (Dojindo Laboratories)
  0.1 M hydrochloric acid
Reagent D2: Sample Pre-Treatment Solution
  8.3% polyoxethylene (20) cetyl ether (Brij58, Wako Pure Chemical Industries, Ltd.)
  0.1 M hydrochloric acid
Reagent E: Leucodye Solution
  30 mM Tris-potassium phosphate buffer (pH 9.0)
  290 mM potassium phosphate buffer (pH 6.5)
  0.16 mM N-(carboxymethylaminocarbonyl)-4,4'-bis(dimethylamino)diphenylamine sodium (DA-64, Wako Pure Chemical Industries, Ltd.)
Reagent F1: Peroxidase, CFP-T7-H35 Solution
  100 mM potassium phosphate buffer (pH 6.5)
  40 U/ml peroxidase (Kikkoman Corporation)
  180 U/ml (42 mg/ml) CFP-T7-H35 (Amadoriase 25)
Reagent F2: Peroxidase, EFP-T5-62D/63H/106K/110L/113K/355S
  100 mM potassium phosphate buffer (pH 6.5)
  40 U/ml peroxidase (Kikkoman Corporation)
  30 U/ml (27 mg/ml) EFP-T5-62D/63H/106K/110L/113K/355S solution (Amadoriase 28)

Figure 5:
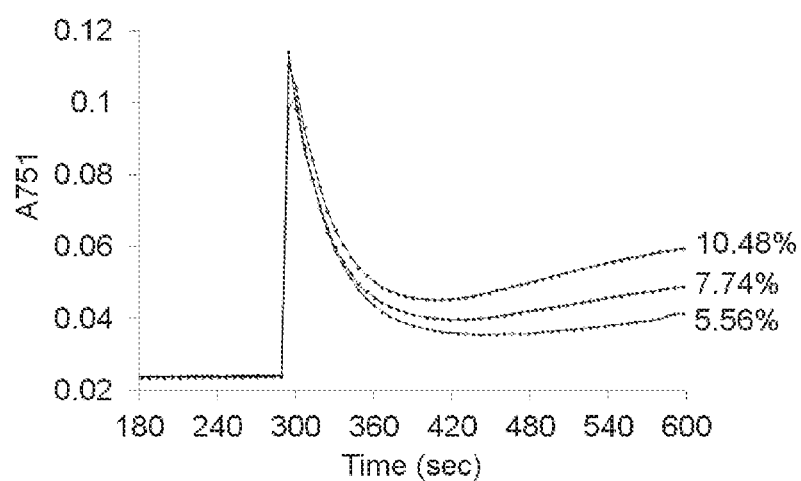

A sample diluted 30 fold with Reagent D1 or Reagent D2 (25 μl) was added to 125 μl of Reagent E, the mixture was incubated at 37° C. for 5 minutes, 50 μl of Reagent F1 was added thereto, and quantification of hydrogen peroxide generated upon oxidation of the HbA1c β-chain amino terminus was then allowed to proceed at 37° C. for 5 minutes. Also, a sample diluted 30 fold with Reagent D1 (25 μl) was added to 125 μl of Reagent E, the mixture was incubated at 37° C. for 5 minutes, 50 μl of Reagent F2 was added thereto, and quantification of hydrogen peroxide generated upon oxidation of the HbA1c β-chain amino terminus was then allowed to proceed at 37° C. for 5 minutes. As an example, the correlation between the time elapsed after the sample diluted with Reagent D1 was mixed with Reagent E and the absorbance is shown in FIG. 5-1. In this case, an increased absorbance caused by generation of hydrogen peroxide was observed immediately alter the addition of the CFP-T7-H35 solution (Reagent F1). On the basis of the results of measurement of HbA1c samples, a chart showing the HbA1c concentration in the sample (i.e., the NGSP level) plotted along the horizontal axis and a difference in the absorbance of light at 751 nm before and after hydrogen peroxide quantification (ΔA) plotted along the vertical axis was prepared.

ΔA was calculated in accordance with the equation below.

$\Delta A$=(absorbance 5 minutes after the addition of Reagent $F1$ or Reagent $F2$)−(absorbance immediately before the addition of Reagent $F1$ or Reagent $F2$×0.75)

Figures 1, 6:
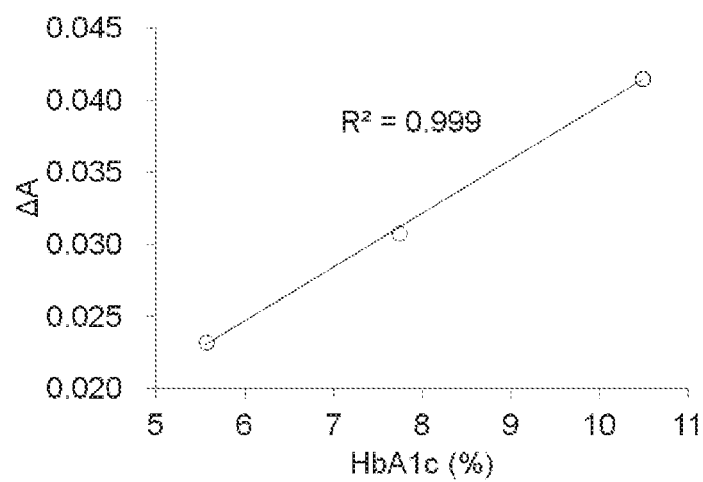
Figures 2, 6:
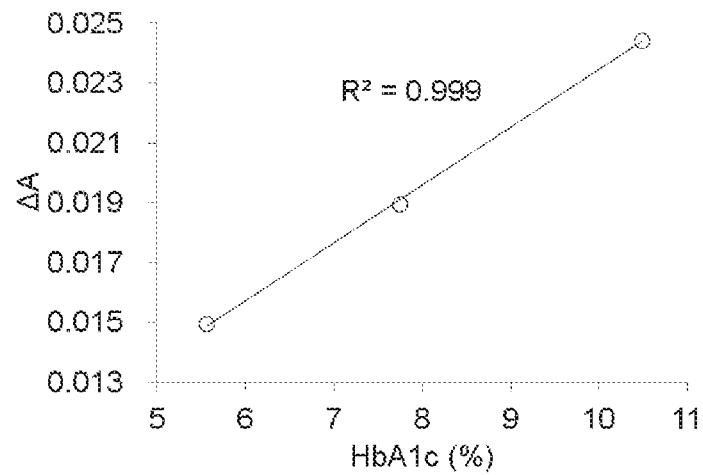
Figures 3, 6:
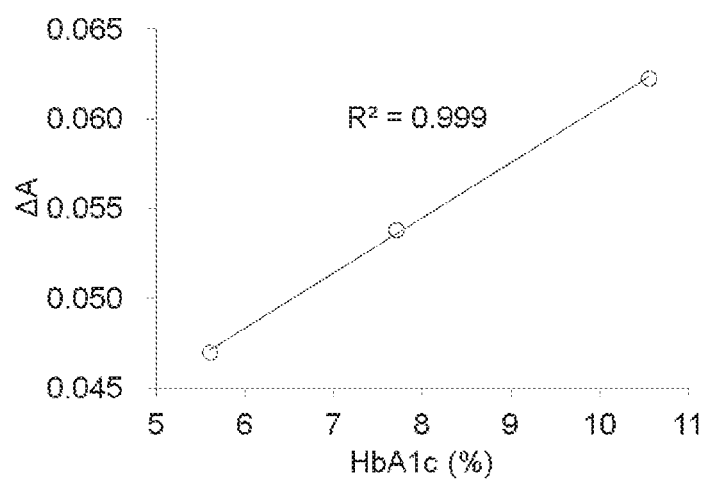

Since the volume of the reaction solution was increased 1.33 fold with the addition of Reagent F1 or Reagent F2, the value attained by multiplying the absorbance immediately before the addition of Reagent F1 or Reagent F2 by 0.75 was considered to be the absorbance immediately after the addition of Reagent F1 or Reagent F2. FIG. 6-1 shows the results attained when the sample was assayed with Reagent D1 and Reagent F1, FIG. 6-2 shows the results attained when the sample was assayed with the use of Reagent D2 and Reagent F1, and FIG. 6-3 shows the results attained when the sample was assayed with the use of Reagent D1 and Reagent F2.

In both cases where the sample was diluted with either Reagent D1 or Reagent D2, a good correlation was established between the HbA1c concentration and ΔA. As such, when denatured HbA1c is measured using an amadoriase exhibiting αF6P oxidation activity, HbA1c quantification can be performed rapidly and accurately even when HbA1c is denatured via acid treatment. Further, when a nonionic surfactant is present in the acidic solution used for denaturation, the type of nonionic surfactant which can be used was not limited. Furthermore, since HbA1c could be directly measured using modified amadoriases from different species, the amadoriase to be used for direct measurement of HbA1c is not limited, provided that such amadoriase exhibits a certain degree of reactivity with αF6P.

Example 7

Quantification of HbA1c Pre-Treated with Ionic Surfactant

Reagents for measurement of HbA1c having the compositions described below were prepared and HbA1c was measured with the use of Bio Majesty JCA-BM1650 (JEOL Ltd.) in the manner described below. In Example 7, an ionic surfactant solution was used as a pretreatment solution for the HbA1c sample.
Sample: HbA1c Solution
  the certified reference material for measurement of HbA1c, JCCRM-423-9b (Reference Material Institute for Clinical Chemistry Standards)
  total hemoglobin concentration: 133 g/l
  three HbA1c concentration levels (NGSP levels: 5.61%, 7.71%, and 10.55%)
Reagent G1: Sample Pre-Treatment Solution
  0.80% tetradecyltrimethylammonium bromide (Tokyo Chemical Industry Co., Ltd.)
Reagent G2: Sample Pre-Treatment Solution
  0.70% hexadecyltrimethylammonium bromide (Tokyo Chemical Industry Co., Ltd.)
Reagent H1: Leucodye Solution
  120 mM MOPS-NaOH buffer (pH 6.5)
  1.6% n-dodecyl-β-D-maltoside (Dojindo Laboratories)
  0.16 mM N-(carboxymethylaminocarbonyl)-4,4'-bis(dimethylamino)diphenylamine sodium (DA-64, Wako Pure Chemical Industries, Ltd.)
Reagent H2: Leucodye Solution
  120 mM PIPES-NaOH buffer (pH 6.5)
  1.6% n-dodecyl-β-D-maltoside (Dojindo Laboratories)
  0.16 mM N-(carboxymethylaminocarbonyl)-4,4'-bis(dimethylamino)diphenylamine sodium (DA-64, Wako Pure Chemical Industries, Ltd.)
Reagent I1: Peroxidase, CFP-DH2 Solution
  100 mM MOPS-NaOH buffer (pH 6.5)
  40 U/ml peroxidase (Kikkoman Corporation)
  160 U/ml (51 mg/ml) CFP-DH2 (Amadoriase 39)
Reagent I2: Peroxidase CFP-DH2 Solution
  100 mM PIPES-NaOH buffer (pH 6.5)
  40 U/ml peroxidase (Kikkoman Corporation)
  160 U/ml CFP-DH2

Figure 7:
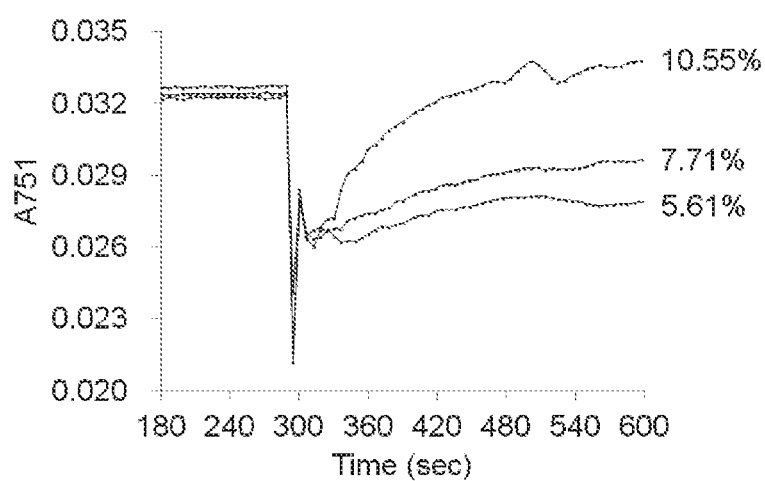
FIG. 7 shows the correlation between the time elapsed after the sample diluent (Reagent G1) has been mixed with a measurement reagent and absorbance, wherein HbA1c is measured using a modified amadoriase. An amadoriase solution is added after the elapse of 300 seconds.

A sample diluted 25 fold with Reagent G1 (25 µl) was added to 125 µl of Reagent H1, the mixture was incubated at 37° C. for 5 minutes, 50 µl of Reagent I1 was added thereto, and quantification of hydrogen peroxide generated upon oxidation of the HbA1c β-chain amino terminus was then allowed to proceed at 37° C. for 5 minutes. When the sample was diluted 25 fold with Reagent G2, 25 µl of the diluted sample was added to 125 µl of Reagent H2, the mixture was incubated at 37° C. for 5 minutes, 50 µl of Reagent I2 was added thereto, and quantification of hydrogen peroxide generated upon oxidation of the HbA1c β-chain amino terminus was then allowed to proceed at 37° C. for 5 minutes. As an example, the correlation between the time elapsed after the sample diluted with Reagent G1 was mixed with Reagent H1 and the absorbance is shown in FIG. 7-1. In this case, an increased absorbance caused by generation of hydrogen peroxide was observed immediately after the addition of the CFP-DH2 solution (Reagent I1). On the basis of the results of measurement of HbA1c samples, a chart showing the HbA1c concentration in the sample (i.e., the NGSP level) plotted along the horizontal axis and a difference in the absorbance of light at 751 nm before and after hydrogen peroxide quantification (ΔA) plotted along the vertical axis was produced.

ΔA was calculated in accordance with the equation below.

$$\Delta A = (\text{absorbance 5 minutes after the addition of Reagent } I1 \text{ or Reagent } I2) - (\text{absorbance immediately before the addition of Reagent } I1 \text{ or Reagent } I2 \times 0.75)$$

Figures 1, 8:
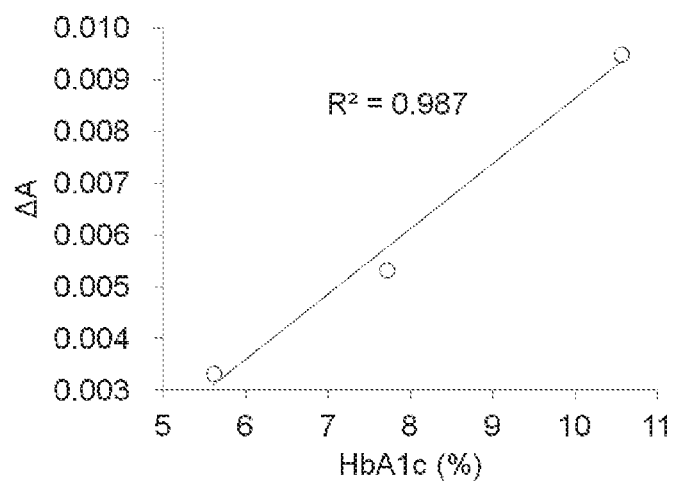
Figures 2, 8:
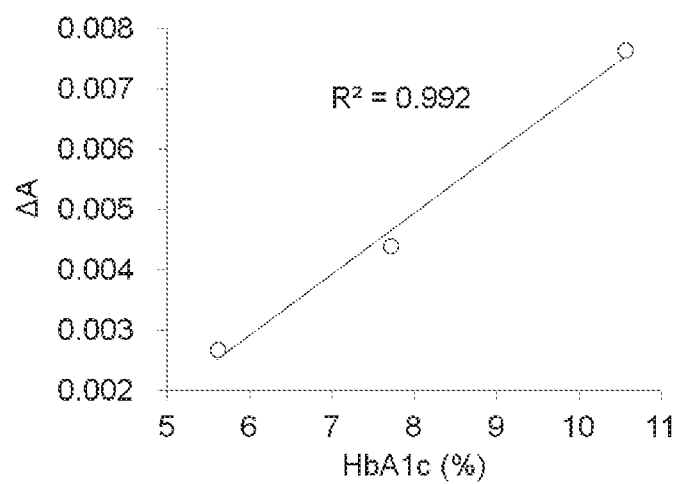

Since the volume of the reaction solution was increased 1.33 fold with the addition of Reagent I1 or Reagent I2, the value attained by multiplying the absorbance immediately before the addition of Reagent I1 or Reagent I2 by 0.75 was considered to be the absorbance immediately after the addition of Reagent I1 or Reagent I2. FIG. 8-1 shows the results attained when the sample was diluted with Reagent G1, and FIG. 8-2 shows the results attained when the sample was diluted with Reagent G2.

In both cases where the sample was diluted with either Reagent G1 or Reagent G2, a good correlation was established between the HbA1c concentration and ΔA. As such, when denatured HbA1c is measured using an amadoriase exhibiting αF6P oxidation activity, HbA1c quantification can be performed rapidly and accurately even when HbA1c is denatured via treatment with an ionic surfactant. Furthermore, it was also demonstrated that the type of ionic surfactant used for denaturing HbA1c is not limited when implementing the present assays.

As described above, CFP-T7-H35 recognized, as a substrate, a glycated peptide with a long peptide chain (i.e., αF6P), which could not serve as a substrate for the wild-type enzyme (CFP-T7). When an attempt of direct measurement of HbA1c was made using CFP-T7-H35 but without the processing step to cleave αF6P from HbA1c with a protease or the like, surprisingly, the HbA1c concentration in the sample could be determined, as described in Example 5. Amadoriases acting directly on HbA1c have not hitherto been found, and there are no reports on such amadoriases. As such, the fact that amadoriases that recognize αF6P as a substrate can act directly on HbA1c is a surprising finding.

However, now that amadoriases recognizing αF6P as a substrate have been demonstrated to act directly on HbA1c in the examples above, as with the case of CFP-T7-H35, it is indicated that other amadoriases exhibiting activity on αF6P may directly recognize the HbA1c β-chain as a substrate. In particular, it is believed to be highly likely that an amadoriase having a high specific activity on αF6P will act directly on HbA1c as with the amadoriase of the present invention and such amadoriases can likely be used for quantification of HbA1c.

Upon verifying whether this is the case, as described in Example 6, Amadoriase 28 from EFP-T5 exhibiting high specific activity on αF6P was also found to act directly on HbA1c (FIG. 6-3). It therefore was demonstrated that Amadoriase 28 acts directly on HbA1c as with the amadoriase of the present invention exhibiting a high degree of activity on αF6P and Amadoriase 28 can be used for quantification of HbA1c. It is believed that the same applies to other amadoriases having high specific activity on αF6P as well. Enzymes exhibiting specific activity of 1.0 U/mg or higher were used above for the convenience of experiments; however, a person skilled in the art will appreciate that enzymes exhibiting specific activity of 0.1 U/mg may be used in amounts of 10 times the amount of enzymes exhibiting specific activity of 1.0 U/mg as well.

The finding of the present invention does not merely demonstrate that an amadoriase exhibiting activity on αF6P can act directly on HbA1c. Rather, amadoriases exhibiting activity on α-fructosyl oligopeptides, such as αF3P, αF4P, αF5P, αF7P, αF8P, αF10P, or αF16P, may also be able to act directly on HbA1c in a similar manner.

As described above, the method for measurement of HbA1c using the amadoriase of the present invention is capable of HbA1c quantification rapidly, simply, accurately, and sufficiently, without the need for treatment of HbA1c with a protease or the like. When denatured HbA1c is to be measured, the technique of denaturing HbA1c is not particularly limited. Thus, direct measurement of HbA1c by an enzymatic method can be realized, and industrial applicability thereof can be expected.

BRIEF DESCRIPTION OF SEQUENCE LISTING

SEQ ID NO: 1: the amino acid sequence of the amadoriase derived from the *Coniochaeta* sp. NISL 9330 strain;
SEQ ID NO: 2: the nucleotide sequence of the amadoriase as shown in SEQ ID NO: 1;
SEQ ID NOs: 3-33: PCR primers;
SEQ ID NO: 34: PCR primer;
SEQ ID NO: 35: PCR primer;
SEQ ID NO: 36: the amino acid sequence of *Aspergillus oryzae* RIB40 (FAOAo2);
SEQ ID NO: 37: the nucleotide sequence of FAOAo2;
SEQ ID NO: 38: the amino acid sequence of *Phaeosphaeria nodorum* (PnFX);
SEQ ID NO: 39: the nucleotide sequence of PnFX;
SEQ ID NO: 40: the amino acid sequence of *Eupenicillium terrenum* (EFP-T5);
SEQ ID NO: 41: the nucleotide sequence of EFP-T5;
SEQ ID NOs: 42-53: PCR primers;
SEQ ID NO: 54: the amino acid sequence of *Neocosmospora vasinfecta* (NvFX);
SEQ ID NO: 55: the nucleotide sequence of NvFX;
SEQ ID NOs: 56-61: PCR primers;
SEQ ID NO: 62: the amino acid sequence of *Aspergillus nidulans* (AnFX) comprising substitution S59G;
SEQ ID NO: 63: the nucleotide sequence of AnFX;
SEQ ID NOs: 64-88: PCR primers;
SEQ ID NO: 89: the amino acid sequence of *Cryptococcus neoformans* (CnFX);
SEQ ID NO: 90: the nucleotide sequence of CnFX;
SEQ ID NOs: 91-98: PCR primers;
SEQ ID NO: 99: the amino acid sequence of the amadoriase (Cc95FX) exhibiting 95% sequence identity with the ketoamine oxidase derived from *Curvularia clavata*;
SEQ ID NO: 100: the nucleotide sequence of Cc95FX;
SEQ ID NOs: 101-112: PCR primers;
SEQ ID NO: 113: the amino acid sequence of the amadoriase derived from *Pyrenochaeta* sp. (Py);
SEQ ID NO: 114: the nucleotide sequence of the amadoriase derived from *Pyrenochaeta* sp. (Py);
SEQ ID NO: 115: the amino acid sequence of the amadoriase derived from *Arthrinium* sp. (Ar);
SEQ ID NO: 116: the nucleotide sequence of the amadoriase derived from *Arthrinium* sp. (Ar);
SEQ ID NO: 117: the amino acid sequence of the amadoriase derived from *Curvularia clavata* (Cc);
SEQ ID NO: 118: the nucleotide sequence of the amadoriase derived from *Curvularia clavata* (Cc);
SEQ ID NO: 119: the amino acid sequence of the amadoriase derived from *Emericella nidulans* (En);
SEQ ID NO: 120: the nucleotide sequence of the amadoriase derived from *Emericella nidulans* (En);
SEQ ID NO: 121: the amino acid sequence of the amadoriase derived from *Ulocladium* sp. (Ul);
SEQ ID NO: 122: the nucleotide sequence of the amadoriase derived from *Ulocladium* sp.;
SEQ ID NO: 123: the amino acid sequence of the amadoriase derived from *Penicillium janthinellum* (Pj);
SEQ ID NO: 124: the nucleotide sequence of the amadoriase derived from *Penicillium janthinellum* (Pj);
SEQ ID NO: 125: the amino acid sequence of Amadoriase 1 derived from *Aspergillus fumigatus*;
SEQ ID NO: 126: the nucleotide sequence of Amadoriase 1;
SEQ ID NO: 127: the amino acid sequence of FAOAo1 derived from *Aspergillus oryzae*;
SEQ ID NO: 128: the nucleotide sequence of FAOAo1;
SEQ ID NO: 129: the amino acid sequence of Amadoriase II derived from *Aspergillus fumigatus*;
SEQ ID NO: 130: the nucleotide sequence of Amadoriase II;
SEQ ID NO: 131: the amino acid sequence of FAOD-A derived from *Aspergillus terreus*;
SEQ ID NO: 132: the nucleotide sequence of FAOD-A;
SEQ ID NO: 133: the amino acid sequence of CFP-T7-H20 (R62D, D106K, Q110L, A113K) derived from *Coniochaeta* sp.;
SEQ ID NO: 134: the nucleotide sequence of CFP-T7-H20;
SEQ ID NO: 135: the amino acid sequence of PnFPOX (S62D, D106K, G110L, A113K) derived from *Phaeosphaeria nodorum*;
SEQ ID NO: 136: the nucleotide sequence encoding the amino acid sequence as shown in SEQ ID NO: 135;
SEQ ID NO: 137: the amino acid sequence of NvFX-62D/106K/110L (R62D, G106K, E110L) derived from *Neocosmospora vasinfecta* (Amadoriase 29);
SEQ ID NO: 138: the nucleotide sequence encoding the amino acid sequence as shown in SEQ ID NO: 137;
SEQ ID NO: 139: The amino acid sequence of AnFX-61D/105K/109L (S59G, R61D, G105K, K1091L) derived from *Aspergillus nidulans* (Amadoriase 30);
SEQ ID NO: 140: The nucleotide sequence encoding the amino acid sequence as shown in SEQ ID NO: 139;
SEQ ID NO: 141: the amino acid sequence of CFP-T7-H35 (R62D, L63H, E102K, D106K, Q110L, A113K, A355S) derived from *Coniochaeta* sp. (Amadoriase 25);
SEQ ID NO: 142: the nucleotide sequence of CFP-T7-H35;
SEQ ID NO: 143: the amino acid sequence of EFP-T5-62D/63H/106K/110L/113K/355S derived from *Eupenicillium terrenum* (Amadoriase 28);
SEQ ID NO: 144: the nucleotide sequence encoding the amino acid sequence as shown in SEQ ID NO: 143;
SEQ ID NO: 145: the amino acid sequence of the wild-type amadoriase derived from *Eupenicillium terrenum*;
SEQ ID NO: 146: the nucleotide sequence of the wild-type amadoriase derived from *Eupenicillium terrenum*;

SEQ ID NO: 147: the amino acid sequence of the wild-type amadoriase (AnFX);
SEQ ID NO: 148: the nucleotide sequence of the wild-type amadoriase (AnFX);
SEQ ID NO: 149: the amino acid sequence of the wild-type amadoriase (CnFX);
SEQ ID NO: 150: the nucleotide sequence of the wild-type amadoriase (CnFX);
SEQ ID NO: 151: the amino acid sequence of CFP-T7-H1 (R62A) derived from Coniochaeta sp. (Amadoriase 1);
SEQ ID NO: 152: the nucleotide sequence of CFP-T7-H1;
SEQ ID NO: 153: the amino acid sequence of CFP-T7-62D (R62D) derived from Coniochaeta sp. (Amadoriase 26);
SEQ ID NO: 154: the nucleotide sequence of CFP-T7-62D;
SEQ ID NO: 155: the amino acid sequence of EFP-15-R62D (R62D) derived from Eupenicillium terrenum (Amadoriase 27);
SEQ ID NO: 156: the nucleotide sequence of EFP-T5-R62D;
SEQ ID NO: 157: the amino acid sequence of CFP-T7-H2 (R62A, Q110L) derived from Coniochaeta sp. (Amadoriase 2);
SEQ ID NO: 158: the nucleotide sequence of CFP-T7-H2;
SEQ ID NO: 159: the amino acid sequence of CFP-T7-H4 (R62A, Q110Y) derived from Coniochaeta sp. (Amadoriase 4);
SEQ ID NO: 160: the nucleotide sequence of CFP-T7-H4;
SEQ ID NO: 161: the amino acid sequence of CFP-T7-H2-62N (R62N, Q110L) derived from Coniochaeta sp. (Amadoriase 5);
SEQ ID NO: 162: the nucleotide sequence of CFP-T7-H2-62N;
SEQ ID NO: 163: the amino acid sequence of CFP-T7-H6 (R62D, Q110L) derived from Coniochaeta sp. (Amadoriase 6);
SEQ ID NO: 164: the nucleotide sequence of CFP-T7-H6;
SEQ ID NO: 165: the amino acid sequence of CFP-T7-H10 (R62D, D106A, Q110L) derived from Coniochaeta sp. (Amadoriase 12);
SEQ ID NO: 166: the nucleotide sequence of CFP-T7-H10;
SEQ ID NO: 167: the amino acid sequence of CFP-T7-H11 (R62D, D106K, Q110L) derived from Coniochaeta sp. (Amadoriase 13);
SEQ ID NO: 168: the nucleotide sequence of CFP-T7-H11;
SEQ ID NO: 169: the amino acid sequence of CFP-T7-H12 (R62D, D106R, Q110L) derived from Coniochaeta sp. (Amadoriase 14);
SEQ ID NO: 170: the nucleotide sequence of CFP-T7-H12;
SEQ ID NO: 171: the amino acid sequence of CFP-T7-H13 (R62D, Q110L, A113K) derived from Coniochaeta sp. (Amadoriase 15);
SEQ ID NO: 172: the nucleotide sequence of CFP-T7-H13;
SEQ ID NO: 173: the amino acid sequence of CFP-T7-H14 (R62D, Q110L, A113R) derived from (Coniochaeta sp. (Amadoriase 16);
SEQ ID NO: 174: the nucleotide sequence of CFP-T7-H14;
SEQ ID NO: 175: the amino acid sequence of CFP-T7-H21 (R62D, D106K, Q110L, A113R) derived from Coniochaeta sp. (Amadoriase 18);
SEQ ID NO: 176: the nucleotide sequence of CFP-T7-H21;
SEQ ID NO: 177: the amino acid sequence of CFP-T7-H24 (R62D, E63A, D106K, Q110L, A113K) derived from Coniochaeta sp. (Amadoriase 19);
SEQ ID NO: 178: the nucleotide sequence of CFP-T7-H24;
SEQ ID NO: 179: the amino acid sequence of CFP-T7-H26 (R62D, L63H, D106K, Q110L, A113K) derived from Coniochaeta sp. (Amadoriase 21);
SEQ ID NO: 180: the nucleotide sequence of CFP-T7-H26;
SEQ ID NO: 181: the amino acid sequence of CFP-T7-H28 (R62D, E63H, E102K, D106K, Q110L, A113K) derived from Coniochaeta sp. (Amadoriase 23);
SEQ ID NO: 182: the nucleotide sequence of CFP-T7-H28;
SEQ ID NO: 183: the amino acid sequence of CFP-T7-H29 (R62D, L63H, D106K, Q110L, A113K, A419K) derived from Coniochaeta sp. (Amadoriase 24);
SEQ ID NO: 184: the nucleotide sequence of CFP-T7-H29;
SEQ ID NO: 185: the amino acid sequence of (AnFX-61D/62H/101K/105K/109L/112K/355S) derived from Aspergillus nidulans (Amadoriase 31);
SEQ ID NO: 186: the nucleotide sequence encoding the amino acid sequence as shown in SEQ ID NO: 185;
SEQ ID NO: 187: the amino acid sequence of (PnFX-62D/63H/106K/110L/113K/351S) derived from Phaeosphaeria nodorum (Amadoriase 33);
SEQ ID NO: 188: the nucleotide sequence encoding the amino acid sequence as shown in SEQ ID NO: 187;
SEQ ID NO: 189: the amino acid sequence of (CnFX-62D/106K/110L/113K) derived from Cryptococcus neoformans (Amadoriase 34);
SEQ ID NO: 190: the nucleotide sequence encoding the amino acid sequence as shown in SEQ ID NO: 189;
SEQ ID NO: 191: the amino acid sequence of (Cc95FX-62D/63H/106K/110L/113K/353S) derived from Curvularia clavata (Amadoriase 35);
SEQ ID NO: 192: the nucleotide sequence encoding the amino acid sequence as shown in SEQ ID NO: 191;
SEQ ID NOs: 193-198: PCR primers;
SEQ ID NO: 199: the amino acid sequence of CFP-DH1 (derived from Coniochaeta sp. NISL 9330) (Modified Amadoriase 36, CFP-T7-H36) (CFP-T7-R62D/L63H/D68N/E102K/D106K/Q110L/A113K/A355S/E44P/E133A/E253K/V257C/N262H/Q337K/E340P/ΔP435/ΔK436/ΔL437);
SEQ ID NO: 200: the nucleotide sequence encoding the amino acid sequence as shown in SEQ ID NO: 199;
SEQ ID NOs: 201-202: PCR primers;
SEQ ID NO: 203: the amino acid sequence of CFP-DH2 (derived from Coniochaeta sp. NISL 9330) (Amadoriase 39);
SEQ ID NO: 204: the nucleotide sequence encoding the amino acid sequence as shown in SEQ ID NO: 203.

All publications, patents, and patent applications cited herein are incorporated herein by reference in their entirety.

The invention claimed is:

1. A reagent kit for measurement of hemoglobin A1c in a sample comprising ingredients (1) and (2) below:
   (1) a modified amadoriase that acts directly on hemoglobin A1c and generates hydrogen peroxide; and
   (2) a reagent for measurement of hydrogen peroxide, wherein the modified amadoriase is selected from:
   (i) a modified amadoriase comprising the amino acid sequence of SEQ ID NO: 1, and wherein the amino acid at position 62 is substituted with aspartic acid; the amino acid at position 63 is substituted with histidine; the amino acid at position 102 is substituted with lysine; the amino acid at position 106 is substituted with lysine; the amino acid at position 110 is substituted with leucine; the amino acid at position 113 is substituted with lysine; and the amino acid at position 355 is substituted with serine, and
   (ii) a modified amadoriase comprising an amino acid sequence that is at least 90% identical to the amadoriase of (i).

2. The method of claim 1, wherein the modified amadoriase is obtained from the genus *Coniochaeta*.

3. A reagent kit for measurement of hemoglobin A1c in a sample comprising ingredients (1) and (2) below:
   (1) a modified amadoriase that acts directly on hemoglobin A1c and generates hydrogen peroxide; and
   (2) a reagent for measurement of hydrogen peroxide, wherein the modified amadoriase is selected from:
   (i) a modified amadoriase comprising the amino acid sequence of SEQ ID NO: 1, and wherein the amino acid at position 62 is substituted with aspartic acid; the amino acid at position 63 is substituted with histidine; the amino acid at position 102 is substituted with lysine; the amino acid at position 106 is substituted with lysine; the amino acid at position 110 is substituted with leucine; the amino acid at position 113 is substituted with lysine; and the amino acid at position 355 is substituted with serine, and
   (ii) a modified amadoriase comprising an amino acid sequence that is at least 90% identical to the amadoriase of (i).

4. The method of claim 1, wherein the modified amadoriase further comprises asparagine at the position corresponding to position 68 of SEQ ID NO: 1 and threonine at the position corresponding to position 356 of SEQ ID NO: 1.

* * * * *

SEQUENCE LISTING

<160> NUMBER OF SEQ ID NOS: 204

<210> SEQ ID NO 1
<211> LENGTH: 437
<212> TYPE: PRT
<213> ORGANISM: Coniochaeta sp.

<400> SEQUENCE: 1

```
Met Thr Ser Asn Arg Ala Asp Thr Arg Val Ile Val Val Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
    195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
    275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
            370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
```

```
                    405                 410                 415
Arg Arg Ala Ala Pro Pro Lys Asp Leu Ala Asp Met Pro Gly Trp Lys
            420                 425                 430

His Asp Pro Lys Leu
        435

<210> SEQ ID NO 2
<211> LENGTH: 1314
<212> TYPE: DNA
<213> ORGANISM: Coniochaeta sp.

<400> SEQUENCE: 2
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atacgactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg gcgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta ccagacgca     960 tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
tcatgggaat agcactgcgc aacaaggtgg                                       30

<210> SEQ ID NO 4
<211> LENGTH: 29
<212> TYPE: DNA
<213> ORGANISM: Artificial
<220> FEATURE:
<223> OTHER INFORMATION: primer
```

```
<400> SEQUENCE: 4
tattcccatg atcttgttga gatcatggc                                29

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
acctgaaaaa gctgtaccag gcactgcac                                29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
acctgaaaaa gttctaccag gcactgcac                                29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
acctgaaaaa gtattaccag gcactgcac                                29

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8 cttttcagg tcctcgatac cctcaggc                                  28

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
tcatgggaat aaacctgcgc aacaaggtgg                               30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
tcatgggaat agatctgcgc aacaaggtgg                               30

<210> SEQ ID NO 11
```

```
<211> LENGTH: 30
<212> TYPE: DNA
<213> ORGANISM: Artificial
<220> FEATURE:
<223> OTHER INFORMATION: primer

<400> SEQUENCE: 11
tcatgggaat acaactgcgc aacaaggtgg                                    30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
tcatgggaat agaactgcgc aacaaggtgg                                    30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
tgggaataga tctggccaac aaggtggacc                                    30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
tgggaataga tctggaaaac aaggtggacc                                    30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
tgggaataga tctgcacaac aaggtggacc                                    30

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cagatctatt cccatgatct tgttgag                                       27

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
```

```
tgagggtatc gaggccctga aaaagctg                                              28
```

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18

```
tgagggtatc gagaaactga aaaagctg                                              28
```

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19

```
tgagggtatc gagcgcctga aaaagctg                                              28
```

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20

```
ctcgataccc tcaggcgtgt gttcgcag                                              28
```

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21

```
aaaaagctgt accagaaact gcacgatgcc                                            30
```

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22

```
gcatcgtgca gtttctggta cagcttttc                                             30
```

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23

```
aaaaagctgt accagcgtct gcacgatgcc                                            30
```

<210> SEQ ID NO 24
<211> LENGTH: 30
<212> TYPE: DNA

```
<213> ORGANISM: Artificial
<220> FEATURE:
<223> OTHER INFORMATION: primer

<400> SEQUENCE: 24
gcatcgtgca gacgctggta cagcttttc                                    30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
tcatgggaat agatgcgcgc aacaaggtgg                                   30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tcatgggaat agatgaccgc aacaaggtgg                                   30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcatgggaat agatcatcgc aacaaggtgg                                   30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tcatgggaat agataagcgc aacaaggtgg                                   30

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
atctattccc atgatcttgt tgagatcat                                    29

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
aggcgtgtgt tcgcagtcca ttctg                                        25
```

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
gcgaacacac gcctaagggt atcgagaaac         30

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
acgtctagac ttgagtgcat cgcctcctg         29

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
tcaagtctag acgtaaggca ccgccaaaag         30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
acagacactg cggactctgc tctcttgatg         30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
gtccgcagtg tctgtacacc agcacaag         28

<210> SEQ ID NO 36
<211> LENGTH: 436
<212> TYPE: PRT
<213> ORGANISM: Aspergillus oryzae

<400> SEQUENCE: 36

Met Thr Val Thr Lys Ser Ser Ser Ile Leu Ile Ile Gly Ala Gly Thr
1               5                   10                  15

Trp Gly Ala Ser Thr Ala Leu His Leu Gly Arg Arg Gly Tyr Thr Asn
            20                  25                  30

Val Thr Val Leu Asp Pro Tyr Thr Val Pro Ser Ala Ile Ser Ala Gly
        35                  40                  45

Asn Asp Val Asn Lys Ile Ile Ser Ser Gly Gln Tyr Ser Asn Lys Lys

```
                50                   55                   60
Asp Glu Ile Glu Val Asn Glu Ile Leu Ala Glu Ala Phe Lys Gly
 65                   70                   75                   80

Trp Thr Thr Asp Pro Leu Phe Lys Pro Tyr Tyr His Asp Thr Gly Val
                     85                   90                   95

Val Met Ser Ala Cys Ser Ser Ala Gly Leu Asp Arg Leu Gly Ile Arg
                    100                  105                  110

Val Arg Pro Glu Glu Pro Asp Val Ser Glu Val Thr Lys Pro Glu
                115                  120                  125

His Phe Arg Gln Leu Ala Pro Ala Val Leu Lys Gly Asn Phe Pro Gly
                130                  135                  140

Trp Arg Gly Tyr His Ile Arg Ser Asn Ala Gly Trp Ala His Ala Arg
145                  150                  155                  160

Asn Ala Leu Val Ala Ala Ile Arg Glu Ala Lys Leu Gly Val Lys
                    165                  170                  175

Phe Val Thr Gly Thr Gln Gly Arg Val Ile Thr Leu Ile Phe Glu Asn
                    180                  185                  190

Asn Asp Val Lys Gly Ala Val Thr Ala Asp Gly Lys Ile Trp Arg Ala
                    195                  200                  205

Glu Gln Thr Val Leu Cys Ala Gly Ala Asn Ala Ala Gln Phe Leu Asp
                    210                  215                  220

Phe Lys Asp Gln Leu Arg Pro Thr Ala Trp Thr Leu Ala His Ile Arg
225                  230                  235                  240

Leu Lys Pro Glu Glu Arg Ala Leu Tyr Lys Asn Leu Pro Val Ile Phe
                    245                  250                  255

Asn Ile Glu Lys Gly Phe Phe Phe Glu Pro Asp Glu Glu Arg Gly Glu
                    260                  265                  270

Ile Lys Ile Cys Asp Glu His Pro Gly Tyr Thr Asn Met Val Lys Ser
                    275                  280                  285

Ala Asp Gly His Leu Thr Ser Leu Pro Phe Glu Lys Thr Gln Ile Pro
                    290                  295                  300

Lys Glu Ser Glu Ala Arg Val Arg Ala Leu Leu Ser Glu Thr Met Pro
305                  310                  315                  320

Gln Leu Ala Asp Arg Pro Phe Ser Phe Ala Arg Val Cys Trp Cys Ala
                    325                  330                  335

Asp Thr Ala Asn Arg Glu Phe Ile Ile Asp Arg His Pro Glu His Pro
                    340                  345                  350

Ser Leu Val Leu Gly Cys Gly Ala Ser Gly Arg Gly Phe Lys Tyr Leu
                    355                  360                  365

Pro Ser Ile Gly Asn Leu Ile Val Asp Ala Ile Glu Asp Lys Val Pro
                    370                  375                  380

Glu Lys Val His Lys Leu Thr Arg Trp Ser Pro Asp Ile Ala Val Asp
385                  390                  395                  400

Arg Lys Trp Arg Asp Thr Leu Gly Arg Phe Gly Gly Pro Asn Arg Val
                    405                  410                  415

Met Asp Phe His Asp Val Lys Glu Trp Thr Asn Val Gln Asn Lys Asp
                    420                  425                  430

Thr Ala Lys Leu
                435

<210> SEQ ID NO 37
<211> LENGTH: 1311
<212> TYPE: DNA
<213> ORGANISM: Aspergillus oryzae
```

<400> SEQUENCE: 37

```
atgactgtca ccaaatcttc ctcaatcctg atcatcggcg caggcacttg gggcgcttca      60
actgcccttc accttggtcg cagaggatac accaatgtca ccgtcctaga cccttacaca     120
gtgccctcag caatttcagc tggaaatgac gtgaacaaga tcatctcctc ggggcaatac     180
agcaacaaaa aggatgagat tgaagttaac gaaattctcg ccgaggaggc attcaaaggc     240
tggacaaccg acccttttgtt caagccatac taccacgaca ctggcgttgt aatgtctgct     300
tgcagcagcg ccggtctgga tcgcctcgga atccgagtaa ggccggaaga ggaacctgat     360
gtttccgaag tcacgaagcc ggagcacttc cgccaactgg ccccgctgt gctgaaagga      420
aacttcccgg ggtggagagg ctaccacatt cgttcgaacg ctggctgggc cacgcccga     480
aatgccctcg tggccgctat acgcgaagca gagaaacttg tgttaaatt cgtaacaggc     540
acccaaggaa gagtcatcac ccttatcttc gagaacaacg acgtcaaggg cgcagtcacc     600
gccgacggaa agatctggcg cgcggagcaa acagttctct cgcgctggcg caaatgctgcg    660
cagttcttgg attttaagga ccagctccgc ccaacggcat ggacactcgc ccatatccgg    720
ctcaaacctg aggaacgcgc gctctacaaa aacttgccgg tgattttcaa cattgagaaa    780
ggattttttct tcgagcctga tgaggagcgc ggggagatca agatctgcga cgaacatccg    840
ggatacacta acatggttaa atctgcggat ggccacttga cgagtttgcc ctttgagaag    900
acccagatcc ccaaggagtc tgaagctaga gtcagagctt actatcggaa gaccatgcct    960
caattagccg atcgcccatt tagcttcgcc cgcgtttgct ggtgtgcgga caccgcaaac    1020
cgtgaattca tcattgaccg ccaccctgaa cacccgtctc ttgttttggg atgcggtgct    1080
tccggaaggg gtttcaaata tctcccctca atcggcaacc tcattgttga cgccattgaa    1140
gacaaagtcc cagagaaagt tcacaagctt acgaggtgga gtccagacat tgctgttgac    1200
agaaagtgga gggacactct ggggcgcttt ggagggccta accgtgtcat ggacttccat    1260
gatgtcaagg aatggactaa cgtgcagaac aaggatactg cgaagctgta g             1311
```

<210> SEQ ID NO 38
<211> LENGTH: 437
<212> TYPE: PRT
<213> ORGANISM: Phaeosphaeria nodorum

<400> SEQUENCE: 38

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Ser Leu Arg
        50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125
```

| | | | | | | | | | | | | |
|---|---|---|---|---|---|---|---|---|---|---|---|---|
|Glu|Asp|Glu|Ile|Leu|Lys|Arg|Met|Pro|Leu|Leu|Ser|Arg|Asp|Gln|Ile|
| |130| | | |135| | | |140| | | | |

Glu Asp Glu Ile Leu Lys Arg Met Pro Leu Leu Ser Arg Asp Gln Ile
        130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
            165                 170                 175

Arg Phe Gly Phe Tyr Gly Ala Gly Ser Phe Lys Ala Pro Leu Leu Ala
        180                 185                 190

Glu Gly Val Cys Ile Gly Val Glu Thr Val Asp Gly Thr Arg Tyr Tyr
            195                 200                 205

Ala Asp Lys Val Val Leu Ala Ala Gly Ala Trp Ser Pro Thr Leu Val
210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
                340                 345                 350

Leu Leu Ile Cys Glu His Pro Glu Trp Lys Asn Phe Val Leu Ala Thr
            355                 360                 365

Gly Asp Ser Gly His Ser Phe Lys Leu Leu Pro Asn Ile Gly Lys His
370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 39
<211> LENGTH: 1314
<212> TYPE: DNA
<213> ORGANISM: Phaeosphaeria nodorum

<400> SEQUENCE: 39
atggccccgt cgcgtgctaa tacgtcggtc attgtggttg gtggtggtgg tacgattggc      60
tcatctacgg ctctgcatct ggtccgctca ggctataccc cgtcgaacgt gacggttctg     120
gatgcatacc cgattccgag ctctcagagc gctggcaacg acctgaataa aatcatgggt     180
gtctctctgc gtaatccggt ggatctgcag ctggctctgg aagcgcgcca aatgtggaac     240
gaagacgaac tgttcaagaa ttttttccat aacaccggcc gtctggattg cgcgcacggt     300 gaaaagata ttgccgacct gaagagcggc tatcaggctc tggtggatgc gggtctggac      360

-continued

```
gccacgaacg aatggctgga tagtgaagac gaaatcctga aacgtatgcc gctgctgtcc    420
cgcgatcaaa ttaaaggctg gaaggcgatc ttttcaaaag acgtggttg gctggcagca     480
gcaaaggcaa ttaatgcagt tggtgaatat ctgcgtgatc agggcgtccg cttcggtttt    540
tacggcgccg gttctttcaa agcaccgctg ctggctgaag cgtctgcat cggtgtcgaa     600
accgtggatg gcacgcgcta ttacgcagac aaagtggttc tggctgcagg tgcatggtcg    660
ccgaccctgg ttgaactgca tgaacagtgt gtgagcaaag cgtgggttta cggccacatt    720
caactgacgc cggaagaagc cgcacgttat aagaacagcc cggtcgtgta caatggcgat    780
gtgggctttt tctttgaacc gaacgaacat ggcgttatca aagtctgcga tgaatttccg    840
ggttttaccc gcttcaagat gcaccagccg tttggtgcca aagcaccgaa gcgtattagt    900
gtgccgcgct cccatgccaa acacccgacc gatacgatcc cggatgcaag tgacgtttcc    960
attcgtcgcg ctatcgcgac ctttatgccg cagttcaaga acaaaaagat gttcaaccaa   1020
gcgatgtgct ggtgtaccga tacggccgac gctgcgctgc tgatttgtga acatccggaa   1080
tggaaaaact ttgttctggc gaccggcgat tcaggtcatt cgttcaaact gctgccgaat   1140
atcggcaagc acgttgtcga actgctggag ggtacgctgg cagatgacct ggcacacgca   1200
tggcgttggc gtccgggtag tggtgatgca ctgaaaagcc gtcgctctgc tccggcgaaa   1260
gacctggctg atatgccggg ctggaaccat gacaaaccgc gtgctaatct gtaa         1314
```

<210> SEQ ID NO 40
<211> LENGTH: 437
<212> TYPE: PRT
<213> ORGANISM: Eupenicillium terrenum

<400> SEQUENCE: 40

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe His Gln Val Gly Met Ile Asp
                85                  90                  95

Cys Ser Ser Lys Glu Gly Ile Glu Asn Leu Arg Arg Lys Tyr Gln
                100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205
```

```
Thr Lys Tyr Phe Ala Asp Lys Val Val Leu Ala Ala Gly Ala Trp Ser
    210                 215                 220
Pro Thr Leu Val Asp Leu Glu Asp Gln Cys Val Ser Lys Ala Trp Val
225                 230                 235                 240
Phe Ala His Ile Gln Leu Thr Pro Lys Glu Ala Asp Ala Tyr Lys Asn
                245                 250                 255
Val Pro Val Val Tyr Asp Gly Glu Tyr Gly Phe Phe Glu Pro Asp
            260                 265                 270
Glu Tyr Gly Val Ile Lys Val Cys Asp Glu Phe Pro Gly Phe Ser Arg
        275                 280                 285
Phe Lys Leu His Gln Pro Tyr Gly Ala Ala Ser Pro Lys Met Ile Ser
    290                 295                 300
Val Pro Arg Ser His Ala Lys His Pro Thr Asp Thr Tyr Pro Asp Ala
305                 310                 315                 320
Ser Glu Val Thr Ile Arg Lys Ala Ile Ala Arg Phe Leu Pro Glu Phe
                325                 330                 335
Lys Asp Lys Glu Leu Phe Asn Arg Thr Met Cys Trp Cys Thr Asp Thr
            340                 345                 350
Ala Asp Ala Asn Leu Leu Ile Cys Glu His Pro Lys Trp Lys Asn Phe
        355                 360                 365
Ile Leu Ala Thr Gly Asp Ser Gly His Ser Phe Lys Leu Leu Pro Asn
    370                 375                 380
Ile Gly Lys Tyr Val Val Glu Leu Leu Glu Gly Ser Leu Ser Gln Glu
385                 390                 395                 400
Met Ala Gly Ala Trp Arg Trp Arg Pro Gly Asp Ala Leu Arg Ser
                405                 410                 415
Arg Arg Gly Ala Pro Ala Lys Asp Leu Ala Glu Met Pro Gly Trp Lys
            420                 425                 430
His Asp Ala His Leu
        435

<210> SEQ ID NO 41
<211> LENGTH: 1314
<212> TYPE: DNA
<213> ORGANISM: Eupenicillium terrenum

<400> SEQUENCE: 41
atggctcatt cgcgtgcaag caccaaagtc gtcgtggttg ggggaggtgg tacgatcggg    60
tcttcgacgg ctctgcactt aatccgctct ggatatacccc cctcaaatat caccgtgctt   120
gacgtataca agacccccttc attgcaatct gcaggacatg atttgaacaa gatcatgggc   180
attgattgc gcaacgggcc tgacttgcag cttttcgctgg aatcactcga catgtggcaa   240
aacgatgagt tgttcaagcc attctttcac caagtgggca tgattgattg tcgtcatcc   300
aaagaggta ttgaaaatct tcgacgaaaa taccagaccc tcctcgatgc gggcattggg   360
ctggagaaga cgaacgtttg ctggaatct gaagatgaga tcctcgccaa agcgccgaat   420
ttcacgcgtg aacaagtcaa ggggtggaaa ggcttattt gcactgatgg aggctggctt   480
gctgcagcca aggctatcaa tgcgatcgga attttcctcc aggacaaagg tgtcaagttt   540
ggctttggag atgctggtac cttcagcaa cctctgttcg ccgctgatgg aaaaacttgc   600
atcggacttg aaactacaga cggaaccaag tactttgctg acaaggttgt cttggctgct   660
ggtgcgtgga gtcccacctt ggtggatcta aagatcagt gtgtttcaaa ggcctgggtt   720
ttcgctcata ttcaactcac acccaaagaa gcggacgcgt acaagaatgt gcctgtggtc   780
```

```
tatgatggtg aatatgggtt cttttttcgaa cccgacgagt atggggtgat caaagtctgt    840
gacgagttcc ctggtttctc tcgcttcaaa ctgcatcaac cgtacggggc tgcatctccc    900
aagatgatat ccgtaccgcg atcacacgcc aagcatccca cagataccta ccctgatgcc    960
tccgaagtca ccatacgcaa agcgatcgca aggttcctgc cagaatttaa agacaaggag   1020
ctcttcaacc gtaccatgtg ctggtgtaca gatacggccg atgctaactt attgatttgc   1080
gaacacccga agtggaagaa tttcattctg gccactggag atagcggaca ttccttcaag   1140
ctgttgccaa acatcgggaa atacgtagtt gagcttttag agggatctct atcgcaggaa   1200
atggctggtg cctggagatg gagacccgga ggtgatgctc ttagatctag acgcggtgct   1260
ccggcaaagg atcttgctga gatgccggga tggaagcatg atgcacattt gtga         1314
```

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42

```
aagatcatgg gcattgattt gcgcaacggg                                      30
```

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43

```
aatgcccatg atcttgttca aatcatgtcc                                      30
```

<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44

```
gagggtattg aaaaacttcg acgaaaatac                                      30
```

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45

```
ttcaataccc tctttggatg acgaac                                          26
```

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46

```
aaaaacttcg acgattatac cagaccctcc                                      30
```

```
<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
tcgtcgaagt ttttcaatac cctctttgg                                       29

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
cgacgattat accagaaact cctcgatgcg                                      30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ctggtataat cgtcgaagtt tttcaatacc                                      30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
agatacggcc gattctaact tattgatttg                                      30

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51
atcggccgta tctgtacacc agcacatgg                                       29

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
tcatgggcat tgatcatcgc aacgggcctg                                      30

<210> SEQ ID NO 53
<211> LENGTH: 29
<212> TYPE: DNA
<213> ORGANISM: Artificial
<220> FEATURE:
<223> OTHER INFORMATION: primer
```

<400> SEQUENCE: 53
atcaatgccc atgatcttgt tcaaatcat                                          29

<210> SEQ ID NO 54
<211> LENGTH: 441
<212> TYPE: PRT
<213> ORGANISM: Neocosmospora vasinfecta

<400> SEQUENCE: 54

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe His Asn Thr Gly Arg Leu Asp
                85                  90                  95

Cys Glu Ser Ser Ala Glu Gly Val Glu Gly Leu Arg Arg Glu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Leu Gln Arg Gln
                165                 170                 175

Gly Val Arg Phe Gly Phe Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350
```

Ala Asp Ser Ala Leu Leu Ile Cys Glu His Pro Arg Trp Lys Asn Phe
            355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
            435                 440

<210> SEQ ID NO 55
<211> LENGTH: 1326
<212> TYPE: DNA
<213> ORGANISM: Neocosmospora vasinfecta

<400> SEQUENCE: 55
atgacgaccc cgcgtaaaga aacgacggtc ctgattattg gtggtggtgg cacgattggt      60
agctcgacgg ctctgcatct gctgcgtgcc ggctataccc cgtctaacat taccgtgctg     120
gatacgtacc cgatcccgag tgcccagtcc gcaggcaacg acctgaataa aattatgggt     180
atccgtctgc gcaataaagt tgatctgcaa ctgagcctgg aagcccgtga tatgtggcgc     240
aacgacgcac tgtttcgtcc gttttttcca ataccggcc gcctggactg cgaaagctct     300
gctgaaggcg tggaaggtct cgtcgcgaa tatcagaaac tggtggaagc aggcgttggt     360
ctggaagaaa cgcacgaatg gctggatagc gaagaagcta ttctggaaaa agcgccgctg     420
ctgcaacgtg aagaaattga aggttggaaa gccatctggt ctgaagaagg cggttggctg     480
gcggccgcaa aagctattaa cgcgatcggc gaagaactgc agcgtcaagg cgttcgcttc     540
ggttttggcg gtgccggtag tttttaaacgc ccgctgttcg cagatgacgg caccacgtgt     600
atcggtgtcg aaaccgtgga tggcacgcag tatcatgcgg acaaagtggt tctggctgca     660
ggtgcttggt caccggcgct ggtcgatctg gaagaacagt gctgttcgaa agcctgggtg     720
tacgcacaca tgcaactgac cccggaagaa gccgcagttt ataaaggctg cccggtcgtg     780
taccacggcg atgtcggctt ttttctttgaa ccgaacgaaa atggcgttat taaagtctgt     840
gacgaattcc cgggttttac gcgtttcaaa cagcatcaac cgtatggtgc cccggcaccg     900
aaacctgtga gtgttccgcg ctcccatgcg aaacacccga ccgatacgta cccggacgct     960
tcagaagaat cgatcaaacg tgccgtgagt acctttctgc cgcgcttcaa agataaaccg    1020
ctgtttaacc gtgcactgtg ctggtgtacc gatacggccg actccgcact gctgatttgc    1080
gaacacccgc gctggaaaaa ttttatcctg gcgaccggcg atagcggtca ttctttcaaa    1140
ctgctgccga ttatcggcaa acacgttgtc gaactggttg aaggtcgtct ggcggatgac    1200
ctggctgaag cgtggcgttg cgtccgggt cagggtgatg cacgtaaaag cattcgcgct    1260
gcgccggcga aagacctggc ggatatgccg ggctggaaac acgaccaaga ctcggaatca    1320
cgctga                                                             1326

<210> SEQ ID NO 56
<211> LENGTH: 29
<212> TYPE: DNA
<213> ORGANISM: Artificial
<220> FEATURE:
<223> OTHER INFORMATION: primer

<400> SEQUENCE: 56
ttatgggtat cgatctgcgc aataaagtt                                29

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57
gctcagttgc agatcaactt tattgcgcag                               30

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58
gaaggcgtgg aaaaactgcg tcgcgaatat                               30

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59
ttccaccagt ttctgatatt cgcgacgcag                               30

<210> SEQ ID NO 60
<211> LENGTH: 27
<212> TYPE: DNA
<213> ORGANISM: Artificial
<220> FEATURE:
<223> OTHER INFORMATION: primer

<400> SEQUENCE: 60
ctgcgtcgcc tgtatcagaa actggtg                                  27

<210> SEQ ID NO 61
<211> LENGTH: 30
<212> TYPE: DNA
<213> ORGANISM: Artificial
<220> FEATURE:
<223> OTHER INFORMATION: primer

<400> SEQUENCE: 61
accaacgcct gcttccacca gtttctgata                               30

<210> SEQ ID NO 62
<211> LENGTH: 438
<212> TYPE: PRT
<213> ORGANISM: Aspergillus nidulans

<400> SEQUENCE: 62

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

```
Pro Ser Asn Ile Thr Val Leu Asp Thr Cys Pro Ile Pro Ser Ala Gln
         35                  40                  45

Ser Ala Gly Tyr Asp Leu Asn Lys Ile Met Gly Ile Arg Leu Arg Asn
 50                  55                  60

Lys Pro Asp Leu Gln Leu Ser Leu Glu Ala Leu Asp Met Trp Lys Asn
 65                  70                  75                  80

Asp Pro Leu Phe Lys Pro Phe Phe His Asn Val Gly Met Ile Asp Val
                 85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
            115                 120                 125

Ser Glu Asp Glu Ile Leu Ala Lys Ala Pro His Phe Thr Gln Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
            195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
            275                 280                 285

Phe Lys Met His Gln Pro Tyr Gly Ser Pro Ala Pro Lys Pro Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435
```

<210> SEQ ID NO 63
<211> LENGTH: 1317
<212> TYPE: DNA
<213> ORGANISM: Aspergillus nidulans

<400> SEQUENCE: 63

```
atgacgcccc gagccaacac caaaatcatt gtcgtcggcg gcggcggcac aatgggctcg      60
tcgacagccc tacacctcct gcgcgccggc tacacgccgt ccaacattac agtgctcgac     120
acgtgcccta tccccctccgc acagtctgca ggctacgacc tgaacaaaat catggggatc     180
cgtctgcgca caagcctga tttacagctc tctcttgagg cgctggacat gtggaaaaat     240
gatcctctct tcaagccgtt tttccacaat gttggaatga tcgacgtctc ttcaacagag     300
gaaggcatcg agggtcttcg gaagaaatac cagtctcttc tcgacgcagg cattgggctc     360
gagaagacga atttcatgct ggaaagtgaa gacgagatcc tggctaaagc gccgcatttc     420
acgcaggagc agattaaagg ctggaaaggc ctgttctgtg gcgacggcgg ctggctcgct     480
gcagccaaag ccatcaatgc cattgggcag ttcctcaagg aacagggcgt caagtttgga     540
ttcggcggcg ccggcacgtt caaaaagcca ctcttcgccg atgcccacga agacgtgc      600
atcggcgtcg agactgtaga cggcacaaag tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt ataagaacac tcctgttata     780
tacgacggtg actatgggtt tttctttgag ccgaatgaaa acggcatcat aaaagtctgt     840
gacgaattcc ctggcttcac gcatttcaaa atgcaccagc cgtacggctc gccggcgccc     900
aaacccatct ctgtgcctcg ttcccatgcg aagcacccca cagatacata cccgcacgcg     960
tcggaggtca cgatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagtgggca ttcgttcaag    1140
ttgctgccga atattggaaa gcatgttgtc gagttattgg aggagaggct ggaaagtgtg    1200
tttaaggatg cttggaggtg gaggcctggc agtggggatg cattaaaaag tagacgggct    1260
gcgcctgcga aggacctggc ggatatgccg gggtggagga tgaggcaaa gatgtag      1317
```

<210> SEQ ID NO 64
<211> LENGTH: 30
<212> TYPE: DNA
<213> ORGANISM: Artificial
<220> FEATURE:
<223> OTHER INFORMATION: primer

<400> SEQUENCE: 64

```
atcatgggca tcgatctgcg caacaagcct                                       30
```

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65

```
agagagctgt aaatcaggct tgttgcgcag                                       30
```

<210> SEQ ID NO 66
<211> LENGTH: 30
<212> TYPE: DNA

```
<213> ORGANISM: Artificial
<220> FEATURE:
<223> OTHER INFORMATION: primer

<400> SEQUENCE: 66
gaaggcatcg agaaacttcg gaagaaatac                                              30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gtcgagaaga gactggtatt tcttccgaag                                              30

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
cttcggaagc tgtaccagtc tcttctc                                                 27

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
cccaatgcct gcgtcgagaa gagactggta                                              30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
cttctcgagc ccaatgcctg cgtcgagaag                                              30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
gataccgcgg atagcaatct gcttgtttgt                                              30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ccagcgtgga tgctcacaaa caagcagatt                                              30
```

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
atcatgggca tcgatcatcg caacaagcct                                      30

<210> SEQ ID NO 74
<211> LENGTH: 27
<212> TYPE: DNA
<213> ORGANISM: Artificial
<220> FEATURE:
<223> OTHER INFORMATION: primer

<400> SEQUENCE: 74
agagagctgt aaatcaggct tgttgcg                                         27

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
tcttcaacag agaaaggcat cgagaaactt                                      30

<210> SEQ ID NO 76
<211> LENGTH: 27
<212> TYPE: DNA
<213> ORGANISM: Artificial
<220> FEATURE:
<223> OTHER INFORMATION: primer

<400> SEQUENCE: 76
gtacagcttc cgaagtttct cgatgcc                                         27

<210> SEQ ID NO 77
<211> LENGTH: 29
<212> TYPE: DNA
<213> ORGANISM: Artificial
<220> FEATURE:
<223> OTHER INFORMATION: primer

<400> SEQUENCE: 77
atcatgggtg tcgatctgcg taatccggt                                       29

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
agccagctgc agatccaccg gattacgcag                                      30

<210> SEQ ID NO 79
<211> LENGTH: 30
<212> TYPE: DNA
<213> ORGANISM: Artificial
<220> FEATURE:

<223> OTHER INFORMATION: primer

<400> SEQUENCE: 79
aaagatattg ccaaactgaa gagcggctat                                              30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
atccaccaga gcctgatagc cgctcttcag                                              30

<210> SEQ ID NO 81
<211> LENGTH: 27
<212> TYPE: DNA
<213> ORGANISM: Artificial
<220> FEATURE:
<223> OTHER INFORMATION: primer

<400> SEQUENCE: 81
ctgaagagcc tgtatcaggc tctggtg                                                 27

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
gtccagaccc gcatccacca gagcctgata                                              30

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
agcctgtatc agaaactggt ggatgcgggt                                              30

<210> SEQ ID NO 84
<211> LENGTH: 30
<212> TYPE: DNA
<213> ORGANISM: Artificial
<220> FEATURE:
<223> OTHER INFORMATION: primer

<400> SEQUENCE: 84
gttcgtggcg tccagacccg catccaccag                                              30

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
gatacggccg acagcgcgct gctgatttgt                                              30

```
<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
ccattccgga tgttcacaaa tcagcagcgc                                          30

<210> SEQ ID NO 87
<211> LENGTH: 29
<212> TYPE: DNA
<213> ORGANISM: Artificial
<220> FEATURE:
<223> OTHER INFORMATION: primer

<400> SEQUENCE: 87
atgggtgtcg atcatcgtaa tccggtgga                                           29

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
cagagccagc tgcagatcca ccggattacg                                          30

<210> SEQ ID NO 89
<211> LENGTH: 443
<212> TYPE: PRT
<213> ORGANISM: Cryptococcus neoformans

<400> SEQUENCE: 89
```

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
            195                 200                 205

Thr Gln Tyr Phe Ala Asp Lys Val Val Leu Ala Ala Gly Ala Trp Ser
        210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
        290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp
            435                 440

<210> SEQ ID NO 90
<211> LENGTH: 1332
<212> TYPE: DNA
<213> ORGANISM: Cryptococcus neoformans

<400> SEQUENCE: 90

```
atgccgccgt cccgtgcttc aacgaaagtg attgtcattg gtggtggtgg tacgctgggc      60
tcctcaaccg ccctgcatct gctgcgcgcg ggctataccc cgagtaacat taccgtgctg     120
gatacgtacc tgatcccgag tgcccagtcc gcaggcaacg acctgaataa aattatgggt     180
attcgtatcc gcaatccggt ggataaacaa ctgagcctgg aagcccgtga tatgtggcgc     240
aacgacgaag ttttcaaacc gtacttccat aacaccggtc gtctggactg cgctcacacg     300
ccggaatcaa ttgcgtcgct gcgtaaaagc tacgaagcca tcctgaaagc aggctcaggt     360
ctggaaaaaa cccatcactg gctgtcgacg gaagatgaaa tcctggcacg tgcaccgctg     420
ctggaccgta acagattaa aggttggaaa gcaatctata tgaagatgg cggttggctg     480 gcggccgcaa aagctattaa ctccatcggc caagtcctga agaaaaagg tgtgaccttc     540 ggctttggta gcgcaggctc ttttaaaaaa ccgctgttcg atgaagacgg cacgaaagcc     600
attggtatcg aaaccgttga tggtacgcag tattttgccg acaaagtggt tctggctgca     660
ggtgcatgga gcccgaccct ggttgatctg gaaggccagt gctgttctaa agcttgggtc     720
```

-continued

```
tacgcgcaca tgcaactgac gccggaagaa gccgcagaat ataaagaatg cccggtcgtg    780
tacaacagcg aactgggctt tttctttgaa ccgaacgaaa aaggtgtgat caaagtttgt    840
gatgaattcc cgggctttac ccgtttcaaa cagcatcaac cgtacggtgc tagctctacg    900
aaacacatta gctttccgcg ctctcatgcg aaacacccga ccgatacgat cccggatgaa    960
agtgacgcct ccattcgtcg cgctatctct gcgtttctgc cgcgtttcaa agaaaaagaa   1020
ctgtttaacc gcgcgctgtg ctggtgtacc gatacggctg acgcgaacct gctgatttgt   1080
gaacacccga atggaaaaa ttttatcctg gccaccggcg attcaggtca ttcgttcaaa    1140
attctgccga atatcggcaa acacgttgtc gaactgattg aagtaccct ggccgaagat    1200 ctggcagaaa gctggcgttg gcgtccgggc agtggtgacc cgctgatctc ccgtcgcgct   1260
gcgccggcgc gcgacctggc ggacctgccg ggctggaacc acgacgaacc gagcgacgat   1320
gacatggact ga                                                        1332
```

<210> SEQ ID NO 91
<211> LENGTH: 30
<212> TYPE: DNA
<213> ORGANISM: Artificial
<220> FEATURE:
<223> OTHER INFORMATION: primer

<400> SEQUENCE: 91
attatgggta ttgatatccg caatccggtg                                      30

<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92
gctcagttgt ttatccaccg gattgcggat                                      30

<210> SEQ ID NO 93
<211> LENGTH: 30
<212> TYPE: DNA
<213> ORGANISM: Artificial
<220> FEATURE:
<223> OTHER INFORMATION: primer

<400> SEQUENCE: 93
gaatcaattg cgaaactgcg taaaagctac                                      30

<210> SEQ ID NO 94
<211> LENGTH: 30
<212> TYPE: DNA
<213> ORGANISM: Artificial
<220> FEATURE:
<223> OTHER INFORMATION: primer

<400> SEQUENCE: 94
tttcaggatg gcttcgtagc ttttacgcag                                      30

<210> SEQ ID NO 95
<211> LENGTH: 30
<212> TYPE: DNA
<213> ORGANISM: Artificial
<220> FEATURE:
<223> OTHER INFORMATION: primer

<400> SEQUENCE: 95
ctgcgtaaac tgtacgaagc catcctgaaa                                30

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
acctgagcct gctttcagga tggcttcgta                                30

<210> SEQ ID NO 97
<211> LENGTH: 30
<212> TYPE: DNA
<213> ORGANISM: Artificial
<220> FEATURE:
<223> OTHER INFORMATION: primer

<400> SEQUENCE: 97
aaactgtacg aaaaaatcct gaaagcaggc                                30

<210> SEQ ID NO 98
<211> LENGTH: 30
<212> TYPE: DNA
<213> ORGANISM: Artificial
<220> FEATURE:
<223> OTHER INFORMATION: primer

<400> SEQUENCE: 98
tttttccaga cctgagcctg ctttcaggat                                30

<210> SEQ ID NO 99
<211> LENGTH: 440
<212> TYPE: PRT
<213> ORGANISM: Curvularia clavata

<400> SEQUENCE: 99

Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Ile Thr Val Leu Asp Ala Tyr Pro Ile Pro Ser Ser
                35                  40                  45

Gln Ser Ala Gly Asn Asp Leu Asn Lys Ile Met Gly Ile Arg Leu Arg
        50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
                100                 105                 110

Ala Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Ser Arg Asp
        130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln

```
                165                 170                 175
Gly Val Lys Phe Gly Phe Gly Gly Ala Gly Ser Phe Lys Gln Pro Leu
            180                 185                 190
Leu Ala Glu Gly Val Cys Ile Gly Val Glu Thr Val Asp Gly Thr Arg
        195                 200                 205
Tyr Tyr Ala Asp Lys Val Val Leu Ala Ala Gly Ala Trp Ser Pro Thr
    210                 215                 220
Leu Val Glu Leu His Glu Gln Cys Val Ser Lys Ala Trp Val Tyr Gly
225                 230                 235                 240
His Ile Gln Leu Thr Pro Glu Glu Ala Glu Tyr Lys Asn Ser Pro
            245                 250                 255
Val Val Tyr Asn Gly Asp Val Gly Phe Phe Glu Pro Asn Glu His
        260                 265                 270
Gly Val Ile Lys Val Cys Asp Glu Phe Pro Gly Phe Thr Arg Phe Lys
    275                 280                 285
Met His Gln Pro Phe Gly Ala Lys Ala Pro Lys Arg Ile Ser Val Pro
    290                 295                 300
Arg Ser His Ala Lys His Pro Thr Asp Thr Ile Pro Asp Ala Ser Glu
305                 310                 315                 320
Lys Ser Ile Arg Lys Ala Ile Ala Thr Phe Leu Pro Lys Phe Thr Glu
            325                 330                 335
Lys Glu Leu Phe Asn Arg His Leu Cys Trp Cys Thr Asp Thr Ala Asp
        340                 345                 350
Ala Ala Leu Leu Ile Cys Glu His Pro Glu Trp Lys Asn Phe Val Leu
    355                 360                 365
Ala Thr Gly Asp Ser Gly His Ser Phe Lys Leu Leu Pro Asn Ile Gly
    370                 375                 380
Lys His Val Val Glu Leu Leu Glu Gly Thr Leu Ala Asp Asp Leu Ala
385                 390                 395                 400
His Ala Trp Arg Trp Arg Pro Gly Ser Gly Asp Ala Leu Lys Ser Arg
            405                 410                 415
Arg Ser Ala Pro Ala Lys Asp Leu Ala Asp Met Pro Gly Trp Lys His
        420                 425                 430
Asp Asp Val Val Lys Ser Lys Leu
    435                 440

<210> SEQ ID NO 100
<211> LENGTH: 1323
<212> TYPE: DNA
<213> ORGANISM: Curvularia clavata

<400> SEQUENCE: 100
atggccccgt cgcgtgctaa tacgtcggtc attgtggttg gtggtggtgg tacgattggc    60
tcatctacgg ctctgcatct ggtccgctca ggctataccc cgtcgaacat tacggttctg   120
gatgcatacc cgattccgag ctctcagagc gctggcaacg acctgaataa atcatgggt   180 atccgtctgc gtaataaggt ggatctgcag ctgtctctgg aagcgcgcca atgtggcgc   240 gaagacgatc tgttcaagga gtatttccat aacaccggcc gtctggattg cgcgcacggt   300
gaagaaggtc ttgccgacct gcgtcaagcc tatcaggctc tgctggatgc gaatgcgggt   360
ctggaagaga cgaccgaatg gctggatagt gaagacgaaa tcctgaaaaa aatgccgctg   420
ctgtcccgcg atcaaattaa aggctggaag gcggtgtatt cacaggacgg tggttggctg   480
gcagcagcaa aggcaattaa tgcaattggt gaatatctgc gtgctcaggg cgtcaaattc   540
```

```
ggttttggcg gcgccggttc tttcaaacaa ccgctgctgg ctgaaggcgt ctgcatcggt    600
gtcgaaaccg tggatggcac gcgctattac gcagacaaag tggttctggc tgcaggtgca    660
tggtcgccga ccctggttga actgcatgaa cagtgtgtga gcaaagcgtg ggtttacggc    720
cacattcaac tgacgccgga agaagccgca gaatataaga acagcccggt cgtgtacaat    780
ggcgatgtgg gcttttttctt tgaaccgaac gaacatggcg ttatcaaagt ctgcgatgaa    840
tttccgggtt ttacccgctt caagatgcac cagccgtttg gtgccaaagc accgaagcgt    900
attagtgtgc cgcgctccca tgccaaacac ccgaccgata cgatcccgga tgcaagtgaa    960
aaatccattc gtaaagctat cgcgaccttt ctgccgaagt tcacggagaa agagctgttc   1020
aaccgtcatc tgtgctggtg taccgatacg gccgacgctg cgctgctgat tgtgaacat   1080 ccggaatgga aaactttgt tctggcgacc ggcgattcag gtcattcgtt caaactgctg   1140
ccgaatatcg gcaagcacgt tgtcgaactg ctggagggta cgctggcaga tgacctggca   1200
cacgcatggc gttggcgtcc gggtagtggt gatgcactga aaagccgtcg ctctgctccg   1260
gcgaaagacc tggctgatat gccgggctgg aaacatgacg atgtggtgaa aagcaaactg   1320
taa                                                                  1323

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
atcatgggta tcgatctgcg taataaggtg                                       30

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102
cagagacagc tgcagatcca ccttattacg                                       30

<210> SEQ ID NO 103
<211> LENGTH: 30
<212> TYPE: DNA
<213> ORGANISM: Artificial
<220> FEATURE:
<223> OTHER INFORMATION: primer

<400> SEQUENCE: 103
gaaggtcttg ccaaactgcg tcaagcctat                                       30

<210> SEQ ID NO 104
<211> LENGTH: 30
<212> TYPE: DNA
<213> ORGANISM: Artificial
<220> FEATURE:
<223> OTHER INFORMATION: primer

<400> SEQUENCE: 104
atccagcaga gcctgatagg cttgacgcag                                       30

<210> SEQ ID NO 105
<211> LENGTH: 30
```

```
<212> TYPE: DNA
<213> ORGANISM: Artificial
<220> FEATURE:
<223> OTHER INFORMATION: primer

<400> SEQUENCE: 105
cttgccaaac tgcgtcaact gtatcaggct                                      30

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
acccgcattc gcatccagca gagcctgata                                      30

<210> SEQ ID NO 107
<211> LENGTH: 30
<212> TYPE: DNA
<213> ORGANISM: Artificial
<220> FEATURE:
<223> OTHER INFORMATION: primer

<400> SEQUENCE: 107
cgtcaactgt atcagaaact gctggatgcg                                      30

<210> SEQ ID NO 108
<211> LENGTH: 30
<212> TYPE: DNA
<213> ORGANISM: Artificial
<220> FEATURE:
<223> OTHER INFORMATION: primer

<400> SEQUENCE: 108
ctcttccaga cccgcattcg catccagcag                                      30

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
gatacggccg acagcgcgct gctgatttgt                                      30

<210> SEQ ID NO 110
<211> LENGTH: 30
<212> TYPE: DNA
<213> ORGANISM: Artificial
<220> FEATURE:
<223> OTHER INFORMATION: primer

<400> SEQUENCE: 110
ccattccgga tgttcacaaa tcagcagcgc                                      30

<210> SEQ ID NO 111
<211> LENGTH: 30
<212> TYPE: DNA
<213> ORGANISM: Artificial
<220> FEATURE:
<223> OTHER INFORMATION: primer

<400> SEQUENCE: 111
```

```
atcatggta tcgatcatcg taataaggtg                                         30
```

<210> SEQ ID NO 112
<211> LENGTH: 30
<212> TYPE: DNA
<213> ORGANISM: Artificial
<220> FEATURE:
<223> OTHER INFORMATION: primer

<400> SEQUENCE: 112

```
aagctgtacc agaaacttct cgacgcaggc                                        30
```

<210> SEQ ID NO 113
<211> LENGTH: 440
<212> TYPE: PRT
<213> ORGANISM: Pyrenochaeta sp.

<400> SEQUENCE: 113

```
Met Ala Ala Ser Arg Ala Lys Thr Thr Val Ile Val Gly Gly Gly
1               5                   10                  15

Gly Thr Ile Gly Ser Ser Thr Ala Leu His Leu Arg Ser Gly Tyr
                20                  25                  30

Thr Pro Ser Asn Ile Thr Val Leu Asp Thr Tyr Pro Ile Pro Ser Leu
            35                  40                  45

Gln Ser Ala Gly Asn Asp Leu Asn Lys Ile Met Gly Ile Arg Leu Arg
50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Ala Gly Ser Phe Gln Gln Pro Leu
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
        290                 295                 300
```

```
Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
            325                 330                 335

Lys Glu Leu Phe Asn Arg Ala Met Cys Trp Cys Thr Asp Thr Ala Asp
        340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
            405                 410                 415

Arg Ala Ala Pro Ala Lys Asp Leu Ala Asp Met Pro Gly Trp Asn His
        420                 425                 430

Asp Glu Ser Pro Arg Ala Lys Leu
        435                 440

<210> SEQ ID NO 114
<211> LENGTH: 1323
<212> TYPE: DNA
<213> ORGANISM: Pyrenochaeta sp.

<400> SEQUENCE: 114
atggccgctt cacgagcaaa gacgacagtg atcgtcgtgg gtggcggcgg taccattggg      60
tcatcaacag cgctccacct tctacgttca ggttatactc catcgaatat cacagttttg     120
gacacatatc caattccttc attacagtcc gcgggcaatg atttaaacaa gattatgggc     180
attcgcttgc gaaacaaagt cgacctccaa ttgagtttag aggctaggga gatgtggaga     240
gaagatgaac ttttagaga tttttttcac aatactgggc gactggattg tgcccatggc      300
gaaaaaggaa tcaatgatct taggcaggca tatcaaacac tactcgacgc caatgccggt     360
ttggaagaga cgaacgagtg gctggactct gaggacgaaa ttctggcaag aatgccgctc     420
ttgagtcgag agcagatcaa gggctggaaa gcggtcttca gccgagacgg cggttggctc     480
gccgcaggta aggccatcaa tgcaattggc gagtatctgc gcaaggaagg agtcaagttt     540
ggctttggcg gcgcgggatc gttccagcag ccgcttcttg cagagggtat ttgcattggc     600
gtggaaacaa cggatggaac tagatactac gccgacaaag ttgtcctggc agctggtgca     660
tggagtcctg cattggtgga cttggaagac cagtgtgttt caaaagcatg gtctatgct      720 cacatgcagc tcaccccgaa ggaggctgcg gcatacaaag acacaccagt agtctacaat     780
ggcgatctgg gattttttctt tgaaccaaac gagcatggcg tgatcaaagt ctgcgacgag     840
ttcccaggct tcacacgttt taagaagcat caaccatttg gtgcaagggc accaaaacgg     900
atatcggttc ccagatctca tgccaaacac cctactgata cttatcctca cgcatccgaa     960
gccagtatca agaaagctat tgcggcattc ttaccacagt tcaaggacaa ggagctgttc    1020
aaccgcgcaa tgtgctggtg cacagataca gctgatgcag ccttgttgat ctgcgaacac    1080
ccgcaatgga gaaatttcat gcttgctact ggagacagcg gcactcatt taagctctta    1140 ccaaatatcg gcaagcatgt agttgaactg attgaaggca ctctggcggc agatcttgcc    1200
catgcttgga ggtggcgacc tgggattggt gacgctttgc agtcaaggcg agcggcacct    1260
gcgaaggatc tggcggacat gccaggatgg aatcatgatg aatctcctag ggcgaaattg    1320
```

```
taa                                                                     1323
```

<210> SEQ ID NO 115
<211> LENGTH: 452
<212> TYPE: PRT
<213> ORGANISM: Arthrinium sp.

<400> SEQUENCE: 115

```
Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365
```

```
Phe Ile Leu Ala Thr Gly Asp Ser Gly His Ser Phe Lys Leu Leu Pro
    370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
            435                 440                 445

Glu His Lys Leu
    450

<210> SEQ ID NO 116
<211> LENGTH: 1359
<212> TYPE: DNA
<213> ORGANISM: Arthrinium sp.

<400> SEQUENCE: 116
atggcggcgt cacgaaagac caccaaagtg attgtcgtgg gcggcggagg caccatcggc    60
tcatccacgg ctctacatct tctccggtcg gggtatacgg ccaccaacat taccgtcctg   120
gacacctacc ccatcccctc ggcgcagtcg gccggcaacg acctgaacaa gattatgggg   180
atccgcctgc ggaacccggt cgacaagcag ctcagccttg aagcccagga catgtggtgc   240
catgacgagc tcttcaagcc ctacttccac aacaccggca ggatggactg cgagggcacc   300
gagaagggca tcgcggcgct caagcagcag taccagacct tgcttgacgc cgacgtgggc   360
ctcgagaaga cgacggagtg gctcgacagt gaggatgcca tcctggcaaa gatgccactc   420
ctggagcgcg accaaatcaa aggatggaaa gcgatattta gccaggacgg cggttggctg   480
gccgcagcta agccatcaa cgcgataggc gaggaactga agaggcaggg cgtcaacttc   540
gggttcggcg gggcgggcgc cttcaagaag ccccttttcg ccccggacgg atccacctgc   600
atcggcgtcg agacggtgga tggaaccaag tactacggcg acaaggtcgt cctggccgcg   660
ggcgcgtgga gccctgcgct ggtcgacctg aagagcagt gctgctccaa ggcctgggtg   720
tacgcccaca tgcagctgac gccgcacgag gcagccgagt accagggctg tccggtcgtg   780
taccacggcg acctcggctt cttcttcgag cccaacgagc acggcgtcat caaggtgtgc   840
gacgagttcc ccggcttcac gcggttcctc gagcagcacc agtcgtacgg cgcgccggcg   900
ccgacgcgcg tctcggtgcc ccggtcgcac gcgaagcacc ccaccgacac atacccggac   960
gcgtcggagc agtcgatccg gcgggccgtg gccgcgttcc tgccgcgatt ccaaagcaaa  1020
gagcttttca accgcgccat gtgctggtgc accgacacgg ccgacgccgc gctgctgatc  1080
tgcgagcacc cccgctggcg caattttatt ctggctacgg gcgacagcgg acactcgttc  1140
aagctcctgc ccaacatcgg caagcacgtg gtcgagctgc tggaaggccg gctagcggat  1200
gacctggcgc aggcgtggag gtggcgcccc ggtcaggggg atgcgttgaa gtctagacgg  1260
gcggctccgg ctaaggatct ggcggatatg ccagggtgga atcatgacgg ggattcaggg  1320
aatgctacgt ctggaacaag ctcggagcac aaattgtag                          1359

<210> SEQ ID NO 117
<211> LENGTH: 440
<212> TYPE: PRT
<213> ORGANISM: Curvularia clavata

<400> SEQUENCE: 117
```

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
                100                 105                 110

Ala Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
            275                 280                 285

Gln His Gln Pro Tyr Gly Ala Lys Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
            325                 330                 335

Lys Glu Leu Phe Asn Arg His Leu Cys Trp Cys Thr Asp Thr Ala Asp
                340                 345                 350

Ala Ala Leu Leu Met Cys Glu His Pro Glu Trp Lys Asn Phe Val Leu
            355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415
```

Arg Ala Ala Pro Ala Lys Asp Leu Ala Asp Met Pro Gly Trp Lys His
            420                 425                 430

Asp Asp Val Val Lys Ser Lys Leu
        435                 440

<210> SEQ ID NO 118
<211> LENGTH: 1323
<212> TYPE: DNA
<213> ORGANISM: Curvularia clavata

<400> SEQUENCE: 118

| | | | | | |
|---|---|---|---|---|---|
| atggcgccct | caagagcaaa | cacttctgtt | atcgttgtcg | gtggcggtgg | cactattggc | 60 |
| tcttcaaccg | ctcttcatct | agtccgctcg | ggctacacac | catctaacat | caccgttctt | 120 |
| gacacatacc | ctatcccatc | agcgcagtca | gctggaaatg | acctgaataa | gatcatgggt | 180 |
| atccgcttgc | ggaacaaggt | cgatctccaa | ttgagtctag | aagccaggca | gatgtggaga | 240 |
| gaggatgacc | tattcaaaga | gtatttccac | aacactggaa | gactcgactg | tgcacatggg | 300 |
| gaagagggac | ttgcagattt | gagacaggca | taccaggctc | tgctcgacgc | taacgcgggt | 360 |
| ctcgaagaaa | caacagaatg | gcttgactcc | gaagacgaaa | ttctaaagaa | atgccgcctt | 420 |
| ctggaccgcg | agcaaatcaa | gggctggaaa | gcggtttaca | gccaagacgg | cggctggctg | 480 |
| gctgcagcaa | aagccatcaa | tgctataggc | gagtacttgc | gagcccaagg | agttaagttt | 540 |
| ggttttggtg | gtgctggatc | gttcaagcag | cctcttttgg | ccgagggagt | gtgcattggc | 600 |
| gtagagacag | tcgacgggac | gaggtactac | gccgataaag | ttgtgcttgc | agctggtgct | 660 |
| tggagtccgg | tattggtcga | cctggaagat | caatgcgttt | caaaagcttg | gtatatgct | 720 |
| cacatacagc | ttacgcctga | ggaagcagca | gagtacaaaa | acgtgcctgt | ggtatacaac | 780 |
| ggcgacgtcg | gcttcttctt | cgagcctgac | gagcacggcg | ttatcaaggt | ttgtgacgaa | 840 |
| tttccaggtt | ttacacgctt | caagcaacat | cagccatatg | cgccaaagc | accgaaacgt | 900 |
| atctccgtgc | ccagatcggc | agcgaagcac | ccgacggata | cttaccccga | tgcgtcggag | 960 |
| aagagcatcc | gcaaggccat | tgcaactttc | ctgcccaagt | tcacagagaa | ggagctattc | 1020 |
| aaccggcatc | tatgttggtg | tacggatacg | gctgacgctg | cgctattgat | gtgtgagcat | 1080 |
| cccgagtgga | agaactttgt | gctggcgaca | ggggacagcg | gcacacatt | caaacttttg | 1140 |
| ccaaatatcg | gcaagcatgt | ggttgagctt | ctcgagggta | cactcgcgga | ggatctggca | 1200 |
| catgcatgga | gatggcggcc | tggtactggc | gatgcgctga | atcaagaag | agcggcaccg | 1260 |
| gcgaaggatt | tagcagatat | gcctggctgg | aagcatgacg | atgttgtcaa | gtccaagtta | 1320 |
| tag | | | | | | 1323 |

<210> SEQ ID NO 119
<211> LENGTH: 438
<212> TYPE: PRT
<213> ORGANISM: Emericella nidulans

<400> SEQUENCE: 119

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
            85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
        210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
        290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 120
<211> LENGTH: 1317
<212> TYPE: DNA
<213> ORGANISM: Emericella nidulans

<400> SEQUENCE: 120

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaaat cttcggcatc     180
aggctgcgca acaagcctga cttacaactc tatcttgagg cgctggacat gtggaaaaat     240
gatcctctat tcaagccgtt tttccacaat gttggacaga tggacgtctc ttcaacagaa     300
gaaggcatca aaaagcttcg catgagatac cagtctcttc tcgacgcagg cattgggctc     360
gagaagacga atttcctgct ggaaagtgaa gacgagatcc tggctaaagc cgcatttc      420
acgcgggagc agattaaagg ctggaaaggg ctgttctgtg gcgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga agacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgaggcaaa gatgtag       1317
```

<210> SEQ ID NO 121
<211> LENGTH: 441
<212> TYPE: PRT
<213> ORGANISM: Ulocladium sp.

<400> SEQUENCE: 121

```
Met Ala Pro Asn Arg Ala Asn Ile Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
```

```
                130                 135                 140
Gln Ile Lys Gly Trp Lys Ala Val Phe Ser Glu Asp Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Ala Gly Ser Phe Lys Gln Pro Leu
                180                 185                 190

Leu Ala Glu Gly Val Cys Val Gly Val Glu Thr Val Asp Gly Thr Arg
                195                 200                 205

Tyr Tyr Ala Asp Lys Val Val Leu Ala Ala Gly Ala Trp Ser Pro Ala
                210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
                260                 265                 270

Gly Val Ile Lys Val Cys Asp Glu Phe Pro Gly Phe Thr Arg Phe Lys
                275                 280                 285

Gln His Gln Pro Phe Gly Ala Ser Ala Pro Lys Arg Ile Ser Val Pro
290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
                340                 345                 350

Ala Ala Leu Leu Met Cys Glu His Pro Glu Trp Lys Asn Phe Val Leu
                355                 360                 365

Ala Thr Gly Asp Ser Gly His Thr Phe Lys Leu Leu Pro Asn Ile Gly
                370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
                420                 425                 430

Asp Gly Glu Ala Pro Arg Ala Lys Leu
                435                 440

<210> SEQ ID NO 122
<211> LENGTH: 1326
<212> TYPE: DNA
<213> ORGANISM: Ulocladium sp.

<400> SEQUENCE: 122
atggcaccta acagagctaa tatttctgtc atcgtcgtgg gtggtggcgg caccattggg      60
tcttcaacgg cccttcatct cgtacgctcg ggatacacac cgtcgaatat cacggttctg     120
gacacttatc caattccatc agcgcaatca gctggcaatg acttgaacaa gatcatgggt     180
atccgtttgc ggaacaaggt ggatttgcag ttgagcttag aggcgagaca aatgtggaca     240
gaagacgatc tgttcaagga gtactttcat aaaaccgggc ggctcgactg cgcacatggc     300
gagaaaggcc ttgcagatct caaacaagcc taccagcccc tcttgatgc gaacgctggc     360
```

```
ctggaggcga cgacagaatg gttagattcc gaggacaaga ttcttgagaa gatgccgctt    420
ctcaatcgcg atcagatcaa aggatggaaa gccgtcttca gcgaagacgg cggatggctc    480
gctgcggcaa aagccatcaa cgctatcggt agatttctgc gcgatcaagg cgtcaagttt    540
ggctttggcg gagcaggatc attcaaacaa cctcttcttg ccgagggtgt ttgtgttggt    600
gttgaaacag ttgacgggac gagatattat gctgacaagg ttgtgttggc ggctggtgcg    660
tggagtcctg cattggtcga tctacaagac caatgtgtgt cgaaagcatg ggtatacgct    720
cacatccaac tgtccccgag cgaggcggcg gaatacaaaa atgttcctgt agtctataat    780
ggcgacgtgg gcttcttctt cgagcctgac gaatacggcg tcatcaaagt ctgtgacgag    840
tttccaggtt ttacgcgctt caagcagcat caaccttttcg gcgcatcggc tccaaagcgc    900
atttctgtgc ctcgatctgc cgcaaaacac cccacagata cctatccgga cgcctcggaa    960
gtcagtatcc gcaaggccat cgcgacgttc ctgcccaagt tcacagaaaa ggaagtgttc   1020
aacaggcatc tgtgttggtg tactgatacg gctgatgcgg cgcttttgat gtgcgaacat   1080
cctgagtgga agaactttgt tttggccacg ggtgacagtg tcacaccttc aagcttcta    1140 cctaacatcg gtaagcatgt ggtcgagcta ctagagggta cattagcaga cgacctagcg   1200
catgcgtgga gatggcgtcc cggtaccggc gatgcgctga gtcgcgaagg gcggcgcgt    1260 gcgaaagacc ttgcagatat gccaggatgg aatcatgacg gggaagcccc cagagcgaag   1320
ctgtga                                                               1326
```

<210> SEQ ID NO 123
<211> LENGTH: 437
<212> TYPE: PRT
<213> ORGANISM: Penicillium janthinellum

<400> SEQUENCE: 123

```
Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
```

|  |  |  | 195 |  |  |  | 200 |  |  |  | 205 |  |
|---|---|---|---|---|---|---|---|---|---|---|---|---|
| Thr | Lys | Tyr | Phe | Ala | Asp | Lys | Val | Val | Leu | Ala | Ala | Gly Ala Trp Ser |

| Ser | Thr | Leu | Val | Asp | Leu | Glu | Asp | Gln | Cys | Val | Ser | Lys | Ala | Trp | Val |
|---|---|---|---|---|---|---|---|---|---|---|---|---|---|---|---|
| 225 |  |  |  |  | 230 |  |  |  |  | 235 |  |  |  |  | 240 |

Phe Ala His Ile Gln Leu Thr Pro Gln Glu Ser Ala Gln Tyr Lys Asp
                245                    250                    255

Val Pro Val Val Tyr Asp Gly Asp Tyr Gly Phe Phe Glu Pro Asn
          260                    265                    270

Glu His Gly Val Ile Lys Val Cys Asp Glu Phe Pro Gly Phe Ser Arg
275                  280                    285

Phe Lys Leu His Gln Pro Tyr Gly Ala Thr Ser Pro Lys Leu Ile Ser
          290                    295                    300

Val Pro Arg Ser His Ala Lys His Pro Thr Asp Thr Tyr Pro Asp Ser
305                  310                    315                    320

Ser Glu Glu Thr Ile Arg Lys Ala Ile Ala Arg Phe Met Pro Arg Phe
                  325                    330                    335

Lys Asp Lys Glu Leu Phe Asn Arg Ser Met Cys Trp Cys Thr Asp Thr
              340                    345                    350

Ala Asp Ala Asn Leu Leu Ile Cys Glu His Pro Lys Trp Lys Asn Phe
              355                    360                    365

Ile Leu Ala Thr Gly Asp Ser Gly His Ser Phe Lys Val Leu Pro Asn
          370                    375                    380

Ile Gly Lys His Val Val Glu Leu Ile Glu Gly Arg Leu Pro Gln Asp
385                  390                    395                    400

Leu Ala Gly Ala Trp Arg Trp Arg Pro Gly Gly Asp Ala Leu Lys Ser
                  405                    410                    415

Lys Arg Ser Ala Pro Ala Lys Asp Leu Ala Glu Met Pro Gly Trp Lys
              420                    425                    430

His Asp Ala Lys Leu
        435

<210> SEQ ID NO 124
<211> LENGTH: 1314
<212> TYPE: DNA
<213> ORGANISM: Penicillium janthinellum

<400> SEQUENCE: 124

| atggctcatt | cgcgagaaag | cacaaagatt | gtcattgtcg | ggggaggtgg | cacaatggga | 60 |
|---|---|---|---|---|---|---|
| tcttcaaccg | cgctacacct | gatacgctct | ggatacaccc | cgtcaaacat | caccgtcctt | 120 |
| gatgtatacc | caattccatc | cttgcaatcc | gcaggatatg | atcttaacaa | gatcatgagc | 180 |
| atccgattac | gcaacgggcc | tgacttgcaa | ctttccctgg | aggctctcga | tatgtggaaa | 240 |
| aacgatccgt | tgttcaagcc | tttctttcac | aacgttggca | tgctagactg | ttcatcgtca | 300 |
| caagagggta | ttgcaagcct | tcgacggaag | caccaagacc | tcatagacgc | gaatatcgga | 360 |
| ctagagaaga | cgaatatctg | gttagagagt | gaagatgata | ttctggcaaa | agccccgcac | 420 |
| ttcacgcggg | aacagatcaa | ggggtggaag | ggcttgtttt | gcggcgatgg | aggatggctt | 480 |
| gctgcagcca | aggccatcaa | tgcgatcgga | acctttctaa | aaagtcaagg | cgtcaagttc | 540 |
| ggatttggaa | gtgccgggac | tttcaagcga | cctttgtttg | ctccagatgg | ggcgacatgc | 600 |
| agcggtgttg | agacagtaga | tggaacaaaa | tacttcgccg | acaaggtggt | tttggccgct | 660 |
| ggtgcttgga | gttcgacgtt | agtagatttg | gaggaccaat | gtgtttcgaa | ggcctgggtc | 720 |

```
ttcgctcata tccaactcac gccccaagaa tcggcccagt acaaggacgt gcccgtagta    780
tacgacggtg attatggctt tttcttcgag cccaacgaac acggagtaat caaagtctgc    840
gatgagttcc ccgggttctc ccgcttcaag ctgcatcaac cttacggtgc cacctctcct    900
aagcttatat ccgttcctcg atcacacgcc aagcatccca ccgatacctc cccagattct    960
tctgaagaga ccattcgaaa agcgattgcg aggtttatgc cacgcttcaa ggataaggag   1020 cttttaata ggagcatgtg ctggtgcacc gatactgctg atgccaactt gttgatctgc   1080
gagcacccca gtggaagaa ctttatcttg gccacaggag acagcggcca tagtttcaag   1140
gttttgccca ataggaaa acatgtcgtt gagttgatag aaggacgcct accacaagac   1200
ctggctggtg cgtggagatg gagaccaggg ggagatgccc ttaagtccaa acgcagtgct   1260
ccggcaaagg accttgctga aatgccgggc tggaagcatg atgcgaagct ctga         1314
```

<210> SEQ ID NO 125
<211> LENGTH: 445
<212> TYPE: PRT
<213> ORGANISM: Aspergillus fumigatus

<400> SEQUENCE: 125

```
Met Ala Pro Ser Ile Leu Ser Thr Glu Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270
```

```
Pro Asp Glu Asp Lys His Glu Leu Lys Ile Cys Asp Glu His Pro Gly
            275                 280                 285
Tyr Cys Asn Phe Leu Pro Asp Pro Asn Arg Pro Gly Gln Glu Lys Ser
        290                 295                 300
Val Pro Phe Ala Lys His Gln Ile Pro Leu Glu Ala Glu Ala Arg Ala
305                 310                 315                 320
Arg Asp Phe Leu His Asp Thr Met Pro His Leu Ala Asp Arg Pro Leu
                325                 330                 335
Ser Phe Ala Arg Ile Cys Trp Asp Ala Asp Thr Pro Asp Arg Ala Phe
            340                 345                 350
Leu Ile Asp Arg His Pro Glu His Pro Ser Leu Leu Val Ala Val Gly
        355                 360                 365
Gly Ser Gly Asn Gly Ala Met Gln Met Pro Thr Ile Gly Gly Phe Ile
    370                 375                 380
Ala Asp Ala Leu Glu Ser Lys Leu Gln Lys Glu Val Lys Asp Ile Val
385                 390                 395                 400
Arg Trp Arg Pro Glu Thr Ala Val Asp Arg Asp Trp Arg Ala Thr Gln
                405                 410                 415
Asn Arg Phe Gly Gly Pro Asp Arg Ile Met Asp Phe Gln Gln Val Gly
            420                 425                 430
Glu Asp Gln Trp Thr Lys Ile Gly Glu Ser Arg Gly Pro
            435                 440                 445

<210> SEQ ID NO 126
<211> LENGTH: 1338
<212> TYPE: DNA
<213> ORGANISM: Aspergillus fumigatus

<400> SEQUENCE: 126
atggcgcctt caattttgag cactgaatct tccattatcg ttatcggagc aggcacatgg      60
ggctgctcaa ctgctctgca cctcgctcgt cgaggctaca agatgtcac tgttctcgac     120 cctcatccag ttccttcgcc cattgcagca ggcaatgaca tcaacaagat tatggagcac     180
agcgagctga agatggctc atccgaccct cgaagcgcag ccttctcgac atttacgcga     240
gctgctctta aggcgtggaa aactgacccg ttttccagc cttactttca cgaaactggc     300
tttatcatat cggggcacac acctgctctg attgaccaca tacgaaaaga cgaggtagaa     360
ccgtcagaaa caaacttcgt caagctggag acagccgagg acttccgccg gaccatgccg     420
ccaggtgtac tgacaggcga cttccctggc tggaaaggct ggttgcacaa gtctggtgct     480
gggtggattc atgccaaaaa ggctatgatc tctgctttca atgaagctaa cgcttgggga     540
gtcagatttg tcactggctc tccggaaggg aatgttgtat cgttggtata cgaggacgga     600
gacgtcgttg gagccagaac tgccgatggt cgcgtgcaca agcccatcg cactattctt     660 tcggcaggtg ctggcagtga cagtctccta gacttcaaga gcagcttcg gcctaccgcg     720 tggactctct gtcatattca gatgggccct gaagaggtca gcaatatcg gaaccttcct     780 gtgttgttca acatcgccaa agggttcttc atggagcctg atgaggataa acacgagctc     840
aagatttgtg acgagcatcc agggtactgc aactttctcc ctgacccaaa cagaccgggc     900
caggagaaga gtgtcccctt cgcaaagcat cagatcccgc tcgaggccga agcccgcgca     960
cgagactttc tccatgatac aatgccgcat ctggctgacc ggccactgtc tttcgcgcgt    1020
atttgctggg atgctgatac cccagaccgt gctttcttga tcgatagaca tcctgaacac    1080
ccctcactgc tagtcgctgt tggaggttcc ggcaatggcg ccatgcaaat gcctacaatt    1140
```

```
ggcggtttta tcgcagatgc tctagagagt aaactacaga aggaggtgaa ggacatcgtt       1200
cgatggaggc cagagacggc tgtcgatcga gattggagag cgactcagaa tcgctttggc       1260
gggcctgaca ggatcatgga ttttcagcag gtcggagagg atcagtggac caagattgga       1320
gagagcagag gtccgtaa                                                    1338
```

<210> SEQ ID NO 127
<211> LENGTH: 445
<212> TYPE: PRT
<213> ORGANISM: Aspergillus oryzae

<400> SEQUENCE: 127

```
Met Thr Ser Ser Lys Leu Thr Pro Thr Ser Ile Leu Ile Val Gly
1               5                  10                  15

Ala Gly Thr Trp Gly Cys Ser Thr Ala Leu His Leu Ala Arg Arg Gly
                20                  25                  30

Tyr Lys Asn Val Thr Val Leu Asp Pro His Pro Val Pro Ser Pro Ile
                35                  40                  45

Ala Ala Gly Asn Asp Ile Asn Lys Ile Met Glu His Arg Glu Val Lys
            50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
                100                 105                 110

His Ile Gln Glu His Glu Ile Asp Ser Ser Asp Ala Glu Phe Ile Lys
            115                 120                 125

Leu Asn Thr Ala Glu Asp Phe Arg Lys Thr Met Pro Pro Gly Ile Leu
            130                 135                 140

Thr Gly Asn Phe Pro Gly Trp Lys Gly Trp Leu Asn Lys Thr Gly Ala
145                 150                 155                 160

Gly Trp Ile His Ala Lys Lys Ala Met Phe Ser Ala Tyr Thr Glu Ala
                165                 170                 175

Lys Arg Leu Gly Val Thr Phe Ile Thr Gly Ser Pro Glu Gly Asp Val
                180                 185                 190

Val Ser Leu Ile Tyr Glu Asn Gly Asp Val Val Gly Ala Arg Thr Ala
            195                 200                 205

Asp Gly Thr Val His Arg Ala Asp His Thr Ile Leu Ser Ala Gly Ala
            210                 215                 220

Gly Ser Asp Arg Leu Leu Asp Phe Lys Lys Gln Leu Arg Pro Thr Ala
225                 230                 235                 240

Trp Thr Leu Cys His Ile Arg Met Thr Pro Asp Glu Ala Lys Lys Tyr
                245                 250                 255

Arg Asn Leu Pro Val Leu Phe Asn Val Ala Lys Gly Phe Phe Met Glu
                260                 265                 270

Pro Asp Glu Asp Asn His Glu Leu Lys Ile Cys Asp Glu His Pro Gly
            275                 280                 285

Tyr Cys Asn Phe Val Pro Asp Pro Lys His Gly Gly Glu Val Arg Ser
            290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                325                 330                 335
```

```
Ser Phe Ala Arg Ile Cys Trp Asp Ala Asp Thr Val Asp Arg Ala Phe
            340                 345                 350

Leu Ile Asp Arg His Pro Glu Tyr Arg Ser Leu Leu Leu Ala Val Gly
        355                 360                 365

Gly Ser Gly Asn Gly Ala Met Gln Met Pro Thr Ile Gly Gly Phe Ile
370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                405                 410                 415

Asn Arg Phe Gly Gly Pro Asn Lys Val Met Asp Phe Gln Lys Val Gly
            420                 425                 430

Glu Asn Glu Trp Thr Lys Ile Gly Asp Lys Ser Arg Leu
        435                 440                 445

<210> SEQ ID NO 128
<211> LENGTH: 1338
<212> TYPE: DNA
<213> ORGANISM: Aspergillus oryzae

<400> SEQUENCE: 128
atgacatcct ccaagttgac tcccacatca tctatcttaa ttgtcggtgc agggacctgg      60
ggttgttcta ctgctttaca tcttgcccgt cgaggataca aaaatgtcac ggtcctagat     120
ccgcacccgg tcccttctcc cattgcagct ggcaatgaca ttaacaagat tatggagcac     180
agggaggtaa aagcctctga accgatcct tggagtatcg ccttctcaac atgcacacga      240
gctgcactga aaggttggaa aaacgaccca gtattccagc catacttcca tgaaacgggg     300
gcaatagttt ctggccacac cgcctctttg attaaacata caagaaaca cgaaatcgac      360 tcgtcagacg ccgagttcat aaaattgaac accgcagagg atttccgcaa aactatgccc     420
ccgggaatcc tcactggcaa cttccccggc tggaagggct ggctgaacaa gaccggcgcc     480
ggatggatcc acgccaagaa ggccatgttc tccgcataca ccgaagcaaa gcgcctagga     540
gtcactttca tcaccggctc ccctgaagga gacgttgtat ctctaattta cgagaatgga     600
gacgtagtcg gagccagaac ggccgacggc accgtccacc gagcagacca taccattctt     660
tccgcagggg ctggcagtga tcgtctcctg gactttaaga aacagctccg tcctaccgcc     720
tggacgctct gccacatcag aatgacgccc gacgaggcca agaagtaccg aatcttcct      780 gtgctgttca acgtcgctaa ggggttcttc atggaacctg atgaggataa tcatgagctt     840
aagatctgcg acgagcatcc tggatattgc aacttcgtcc cggacccgaa gcacggcggt     900
gaggtgcgca gtatcccatt tgcaaagcat cagattcctc ttgaagccga ggcccgtgca     960
agggacttcc tccgtgatac gatgcctcat cttgctgatc gaccactgtc ttttgctcgt    1020
atatgctggg atgctgatac agtggatcgc gccttcttga tcgataggca tcctgagtat    1080
cgctctttac tgcttgctgt cggtggatct ggtaatggag ccatgcaaat gcctaccatt    1140
ggtgggttca tagcggatgc tctggaggga aacctgcaaa aggaactgaa gcatgcacta    1200
cggtggaggc ctgagattgc cgcccaacga gactggaagg atacgcaaaa tagattcgga    1260
ggtccgaata aagtaatgga tttccaaaag gttggagaga tgagtggac caagattggc     1320 gataagagtc ggctttaa                                                   1338

<210> SEQ ID NO 129
<211> LENGTH: 438
<212> TYPE: PRT
```

<213> ORGANISM: Aspergillus fumigatus

<400> SEQUENCE: 129

```
Met Ala Val Thr Lys Ser Ser Leu Leu Ile Val Gly Ala Gly Thr
 1               5                  10                  15

Trp Gly Thr Ser Thr Ala Leu His Leu Ala Arg Arg Gly Tyr Thr Asn
                20                  25                  30

Val Thr Val Leu Asp Pro Tyr Pro Val Pro Ser Ala Ile Ser Ala Gly
             35                  40                  45

Asn Asp Val Asn Lys Val Ile Ser Ser Gly Gln Tyr Ser Asn Asn Lys
 50                  55                  60

Asp Glu Ile Glu Val Asn Glu Ile Leu Ala Glu Ala Phe Asn Gly
 65                  70                  75                  80

Trp Lys Asn Asp Pro Leu Phe Lys Pro Tyr Tyr His Asp Thr Gly Leu
                 85                  90                  95

Leu Met Ser Ala Cys Ser Gln Glu Gly Leu Asp Arg Leu Gly Val Arg
                100                 105                 110

Val Arg Pro Gly Glu Asp Pro Asn Leu Val Glu Leu Thr Arg Pro Glu
            115                 120                 125

Gln Phe Arg Lys Leu Ala Pro Glu Gly Val Leu Gln Gly Asp Phe Pro
130                 135                 140

Gly Trp Lys Gly Tyr Phe Ala Arg Ser Gly Ala Gly Trp Ala His Ala
145                 150                 155                 160

Arg Asn Ala Leu Val Ala Ala Arg Glu Ala Gln Arg Met Gly Val
                165                 170                 175

Lys Phe Val Thr Gly Thr Pro Gln Gly Arg Val Val Thr Leu Ile Phe
                180                 185                 190

Glu Asn Asn Asp Val Lys Gly Ala Val Thr Gly Asp Gly Lys Ile Trp
            195                 200                 205

Arg Ala Glu Arg Thr Phe Leu Cys Ala Gly Ala Ser Ala Gly Gln Phe
210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
            275                 280                 285

Gln Ser Ala Asp Gly Thr Met Met Ser Ile Pro Phe Glu Lys Thr Gln
290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                325                 330                 335

Cys Ala Asp Thr Ala Asn Arg Glu Phe Leu Ile Asp Arg His Pro Gln
            340                 345                 350

Tyr His Ser Leu Val Leu Gly Cys Gly Ala Ser Gly Arg Gly Phe Lys
            355                 360                 365

Tyr Leu Pro Ser Ile Gly Asn Leu Ile Val Asp Ala Met Glu Gly Lys
        370                 375                 380

Val Pro Gln Lys Ile His Glu Leu Ile Lys Trp Asn Pro Asp Ile Ala
385                 390                 395                 400
```

Ala Asn Arg Asn Trp Arg Asp Thr Leu Gly Arg Phe Gly Gly Pro Asn
            405                 410                 415

Arg Val Met Asp Phe His Asp Val Lys Glu Trp Thr Asn Val Gln Tyr
        420                 425                 430

Arg Asp Ile Ser Lys Leu
        435

<210> SEQ ID NO 130
<211> LENGTH: 1317
<212> TYPE: DNA
<213> ORGANISM: Aspergillus fumigatus

<400> SEQUENCE: 130

```
atggcggtaa ccaagtcatc ttcccttttg atcgtggggg caggcacctg ggcacatcg      60
actgctctcc acctggcacg aagaggatac acaaatgtga cggttctaga tccctacccc    120
gttccctcag ccatctcggc tgggaatgat gtgaacaagg tcatctcctc cggccaatat    180
agcaacaaca aggacgaaat tgaggtcaac gagattctgg ctgaagaagc gttcaatggc    240
tggaagaacg accccttgtt caaaccatac tatcacgata ctggattgct catgtccgcc    300
tgctcccagg aaggcttgga ccgccttgga gtccgtgtca ggcccggtga ggaccccaac    360
cttgtggaac tgacacggcc ggagcaattc cgcaaattag ctcctgaggg tgttctacag    420
ggagatttcc ccggctggaa gggctacttt cgcgcgttcag gagctggttg ggcccatgct    480
cgcaatgcac tcgtggctgc tgcaagggag gctcagagaa tgggcgtgaa gttcgtaact    540
ggcactcctc agggcagagt agtcactcta atatttgaga ataacgatgt caaaggtgcc    600
gttaccggag acggcaagat ttggcgtgca gagcgcacat tcctctgcgc cggtgccagc    660
gctggtcagt cctcgactt caagaatcag ttgcgtccaa cggcatggac gctggttcat    720
attgctctga gcctgagga gcgggctctt tacaagaata tcccagttat cttcaacatt    780
gagagggggt tcttcttcga accagatgag gagcgcggtg agattaagat ctgcgacgaa    840
catccggggt ataccaatat ggtacagtct gccgacggca cgatgatgag cattcctttt    900
gaaaagactc agattcctaa gaagccgag acgagggtta gagctctgct taaagagacg    960
atgccacagc ttgcagaccg tccattcagt ttcgccagga tttgctggtg cgccgacact   1020
gccaaccggg agttcttgat cgatcgccat cctcagtacc attcgcttgt gctgggctgc   1080
ggcgcttccg gcagaggatt caaatatcta ccttcaattg caatctcat cgttgatgct   1140
atggaaggca aggtccctca aaagatccac gaactgatta atggaacccc agatattgct   1200
gccaatcgca actggaggga tactttgggg agattcgggg gtcccaacag agtaatggac   1260
ttccacgacg tcaaggagtg gacaaatgta caatatagag atatttccaa gttataa      1317
```

<210> SEQ ID NO 131
<211> LENGTH: 437
<212> TYPE: PRT
<213> ORGANISM: Aspergillus terreus

<400> SEQUENCE: 131

Met Pro Val Thr Lys Ser Ser Ser Ile Leu Ile Gly Ala Gly Thr
1               5                   10                  15

Trp Gly Cys Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
        35                  40                  45

Asn Asp Val Asn Lys Ile Ile Ser Ser Gly Gln Tyr Ser Ser Lys Lys

```
            50                  55                  60
Asp Glu Val Glu Val Asn Glu Ile Ile Ala Glu Gln Ala Phe Asn Gly
65                  70                  75                  80

Trp Lys Asn Asp Pro Ile Phe Lys Pro Tyr Tyr His Asp Thr Gly Val
                85                  90                  95

Val Met Ser Ala Thr Thr Gln Glu Gly Leu Glu Arg Leu Gly Val Arg
            100                 105                 110

Val Arg Pro Glu Asp Glu Pro Asp Val Ala Glu Leu Thr Arg Pro Glu
        115                 120                 125

Gln Phe Arg Gln Leu Ala Pro Gly Val Leu Lys Gly Asn Phe Pro Gly
    130                 135                 140

Trp Arg Gly Tyr His Ile Arg Ser Asn Ala Gly Trp Ala His Ala Arg
145                 150                 155                 160

Asn Ala Leu Val Ala Ala Arg Glu Ala Gln Arg Leu Gly Val Arg
                165                 170                 175

Phe Val Ala Gly Ser Pro Gln Gly Arg Val Ile Thr Leu Ile Phe Glu
            180                 185                 190

Asn Asn Asp Val Lys Gly Ala Val Thr Ala Asp Gly Lys Ile Trp Arg
        195                 200                 205

Ala Glu Gln Thr Ile Leu Cys Ala Gly Ala Ala Gly Gln Phe Leu
    210                 215                 220

Asp Phe Lys Asp Gln Leu Arg Pro Thr Ala Trp Thr Leu Val His Ile
225                 230                 235                 240

Gln Leu Lys Pro Glu Glu Arg Ala Gln Tyr Lys Asn Met Pro Val Val
                245                 250                 255

Phe Asn Ile Glu Lys Gly Phe Phe Glu Pro Asp Glu Glu Arg Gly
            260                 265                 270

Glu Ile Lys Ile Cys Asp Glu His Pro Gly Tyr Thr Asn Met Thr Thr
        275                 280                 285

Gly Ala Asp Gly Arg Val Arg Ser Ile Pro Phe Glu Lys Thr Gln Val
    290                 295                 300

Pro Arg Glu Ala Glu Met Arg Val Arg Lys Leu Leu Ser Glu Thr Met
305                 310                 315                 320

Pro Gln Leu Ala Asp Arg Pro Phe Ser Phe Ala Arg Ile Cys Trp Cys
                325                 330                 335

Ala Asp Thr Pro Asn Arg Glu Phe Ile Ile Asp Arg His Pro Glu Tyr
            340                 345                 350

Pro Ser Leu Val Leu Gly Cys Gly Ala Ser Gly Arg Gly Phe Lys Tyr
        355                 360                 365

Leu Pro Ser Ile Gly Ser Ile Ile Ala Asp Ala Met Glu Asp Lys Thr
    370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Gly Pro Asn Arg
                405                 410                 415

Val Met Asp Phe Asn Glu Val Lys Glu Trp Thr Asn Val Thr Gln Arg
            420                 425                 430

Asp Ile Ser Lys Leu
        435

<210> SEQ ID NO 132
<211> LENGTH: 1314
<212> TYPE: DNA
<213> ORGANISM: Aspergillus terreus
```

<400> SEQUENCE: 132

```
atgccagtca ccaagtcttc gtcgatattg atcatcgggg cgggcacctg gggttgctca      60
actgccctgc atcttgcccg cagaggatac accaatgtca ctgtccttga cccgtacccg     120
gttccatcag ccatttcggc cggcaacgac gtcaacaaga tcatctcgtc cggccagtac     180
agcagcaaga aggacgaggt cgaagtcaat gagattatcg ccgaacaggc cttcaatggc     240
tggaaaaatg accccatctt caagccgtac taccacgaca ccggcgtcgt gatgtccgcc     300
accacacagg aaggattgga gcgtctgggg gtccgcgtgc gacctgaaga tgaacccgat     360
gtagccgaat tgactcggcc ggagcagttc cgccagctgg cccccggcgt cttgaagggt     420
aacttccccg gttggagggg gtaccacatt cgctcaaacg cgggctgggc gcatgcgcgc     480
aacgccctgg tcgccgcggc gcgggaggca cagcgcctgg tgtgcgcgctt cgtcgcggga    540
tcgccgcagg gcagagtcat cacgttgatt tttgagaaca acgatgtgaa gggtgccgtc     600
acggcggacg gcaagatctg gcgggccgag cagactatcc tctgcgctgg tcggccgcc     660
ggccagtttc tggatttcaa ggaccaactg cgtcccactg cgtggactct ggtccacatc     720
cagttgaagc cggaagagcg tgcccagtat aaaaacatgc cggtggtctt caacatcgag     780
aagggggttct tcttcgagcc ggatgaggag cgtggtgaaa tcaagatctg cgacgaacac     840
cccgggtaca cgaatatgac cacgggggcc gacggccgcg tgaggagcat tcccttcgag     900
aagacgcagg ttcctcgaga gcggagatg cgcgtccgca agcttctgtc tgaaacgatg      960
cctcagcttg cggaccggcc gttcagtttc gcaaggatct gctggtgtgc ggataccccc    1020
aatcgcgagt ttatcattga ccgtcatccc gaatacccgt cgcttgttct tgggtgtggt    1080
gcttcaggac gaggcttcaa atatcttccc tcgatcggaa gcatcatcgc agacgccatg    1140
gaggacaaaa ccccggcaaa aatccacaag ctgatccgct ggagcccgga aatcgcgatc    1200
aaccgtaact gggggacag attaggtcga tttggagggc ccaaccgggt catggatttc     1260
aatgaagtga aggagtggac taatgtcacc caaagggaca tctcgaagtt atag           1314
```

<210> SEQ ID NO 133
<211> LENGTH: 437
<212> TYPE: PRT
<213> ORGANISM: Coniochaeta sp.

<400> SEQUENCE: 133

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp Leu Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125
```

Asp Asn Glu Asp Glu Ile Leu Ser Lys Met Pro Leu Leu Gln Arg Asp
    130                 135                 140

Gln Ile Gln Gly Trp Lys Ala Ile Trp Ser Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 134
<211> LENGTH: 1314
<212> TYPE: DNA
<213> ORGANISM: Coniochaeta sp.

<400> SEQUENCE: 134
atgacgtcga atcgtgcaga tacaaggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360

```
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtgg tgtaaagttc     540 ggattcggcg cgctggatc cttcaagcaa ccccttttcg acgatgaagg cacaacttgc     600
attggcgttg agacggcaga tggtaccaaa tattacgctg acaaggtggt cttagcagct    660
ggcgcatgga gcccaaccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag aacatcaac cctatggcgc cccatctccg     900
aaacggatat cagtaccacg atcgcacgcc aagcatccca cagacactta tccgagacgca  960 tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 135
<211> LENGTH: 437
<212> TYPE: PRT
<213> ORGANISM: Phaeosphaeria nodorum

<400> SEQUENCE: 135

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
                20                  25                  30

Thr Pro Ser Asn Val Thr Val Leu Asp Ala Tyr Pro Ile Pro Ser Ser
            35                  40                  45

Gln Ser Ala Gly Asn Asp Leu Asn Lys Ile Met Gly Val Asp Leu Arg
        50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Lys Leu Lys Ser Leu Tyr Gln
            100                 105                 110

Lys Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205
```

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
    245                 250                 255

Tyr Asn Gly Asp Val Gly Phe Phe Glu Pro Asn Glu His Gly Val
    260                 265                 270

Ile Lys Val Cys Asp Glu Phe Pro Gly Phe Thr Arg Phe Lys Met His
    275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435

<210> SEQ ID NO 136
<211> LENGTH: 1314
<212> TYPE: DNA
<213> ORGANISM: Phaeosphaeria nodorum

<400> SEQUENCE: 136
atggccccgt cgcgtgctaa tacgtcggtc attgtggttg gtggtggtgg tacgattggc      60
tcatctacgg ctctgcatct ggtccgctca ggctatatcc cgtcgaacgt gacggttctg     120
gatgcatacc cgattccgag ctctcagagc gctggcaacg acctgaataa aatcatgggt     180
gtcgatctgc gtaatccggt ggatctgcag ctggctctgg aagcgcgcca aatgtggaac     240
gaagacgaac tgttcaagaa gtttttccat aacaccggcc gtctggattg cgcgcacggt     300
gaaaaagata ttgccaaact gaagagcctg tatcagaaac tggtggatgc gggtctggac     360
gccacgaacg aatggctgga tagtgaagac gaaatcctga acgtatgcc gctgctgtcc     420 cgcgatcaaa ttaaaggctg gaaggcgatc ttttcaaaag acgtggttg ctggcagca     480 gcaaaggcaa ttaatgcagt tggtgaatat ctgcgtgatc agggcgtccg cttcggtttt     540
tacggcgccg gttctttcaa agcaccgctg ctggctgaag cgtctgcat cggtgtcgaa     600 accgtggatg cacgcgcta ttacgcagac aaagtggttc tggctgcagg tgcatggtcg     660
ccgaccctgg ttgaactgca tgaacagtgt gtgagcaaag cgtgggttta cggccacatt     720
caactgacgc cggaagaagc cgcacgttat aagaacagcc cggtcgtgta caatggcgat     780

```
gtgggctttt tctttgaacc gaacgaacat ggcgttatca aagtctgcga tgaatttccg    840
ggttttaccc gcttcaagat gcaccagccg tttggtgcca agcaccgaa gcgtattagt     900 gtgccgcgct cccatgccaa acacccgacc gatacgatcc cggatgcaag tgacgtttcc    960
attcgtcgcg ctatcgcgac ctttatgccg cagttcaaga acaaaaagat gttcaaccaa   1020
gcgatgtgct ggtgtaccga tacggccgac gctgcgctgc tgatttgtga acatccggaa   1080
tggaaaaact ttgttctggc gaccggcgat tcaggtcatt cgttcaaact gctgccgaat   1140
atcggcaagc acgttgtcga actgctggag ggtacgctgg cagatgacct ggcacacgca   1200
tggcgttggc gtccgggtag tggtgatgca ctgaaaagcc gtcgctctgc tccggcgaaa   1260
gacctggctg atatgccggg ctggaaccat gacaaaccgc gtgctaatct gtaa         1314
```

<210> SEQ ID NO 137
<211> LENGTH: 441
<212> TYPE: PRT
<213> ORGANISM: Neocosmospora vasinfecta

<400> SEQUENCE: 137

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Asp Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe His Asn Thr Gly Arg Leu Asp
                85                  90                  95

Cys Glu Ser Ser Ala Glu Gly Val Glu Lys Leu Arg Arg Leu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Gly Gly Trp Leu
145                 150                 155                 160

Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Val Tyr Lys Gly
                245                 250                 255

Cys Pro Val Val Tyr His Gly Asp Val Gly Phe Phe Glu Pro Asn
            260                 265                 270

Glu Asn Gly Val Ile Lys Val Cys Asp Glu Phe Pro Gly Phe Thr Arg
```

```
            275                 280                 285
    Phe Lys Gln His Gln Pro Tyr Gly Ala Pro Ala Pro Lys Pro Val Ser
        290                 295                 300
    Val Pro Arg Ser His Ala Lys His Pro Thr Asp Thr Tyr Pro Asp Ala
    305                 310                 315                 320
    Ser Glu Glu Ser Ile Lys Arg Ala Val Ser Thr Phe Leu Pro Arg Phe
                    325                 330                 335
    Lys Asp Lys Pro Leu Phe Asn Arg Ala Leu Cys Trp Cys Thr Asp Thr
                340                 345                 350
    Ala Asp Ser Ala Leu Leu Ile Cys Glu His Pro Arg Trp Lys Asn Phe
            355                 360                 365
    Ile Leu Ala Thr Gly Asp Ser Gly His Ser Phe Lys Leu Leu Pro Ile
        370                 375                 380
    Ile Gly Lys His Val Val Glu Leu Val Glu Gly Arg Leu Ala Asp Asp
    385                 390                 395                 400
    Leu Ala Glu Ala Trp Arg Trp Arg Pro Gly Gln Gly Asp Ala Arg Lys
                    405                 410                 415
    Ser Ile Arg Ala Ala Pro Ala Lys Asp Leu Ala Asp Met Pro Gly Trp
                420                 425                 430
    Lys His Asp Gln Asp Ser Glu Ser Arg
            435                 440
```

<210> SEQ ID NO 138
<211> LENGTH: 1326
<212> TYPE: DNA
<213> ORGANISM: Neocosmospora vasinfecta

<400> SEQUENCE: 138

```
atgacgaccc cgcgtaaaga acgacggtc ctgattattg gtggtggtgg cacgattggt    60
agctcgacgg ctctgcatct gctgcgtgcc ggctataccc cgtctaacat taccgtgctg   120
gatacgtacc cgatcccgag tgcccagtcc gcaggcaacg acctgaataa aattatgggt   180
atcgatctgc gcaataaagt tgatctgcaa ctgagcctgg aagcccgtga tatgtggcgc   240
aacgacgcac tgtttcgtcc gttttttccat aataccggcc gctggactg cgaaagctct   300
gctgaaggcg tggaaaaact gcgtcgcctg tatcagaaac tggtggaagc aggcgttggt   360
ctggaagaaa cgcacgaatg gctggatagc gaagaagcta ttctggaaaa agcgccgctg   420
ctgcaacgtg aagaaattga aggttggaaa gccatctggt ctgaagaagg cggttggctg   480
gcggccgcaa aagctattaa cgcgatcggc gaagaactgc agcgtcaagg cgttcgcttc   540
ggttttggcg gtgccggtag ttttaaacgc ccgctgttcg cagatgacgg caccacgtgt   600
atcggtgtcg aaaccgtgga tggcacgcag tatcatgcgg acaaagtggt tctggctgca   660
ggtgcttggt caccggcgct ggtcgatctg aagaacagt gctgttcgaa agcctgggtg   720
tacgcacaca tgcaactgac cccggaagaa gccgcagttt ataaaggctg cccggtcgtg   780
taccacggcg atgtcggctt ttctctttgaa ccgaacgaaa atggcgttat taaagtctgt   840
gacgaattcc cgggttttac gcgtttcaaa cagcatcaac cgtatggtgc cccggcaccg   900
aaacctgtga gtgttccgcg ctcccatgcg aaacacccga ccgatacgta cccggacgct   960
tcagaagaat cgatcaaacg tgccgtgagt accttctctgc cgcgcttcaa agataaaccg  1020
ctgtttaacc gtgcactgtg ctggtgtacc gatacggccg actccgcact gctgatttgc  1080
gaacacccgc gctggaaaaa ttttatcctg gcgaccggcg atagcggtca ttcttttcaaa 1140
ctgctgccga ttatcggcaa acacgttgtc gaactggttg aaggtcgtct ggcggatgac  1200
```

```
ctggctgaag cgtggcgttg gcgtccgggt cagggtgatg cacgtaaaag cattcgcgct   1260
gcgccggcga agacctggc ggatatgccg ggctggaaac acgaccaaga ctcggaatca   1320
cgctga                                                              1326
```

<210> SEQ ID NO 139
<211> LENGTH: 438
<212> TYPE: PRT
<213> ORGANISM: Aspergillus nidulans

<400> SEQUENCE: 139

```
Met Thr Pro Arg Ala Asn Thr Lys Ile Ile Val Val Gly Gly Gly Gly
 1               5                  10                  15

Thr Met Gly Ser Ser Thr Ala Leu His Leu Leu Arg Ala Gly Tyr Thr
                20                  25                  30

Pro Ser Asn Ile Thr Val Leu Asp Thr Cys Pro Ile Pro Ser Ala Gln
            35                  40                  45

Ser Ala Gly Tyr Asp Leu Asn Lys Ile Met Gly Ile Asp Leu Arg Asn
        50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Lys Leu Arg Lys Leu Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
```

```
                340             345             350
Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435
```

<210> SEQ ID NO 140
<211> LENGTH: 1317
<212> TYPE: DNA
<213> ORGANISM: Aspergillus nidulans

<400> SEQUENCE: 140

```
atgacgcccc gagccaacac caaaatcatt gtcgtcggcg gcggcggcac aatgggctcg      60
tcgacagccc tacacctcct gcgcgccggc tacacgccgt ccaacattac agtgctcgac     120
acgtgcccta tccctccgc acagtctgca ggctacgacc tgaacaaaat catgggcatc     180
gatctgcgca caagcctga tttacagctc tctcttgagg cgctggacat gtggaaaaat     240
gatcctctct tcaagccgtt tttccacaat gttggaatga tcgacgtctc ttcaacagag     300
gaaggcatcg agaaacttcg gaagctgtac cagtctcttc tcgacgcagg cattgggctc     360
gagaagacga atttcatgct ggaaagtgaa gacgagatcc tggctaaagc gccgcatttc     420
acgcaggagc agattaaagg ctggaaaggc ctgttctgtg gcgacggcgg ctggctcgct     480
gcagccaaag ccatcaatgc cattgggcag ttcctcaagg aacagggcgt caagtttgga     540
ttcggcggcg ccggcacgtt caaaaagcca ctcttcgccg atgcccacga agacgtgc      600
atcgcgtcg agactgtaga cggcacaaag tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt ataagaacac tcctgttata     780
tacgacggtg actatgggtt tttctttgag ccgaatgaaa acggcatcat aaaagtctgt     840
gacgaattcc ctggcttcac gcatttcaaa atgcaccagc cgtacggctc gccggcgccc     900
aaacccatct ctgtgcctcg ttcccatgcg aagcaccca cagatacata cccgcacgcg     960
tcggaggtca cgatcaaaaa ggctatcaac cggttcctgc cgaggttcaa tgacaaggaa    1020
ctgtttaaca gggccatgtg ctggtgcacc gataccgcgg atgcaaatct gcttgtttgt    1080
gagcatccac gctggaaggg gttttatctt gcaacagggg acagtgggca ttcgttcaag    1140
ttgctgccga atattggaaa gcatgttgtc gagttattgg aggagaggct ggaaagtgtg    1200
tttaaggatg cttggaggtg gaggcctggc agtggggatg cattaaaaag tagacgggct    1260
gcgcctgcga aggacctggc ggatatgccg gggtggagga atgaggcaaa gatgtag       1317
```

<210> SEQ ID NO 141
<211> LENGTH: 437
<212> TYPE: PRT
<213> ORGANISM: Coniochaeta sp.

<400> SEQUENCE: 141

-continued

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20              25                  30

Ala Pro Ala Asn Ile Thr Val Leu Asp Thr Phe Glu Ile Pro Ser Ala
            35              40                  45

Gln Ser Ala Gly His Asp Leu Asn Lys Ile Met Gly Ile Asp His Arg
    50              55                  60

Asn Lys Val Asp Leu Gln Met Ser Leu Glu Ala Arg Gln Met Trp Lys
65              70                  75                      80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
                100                 105             110

Lys Leu His Asp Ala Gly Ala Gly Leu Glu Lys Thr His Ala Trp Leu
            115             120                 125

Asp Asn Glu Asp Glu Ile Leu Ser Lys Met Pro Leu Leu Gln Arg Asp
        130                 135             140

Gln Ile Gln Gly Trp Lys Ala Ile Trp Ser Asp Gly Gly Trp Leu
145             150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180             185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415
```

Arg Arg Ala Ala Pro Pro Lys Asp Leu Ala Asp Met Pro Gly Trp Lys
             420                 425                 430

His Asp Pro Lys Leu
        435

<210> SEQ ID NO 142
<211> LENGTH: 1314
<212> TYPE: DNA
<213> ORGANISM: Coniochaeta sp.

<400> SEQUENCE: 142

| | | |
|---|---|---|
| atgacgtcga atcgtgcaga tacaagggtg attgtcgtcg gtggcggagg aacgattggt | 60 |
| tcctcgacag cgctgcatct tgtgaggagt ggttatgctc ccgcaaatat cacggtcttg | 120 |
| gacacatttg agattccatc ggctcaatca gccggccatg atctcaacaa gatcatggga | 180 |
| atagatcatc gcaacaaggt ggacctgcaa atgagtctag aggctagaca gatgtggaag | 240 |
| gaggatgagt tattccagcc cttctttcac aataccggca gaatggactg cgaacacacg | 300 |
| cctaagggta tcgagaaact gaaaaagctg taccagaaac tgcacgatgc cggtgcgggt | 360 |
| ctggagaaga ctcatgcctg gttggacaac gaggatgaga tcttatccaa gatgccgttg | 420 |
| cttcaacgtg accaaataca aggatggaaa gcaatatgga gtcaagatgg cggctggtta | 480 |
| gctgcggcaa aggccatcaa tgcgatcgga cagttcttga agaacgtggt gtaaagttc | 540 |
| ggattcggcg cgctggatc cttcaagcaa ccccttttcg acgatgaagg cacaacttgc | 600 |
| attggcgttg agacggcaga tggtaccaaa tattacgctg acaaggtggt cttagcagct | 660 |
| ggcgcatgga gcccaacct ggtggacctg aagatcaat gttgctcgaa ggcttgggtg | 720 |
| tatgctcata ttcagttgac gcctgaagag gccgctgagt ataagggtgt cccagttgtg | 780 |
| tataatggcg aatttggctt cttctttgag cctgatgagt ttggtgtaat aaaggtgtgc | 840 |
| gacgagttcc caggattctc gcgcttcaag gaacatcaac cctatggcgc cccatctccg | 900 |
| aaacggatat cagtaccacg atcgcacgcc aagcatccca cagacactta tccagacgca | 960 |
| tccgaagtca gcatcaaaaa agcaatcgcg acgtttctcc ctcgatttca ggacaaggag | 1020 |
| ctcttcaatc gcgccttgtg ctggtgtaca gacactgcgg actctgctct cttgatgtgt | 1080 |
| gaacacccca atggaagaa tttcattcta gcgaccggcg acagcggaca ctcattcaaa | 1140 |
| atcttgccta acgtcggaaa atacgtagtc gagttgatag agggccgcct gccgaggaa | 1200 |
| atggcttatc aatggaggtg gcggccagga ggcgatgcac tcaagtctag acgtgcggca | 1260 |
| ccgccaaaag atcttgcaga catgccagga tggaaacatg atccgaaatt gtaa | 1314 |

<210> SEQ ID NO 143
<211> LENGTH: 437
<212> TYPE: PRT
<213> ORGANISM: Eupenicillium terrenum

<400> SEQUENCE: 143

Met Ala His Ser Arg Ala Ser Thr Lys Val Val Val Gly Gly Gly
1               5                  10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp His Arg
    50                  55                  60

Asn Gly Pro Asp Leu Gln Leu Ser Leu Glu Ser Leu Asp Met Trp Gln 65                  70                  75                  80
Asn Asp Glu Leu Phe Lys Pro Phe Phe His Gln Val Gly Met Ile Asp
                    85                  90                  95

Cys Ser Ser Lys Glu Gly Ile Glu Lys Leu Arg Arg Leu Tyr Gln
                100                 105                 110

Lys Leu Leu Asp Ala Gly Ile Gly Leu Glu Lys Thr Asn Val Trp Leu
                115                 120                 125

Glu Ser Glu Asp Glu Ile Leu Ala Lys Ala Pro Asn Phe Thr Arg Glu
        130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Pro Leu
                180                 185                 190

Phe Ala Ala Asp Gly Lys Thr Cys Ile Gly Leu Glu Thr Thr Asp Gly
            195                 200                 205

Thr Lys Tyr Phe Ala Asp Lys Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
                260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
                340                 345                 350

Ala Asp Ser Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Asp Ala Leu Arg Ser
                405                 410                 415

Arg Arg Gly Ala Pro Ala Lys Asp Leu Ala Glu Met Pro Gly Trp Lys
                420                 425                 430

His Asp Ala His Leu
        435

<210> SEQ ID NO 144
<211> LENGTH: 1314
<212> TYPE: DNA
<213> ORGANISM: Eupenicillium terrenum

<400> SEQUENCE: 144

```
atggctcatt cgcgtgcaag caccaaagtc gtcgtggttg ggggaggtgg tacgatcggg    60
tcttcgacgg ctctgcactt aatccgctct ggatataccc cctcaaatat caccgtgctt   120
gacgtataca agaccccttc attgcaatct gcaggacatg atttgaacaa gatcatgggc   180
attgatcatc gcaacgggcc tgacttgcag ctttcgctgg aatcactcga catgtggcaa   240
aacgatgagt tgttcaagcc attctttcac caagtgggca tgattgattg ttcgtcatcc   300
aaagagggta ttgaaaaact tcgacgatta taccagaaac tcctcgatgc gggcattggg   360
ctggagaaga cgaacgtttg ctggaatct gaagatgaga tcctcgccaa agcgccgaat   420
ttcacgcgtg aacaagtcaa ggggtggaaa ggcttatttt gcactgatgg aggctggctt   480
gctgcagcca aggctatcaa tgcgatcgga attttcctcc aggacaaagg tgtcaagttt   540
ggctttggag atgctggtac ctttcagcaa cctctgttcg ccgctgatgg aaaaacttgc   600
atcggacttg aaactacaga cggaaccaag tactttgctg acaaggttgt cttggctgct   660
ggtgcgtgga gtcccacctt ggtggatcta gaagatcagt gtgtttcaaa ggcctgggtt   720
ttcgctcata ttcaactcac acccaaagaa gcggacgcgt acaagaatgt gcctgtggtc   780
tatgatggtg aatatgggtt cttttttcgaa cccgacgagt atggggtgat caaagtctgt   840
gacgagttcc ctggtttctc tcgcttcaaa ctgcatcaac cgtacggggc tgcatctccc   900
aagatgatat ccgtaccgcg atcacacgcc aagcatccca cagataccta ccctgatgcc   960
tccgaagtca ccatacgcaa agcgatcgca aggttcctgc agaatttaa agacaaggag  1020
ctcttcaacc gtaccatgtg ctggtgtaca gatacggccg attctaactt attgatttgc  1080
gaacacccga gtggaagaa tttcattctg gccactggag atagcggaca ttccttcaag  1140
ctgttgccaa acatcgggaa atacgtagtt gagcttttag agggatctct atcgcaggaa  1200
atggctggtg cctggagatg gagacccgga ggtgatgctc ttagatctag acgcggtgct  1260
ccggcaaagg atcttgctga gatgccggga tggaagcatg atgcacattt gtga        1314
```

<210> SEQ ID NO 145
<211> LENGTH: 437
<212> TYPE: PRT
<213> ORGANISM: Eupenicillium terrenum

<400> SEQUENCE: 145

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe His Gln Val Gly Met Ile Asp
                85                  90                  95

Cys Ser Ser Lys Glu Gly Ile Glu Asn Leu Arg Arg Lys Tyr Gln
                100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140
```

```
Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Glu Pro Asn
            260                 265                 270

Glu Tyr Gly Val Ile Lys Val Cys Asp Glu Phe Pro Gly Phe Ser Arg
            275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
            435

<210> SEQ ID NO 146
<211> LENGTH: 1314
<212> TYPE: DNA
<213> ORGANISM: Eupenicillium terrenum

<400> SEQUENCE: 146
atggctcatt cgcgtgcaag caccaaagtc gtcgtggttg ggggaggtgg tacgatcggg    60
tcttcgacgg ctctgcactt aatccgctct ggatataccc cctcaaatat caccgtgctt   120
gacgtataca agacccctttc attgcaatct gcaggacatg attttgaacaa gatcatgggc   180 attcgattgc gcaacgggcc tgacttgcag ctttcgctgg aatcactcga catgtggcaa   240
aacgatgagt tgttcaagcc attctttcac caagtgggca tgattgattg ttcgtcatcc   300
aaagagggta ttgaaaatct tcgacgaaaa taccagaccc cctcgatgc gggcattggg   360 ctggagaaga cgaacgtttg gctggaatct gaagatgaga tcctcgccaa agcgccgaat   420
```

-continued

```
ttcacgcgtg aacaagtcaa ggggtggaaa ggcttatttt gcactgatgg aggctggctt      480
gctgcagcca aggctatcaa tgcgatcgga attttcctcc aggacaaagg tgtcaagttt      540
ggctttggag gtgctggaac atttcagcaa cctctgttcg ccgctgatgg aaaaacttgc      600
atcggacttg aaactacaga cggaaccaag tactttgctg acaaggttgt cttggctgct      660
ggtgcgtgga gtcccacctt ggtggatcta aagatcagt gtgtttcaaa ggcctgggtt       720
ttcgctcata ttcaactcac acccaaagaa gcggacgcgt acaagaatgt gcctgtggtc      780
tatgatggtg aatatgggtt ctttttttgag cccaacgagt atggggtgat caaagtctgt     840
gacgagttcc ctggtttctc tcgcttcaaa ctgcatcaac cgtacggggc tgcatctccc      900
aagatgatat ccgtaccgcg atcacacgcc aagcatccca cagataccta ccctgatgcc      960
tccgaagtca ccatacgcaa agcgatcgca aggttcctgc cagaatttaa agacaaggag     1020
ctcttcaacc gtaccatgtg ctggtgtaca gatacggccg atgctaactt attgatttgc     1080
gaacacccga gtggaagaa tttcattctg gccactggag atagcggaca ttccttcaag      1140
ctgttgccaa acatcgggaa acacgttgtt gagcttttag agggatctct atcgcaggaa     1200
atggctggtg cctggagatg gagacccgga ggtgatgctc ttagatctag acgcggtgct     1260
ccggcaaagg atcttgctga gatgccggga tggaagcatg atgcacattt gtga           1314
```

```
<210> SEQ ID NO 147
<211> LENGTH: 438
<212> TYPE: PRT
<213> ORGANISM: Aspergillus nidulans

<400> SEQUENCE: 147

Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220
```

```
Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Glu Pro Asn
            260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Ala Pro Lys Pro Ile Ser
            290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
            370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
            435

<210> SEQ ID NO 148
<211> LENGTH: 1317
<212> TYPE: DNA
<213> ORGANISM: Aspergillus nidulans

<400> SEQUENCE: 148
atgacgcccc gagccaacac caaaatcatt gtcgtcggcg gcggcggcac aatgggctcg    60
tcgacagccc tacacctcct gcgcgccggc tacacgccgt ccaacattac agtgctcgac   120
acgtgcccta tccctccgc acagtctgca ggctacgacc tgaacaaaat catgagcatc   180
aggctgcgca acaagcctga tttacagctc tctcttgagg cgctggacat gtggaaaaat   240
gatcctctct tcaagccgtt tttccacaat gttggaatga tcgacgtctc ttcaacagag   300
gaaggcatcg agggtcttcg aagaaatac cagtctcttc tcgacgcagg cattgggctc   360
gagaagacga atttcatgct ggaaagtgaa gacgagatcc tggctaaagc gccgcatttc   420
acgcaggagc agattaaagg ctggaaaggc ctgttctgtg cgacggcgg ctggctcgct   480 gcagccaaag ccatcaatgc cattgggcag ttcctcaagg aacagggcgt caagtttgga   540
ttcggcggcg ccggcacgtt caaaaagcca ctcttcgccg atgcccacga agacgtgc    600 atcgcgtcg agactgtaga cggcacaaag tactacgccg acaaggtcgt tctagcagct   660
ggtgcctgga gttcgacgtt ggtcgatctg gaggagcagt gcgtttcaaa ggcctgggtc   720
tttgcccaca tccaactgac gcccgctgaa gcagccgcgt ataagaacac tcctgttata   780
tacgacggtg actatgggtt tttctttgag ccgaatgaaa acggcatcat aaaagtctgt   840
```

```
gacgaattcc ctggcttcac gcatttcaaa atgcaccagc cgtacggctc gccggcgccc    900
aaacccatct ctgtgcctcg ttcccatgcg aagcacccca cagatacata cccgcacgcg    960
tcggaggtca cgatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagtgggca ttcgttcaag   1140
ttgctgccga atattggaaa gcatgttgtc gagttattgg aggagaggct ggaaagtgtg   1200
tttaaggatg cttggaggtg gaggcctggc agtggggatg cattaaaaag tagacgggct   1260
gcgcctgcga aggacctggc ggatatgccg gggtggagga tgaggcaaa gatgtag      1317
```

<210> SEQ ID NO 149
<211> LENGTH: 477
<212> TYPE: PRT
<213> ORGANISM: Cryptococcus neoformans

<400> SEQUENCE: 149

```
Met Pro Pro Ser Arg Ala Ser Thr Lys Val Ile Val Ile Gly Gly Gly
 1               5                  10                  15

Gly Thr Leu Gly Ser Ser Thr Ala Leu His Leu Leu Arg Ala Gly Tyr
             20                  25                  30

Thr Pro Ser Asn Ile Thr Val Leu Asp Thr Tyr Leu Ile Pro Ser Ala
         35                  40                  45

Gln Ser Ala Gly Asn Asp Leu Asn Lys Ile Met Gly Ile Arg Ile Arg
     50                  55                  60

Asn Pro Val Asp Lys Gln Leu Ser Leu Glu Ala Arg Asp Met Trp Arg
 65                  70                  75                  80

Asn Asp Glu Val Phe Lys Pro Tyr Phe His Asn Thr Gly Arg Leu Asp
                 85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
```

```
                290              295              300

Phe Pro Arg Ser His Ala Lys His Pro Thr Asp Thr Ile Pro Asp Glu
305              310              315              320

Ser Asp Ala Ser Ile Arg Arg Ala Ile Ser Ala Phe Leu Pro Arg Phe
                325              330              335

Lys Glu Lys Glu Leu Phe Asn Arg Ala Leu Cys Trp Cys Thr Asp Thr
            340              345              350

Ala Asp Ala Asn Leu Leu Ile Cys Glu His Pro Lys Trp Lys Asn Phe
        355              360              365

Ile Leu Ala Thr Gly Asp Ser Gly His Ser Phe Lys Ile Leu Pro Asn
370              375              380

Ile Gly Lys His Val Val Glu Leu Ile Glu Gly Thr Leu Ala Glu Asp
385              390              395              400

Leu Ala Glu Ser Trp Arg Trp Arg Pro Gly Ser Gly Asp Pro Leu Ile
                405              410              415

Ser Arg Arg Ala Ala Pro Ala Arg Asp Leu Ala Asp Leu Pro Gly Trp
            420              425              430

Asn His Asp Glu Pro Ser Asp Asp Met Asp Val Lys Asp Val Ala
        435              440              445

Val Ser Leu Ala Ser Val Lys Ile Gly Glu Asn Ile Gly Glu Lys Val
    450              455              460

Val Glu Asp Gly Ala Arg Val Gly Val Lys Val Leu Ala
465              470              475

<210> SEQ ID NO 150
<211> LENGTH: 1434
<212> TYPE: DNA
<213> ORGANISM: Cryptococcus neoformans

<400> SEQUENCE: 150
atgccacctt cgcgcgccag tactaaggtc atagttatcg ggggcggtgg tactctcggg      60
tcctctactg ctcttcacct tttacgagcc ggttacactc catccaacat cactgtgctt    120
gacacgtatc taatcccatc agcacagtcg gctggcaatg acctcaataa gatcatgggt    180
attcgtatca ggaatcctgt agataaacag ttgagcctgg aagcaagaga catgtggagg    240
aatgatgaag ttttcaagcc ttatttccac aacacgggaa gacttgattg tgctcataca    300
ccggagagca ttgcatcttt gcgtaaatcg tacgaggcta tcttaaaggc cgggagcggg    360
ctcgagaaga cccaccattg gctgagtaca gaagatgaaa tactggctag agccccttg    420 ttggatcgga aacagatcaa aggatggaaa gctatttaca gcgaagatgg gggctggctt    480
gcggcggcga agctatcaa cagtatcggc caggtgttga agagaaagg tgtgacattc     540 ggattcggga gtgcgggctc attcaagaaa cccttgtttg acgaagacgg taccaaggcc    600
atcggcattg agacagttga tggtacgcaa tattttgccg acaaggtcgt tctggctgcc    660
ggagcttgga gtcctaccct cgtggatttg aagggcaat gctgttcaaa ggcttgggtt    720
tacgcccata tgcaattgac accagaagag gctgccgaat acaaggagtg tcctgtggtg    780
tacaactctg aacttgggtt cttcttcgag cccaatgaaa aaggagtcat caaagtgtgc    840
gacgaattcc agggttcac ccgtttcaag caacatcaac cttacggcgc ctcctctact    900
aaacacatct ctttcccgcg ctcccatgcc aaacacccta ccgataccat tccggacgag    960
tcggacgcat ctatccgccg tgctatctct gcctttttac cgagattcaa agaaaaagaa   1020
ctgttcaaca gagcactgtg ctggtgtaca gataccgccg atgccaatct tttgatatgc   1080
```

```
gaacatccca aatggaaaaa ttttatctta gctacagggg atagtggaca ttcattcaaa    1140
attcttccca atatcggtaa acatgtcgtt gaacttatag aaggtaccct tgccgaggac    1200
ttggctgaga gctggagatg gagacctgga agcggtgacc ccctgatctc tcgtcgggca    1260 gccctgcaa gggatcttgc tgatcttcca ggatggaacc atgatgagcc ctcggatgac    1320
gatatggatg taaaggatgt cgctgtatcg cttgcttctg tgaaaattgg cgaaaacatc    1380
ggggagaagg ttgtggaaga tggagcacga gtcggagtca aagttctagc ttag         1434
```

<210> SEQ ID NO 151
<211> LENGTH: 437
<212> TYPE: PRT
<213> ORGANISM: Coniochaeta sp.

<400> SEQUENCE: 151

```
Met Thr Ser Asn Arg Ala Asp Thr Arg Val Ile Val Val Gly Gly Gly
1               5                  10                   15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Pro Lys Arg Ile Ser
    290                 295                 300

Val Pro Arg Ser His Ala Lys His Pro Thr Asp Thr Tyr Pro Asp Ala
305                 310                 315                 320
```

```
Ser Glu Val Ser Ile Lys Lys Ala Ile Ala Thr Phe Leu Pro Arg Phe
            325                 330                 335

Gln Asp Lys Glu Leu Phe Asn Arg Ala Leu Cys Trp Cys Thr Asp Thr
        340                 345                 350

Ala Asp Ala Ala Leu Leu Met Cys Glu His Pro Lys Trp Lys Asn Phe
    355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 152
<211> LENGTH: 1314
<212> TYPE: DNA
<213> ORGANISM: Coniochaeta sp.

<400> SEQUENCE: 152
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagcactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagcag taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540 ggattcggcg cgctggatc cttcaagcaa ccccttttcg acgatgaagg cacaacttgc      600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc ccatctccg      900 aaacggatat cagtaccacg atcgcacgcc aagcatccca cagacactta ccagacgca      960 tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa     1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa           1314

<210> SEQ ID NO 153
```

<211> LENGTH: 437
<212> TYPE: PRT
<213> ORGANISM: Coniochaeta sp.

<400> SEQUENCE: 153

```
Met Thr Ser Asn Arg Ala Asp Thr Arg Val Ile Val Val Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp Leu Arg
50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Gln Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
```

```
                385           390           395           400
Met Ala Tyr Gln Trp Arg Trp Arg Pro Gly Gly Asp Ala Leu Lys Ser
            405                   410                   415

Arg Arg Ala Ala Pro Pro Lys Asp Leu Ala Asp Met Pro Gly Trp Lys
            420                   425                   430

His Asp Pro Lys Leu
        435
```

<210> SEQ ID NO 154
<211> LENGTH: 1314
<212> TYPE: DNA
<213> ORGANISM: Coniochaeta sp.

<400> SEQUENCE: 154

| | | | | | |
|---|---|---|---|---|---|
| atgacgtcga | atcgtgcaga | tacaagggtg | attgtcgtcg | gtggcggagg | aacgattggt | 60 |
| tcctcgacag | cgctgcatct | tgtgaggagt | ggttatgctc | ccgcaaatat | cacggtcttg | 120 |
| gacacatttg | agattccatc | ggctcaatca | gccggccatg | atctcaacaa | gatcatggga | 180 |
| atagatctgc | gcaacaaggt | ggacctgcaa | atgagtctag | aggctagaca | gatgtggaag | 240 |
| gaggatgagt | tattccagcc | cttctttcac | aataccggca | gaatgactg | cgaacacacg | 300 |
| cctgagggta | tcgaggacct | gaaaaagcag | taccaggcac | tgcacgatgc | cggtgcgggt | 360 |
| ctggagaaga | ctcatgcctg | gttggacaac | gaggatgaga | tcttatccaa | gatgccgttg | 420 |
| cttcaacgtg | accaaataca | aggatggaaa | gcaatatgga | gtcaagatgg | cggctggtta | 480 |
| gctgcggcaa | aggccatcaa | tgcgatcgga | cagttcttga | agaacgtgg | tgtaaagttc | 540 |
| ggattcggcg | gcgctggatc | cttcaagcaa | ccccttttcg | acgatgaagg | cacaacttgc | 600 |
| attggcgttg | agacggcaga | tggtaccaaa | tattacgctg | acaaggtggt | cttagcagct | 660 |
| ggcgcatgga | gcccaaccct | ggtggacctg | aagatcaat | gttgctcgaa | ggcttgggtg | 720 |
| tatgctcata | ttcagttgac | gcctgaagag | gccgctgagt | ataagggtgt | cccagttgtg | 780 |
| tataatggcg | aatttggctt | cttctttgag | cctgatgagt | ttggtgtaat | aaaggtgtgc | 840 |
| gacgagttcc | caggattctc | gcgcttcaag | gaacatcaac | cctatggcgc | cccatctccg | 900 |
| aaacggatat | cagtaccacg | atcgcacgcc | aagcatccca | cagacactta | tccgacgca | 960 |
| tccgaagtca | gcatcaaaaa | agcaatcgcg | acgtttctcc | ctcgatttca | ggacaaggag | 1020 |
| ctcttcaatc | gcgccttgtg | ctggtgtaca | gacactgcgg | acgctgctct | cttgatgtgt | 1080 |
| gaacacccca | atggaagaa | tttcattcta | gcgaccggcg | acagcggaca | ctcattcaaa | 1140 |
| atcttgccta | acgtcggaaa | atacgtagtc | gagttgatag | agggccgcct | gccggaggaa | 1200 |
| atggcttatc | aatggaggtg | gcggccagga | ggcgatgcac | tcaagtctag | acgtgcggca | 1260 |
| ccgccaaaag | atcttgcaga | catgccagga | tggaaacatg | atccgaaatt | gtaa | 1314 |

<210> SEQ ID NO 155
<211> LENGTH: 437
<212> TYPE: PRT
<213> ORGANISM: Eupenicillium terrenum

<400> SEQUENCE: 155

```
Met Ala His Ser Arg Ala Ser Thr Lys Val Val Val Gly Gly Gly
1               5                   10                  15

Gly Thr Ile Gly Ser Ser Thr Ala Leu His Leu Ile Arg Ser Gly Tyr
                20                  25                  30

Thr Pro Ser Asn Ile Thr Val Leu Asp Val Tyr Lys Thr Pro Ser Leu
            35                  40                  45
```

```
Gln Ser Ala Gly His Asp Leu Asn Lys Ile Met Gly Ile Asp Leu Arg
 50                  55                  60

Asn Gly Pro Asp Leu Gln Leu Ser Leu Glu Ser Leu Asp Met Trp Gln
 65                  70                  75                  80

Asn Asp Glu Leu Phe Lys Pro Phe Phe His Gln Val Gly Met Ile Asp
                 85                  90                  95

Cys Ser Ser Lys Glu Gly Ile Glu Asn Leu Arg Arg Lys Tyr Gln
                100                 105                 110

Thr Leu Leu Asp Ala Gly Ile Gly Leu Glu Lys Thr Asn Val Trp Leu
            115                 120                 125

Glu Ser Glu Asp Glu Ile Leu Ala Lys Ala Pro Asn Phe Thr Arg Glu
130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
            435

<210> SEQ ID NO 156
<211> LENGTH: 1314
```

```
<212> TYPE: DNA
<213> ORGANISM: Eupenicillium terrenum

<400> SEQUENCE: 156
atggctcatt cgcgtgcaag caccaaagtc gtcgtggttg ggggaggtgg tacgatcggg      60
tcttcgacgg ctctgcactt aatccgctct ggatataccc cctcaaatat caccgtgctt     120
gacgtataca agaccccttc attgcaatct gcaggacatg atttgaacaa gatcatgggc     180
attgatttgc gcaacgggcc tgacttgcag ctttcgctgg aatcactcga catgtggcaa     240
aacgatgagt tgttcaagcc attctttcac caagtgggca tgattgattg ttcgtcatcc     300
aaagagggta ttgaaaatct tcgacgaaaa taccagaccc tcctcgatgc gggcattggg     360
ctggagaaga cgaacgtttg gctggaatct gaagatgaga tcctcgccaa agcgccgaat     420
ttcacgcgtg aacaagtcaa ggggtggaaa ggcttatttt gcactgatgg aggctggctt     480
gctgcagcca aggctatcaa tgcgatcgga attttcctcc aggacaaagg tgtcaagttt     540
ggctttggag atgctggtac ctttcagcaa cctctgttcg ccgctgatgg aaaaacttgc     600
atcggacttg aaactacaga cggaaccaag tactttgctg acaaggttgt cttggctgct     660
ggtgcgtgga gtcccacctt ggtggatcta aagatcagt gtgtttcaaa ggcctgggtt      720
ttcgctcata ttcaactcac acccaaagaa gcggacgcgt acaagaatgt gcctgtggtc     780
tatgatggtg aatatgggtt cttttttcgaa cccgacgagt atggggtgat caaagtctgt   840
gacgagttcc ctggtttctc tcgcttcaaa ctgcatcaac cgtacggggc tgcatctccc     900
aagatgatat ccgtaccgcg atcacacgcc aagcatccca cagataccta ccctgatgcc     960
tccgaagtca ccatacgcaa agcgatcgca aggttcctgc agaatttaa agacaaggag    1020
ctcttcaacc gtaccatgtg ctggtgtaca gatacggccg atgctaactt attgattgc    1080
gaacacccga agtggaagaa tttcattctg gccactggag atagcggaca ttccttcaag    1140
ctgttgccaa acatcgggaa atacgtagtt gagctttag agggatctct atcgcaggaa    1200
atggctggtg cctggagatg gagacccgga ggtgatgctc ttagatctag acgcggtgct    1260
ccggcaaagg atcttgctga gatgccggga tggaagcatg atgcacattt gtga          1314

<210> SEQ ID NO 157
<211> LENGTH: 437
<212> TYPE: PRT
<213> ORGANISM: Coniochaeta sp.

<400> SEQUENCE: 157
```

Met Thr Ser Asn Arg Ala Asp Thr Arg Val Ile Val Gly Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu

```
                115                 120                 125
Asp Asn Glu Asp Glu Ile Leu Ser Lys Met Pro Leu Leu Gln Arg Asp
            130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
                180                 185                 190

Phe Asp Asp Glu Gly Thr Thr Cys Ile Gly Val Glu Thr Ala Asp Gly
                195                 200                 205

Thr Lys Tyr Tyr Ala Asp Lys Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
                290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
                340                 345                 350

Ala Asp Ala Ala Leu Leu Met Cys Glu His Pro Lys Trp Lys Asn Phe
                355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp Pro Lys Leu
        435

<210> SEQ ID NO 158
<211> LENGTH: 1314
<212> TYPE: DNA
<213> ORGANISM: Coniochaeta sp.

<400> SEQUENCE: 158
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagcactgc gcaacaaggt ggacctgcaa atgagtctag aggctagaca gatgtggaag     240
gaggatgagt tattccagcc cttctttcac aataccggca gaatggactg cgaacacacg     300
```

```
cctgagggta tcgaggacct gaaaaagctg taccaggcac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtgg tgtaaagttc      540 ggattcggcg gcgctggatc cttcaagcaa ccccttttcg acgatgaagg cacaacttgc    600
attggcgttg agacggcaga tggtaccaaa tattacgctg acaaggtggt cttagcagct    660
ggcgcatgga gcccaacccct ggtggacctg aagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314

<210> SEQ ID NO 159
<211> LENGTH: 437
<212> TYPE: PRT
<213> ORGANISM: Coniochaeta sp.

<400> SEQUENCE: 159

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Tyr Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190
```

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
        340                 345                 350

Ala Asp Ala Ala Leu Leu Met Cys Glu His Pro Lys Trp Lys Asn Phe
    355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
        420                 425                 430

His Asp Pro Lys Leu
        435

<210> SEQ ID NO 160
<211> LENGTH: 1314
<212> TYPE: DNA
<213> ORGANISM: Coniochaeta sp.

<400> SEQUENCE: 160
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagcactgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagtat taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540 ggattcggcg cgctggatc cttcaagcaa cccctttcg acgatgaagg cacaacttgc      600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720

```
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 161
<211> LENGTH: 437
<212> TYPE: PRT
<213> ORGANISM: Coniochaeta sp.

<400> SEQUENCE: 161

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asn Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270
```

```
Glu Phe Gly Val Ile Lys Val Cys Asp Glu Phe Pro Gly Phe Ser Arg
        275                 280                 285
Phe Lys Glu His Gln Pro Tyr Gly Ala Pro Ser Pro Lys Arg Ile Ser
    290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
            340                 345                 350
Ala Asp Ala Ala Leu Leu Met Cys Glu His Pro Lys Trp Lys Asn Phe
        355                 360                 365
Ile Leu Ala Thr Gly Asp Ser Gly His Ser Phe Lys Ile Leu Pro Asn
    370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
            420                 425                 430
His Asp Pro Lys Leu
        435

<210> SEQ ID NO 162
<211> LENGTH: 1314
<212> TYPE: DNA
<213> ORGANISM: Coniochaeta sp.

<400> SEQUENCE: 162
atgacgtcga atcgtgcaga tacaaggtg attgtcgtcg gtggcggagg aacgattggt      60
tcctcgacag cgctgcatct tgtgaggagt ggttatgctc ccgcaaatat cacggtcttg    120
gacacatttg agattccatc ggctcaatca gccggccatg atctcaacaa gatcatggga    180
ataaacctgc gcaacaaggt ggacctgcaa atgagtctag aggctagaca gatgtggaag    240
gaggatgagt tattccagcc cttctttcac aataccggca gaatggactg cgaacacacg    300
cctgagggta tcgaggacct gaaaaagctg taccaggcac tgcacgatgc cggtgcgggt    360
ctggagaaga ctcatgcctg gttggacaac gaggatgaga tcttatccaa gatgccgttg    420
cttcaacgtg accaaataca aggatggaaa gcaatatgga gtcaagatgg cggctggtta    480
gctgcggcaa aggccatcaa tgcgatcgga cagttcttga agaacgtgg tgtaaagttc     540 ggattcggcg cgctggatc cttcaagcaa ccccttttcg acgatgaagg cacaacttgc    600
attggcgttg agacggcaga tggtaccaaa tattacgctg acaaggtggt cttagcagct    660
ggcgcatgga gcccaacccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag aacatcaac cctatggcgc ccatctccg     900 aaacggatat cagtaccacg atcgcacgcc aagcatccca cagacactta ccagacgca    960 tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa   1140
```

```
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 163
<211> LENGTH: 437
<212> TYPE: PRT
<213> ORGANISM: Coniochaeta sp.

<400> SEQUENCE: 163

```
Met Thr Ser Asn Arg Ala Asp Thr Arg Val Ile Val Gly Gly Gly
1               5                  10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
```

```
                340              345             350
Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 164
<211> LENGTH: 1314
<212> TYPE: DNA
<213> ORGANISM: Coniochaeta sp.

<400> SEQUENCE: 164
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540 ggattcggcg cgctggatc cttcaagcaa cccctttcg acgatgaagg cacaacttgc      600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc ccatctccg      900 aaacggatat cagtaccacg atcgcacgcc aagcatccca cagacactta ccagacgca      960 tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314

<210> SEQ ID NO 165
<211> LENGTH: 437
<212> TYPE: PRT
<213> ORGANISM: Coniochaeta sp.

<400> SEQUENCE: 165
```

```
Met Thr Ser Asn Arg Ala Asp Thr Arg Val Ile Val Gly Gly Gly
1               5                  10                 15

Gly Thr Ile Gly Ser Ser Thr Ala Leu His Leu Val Arg Ser Gly Tyr
            20              25                  30

Ala Pro Ala Asn Ile Thr Val Leu Asp Thr Phe Glu Ile Pro Ser Ala
                35              40                  45

Gln Ser Ala Gly His Asp Leu Asn Lys Ile Met Gly Ile Asp Leu Arg
    50              55                  60

Asn Lys Val Asp Leu Gln Met Ser Leu Glu Ala Arg Gln Met Trp Lys
65              70                  75                  80

Glu Asp Glu Leu Phe Gln Pro Phe Phe His Asn Thr Gly Arg Met Asp
                85                  90                  95

Cys Glu His Thr Pro Glu Gly Ile Glu Ala Leu Lys Lys Leu Tyr Gln
                100                 105                 110

Ala Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
            165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
                260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415
```

Arg Arg Ala Ala Pro Pro Lys Asp Leu Ala Asp Met Pro Gly Trp Lys
            420                 425                 430

His Asp Pro Lys Leu
        435

<210> SEQ ID NO 166
<211> LENGTH: 1314
<212> TYPE: DNA
<213> ORGANISM: Coniochaeta sp.

<400> SEQUENCE: 166

| | |
|---|---|
| atgacgtcga atcgtgcaga tacaagggtg attgtcgtcg gtggcggagg aacgattggt | 60 |
| tcctcgacag cgctgcatct tgtgaggagt ggttatgctc ccgcaaatat cacggtcttg | 120 |
| gacacatttg agattccatc ggctcaatca gccggccatg atctcaacaa gatcatggga | 180 |
| atagatctgc gcaacaaggt ggacctgcaa atgagtctag aggctagaca gatgtggaag | 240 |
| gaggatgagt tattccagcc cttctttcac aataccggca gaatggactg cgaacacacg | 300 |
| cctgagggta tcgaggccct gaaaaagctg taccaggcac tgcacgatgc cggtgcgggt | 360 |
| ctggagaaga ctcatgcctg gttggacaac gaggatgaga tcttatccaa gatgccgttg | 420 |
| cttcaacgtg accaaataca aggatggaaa gcaatatgga gtcaagatgg cggctggtta | 480 |
| gctgcggcaa aggccatcaa tgcgatcgga cagttcttga agaacgtggt gtaaagttc | 540 |
| ggattcggcg cgctggatc cttcaagcaa cccctttttcg acgatgaagg cacaacttgc | 600 |
| attggcgttg agacggcaga tggtaccaaa tattacgctg acaaggtggt cttagcagct | 660 |
| ggcgcatgga gcccaaccct ggtggacctg aagatcaat gttgctcgaa ggcttgggtg | 720 |
| tatgctcata ttcagttgac gcctgaagag gccgctgagt ataagggtgt cccagttgtg | 780 |
| tataatggcg aatttggctt cttctttgag cctgatgagt ttggtgtaat aaaggtgtgc | 840 |
| gacgagttcc caggattctc gcgcttcaag gaacatcaac cctatggcgc cccatctccg | 900 |
| aaacggatat cagtaccacg atcgcacgcc aagcatccca cagacactta tccagacgca | 960 |
| tccgaagtca gcatcaaaaa agcaatcgcg acgtttctcc ctcgatttca ggacaaggag | 1020 |
| ctcttcaatc gcgccttgtg ctggtgtaca gacactgcgg acgctgctct cttgatgtgt | 1080 |
| gaacaccca atggaagaa tttcattcta gcgaccggcg acagcggaca ctcattcaaa | 1140 |
| atcttgccta acgtcggaaa atacgtagtc gagttgatag agggccgcct gccggaggaa | 1200 |
| atggcttatc aatggaggtg gcggccagga ggcgatgcac tcaagtctag acgtgcggca | 1260 |
| ccgccaaaag atcttgcaga catgccagga tggaaacatg atccgaaatt gtaa | 1314 |

<210> SEQ ID NO 167
<211> LENGTH: 437
<212> TYPE: PRT
<213> ORGANISM: Coniochaeta sp.

<400> SEQUENCE: 167

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys

```
            65                  70                  75                  80
Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 168
<211> LENGTH: 1314
<212> TYPE: DNA
<213> ORGANISM: Coniochaeta sp.

<400> SEQUENCE: 168
```

-continued

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccaggcac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc     540
ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg gaagatcaat gttgctcgaa ggcttgggtg     720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 169
<211> LENGTH: 437
<212> TYPE: PRT
<213> ORGANISM: Coniochaeta sp.

<400> SEQUENCE: 169

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Arg Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140
```

```
Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 170
<211> LENGTH: 1314
<212> TYPE: DNA
<213> ORGANISM: Coniochaeta sp.

<400> SEQUENCE: 170
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagcgcct gaaaaagctg taccaggcac tgcacgatgc cggtgcgggt     360
ctggagaaga ctcatgcctg gttggacaac gaggatgaga tcttatccaa gatgccgttg     420
```

```
cttcaacgtg accaaataca aggatggaaa gcaatatgga gtcaagatgg cggctggtta    480
gctgcggcaa aggccatcaa tgcgatcgga cagttcttga agaacgtgg tgtaaagttc     540
ggattcggcg gcgctggatc cttcaagcaa cccctttcg acgatgaagg cacaacttgc     600
attggcgttg agacggcaga tggtaccaaa tattacgctg acaaggtggt cttagcagct    660
ggcgcatgga gcccaaccct ggtggacctg aagatcaat gttgctcgaa ggcttgggtg     720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca atggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

<210> SEQ ID NO 171
<211> LENGTH: 437
<212> TYPE: PRT
<213> ORGANISM: Coniochaeta sp.

<400> SEQUENCE: 171

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220
```

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
            245                 250                 255

Val Pro Val Tyr Asn Gly Glu Phe Gly Phe Phe Glu Pro Asp
        260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
        290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp Pro Lys Leu
        435

<210> SEQ ID NO 172
<211> LENGTH: 1314
<212> TYPE: DNA
<213> ORGANISM: Coniochaeta sp.

<400> SEQUENCE: 172
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatggactg cgaacacacg     300
cctgagggta tcgaggacct gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540 ggattcggcg cgctggatc cttcaagcaa cccctttcg acgatgaagg cacaacttgc      600
attggcgttg acggcaga tggtaccaaa tattacgctg acaaggtggt cttagcagct      660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840

```
gacgagttcc caggattctc gcgcttcaag gaacatcaac cctatggcgc cccatctccg    900
aaacggatat cagtaccacg atcgcacgcc aagcatccca cagacactta tccagacgca    960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa    1140
atcttgccta acgtcggaaa atacgtagtc gagttgatag agggccgcct gccgaggaa     1200 atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 173
<211> LENGTH: 437
<212> TYPE: PRT
<213> ORGANISM: Coniochaeta sp.

<400> SEQUENCE: 173

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Glu Gly Ile Glu Asp Leu Lys Lys Leu Tyr Gln
                100                 105                 110

Arg Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
                180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
        210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
                260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
```

```
                290               295               300
Val Pro Arg Ser His Ala Lys His Pro Thr Asp Thr Tyr Pro Asp Ala
305               310               315               320

Ser Glu Val Ser Ile Lys Lys Ala Ile Ala Thr Phe Leu Pro Arg Phe
                325               330               335

Gln Asp Lys Glu Leu Phe Asn Arg Ala Leu Cys Trp Cys Thr Asp Thr
            340               345               350

Ala Asp Ala Ala Leu Leu Met Cys Glu His Pro Lys Trp Lys Asn Phe
            355               360               365

Ile Leu Ala Thr Gly Asp Ser Gly His Ser Phe Lys Ile Leu Pro Asn
        370               375               380

Val Gly Lys Tyr Val Val Glu Leu Ile Glu Gly Arg Leu Pro Glu Glu
385               390               395               400

Met Ala Tyr Gln Trp Arg Trp Arg Pro Gly Gly Asp Ala Leu Lys Ser
                405               410               415

Arg Arg Ala Ala Pro Pro Lys Asp Leu Ala Asp Met Pro Gly Trp Lys
            420               425               430

His Asp Pro Lys Leu
        435

<210> SEQ ID NO 174
<211> LENGTH: 1314
<212> TYPE: DNA
<213> ORGANISM: Coniochaeta sp.

<400> SEQUENCE: 174
atgacgtcga atcgtgcaga tacaagggtg attgtcgtcg gtggcggagg aacgattggt    60
tcctcgacag cgctgcatct tgtgaggagt ggttatgctc ccgcaaatat cacggtcttg   120
gacacatttg agattccatc ggctcaatca gccggccatg atctcaacaa gatcatggga   180
atagatctgc gcaacaaggt ggacctgcaa atgagtctag aggctagaca gatgtggaag   240
gaggatgagt tattccagcc cttctttcac aataccggca gaatggactg cgaacacacg   300
cctgagggta tcgaggacct gaaaaagctg taccagcgtc tgcacgatgc cggtgcgggt   360
ctggagaaga ctcatgcctg gttggacaac gaggatgaga tcttatccaa gatgccgttg   420
cttcaacgtg accaaataca aggatggaaa gcaatatgga gtcaagatgg cggctggtta   480
gctgcggcaa aggccatcaa tgcgatcgga cagttcttga agaacgtggt gtaaagttc   540 ggattcggcg cgctggatc cttcaagcaa cccctttcg acgatgaagg cacaacttgc    600
attggcgttg agacgcaga tggtaccaaa tattacgctg acaaggtggt cttagcagct    660
ggcgcatgga gcccaaccct ggtggacctg aagatcaat gttgctcgaa ggcttgggtg   720
tatgctcata ttcagttgac gcctgaagag gccgctgagt ataagggtgt cccagttgtg   780
tataatggcg aatttggctt cttctttgag cctgatgagt ttggtgtaat aaaggtgtgc   840
gacgagttcc caggattctc gcgcttcaag aacatcaac cctatggcgc ccatctccg    900 aaacggatat cagtaccacg atcgcacgcc aagcatccca cagacactta ccagacgca    960 tccgaagtca gcatcaaaaa agcaatcgcg acgtttctcc ctcgatttca ggacaaggag  1020
ctcttcaatc gcgccttgtg ctggtgtaca gacactgcgg acgctgctct cttgatgtgt  1080
gaacacccca atggaagaa tttcattcta gcgaccggcg acagcggaca ctcattcaaa  1140
atcttgccta acgtcggaaa atacgtagtc gagttgatag agggccgcct gccgaggaa   1200 atggcttatc aatggaggtg gcggccagga ggcgatgcac tcaagtctag acgtgcggca  1260
```
ccgccaaaag atcttgcaga catgccagga tggaaacatg atccgaaatt gtaa    1314

<210> SEQ ID NO 175
<211> LENGTH: 437
<212> TYPE: PRT
<213> ORGANISM: Coniochaeta sp.

<400> SEQUENCE: 175

Met Thr Ser Asn Arg Ala Asp Thr Arg Val Ile Val Val Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Arg Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp Pro Lys Leu
            435

<210> SEQ ID NO 176
<211> LENGTH: 1314
<212> TYPE: DNA
<213> ORGANISM: Coniochaeta sp.

<400> SEQUENCE: 176

```
atgacgtcga atcgtgcaga tacaagggtg attgtcgtcg gtggcggagg aacgattggt      60
tcctcgacag cgctgcatct tgtgaggagt ggttatgctc cgcaaatat cacggtcttg      120
gacacatttg agattccatc ggctcaatca gccggccatg atctcaacaa gatcatggga     180
atagatctgc gcaacaaggt ggacctgcaa atgagtctag aggctagaca gatgtggaag     240
gaggatgagt tattccagcc cttctttcac aataccggca gaatgactg cgaacacacg      300
cctgagggta tcgagaaact gaaaaagctg taccagcgtc tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540
ggattcggcg gcgctggatc cttcaagcaa cccctttcg acgatgaagg cacaacttgc      600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag aacatcaac cctatggcgc cccatctccg      900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 177
<211> LENGTH: 437
<212> TYPE: PRT
<213> ORGANISM: Coniochaeta sp.

<400> SEQUENCE: 177

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr

```
                20                  25                  30
Ala Pro Ala Asn Ile Thr Val Leu Asp Thr Phe Glu Ile Pro Ser Ala
            35                  40                  45
Gln Ser Ala Gly His Asp Leu Asn Lys Ile Met Gly Ile Asp Ala Arg
        50                  55                  60
Asn Lys Val Asp Leu Gln Met Ser Leu Glu Ala Arg Gln Met Trp Lys
 65                  70                  75                  80
Glu Asp Glu Leu Phe Gln Pro Phe Phe His Asn Thr Gly Arg Met Asp
                85                  90                  95
Cys Glu His Thr Pro Glu Gly Ile Glu Lys Leu Lys Lys Leu Tyr Gln
            100                 105                 110
Lys Leu His Asp Ala Gly Ala Gly Leu Glu Lys Thr His Ala Trp Leu
        115                 120                 125
Asp Asn Glu Asp Glu Ile Leu Ser Lys Met Pro Leu Leu Gln Arg Asp
    130                 135                 140
Gln Ile Gln Gly Trp Lys Ala Ile Trp Ser Gln Asp Gly Gly Trp Leu
145                 150                 155                 160
Ala Ala Ala Lys Ala Ile Asn Ala Ile Gly Gln Phe Leu Lys Glu Arg
                165                 170                 175
Gly Val Lys Phe Gly Phe Gly Ala Gly Ser Phe Lys Gln Pro Leu
            180                 185                 190
Phe Asp Asp Glu Gly Thr Thr Cys Ile Gly Val Glu Thr Ala Asp Gly
        195                 200                 205
Thr Lys Tyr Tyr Ala Asp Lys Val Val Leu Ala Ala Gly Ala Trp Ser
    210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Glu Tyr Lys Gly
                245                 250                 255
Val Pro Val Val Tyr Asn Gly Glu Phe Gly Phe Phe Glu Pro Asp
            260                 265                 270
Glu Phe Gly Val Ile Lys Val Cys Asp Glu Phe Pro Gly Phe Ser Arg
        275                 280                 285
Phe Lys Glu His Gln Pro Tyr Gly Ala Pro Ser Pro Lys Arg Ile Ser
    290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Gln Asp Lys Glu Leu Phe Asn Arg Ala Leu Cys Trp Cys Thr Asp Thr
            340                 345                 350
Ala Asp Ala Ala Leu Leu Met Cys Glu His Pro Lys Trp Lys Asn Phe
        355                 360                 365
Ile Leu Ala Thr Gly Asp Ser Gly His Ser Phe Lys Ile Leu Pro Asn
    370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Gly Asp Ala Leu Lys Ser
                405                 410                 415
Arg Arg Ala Ala Pro Pro Lys Asp Leu Ala Asp Met Pro Gly Trp Lys
            420                 425                 430
His Asp Pro Lys Leu
            435
```

<210> SEQ ID NO 178
<211> LENGTH: 1314
<212> TYPE: DNA
<213> ORGANISM: Coniochaeta sp.

<400> SEQUENCE: 178

```
atgacgtcga atcgtgcaga tacaagggtg attgtcgtcg gtggcggagg aacgattggt      60
tcctcgacag cgctgcatct tgtgaggagt ggttatgctc ccgcaaatat cacggtcttg     120
gacacatttg agattccatc ggctcaatca gccggccatg atctcaacaa gatcatggga     180
atagatgcgc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtggt gtaaagttc      540
ggattcggcg cgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag    1020
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa    1140
atcttgccta acgtcggaaa atacgtagtc gagttgatag agggccgcct gccggaggaa    1200
atggcttatc aatggaggtg gcggccagga ggcgatgcac tcaagtctag acgtgcggca    1260
ccgccaaaag atcttgcaga catgccagga tggaaacatg atccgaaatt gtaa          1314
```

<210> SEQ ID NO 179
<211> LENGTH: 437
<212> TYPE: PRT
<213> ORGANISM: Coniochaeta sp.

<400> SEQUENCE: 179

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95
```

Cys Glu His Thr Pro Glu Gly Ile Glu Lys Leu Lys Lys Leu Tyr Gln
                100                 105                 110

Lys Leu His Asp Ala Gly Ala Gly Leu Glu Lys Thr His Ala Trp Leu
            115                 120                 125

Asp Asn Glu Asp Glu Ile Leu Ser Lys Met Pro Leu Leu Gln Arg Asp
        130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435

<210> SEQ ID NO 180
<211> LENGTH: 1314
<212> TYPE: DNA
<213> ORGANISM: Coniochaeta sp.

<400> SEQUENCE: 180
atgacgtcga atcgtgcaga tacaagggtg attgtcgtcg gtggcggagg aacgattggt    60
tcctcgacag cgctgcatct tgtgaggagt ggttatgctc ccgcaaatat cacggtcttg   120
gacacatttg agattccatc ggctcaatca gccggccatg atctcaacaa gatcatggga   180

```
atagatcatc gcaacaaggt ggacctgcaa atgagtctag aggctagaca gatgtggaag     240
gaggatgagt tattccagcc cttctttcac aataccggca gaatggactg cgaacacacg     300
cctgagggta tcgagaaact gaaaaagctg taccagaaac tgcacgatgc cggtgcgggt     360
ctggagaaga ctcatgcctg gttggacaac gaggatgaga tcttatccaa gatgccgttg     420
cttcaacgtg accaaataca aggatggaaa gcaatatgga gtcaagatgg cggctggtta     480
gctgcggcaa aggccatcaa tgcgatcgga cagttcttga agaacgtgg tgtaaagttc      540
ggattcggcg gcgctggatc cttcaagcaa ccccttttcg acgatgaagg cacaacttgc     600
attggcgttg agacggcaga tggtaccaaa tattacgctg acaaggtggt cttagcagct     660
ggcgcatgga gcccaaccct ggtggacctg aagatcaat gttgctcgaa ggcttgggtg      720
tatgctcata ttcagttgac gcctgaagag gccgctgagt ataagggtgt cccagttgtg     780
tataatggcg aatttggctt cttctttgag cctgatgagt ttggtgtaat aaaggtgtgc     840
gacgagttcc caggattctc gcgcttcaag gaacatcaac cctatggcgc cccatctccg     900
aaacggatat cagtaccacg atcgcacgcc aagcatccca cagacactta tccagacgca     960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt    1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa          1314
```

<210> SEQ ID NO 181
<211> LENGTH: 437
<212> TYPE: PRT
<213> ORGANISM: Coniochaeta sp.

<400> SEQUENCE: 181

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Glu Ile Pro Ser Ala
            35                  40                  45

Gln Ser Ala Gly His Asp Leu Asn Lys Ile Met Gly Ile Asp His Arg
        50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175
```

Gly Val Lys Phe Gly Phe Gly Ala Gly Ser Phe Lys Gln Pro Leu
            180                 185                 190

Phe Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Tyr Asn Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
            435

<210> SEQ ID NO 182
<211> LENGTH: 1314
<212> TYPE: DNA
<213> ORGANISM: Coniochaeta sp.

<400> SEQUENCE: 182
atgacgtcga atcgtgcaga tacaagggtg attgtcgtcg gtggcggagg aacgattggt        60
tcctcgacag cgctgcatct tgtgaggagt ggttatgctc ccgcaaatat cacggtcttg       120
gacacatttg agattccatc ggctcaatca gccggccatg atctcaacaa gatcatggga       180
atagatcatc gcaacaaggt ggacctgcaa atgagtctag aggctagaca gatgtggaag       240
gaggatgagt tattccagcc cttctttcac aataccggca gaatggactg cgaacacacg       300
cctaagggta tcgagaaact gaaaaagctg taccagaaac tgcacgatgc cggtgcgggt       360
ctggagaaga ctcatgcctg gttggacaac gaggatgaga tcttatccaa gatgccgttg       420
cttcaacgtg accaaataca aggatggaaa gcaatatgga gtcaagatgg cggctggtta       480
gctgcggcaa aggccatcaa tgcgatcgga cagttcttga agaacgtgg tgtaaagttc        540 ggattcggcg cgctggatc cttcaagcaa cccctttcg acgatgaagg cacaacttgc        600

```
attggcgttg agacggcaga tggtaccaaa tattacgctg acaaggtggt cttagcagct      660
ggcgcatgga gcccaaccct ggtggacctg gaagatcaat gttgctcgaa ggcttgggtg      720
tatgctcata ttcagttgac gcctgaagag ccgctgagt ataagggtgt cccagttgtg      780
tataatggcg aatttggctt cttctttgag cctgatgagt ttggtgtaat aaaggtgtgc      840
gacgagttcc caggattctc gcgcttcaag gaacatcaac cctatggcgc cccatctccg      900
aaacggatat cagtaccacg atcgcacgcc aagcatccca cagacactta tccgacgca      960 tccgaagtca gcatcaaaaa agcaatcgcg acgtttctcc ctcgatttca ggacaaggag     1020
ctcttcaatc gcgccttgtg ctggtgtaca gacactgcgg acgctgctct cttgatgtgt     1080
gaacacccca atggaagaa tttcattcta gcgaccggcg acagcggaca ctcattcaaa      1140
atcttgccta acgtcggaaa atacgtagtc gagttgatag agggccgcct gccggaggaa     1200
atggcttatc aatggaggtg gcggccagga ggcgatgcac tcaagtctag acgtgcggca     1260
ccgccaaaag atcttgcaga catgccagga tggaaacatg atccgaaatt gtaa           1314
```

<210> SEQ ID NO 183
<211> LENGTH: 437
<212> TYPE: PRT
<213> ORGANISM: Coniochaeta sp.

<400> SEQUENCE: 183

```
Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
```

|     | 245 |     |     |     | 250 |     |     |     | 255 |     |     |
|---|---|---|---|---|---|---|---|---|---|---|---|

Val Pro Val Val Tyr Asn Gly Glu Phe Gly Phe Phe Glu Pro Asp
        260               265              270

Glu Phe Gly Val Ile Lys Val Cys Asp Glu Phe Pro Gly Phe Ser Arg
        275               280              285

Phe Lys Glu His Gln Pro Tyr Gly Ala Pro Ser Pro Lys Arg Ile Ser
     290               295              300

Val Pro Arg Ser His Ala Lys His Pro Thr Asp Thr Tyr Pro Asp Ala
305               310              315              320

Ser Glu Val Ser Ile Lys Lys Ala Ile Ala Thr Phe Leu Pro Arg Phe
          325               330              335

Gln Asp Lys Glu Leu Phe Asn Arg Ala Leu Cys Trp Cys Thr Asp Thr
        340               345              350

Ala Asp Ala Ala Leu Leu Met Cys Glu His Pro Lys Trp Lys Asn Phe
     355               360              365

Ile Leu Ala Thr Gly Asp Ser Gly His Ser Phe Lys Ile Leu Pro Asn
370               375              380

Val Gly Lys Tyr Val Val Glu Leu Ile Glu Gly Arg Leu Pro Glu Glu
385               390              395              400

Met Ala Tyr Gln Trp Arg Trp Arg Pro Gly Gly Asp Ala Leu Lys Ser
        405               410              415

Arg Arg Lys Ala Pro Pro Lys Asp Leu Ala Asp Met Pro Gly Trp Lys
        420               425              430

His Asp Pro Lys Leu
     435

<210> SEQ ID NO 184
<211> LENGTH: 1314
<212> TYPE: DNA
<213> ORGANISM: Coniochaeta sp.

<400> SEQUENCE: 184

| | | |
|---|---|---|
| atgacgtcga atcgtgcaga tacaagggtg attgtcgtcg gtggcggagg aacgattggt | 60 |
| tcctcgacag cgctgcatct tgtgaggagt ggttatgctc ccgcaaatat cacggtcttg | 120 |
| gacacatttg agattccatc ggctcaatca gccggccatg atctcaacaa gatcatggga | 180 |
| atagatcatc gcaacaaggt ggacctgcaa atgagtctag aggctagaca gatgtggaag | 240 |
| gaggatgagt tattccagcc cttctttcac aataccggca gaatggactg cgaacacacg | 300 |
| cctgagggta tcgagaaact gaaaaagctg taccagaaac tgcacgatgc cggtgcgggt | 360 |
| ctggagaaga ctcatgcctg gttggacaac gaggatgaga tcttatccaa gatgccgttg | 420 |
| cttcaacgtg accaaataca aggatggaaa gcaatatgga gtcaagatgg cggctggtta | 480 |
| gctgcggcaa aggccatcaa tgcgatcgga cagttcttga agaacgtggt gtaaagttc | 540 |
| ggattcggcg cgctggatc cttcaagcaa cccctttcg acgatgaagg cacaacttgc | 600 |
| attggcgttg agacggcaga tggtaccaaa tattacgctg acaaggtggt cttagcagct | 660 |
| ggcgcatgga gcccaaccct ggtggacctg aagatcaat gttgctcgaa ggcttgggtg | 720 |
| tatgctcata ttcagttgac gcctgaagag gccgctgagt ataagggtgt cccagttgtg | 780 |
| tataatggcg aatttggctt cttctttgag cctgatgagt ttggtgtaat aaaggtgtgc | 840 |
| gacgagttcc caggattctc gcgcttcaag gaacatcaac cctatggcgc cccatctccg | 900 |
| aaacggatat cagtaccacg atcgcacgcc aagcatccca cagacactta tccagacgca | 960 |
| tccgaagtca gcatcaaaaa agcaatcgcg acgtttctcc ctcgatttca ggacaaggag | 1020 |

```
ctcttcaatc gcgccttgtg ctggtgtaca gacactgcgg acgctgctct cttgatgtgt    1080
gaacacccca atggaagaa tttcattcta gcgaccggcg acagcggaca ctcattcaaa     1140
atcttgccta acgtcggaaa atacgtagtc gagttgatag agggccgcct gccggaggaa    1200
atggcttatc aatggaggtg gcggccagga ggcgatgcac tcaagtctag acgtaaggca    1260
ccgccaaaag atcttgcaga catgccagga tggaaacatg atccgaaatt gtaa          1314
```

<210> SEQ ID NO 185
<211> LENGTH: 438
<212> TYPE: PRT
<213> ORGANISM: Aspergillus nidulans

<400> SEQUENCE: 185

```
Met Thr Pro Arg Ala Asn Thr Lys Ile Ile Val Val Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp His Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe His Asn Val Gly Met Ile Asp Val
                85                  90                  95

Ser Ser Thr Glu Lys Gly Ile Glu Lys Leu Arg Lys Leu Tyr Gln Lys
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320
```

```
Ser Glu Val Thr Ile Lys Lys Ala Ile Asn Arg Phe Leu Pro Arg Phe
            325                 330                 335

Asn Asp Lys Glu Leu Phe Asn Arg Ala Met Cys Trp Cys Thr Asp Thr
        340                 345                 350

Ala Asp Ser Asn Leu Leu Val Cys Glu His Pro Arg Trp Lys Gly Phe
            355                 360                 365

Tyr Leu Ala Thr Gly Asp Ser Gly His Ser Phe Lys Leu Leu Pro Asn
        370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 186
<211> LENGTH: 1317
<212> TYPE: DNA
<213> ORGANISM: Aspergillus nidulans

<400> SEQUENCE: 186
atgacgcccc gagccaacac caaaatcatt gtcgtcggcg gcggcggcac aatgggctcg      60
tcgacagccc tacacctcct gcgcgccggc tacacgccgt ccaacattac agtgctcgac     120
acgtgcccta tccctccgc acagtctgca ggctacgacc tgaacaaaat catgggcatc     180
gatcatcgca acaagcctga tttacagctc tctcttgagg cgctggacat gtggaaaaat     240
gatcctctct tcaagccgtt tttccacaat gttggaatga tcgacgtctc ttcaacagag     300
aaaggcatcg agaaacttcg gaagctgtac cagaaacttc tcgacgcagg cattgggctc     360
gagaagacga atttcatgct ggaaagtgaa gacgagatcc tggctaaagc gccgcatttc     420
acgcaggagc agattaaagg ctggaaaggc ctgttctgtg gcgacggcgg ctggctcgct     480
gcagccaaag ccatcaatgc cattgggcag ttcctcaagg aacagggcgt caagtttgga     540
ttcggcggcg ccggcacgtt caaaaagcca ctcttcgccg atgcccacga agacgtgc      600 atcggcgtcg agactgtaga cggcacaaag tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt ataagaacac tcctgttata     780
tacgacggtg actatgggtt tttctttgag ccgaatgaaa acggcatcat aaaagtctgt     840
gacgaattcc ctggcttcac gcatttcaaa atgcaccagc cgtacggctc gccggcgccc     900
aaacccatct ctgtgcctcg ttcccatgcg aagcacccca cagatacata cccgcacgcg     960
tcggaggtca cgatcaaaaa ggctatcaac cggttcctgc cgaggttcaa tgacaaggaa    1020
ctgtttaaca gggccatgtg ctggtgcacc gataccgcgg atagcaatct gcttgtttgt    1080
gagcatccac gctggaaggg gttttatctt gcaacagggg acagtgggca ttcgttcaag    1140
ttgctgccga atattggaaa gcatgttgtc gagttattgg aggagaggct ggaaagtgtg    1200
tttaaggatg cttggaggtg gaggcctggc agtggggatg cattaaaaag tagacgggct    1260
gcgcctgcga aggacctggc ggatatgccg gggtggagga atgaggcaaa gatgtag        1317

<210> SEQ ID NO 187
<211> LENGTH: 437
```

<212> TYPE: PRT
<213> ORGANISM: Phaeosphaeria nodorum

<400> SEQUENCE: 187

```

Trp Arg Trp Arg Pro Gly Ser Gly Asp Ala Leu Lys Ser Arg Arg Ser
            405                 410                 415

Ala Pro Ala Lys Asp Leu Ala Asp Met Pro Gly Trp Asn His Asp Lys
        420                 425                 430

Pro Arg Ala Asn Leu
        435

<210> SEQ ID NO 188
<211> LENGTH: 1314
<212> TYPE: DNA
<213> ORGANISM: Phaeosphaeria nodorum

<400> SEQUENCE: 188

| | | | | | |
|---|---|---|---|---|---|
| atggccccgt | cgcgtgctaa | tacgtcggtc | attgtggttg | gtggtggtgg | tacgattggc | 60 |
| tcatctacgg | ctctgcatct | ggtccgctca | ggctataccc | cgtcgaacgt | gacggttctg | 120 |
| gatgcatacc | cgattccgag | ctctcagagc | gctggcaacg | acctgaataa | aatcatgggt | 180 |
| gtcgatcatc | gtaatccggt | ggatctgcag | ctggctctgg | aagcgcgcca | aatgtggaac | 240 |
| gaagacgaac | tgttcaagaa | gttttttccat | aacaccggcc | gtctggattg | cgcgcacggt | 300 |
| gaaaaagata | ttgccaaact | gaagagcctg | tatcagaaac | tggtggatgc | gggtctggac | 360 |
| gccacgaacg | aatggctgga | tagtgaagac | gaaatcctga | acgtatgcc | gctgctgtcc | 420 |
| cgcgatcaaa | ttaaaggctg | gaaggcgatc | ttttcaaaag | acggtggttg | gctggcagca | 480 |
| gcaaaggcaa | ttaatgcagt | tggtgaatat | ctgcgtgatc | agggcgtccg | cttcggtttt | 540 |
| tacgcgccg | gttctttcaa | agcaccgctg | ctggctgaag | gcgtctgcat | cggtgtcgaa | 600 |
| accgtggatg | gcacgcgcta | ttacgcagac | aaagtggttc | tggctgcagg | tgcatggtcg | 660 |
| ccgaccctgg | ttgaactgca | tgaacagtgt | gtgagcaaag | cgtgggttta | cggccacatt | 720 |
| caactgacgc | cggaagaagc | cgcacgttat | aagaacagcc | cggtcgtgta | caatggcgat | 780 |
| gtgggctttt | tctttgaacc | gaacgaacat | ggcgttatca | aagtctgcga | tgaatttccg | 840 |
| ggttttaccc | gcttcaagat | gcaccagccg | tttggtgcca | aagcaccgaa | gcgtattagt | 900 |
| gtgccgcgct | cccatgccaa | acaccccgacc | gatacgatcc | cggatgcaag | tgacgtttcc | 960 |
| attcgtcgcg | ctatcgcgac | ctttatgccg | cagttcaaga | acaaaaagat | gttcaaccaa | 1020 |
| gcgatgtgct | ggtgtaccga | tacggccgac | agcgcgctgc | tgatttgtga | acatccggaa | 1080 |
| tggaaaaact | tgttctggc | gaccggcgat | tcaggtcatt | cgttcaaact | gctgccgaat | 1140 |
| atcggcaagc | acgttgtcga | actgctggag | ggtacgctgg | cagatgacct | ggcacacgca | 1200 |
| tggcgttggc | gtccgggtag | tggtgatgca | ctgaaaagcc | gtcgctctgc | tccggcgaaa | 1260 |
| gacctggctg | atatgccggg | ctggaaccat | gacaaaccgc | gtgctaatct | gtaa | 1314 |

<210> SEQ ID NO 189
<211> LENGTH: 443
<212> TYPE: PRT
<213> ORGANISM: Cryptococcus neoformans

<400> SEQUENCE: 189

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Asp Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Lys Leu Arg Lys Leu Tyr Glu
            100                 105                 110

Lys Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Leu Ala Ala Gly Ala Trp Ser
210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Met Asp
        435                 440

<210> SEQ ID NO 190
<211> LENGTH: 1332
<212> TYPE: DNA

<213> ORGANISM: Cryptococcus neoformans

<400> SEQUENCE: 190

```
atgccgccgt cccgtgcttc aacgaaagtg attgtcattg gtggtggtgg tacgctgggc    60
tcctcaaccg ccctgcatct gctgcgcgcg ggctataccc cgagtaacat taccgtgctg   120
gatacgtacc tgatcccgag tgcccagtcc gcaggcaacg acctgaataa aattatgggt   180
attgatatcc gcaatccggt ggataaacaa ctgagcctgg aagcccgtga tatgtggcgc   240
aacgacgaag ttttcaaacc gtacttccat aacaccggtc gtctggactg cgctcacacg   300
ccggaatcaa ttgcgaaact gcgtaaactg tacgaaaaaa tcctgaaagc aggctcaggt   360
ctggaaaaaa cccatcactg gctgtcgacg gaagatgaaa tcctggcacg tgcaccgctg   420
ctggaccgta acagattaa aggttggaaa gcaatctata gtgaagatgg cggttggctg   480
gcggccgcaa aagctattaa ctccatcggc caagtcctga agaaaaagg tgtgaccttc   540
ggctttggta gcgcaggctc ttttaaaaaa ccgctgttcg atgaagacgg cacgaaagcc   600
attggtatcg aaaccgttga tggtacgcag tattttgccg acaaagtggt tctggctgca   660
ggtgcatgga gcccgaccct ggttgatctg gaaggccagt gctgttctaa agcttgggtc   720
tacgcgcaca tgcaactgac gccggaagaa gccgcagaat ataagaatg cccggtcgtg   780
tacaacagcg aactgggctt tttctttgaa ccgaacgaaa aaggtgtgat caaagtttgt   840
gatgaattcc cgggctttac ccgtttcaaa cagcatcaac cgtacggtgc tagctctacg   900
aaacacatta gctttccgcg ctctcatgcg aaacacccga ccgatacgat cccggatgaa   960
agtgacgcct ccattcgtcg cgctatctct gcgtttctgc gcgtttcaa agaaaaagaa  1020
ctgtttaacc gcgcgctgtg ctggtgtacc gatacggctg acgcgaacct gctgatttgt  1080
gaacacccga aatggaaaaa ttttatcctg gccaccggcg attcaggtca ttcgttcaaa  1140
attctgccga atatcggcaa acacgttgtc gaactgattg aaggtaccct ggccgaagat  1200
ctggcagaaa gctggcgttg gcgtccgggc agtggtgacc cgctgatctc ccgtcgcgct  1260
gcgccggcgc gcgacctggc ggacctgccg ggctggaacc acgacgaacc gagcgacgat  1320
gacatggact ga                                                      1332
```

<210> SEQ ID NO 191
<211> LENGTH: 440
<212> TYPE: PRT
<213> ORGANISM: Curvularia clavata

<400> SEQUENCE: 191

```
Met Ala Pro Ser Arg Ala Asn Thr Ser Val Ile Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Ala Tyr Pro Ile Pro Ser Ser
        35                  40                  45

Gln Ser Ala Gly Asn Asp Leu Asn Lys Ile Met Gly Ile Asp His Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Lys Leu Arg Gln Leu Tyr Gln
            100                 105                 110
```

```
Lys Leu Leu Asp Ala Asn Ala Gly Leu Glu Glu Thr Thr Glu Trp Leu
            115                 120                 125

Asp Ser Glu Asp Glu Ile Leu Lys Lys Met Pro Leu Leu Ser Arg Asp
130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Ala Gly Ser Phe Lys Gln Pro Leu
            180                 185                 190

Leu Ala Glu Gly Val Cys Ile Gly Val Glu Thr Val Asp Gly Thr Arg
            195                 200                 205

Tyr Tyr Ala Asp Lys Val Val Leu Ala Ala Gly Ala Trp Ser Pro Thr
210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
            275                 280                 285

Met His Gln Pro Phe Gly Ala Lys Ala Pro Lys Arg Ile Ser Val Pro
290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ser Ala Leu Leu Ile Cys Glu His Pro Glu Trp Lys Asn Phe Val Leu
355                 360                 365

Ala Thr Gly Asp Ser Gly His Ser Phe Lys Leu Leu Pro Asn Ile Gly
370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415

Arg Ser Ala Pro Ala Lys Asp Leu Ala Asp Met Pro Gly Trp Lys His
            420                 425                 430

Asp Asp Val Val Lys Ser Lys Leu
            435                 440

<210> SEQ ID NO 192
<211> LENGTH: 1323
<212> TYPE: DNA
<213> ORGANISM: Curvularia clavata

<400> SEQUENCE: 192
atggccccgt cgcgtgctaa tacgtcggtc attgtggttg gtggtggtgg tacgattggc      60
tcatctacgg ctctgcatct ggtccgctca ggctataccc cgtcgaacat tacggttctg     120
gatgcatacc cgattccgag ctctcagagc gctggcaacg acctgaataa aatcatgggt     180
atcgatcatc gtaataaggt ggatctgcag ctgtctctgg aagcgcgcca aatgtggcgc     240
```

```
gaagacgatc tgttcaagga gtatttccat aacaccggcc gtctggattg cgcgcacggt    300
gaagaaggtc ttgccaaact gcgtcaactg tatcagaaac tgctggatgc gaatgcgggt    360
ctggaagaga cgaccgaatg gctggatagt gaagacgaaa tcctgaaaaa aatgccgctg    420
ctgtcccgcg atcaaattaa aggctggaag gcggtgtatt cacaggacgg tggttggctg    480
gcagcagcaa aggcaattaa tgcaattggt gaatatctgc gtgctcaggg cgtcaaattc    540
ggttttggcg cgccggttc tttcaaacaa ccgctgctgg ctgaaggcgt ctgcatcggt    600
gtcgaaaccg tggatggcac gcgctattac gcagacaaag tggttctggc tgcaggtgca    660
tggtcgccga ccctggttga actgcatgaa cagtgtgtga gcaaagcgtg ggtttacggc    720
cacattcaac tgacgccgga agaagccgca gaatataaga acagcccggt cgtgtacaat    780
ggcgatgtgg gcttttttctt tgaaccgaac gaacatggcg ttatcaaagt ctgcgatgaa    840
tttccgggtt ttacccgctt caagatgcac cagccgtttg gtgccaaagc accgaagcgt    900
attagtgtgc cgcgctccca tgccaaacac ccgaccgata cgatcccgga tgcaagtgaa    960
aaatccattc gtaaagctat cgcgaccttt ctgccgaagt tcacggagaa agagctgttc   1020
aaccgtcatc tgtgctggtg taccgatacg gccgacagcg cgctgctgat ttgtgaacat   1080
ccggaatgga aaaactttgt tctggcgacc ggcgattcag gtcattcgtt caaactgctg   1140
ccgaatatcg gcaagcacgt tgtcgaactg ctggagggta cgctggcaga tgacctggca   1200
cacgcatggc gttggcgtcc gggtagtggt gatgcactga aaagccgtcg ctctgctccg   1260
gcgaaagacc tggctgatat gccgggctgg aaacatgacg atgtggtgaa aagcaaactg   1320
taa                                                                 1323

<210> SEQ ID NO 193
<211> LENGTH: 28
<212> TYPE: DNA
<213> ORGANISM: Artificial
<220> FEATURE:
<223> OTHER INFORMATION: primer

<400> SEQUENCE: 193
caccttgttg cgatgatcta ttcccatg                                         28

<210> SEQ ID NO 194
<211> LENGTH: 28
<212> TYPE: DNA
<213> ORGANISM: Artificial
<220> FEATURE:
<223> OTHER INFORMATION: primer

<400> SEQUENCE: 194
cgcaacaagg tgaacctgca aatgagtc                                         28

<210> SEQ ID NO 195
<211> LENGTH: 28
<212> TYPE: DNA
<213> ORGANISM: Artificial
<220> FEATURE:
<223> OTHER INFORMATION: primer

<400> SEQUENCE: 195
agagtccgca gtgtctgtac accagcac                                         28

<210> SEQ ID NO 196
<211> LENGTH: 30
<212> TYPE: DNA
<213> ORGANISM: Artificial
```

```
<220> FEATURE:
<223> OTHER INFORMATION: primer

<400> SEQUENCE: 196
acactgcgga ctctactctc ttgatgtgtg                                      30

<210> SEQ ID NO 197
<211> LENGTH: 10
<212> TYPE: DNA
<213> ORGANISM: Artificial
<220> FEATURE:
<223> OTHER INFORMATION: primer

<400> SEQUENCE: 197
aaaaaaaaaa                                                            10

<210> SEQ ID NO 198
<211> LENGTH: 10
<212> TYPE: DNA
<213> ORGANISM: Artificial
<220> FEATURE:
<223> OTHER INFORMATION: primer

<400> SEQUENCE: 198
cccccccccc                                                            10

<210> SEQ ID NO 199
<211> LENGTH: 434
<212> TYPE: PRT
<213> ORGANISM: Coniochaeta sp. NISL 9330

<400> SEQUENCE: 199
```

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
        35                  40                  45

Gln Ser Ala Gly His Asp Leu Asn Lys Ile Met Gly Ile Asp His Arg
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Ala Ile Leu Ser Lys Met Pro Leu Leu Gln Arg Asp
    130                 135                 140

Gln Ile Gln Gly Trp Lys Ala Ile Trp Ser Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser

```
                 210                 215                 220
Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
                260                 265                 270

Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
                290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
                340                 345                 350

Ala Asp Ser Ala Leu Leu Met Cys Glu His Pro Lys Trp Lys Asn Phe
                355                 360                 365

Ile Leu Ala Thr Gly Asp Ser Gly His Ser Phe Lys Ile Leu Pro Asn
                370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp

<210> SEQ ID NO 200
<211> LENGTH: 1305
<212> TYPE: DNA
<213> ORGANISM: Coniochaeta sp. NISL 9330

<400> SEQUENCE: 200
atgacctcaa accgtgctga tacccgtgtt attgttgttg gtggtggtgg tacgattggc      60
tcctcgaccg ctctgcatct ggtgcgtagt ggctatgctc cggcgaacat taccgtcctg     120
gatacgtttc cgatcccgag cgcccagtct gcaggccatg atctgaataa aattatgggt     180
atcgaccacc gtaacaaagt taatctgcag atgagcctgg aagcgcgcca aatgtggaaa     240
gaagatgaac tgttccagcc gttttttcca acaccggcc gtatggactg cgaacacacg     300
ccgaaaggta tcgaaaaact gaaaaaactg taccaaaaac tgcatgatgc cggcgcaggt     360
ctggaaaaaa cccacgcctg gctggataac gaagacgcaa ttctgagcaa atgccgctg     420
ctgcagcgtg atcagattca aggttggaaa gccatctggt ctcaagacgg cggttggctg     480
gcagcagcaa aagctattaa tgcgatcggc cagtttctga agaacgcgg cgtgaaattc     540
ggttttggcg gtgcaggttc ttttaaacaa ccgctgttcg atgacgaagg caccacgtgt     600
atcggtgttg aaaccgctga tggcacgaaa tattacgcgg acaaagtggt tctggctgca     660
ggtgcatgga gtccgacccct ggtcgatctg aagaccagt gctgttccaa agcgtgggtg     720
tatgcgcata ttcaactgac gccggaagaa gccgcaaaat ataaaggctg cccggtcgtg     780
taccacggcg aatttggctt tttctttgaa ccggatgaat ttggcgtgat caaagtttgt     840
```

```
gacgaatttc cgggttttc acgtttcaaa gaacatcagc cgtatggtgc gccgtcgccg    900
aaacgtatta gcgttccgcg ctctcatgcc aaacacccga ccgatacgta cccggacgca    960
agtgaagtct ccattaagaa agcgatcgcg acctttctgc cgcgtttcaa agataaaccg    1020
ctgtttaatc gcgcactgtg ctggtgtacc gatacggccg acagcgcact gctgatgtgc    1080
gaacatccga atggaaaaa ctttattctg gcgaccggcg attcaggtca ctcgttcaaa    1140
atcctgccga atgtgggcaa atatgttgtc gaactgattg aaggtcgcct gccggaagaa    1200
atggcttacc agtggcgttg gcgtccgggc ggtgatgccc tgaaaagtcg ccgtgctgct    1260
ccgccgaaag acctggctga tatgccgggc tggaaacatg actaa    1305
```

<210> SEQ ID NO 201
<211> LENGTH: 30
<212> TYPE: DNA
<213> ORGANISM: Artificial
<220> FEATURE:
<223> OTHER INFORMATION: primer

<400> SEQUENCE: 201
gctgtcggcc gtatcggtac accagcacag    30

<210> SEQ ID NO 202
<211> LENGTH: 30
<212> TYPE: DNA
<213> ORGANISM: Artificial
<220> FEATURE:
<223> OTHER INFORMATION: primer

<400> SEQUENCE: 202
atacggccga cagcacactg ctgatgtgcg    30

<210> SEQ ID NO 203
<211> LENGTH: 434
<212> TYPE: PRT
<213> ORGANISM: Coniochaeta sp.

<400> SEQUENCE: 203

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
        35                  40                  45

Gln Ser Ala Gly His Asp Leu Asn Lys Ile Met Gly Ile Asp His Arg
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Ala Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg

```
                165                 170                 175
Gly Val Lys Phe Gly Phe Gly Ala Gly Ser Phe Lys Gln Pro Leu
            180                 185                 190

Phe Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
                260                 265                 270

Glu Phe Gly Val Ile Lys Val Cys Asp Glu Phe Pro Gly Phe Ser Arg
                275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
            355                 360                 365

Ile Leu Ala Thr Gly Asp Ser Gly His Ser Phe Lys Ile Leu Pro Asn
        370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
                420                 425                 430

His Asp

<210> SEQ ID NO 204
<211> LENGTH: 1305
<212> TYPE: DNA
<213> ORGANISM: Coniochaeta sp.

<400> SEQUENCE: 204
atgacctcaa accgtgctga tacccgtgtt attgttgttg gtggtggtgg tacgattggc    60
tcctcgaccg ctctgcatct ggtgcgtagt ggctatgctc cggcgaacat taccgtcctg   120
gatacgtttc cgatcccgag cgcccagtct gcaggccatg atctgaataa aattatgggt   180
atcgaccacc gtaacaaagt taatctgcag atgagcctgg aagcgcgcca aatgtggaaa   240
gaagatgaac tgttccagcc gttttttccat aacaccggcc gtatggactg cgaacacacg   300
ccgaaaggta tcgaaaaact gaaaaaactg taccaaaaac tgcatgatgc cggcgcaggt   360
ctggaaaaaa cccacgccct gctggataac gaagacgcaa ttctgagcaa aatgccgctg   420
ctgcagcgtg atcagattca aggttggaaa gccatctggt ctcaagacgg cggttggctg   480
gcagcagcaa aagctattaa tgcgatcggc cagtttctga agaacgcggg cgtgaaattc   540
ggttttggcg gtgcaggttc ttttaaacaa ccgctgttcg atgacgaagg caccacgtgt   600
```

```
atcggtgttg aaaccgctga tggcacgaaa tattacgcgg acaaagtggt tctggctgca      660
ggtgcatgga gtccgaccct ggtcgatctg gaagaccagt gctgttccaa agcgtgggtg      720
tatgcgcata ttcaactgac gccggaagaa gccgcaaaat ataaaggctg cccggtcgtg      780
taccacggcg aatttggctt tttctttgaa ccggatgaat ttggcgtgat caaagtttgt      840
gacgaatttc cgggttttc acgtttcaaa gaacatcagc cgtatggtgc gccgtcgccg       900
aaacgtatta gcgttccgcg ctctcatgcc aaacacccga ccgatacgta cccggacgca      960
agtgaagtct ccattaagaa agcgatcgcg acctttctgc cgcgtttcaa agataaaccg     1020
ctgtttaatc gcgcactgtg ctggtgtacc gatacggccg acagcacact gctgatgtgc     1080
gaacatccga aatggaaaaa ctttattctg gcgaccggcg attcaggtca ctcgttcaaa     1140
atcctgccga atgtgggcaa atatgttgtc gaactgattg aaggtcgcct gccggaagaa     1200
atggcttacc agtggcgttg gcgtccgggc ggtgatgccc tgaaaagtcg ccgtgctgct     1260
ccgccgaaag acctggctga tatgccgggc tggaaacatg actaa                     1305
```